United States Patent
Chen et al.

(10) Patent No.: US 11,046,682 B2
(45) Date of Patent: Jun. 29, 2021

(54) FUSED HETEROCYCLIC DERIVATIVES, THEIR PREPARATION METHODS THEREOF AND MEDICAL USES THEREOF

(71) Applicant: Beijing Innocare Pharma Tech Co., Ltd., Beijing (CN)

(72) Inventors: Xiangyang Chen, Beijing (CN); Yingxiang Gao, Jiangsu (CN)

(73) Assignee: Beijing Innocare Pharma Tech Co., Ltd., Beijing (CN)

( * ) Notice: Subject to any disclaimer, the term of this patent is extended or adjusted under 35 U.S.C. 154(b) by 0 days.

(21) Appl. No.: 16/327,722

(22) PCT Filed: Aug. 16, 2017

(86) PCT No.: PCT/CN2017/097660
§ 371 (c)(1),
(2) Date: Feb. 22, 2019

(87) PCT Pub. No.: WO2018/036414
PCT Pub. Date: Mar. 1, 2018

(65) Prior Publication Data
US 2019/0185472 A1  Jun. 20, 2019

(30) Foreign Application Priority Data
Aug. 23, 2016  (CN) .......................... 201610705318.9

(51) Int. Cl.
| | | |
|---|---|---|
| C07D 471/04 | (2006.01) | |
| A61K 31/437 | (2006.01) | |
| C07D 231/56 | (2006.01) | |
| A61P 35/00 | (2006.01) | |
| A61K 45/06 | (2006.01) | |

(52) U.S. Cl.
CPC .......... *C07D 471/04* (2013.01); *A61K 31/437* (2013.01); *A61P 35/00* (2018.01); *C07D 231/56* (2013.01); *A61K 45/06* (2013.01)

(58) Field of Classification Search
CPC .................................................. C07D 471/04
See application file for complete search history.

(56) References Cited

U.S. PATENT DOCUMENTS

| | | | |
|---|---|---|---|
| 10,280,163 B2 * | 5/2019 | Wang .................... | C07D 471/04 |
| 2005/0137243 A1 | 6/2005 | Souers et al. | |
| 2010/0004269 A1 * | 1/2010 | Price ..................... | C07D 471/04 |
| | | | 514/259.1 |
| 2011/0053941 A1 | 3/2011 | Mautino et al. | |
| 2011/0183973 A1 | 7/2011 | Baldwin et al. | |
| 2012/0245163 A1 | 9/2012 | Gomtsyan et al. | |
| 2012/0245171 A1 | 9/2012 | Baldwin et al. | |

FOREIGN PATENT DOCUMENTS

| | | |
|---|---|---|
| CN | 101932325 A | 12/2010 |
| KR | 10-2014-0095325 A | 8/2014 |
| WO | WO-2007075598 A2 | 7/2007 |
| WO | WO-2011056652 A1 | 5/2011 |
| WO | WO-2014/134388 A1 | 9/2014 |
| WO | WO-2014186035 A1 | 11/2014 |
| WO | WO-2015070007 A1 | 5/2015 |
| WO | WO-2015082499 A2 | 6/2015 |
| WO | WO-2016026772 A1 | 2/2016 |
| WO | WO-2016/044585 A1 | 3/2016 |
| WO | WO-2016037026 A1 | 3/2016 |
| WO | WO-2016051181 A1 | 4/2016 |
| WO | WO-2016/071293 A2 | 5/2016 |
| WO | WO-2016073738 A2 | 5/2016 |
| WO | WO-2016073774 A2 | 5/2016 |
| WO | WO-2016102493 A1 | 6/2016 |

(Continued)

OTHER PUBLICATIONS

Banker et al. "Modern Pharmaceutics", 3rd Ed. p. 596 (1996). (Year: 1996).*
Burger's Medicinal Chemistry,, edited by Manfred E.Wolf, 5th Ed. Part 1, pp. 975-977 (1995). (Year: 1995).*
Evans in "Principles of Radiopharmacology", Colombett, L.G. editor, CRC Press, pp. 11-13 and 24 (1979). (Year: 1979).*
Coletti et al. Med. Chem. Commun., 2017, 8, 1378-1392 . (Year: 2017).*
Yu et al. Org. Lett. 2014, 16, 4826-4829. (Year: 2014).*
Machine translation for WO 2018/171602 (Sep. 27, 2018).*
CN Priority Application No. 201710168579.6 filed Mar. 21, 2017.*

(Continued)

*Primary Examiner* — Emily A Bernhardt
(74) *Attorney, Agent, or Firm* — Foley Hoag LLP

(57) ABSTRACT

The present invention relates to fused heterocyclic derivatives, processes for their preparation and their use in medicine. Specifically, the present invention relates to a novel derivative represented by the formula (I'), or its pharmaceutically acceptable salt thereof, a pharmaceutical composition containing the derivative or its pharmaceutically acceptable salt thereof, and the method for preparing the derivative and its pharmaceutically acceptable salt thereof. The present invention also relates to the use of the derivative and its pharmaceutically acceptable salt thereof, or a pharmaceutical composition containing the derivative and its pharmaceutically acceptable salt thereof in the preparation of medicines, in particularly as IDO inhibitor medicines, for treating and/or preventing cancers. Wherein each substituent of the formula (I') is the same as defined in the specification.

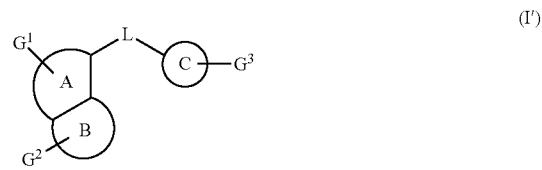

(I')

7 Claims, No Drawings

(56) References Cited

FOREIGN PATENT DOCUMENTS

| WO | WO-2016/126570 A1 | 8/2016 |
| WO | WO-2016/161960 A1 | 10/2016 |
| WO | WO-2018/171602 A1 | 9/2018 |

OTHER PUBLICATIONS

Machine translation for CN Priority Application No. 201710168579.6 filed Mar. 21, 2017.*
Koblish et al., "Hydroxyamidine Inhibitors of Indoleamine-2,3-dioxygenase Potently Suppress Systemic Tryptophan Catabolism and the Growth of IDO-Expressing Tumors," Mol Cancer Ther, 9(2):489-98 (2010).
Mautino et al., "Synergistic antitumor effects of combinatorial immune checkpoint inhibition with anti-PD-1/PD-L antibodies and the IDO pathway inhibitors NLG-919 and indoximod in the context of active immunotherapy," AACR, Abstract 5023 (2014).
RN 1401074-60-9, STN REG, Oct. 16, 2012 (Oct. 16, 2012), p. 3.
RN 1401074-73-4, STN REG, Oct. 16, 2012 (Oct. 16, 2012), p. 3.
RN 1401074-94-9, STN REG, Oct. 16, 2012 (Oct. 16, 2012), p. 3.
RN 1401077-88-0, STN REG, Oct. 16, 2012 (Oct. 16, 2010), p. 2.
RN 145837-71-4, STN REG, Feb. 10, 1993 (Feb. 10, 1993), p. 1.
RN 145837-72-5, STN REG, Feb. 10, 1993 (Feb. 10, 1993), p. 1.
RN 1487677-30-4, STN REG, Dec. 5, 2013 (Dec. 5, 2013), p. 1.
RN 854921-53-2, STN REG, Jul. 13, 2005 (Jul. 13, 2005), p. 4.
International Search Report for International Application No. PCT/CN2017/097660 dated Nov. 14, 2017.
Beyer et al., "Antiallergic activity of some indazole derivatives," CAS-RN 95091-52-4 (1985).
Gomtsyan et al., "Preparation of urea compounds TRPV1 antagonists for treating pain," Abbott Laboratories, USA, CAS-RN 1401077-00-6 (2012).
Supplementary European Search Report for EP 17842837 dated Dec. 3, 2019.
Written Opinion English Translation for International Application No. PCT/CN2017/097660 dated Nov. 14, 2017.

* cited by examiner

FUSED HETEROCYCLIC DERIVATIVES, THEIR PREPARATION METHODS THEREOF AND MEDICAL USES THEREOF

FIELD OF THE INVENTION

The present invention relates to novel fused heterocyclic derivatives or their pharmaceutically acceptable salts thereof, the pharmaceutical compositions containing the fused heterocyclic derivatives or their pharmaceutically acceptable salts thereof, the methods for preparing the fused heterocyclic derivatives or their pharmaceutically acceptable salts thereof, and the uses of the fused heterocyclic derivatives or their pharmaceutically acceptable salts thereof, or the pharmaceutical compositions containing the fused heterocyclic derivatives or their pharmaceutically acceptable salts thereof in the preparation of medicines, in particularly as IDO inhibitor medicines, for treating and/or preventing cancers.

BACKGROUND OF THE INVENTION

Indoleamine 2,3-dioxygenase (IDO) is a heme-containing monomeric protein that is widely distributed in tissues other than liver. It is the rate-limiting enzyme in the kynurenine metabolic pathway and catalyzes the oxidative degradation of tryptophan to kynurenine. Tryptophan is an essential amino acid for T cell proliferation and also a precursor for the synthesis of neurotransmitters. If the concentration of tryptophan in the cell microenvironment decreases, the level of kynurenine increases, resulting in T cells arrested in the middle of G1, thereby affecting proliferation, differentiation and activity of T cells.

IDO is expressed at a low level in normal cells, but overexpressed in many tumor tissues, leading to abnormal local tryptophan metabolism and regulatory T cell formation in tumors. In turn, it mediates local T cell immune tolerance in tumors and plays an important role in occurrence, development and metastasis of malignant tumors. If the activity of IDO is inhibited, the metabolism of tryptophan around the tumor cells is effectively prevented, which promotes the growth of T cells, thereby enhancing the function of the body's immune system against tumors. Therefore, the development of IDO inhibitors has become a hot area in the search for cancer immunotherapeutic drugs. Preclinical studies have shown that a single dose of IDO1 selective inhibitor INCB-024360 could effectively inhibit the activity of plasma IDO1 in nude mice at the level of IDO-deficient mice, and repeated doses prevented the expansion of CT26 tumors (Mol. Cancer Ther., 9(2), 489-98). Currently, small molecule IDO inhibitor drugs are still in clinical trial stages, including Incyte's INCB-024360 (epacadostat), indoximod from NewLink Genetics, NLG-919 from NewLink/Genentech and a molecule from BMS.

IDO inhibitors can also be combined with other anticancer small molecule drugs and immunological checkpoint inhibitors, such as CTLA4, PD-1 and PD-L1, to enhance the anticancer efficacy of the drug. Combination immunotherapy with small molecule IDO inhibitors and immunological checkpoint inhibitors is also in clinical trials, such as indoximod/ipilimumab, epacadostat/pembrolizumab, epacadostat/nivolumab, indoximod/MEDI-4736, NLG-919/atezolizumab, etc. Preliminary results showed that IDO small molecule inhibitors had good additive effects (AACR, Abstract #5023, April 2014).

The development of IDO inhibitors for the treatment of multiple cancers alone and in combination with immunotherapy has attracted the attention of numerous biopharmaceutical companies. A series of patent applications for IDO inhibitors have been published, including WO2007075598A2, WO201507007A1, WO2011056652A1, WO2014186035A1, WO2015082499A2, WO2016026772A1, WO2016073738A2, WO2016073774A2, WO2016051181A1, WO2016037026A1, etc. Through continuous efforts, the present invention has designed compounds having a structure represented by the general formula (I) and shown that the compounds having such a structure exhibited excellent effects and functions of suppressing IDO activity.

SUMMARY OF THE INVENTION

In a first aspect, the present invention provides a compound of Formula (I') or its isomer, prodrug, stable isotope derivative, pharmaceutically acceptable salt or mixture thereof:

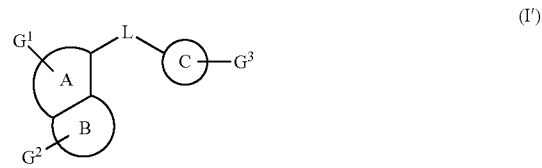

(I')

Wherein:

Ring A is a phenyl ring or a 6-membered heteroaryl ring, wherein the phenyl ring and heteroaryl ring are optionally substituted with one or more $G^1$;

Ring B is a 5-membered heteroaryl ring wherein the heteroaryl ring contains 1-4 heteroatoms independently selected from N, O, S and is optionally substituted with one or more $G^2$;

Ring C is absent, and L is $C_{1-6}$ alkyl, wherein $C_{1-6}$ alkyl is optionally substituted with one or more substituents selected from halogen, cyano, —OR, —NRR', —SR, $C_{3-6}$ cycloalkyl or 3-7 membered heterocyclyl, and/or any of —CH$_2$— within $C_{1-6}$ alkyl is optionally replaced with —O—, —NR$^1$— or —S—, or Ring C is $C_{3-8}$ s cycloalkyl, $C_{3-8}$ cycloalkenyl, 3-8 membered heterocyclyl, $C_{6-10}$ aryl or 5-10 membered heteroaryl, wherein cycloalkyl, cycloalkenyl, heterocyclyl, aryl and heteroaryl are optionally substituted with one or more $G^3$;

L is independently selected from $C_{1-6}$ alkylene, —NR$^1$C(O)NR$^2$—, —C(R$^3$)(R$^4$)C(O)NR$^2$—, —NR$^1$C(O)C(R$^3$)(R$^4$)—, —OC(O)NR$^2$—, —NR$^1$C(O)O—, —NR$^1$S(O)$_m$NR$^2$—, —C(R$^3$)(R$^4$)S(O)$_m$NR$^2$, —NR$^1$S(O)$_m$C(R$^3$)(R$^4$)—, —C(R$^3$)(R$^4$)NR$^1$C(O)—, —C(O)NR$^2$C(R$^3$)(R$^4$)—, wherein alkylene is optionally substituted with substituents selected from halogen, cyano, —OR, —NRR', —SR, $C_{1-6}$ alkyl, $C_{3-6}$ cycloalkyl or 3-7 membered heterocyclyl, and/or any of —CH$_2$— within alkylene is optionally replaced with —O—, —NR$^1$— or —S—;

R and R' are each independently selected from H, $C_{1-6}$ alkyl, $C_{3-6}$ cycloalkyl or 3-7 membered heterocyclyl, wherein $C_{1-6}$ alkyl is optionally substituted with substituents selected from —OR$^5$, —NR$^5$R$^6$, —SR$^5$, and/or any of —CH$_2$— within $C_{1-6}$ alkyl is optionally replaced with —O—, —NR$^5$— or —S—;

$R^1$, $R^2$, $R^3$ and $R^4$ are each independently selected from H, —OH, $C_{1-6}$ alkyl, $C_{3-6}$ cycloalkyl or 3-7 membered heterocyclyl, wherein $C_{1-6}$ alkyl is optionally substituted with substituents selected from —OR$^5$, —NR$^5$R$^6$, —SR$^5$, and/or any of —CH$_2$— within C$_{1-6}$ alkyl is optionally replaced with —O—, —NR$^5$— or —S—;

Alternatively, R$^3$ and R$^4$ together with the carbon atom to which they are attached form a 3-6 membered ring optionally containing heteroatom(s);

G$^1$, G$^2$ and G$^3$ are each independently selected from halogen, cyano, C$_{1-6}$ alkyl, C$_{2-6}$ alkenyl, C$_{2-6}$ alkynyl, C$_{3-8}$ cycloalkyl, C$_{3-8}$ cycloalkenyl, 3-8 membered heterocyclyl, C$_{6-10}$ aryl, 5-10 membered heteroaryl, —OR$^5$, —OC(O)NR$^5$R$^6$, —C(O)OR$^5$, —C(O)NR$^5$R$^6$, —C(O)R$^5$, —NR$^5$R$^6$, —NR$^5$C(O)R$^6$, —NR$^5$C(O)NR$^6$R$^7$, —S(O)$_m$R$^5$ or —NR$^5$S(O)$_m$R$^6$, wherein alkyl, alkenyl, alkynyl, cycloalkyl, cycloalkenyl, heterocyclyl, aryl or heteroaryl is optionally substituted with substituents selected from halogen, cyano, C$_{1-6}$ alkyl, C$_{3-8}$ cycloalkyl, C$_{3-8}$ cycloalkenyl, 3-8 membered heterocyclyl, —OR$^8$, —OC(O)NR$^8$R$^9$, —C(O)OR$^8$, —C(O)NR$^8$R$^9$, —C(O)R$^8$, —NR$^8$R$^9$, —NR$^8$C(O)R$^9$, —NR$^8$C(O)NR$^9$R$^{10}$, —S(O)$_m$R$^8$ or —NR$^8$S(O)$_m$R$^9$, and any of —CH$_2$— within C$_{1-6}$ alkyl is optionally replaced with —O—, —NR$^{11}$— or —S—;

R$^5$, R$^6$, R$^7$, R$^8$, R$^9$ and R$^{10}$ are each independently selected from H, C$_{1-6}$ alkyl, C$_{3-8}$ cycloalkyl, 3-8 membered heterocyclyl, 5-10 membered heteroaryl or C$_{6-10}$ aryl, wherein alkyl, cycloalkyl, heterocyclyl, heteroaryl and aryl are optionally substituted with substituents selected from halogen, cyano, —OR$^{11}$, —NR$^{11}$R$^{12}$, —SR$^{11}$, 4-7 membered heterocyclyl, and/or any of —CH$_2$— within alkyl is optionally replaced with —O—, —NR$^{11}$— or —S—;

R$^{11}$ and R$^{12}$ are each independently selected from H or C$_{1-4}$ alkyl; and m is 1 or 2.

In a second aspect, the present invention provides a compound of Formula (I) or its isomer, prodrug, stable isotope derivative, pharmaceutically acceptable salt or mixture thereof:

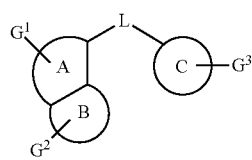

(I)

wherein:

Ring A is a phenyl ring or a 6-membered heteroaryl ring, wherein the phenyl ring and heteroaryl ring are optionally substituted with one or more G$^1$;

Ring B is a 5-membered heteroaryl ring wherein the heteroaryl ring contains 1-4 heteroatoms independently selected from N, O, S and is optionally substituted with one or more G$^2$;

Ring C is C$_{3-8}$ cycloalkyl, C$_{3-8}$ cycloalkenyl, 3-8 membered heterocyclyl, C$_{6-10}$ aryl or 5-10 membered heteroaryl, wherein cycloalkyl, cycloalkenyl, heterocyclyl, aryl and heteroaryl are optionally substituted with one or more G$^3$;

L is independently selected from C$_{1-6}$ alkylene, —NR$^1$C(O)NR$^2$—, —C(R$^3$)(R$^4$)C(O)NR$^2$—, —NR$^1$C(O)C(R$^3$)(R$^4$)—, —OC(O)NR$^2$—, —NR$^1$C(O)O—, —NR$^1$S(O)$_m$NR$^2$—, —C(R$^3$)(R$^4$)S(O)$_m$NR$^2$—, —NR$^1$S(O)$_m$C(R$^3$)(R$^4$)—, —C(R$^3$)(R$^4$)NR$^1$C(O)—, —C(O)NR$^2$C(R$^3$)(R$^4$)—, wherein alkylene is optionally substituted with substituents selected from halogen, cyano, —OR$^1$, —NR$^1$R$^2$, —SR$^1$, C$_{3-6}$ cycloalkyl or 3-7 membered heterocyclyl, and/or any of —CH$_2$— within alkylene is optionally replaced with —O—, —NR$^1$— or —S—;

R$^1$, R$^2$, R$^3$ and R$^4$ are each independently selected from H, C$_{1-6}$ alkyl, C$_{3-6}$ cycloalkyl or 3-7 membered heterocyclyl, wherein C$_{1-6}$ alkyl is optionally substituted with substituents selected from —OR$^5$, —NR$^5$R$^6$, —SR$^5$, and/or any of —CH$_2$— within C$_{1-6}$ alkyl is optionally replaced with —O—, —NR$^5$— or —S—;

Alternatively, R$^3$ and R$^4$ together with the carbon atom to which they are attached form a 3-6 membered ring optionally containing heteroatom(s);

G$^1$, G$^2$ and G$^3$ are each independently selected from halogen, cyano, C$_{1-6}$ alkyl, C$_{2-6}$ alkenyl, C$_{2-6}$ alkynyl, C$_{3-8}$ cycloalkyl, C$_{3-8}$ cycloalkenyl, 3-8 membered heterocyclyl, C$_{6-10}$ aryl, 5-10 membered heteroaryl, —OR$^5$, —OC(O)NR$^5$R$^6$, —C(O)OR$^5$, —C(O)NR$^5$R$^6$, —C(O)R$^5$, —NR$^5$R$^6$, —NR$^5$C(O)R$^6$, —NR$^5$C(O)NR$^6$R$^7$, —S(O)$_m$R$^5$ or —NR$^5$S(O)$_m$R$^6$, wherein alkyl, alkenyl, alkynyl, cycloalkyl, cycloalkenyl, heterocyclyl, aryl or heteroaryl is optionally substituted with substituents selected from halogen, cyano, C$_{1-6}$ alkyl, C$_{3-8}$ cycloalkyl, C$_{3-8}$ cycloalkenyl, 3-8 membered heterocyclyl, —OR$^3$, —OC(O)NR$^8$R$^9$, —C(O)OR$^8$, —C(O)NR$^8$R$^9$, —C(O)R$^8$, —NR$^8$R$^9$, —NR$^8$C(O)R$^9$, —NR$^8$C(O)NR$^9$R$^{10}$, —S(O)$_m$R$^8$ or —NR$^8$S(O)$_m$R$^9$;

R$^5$, R$^6$, R$^7$, R$^8$, R$^9$ and R$^{10}$ are each independently selected from H, C$_{1-6}$ alkyl, C$_{3-8}$ cycloalkyl, 3-8 membered heterocyclyl, 5-10 membered heteroaryl or C$_{6-10}$ aryl, wherein C$_{1-6}$ alkyl is optionally substituted with substituents selected from —OR$^{11}$, —NR$^{11}$R$^{12}$, —SR$^{11}$, and/or any of —CH$_2$— within C$_{1-6}$ alkyl is optionally replaced with —O—, —NR$^{11}$— or —S—; R$^{11}$ and R$^{12}$ are each independently selected from H or C$_{1-4}$ alkyl; and m is 1 or 2.

Another aspect of the invention relates to a pharmaceutical composition comprising a therapeutically effective amount of a compound of Formula (I') or its isomer, prodrug, stable isotope derivative, pharmaceutically acceptable salt or mixture thereof, and pharmaceutically acceptable carriers and excipients. Another aspect of the invention relates to a pharmaceutical composition comprising a therapeutically effective amount of a compound of Formula (I) or its isomer, prodrug, stable isotope derivative, pharmaceutically acceptable salt or mixture thereof, and pharmaceutically acceptable carriers and excipients.

Another aspect of the invention relates to a compound of Formula (I') or its isomer, prodrug, stable isotope derivative, pharmaceutically acceptable salt or mixture thereof, or the use of a pharmaceutical composition comprising a compound represented by Formula (I') or its isomer, prodrug, stable isotope derivative, pharmaceutically acceptable salt or mixture thereof in the preparation of an IDO inhibitor drug. Another aspect of the invention relates to a compound of Formula (I) or its isomer, prodrug, stable isotope derivative, pharmaceutically acceptable salt or mixture thereof, or the use of a pharmaceutical composition comprising a compound represented by Formula (I) or its isomer, prodrug, a stable isotope derivative, pharmaceutically acceptable salt or mixture thereof in the preparation of an IDO inhibitor drug.

Another aspect of the invention relates to a compound of Formula (I') or its isomer, prodrug, stable isotope derivative, pharmaceutically acceptable salt or mixture thereof, or the use of a pharmaceutical composition comprising a compound represented by Formula (I') or its isomer, prodrug, stable isotope derivative, pharmaceutically acceptable salt or mixture thereof in the preparation of medicines for treating and/or preventing cancers. Another aspect of the invention relates to a compound of Formula (I) or its isomer, prodrug, stable isotope derivative, pharmaceutically acceptable salt or mixture thereof, or the use of a pharmaceutical composition comprising a compound represented by Formula (I) or its isomer, prodrug, stable isotope derivative, pharmaceutically acceptable salt, or mixture thereof in the preparation of medicines for treating and/or preventing cancers.

Another aspect of the invention relates to a method for treating and/or preventing cancers, which comprises administration to patients in need of treatment of a therapeutically effective amount of a compound of Formula (I') or its isomer, prodrug, stable isotope derivative, pharmaceutically acceptable salt or mixture thereof or a pharmaceutical composition comprising a compound represented by Formula (I') or its isomer, prodrug, stable isotope derivative, pharmaceutically acceptable salt or mixture thereof. Another aspect of the invention relates to a method for treating and/or preventing cancers, which comprises administration to patients in need of treatment of a therapeutically effective amount of a compound of Formula (I) or its isomer, prodrug, stable isotope derivative, pharmaceutically acceptable salt or mixture thereof or a pharmaceutical composition comprising a compound represented by Formula (I) or its isomer, prodrug, stable isotope derivative, pharmaceutically acceptable salt or mixture thereof.

Another aspect of the invention relates to a compound of Formula (I') or its isomer, prodrug, stable isotope derivative, pharmaceutically acceptable salt or mixture thereof as a medicine for treating and/or preventing cancers. Another aspect of the invention relates to a compound of Formula (I) or its isomer, prodrug, stable isotope derivative, pharmaceutically acceptable salt or mixture thereof as a medicine for treating and/or preventing cancers.

Another aspect of the invention relates to a pharmaceutical combination comprising a therapeutically effective amount of a compound of the formula (I') or its isomer, prodrug, stable isotope derivative, pharmaceutically acceptable salt or mixture thereof and additional anticancer agents. Another aspect of the invention relates to a pharmaceutical combination comprising a therapeutically effective amount of a compound of the formula (I) or its isomer, prodrug, stable isotope derivative, pharmaceutically acceptable salt or mixture thereof and additional anticancer agents.

DETAILED DESCRIPTION OF THE INVENTION

Definitions

Unless otherwise described, the following terms used in the specification and claims of this application have the following definitions.

The description "$C_{x-y}$" as used herein refers to the range of the number of carbon atoms, where x and y are integers. For example, $C_{3-8}$ cycloalkyl means cycloalkyl having 3-8 carbon atoms, with 3, 4, 5, 6, 7, or 8 carbon atoms. It should also be noted that "$C_{3-8}$" also includes any sub-range therein, such as $C_{3-7}$, $C_{3-6}$, $C_{4-7}$, $C_{4-6}$, $C_{5-6}$, etc.

The term "alkyl" refers to a saturated linear or branched hydrocarbon group including 1 to 20 carbon atoms, for example, 1 to 18 carbon atoms, 1 to 12 carbon atoms, 1 to 8 carbon atoms, 1 to 6 carbon atoms or 1 to 4 carbon atoms. Non-limiting examples of an alkyl group include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl and 2-ethylbutyl. The alkyl group can be optionally substituted.

The term "alkenyl" refers to a straight or branched hydrocarbon group containing at least one carbon-carbon double bond and usually 2 to 20 carbon atoms, for example, 2 to 8 carbon atoms, 2 to 6 carbon atoms or 2 to 4 carbon atoms. Non-limiting examples of an alkenyl group include ethenyl, 1-propenyl, 2-propenyl, 1-butenyl, 2-butenyl, 3-butenyl, 2-methyl-2-propenyl, 1,4-pentadienyl and 1,4-butadienyl.

The term "alkynyl" refers to a straight or branched hydrocarbon group containing at least one carbon to carbon triple bond and typically 2 to 20 carbon atoms, for example, 2 to 8 carbon atoms, 2 to 6 carbon atoms or 2 to 4 carbon atoms. Non-limiting examples of an alkynyl group include ethynyl, 1-propynyl, 2-propynyl, 1-butynyl, 2-butynyl and 3-butynyl.

The term "alkylene" refers to a divalent group derived from a saturated straight or branched hydrocarbon group having from 1 to 20 carbon atoms, for example, 1 to 6 carbon atoms or 1 to 4 carbon atoms. Non-limiting examples of an alkylene group include —CH$_2$—, —CH(CH$_3$)—, —CH$_2$CH$_2$—, CH$_2$CH$_2$CH$_2$—, —CH$_2$CH$_2$CH$_2$CH$_2$— and —CH$_2$CH(CH$_3$)CH$_2$—.

The term "cycloalkyl" refers to a saturated cyclic hydrocarbon group containing from 3 to 14 carbon ring atoms. A cycloalkyl group can be a single carbocyclic ring, usually containing from 3 to 7 carbon ring atoms, preferably from 3 to 6 carbon ring atoms. Non-limiting examples of a monocyclic cycloalkyl group include cyclopropyl, cyclobutyl, cyclopentyl, cyclohexyl and cycloheptyl. The cycloalkyl group may alternatively be a bicyclic or tricyclic ring fused together, such as decahydronaphthyl.

The term "cycloalkenyl" refers to a partially unsaturated cyclic hydrocarbon group containing from 3 to 14 carbon ring atoms and at least one carbon-carbon double bond. A cycloalkenyl group can be a single ring and usually contains from 3 to 6 carbon atoms. Non-limiting examples of a monocyclic cycloalkenyl group include cyclopropenyl, cyclobutenyl, cyclopentenyl, and cyclohexenyl. The cycloalkenyl group may alternatively be a bicyclic fused ring. Non-limiting examples of a bicyclic cycloalkenyl group include 4,5,6,7-tetrahydro-3aH-indenyl, octahydronaphthyl and 1,6-dihydro-cyclopentadienyl.

The term "heterocyclic or heterocyclic group" refers to a saturated or partially unsaturated monocyclic or polycyclic group comprising from 3 to 20 ring atoms, for example, 3 to 14, 3 to 12, 3 to 10, 3 to 8, 3 to 7, 4 to 7, or 5 to 6 ring atoms, wherein one or more ring atoms are selected from nitrogen, oxygen or S(O)$_m$ (where m is an integer from 0 to 2), but does not include the ring portion of —OO—, —OS— or —SS—, and the remaining ring atoms are carbon. Preferably, it comprises from 3 to 12 ring atoms, more preferably from 4 to 7 ring atoms, most preferably 5 or 6 ring atoms, of which 1 to 4 atoms are heteroatoms, more preferably 1 to 3 are heteroatoms, most preferably 1 to 2 are heteroatoms. Non-limiting examples of a monocyclic heterocyclic group include pyrrolidinyl, piperidinyl, piperazinyl, morpholinyl, thiomorpholinyl, homopiperazinyl and azetidinyl. Polycyclic heterocyclic groups include fused, bridged or spiro polycyclic heterocyclic groups. The heterocyclyl ring may be fused to an aryl, heteroaryl or cycloalkyl ring, wherein the ring to which the parent structure is attached is a heterocyclic group. Non-limiting examples include:

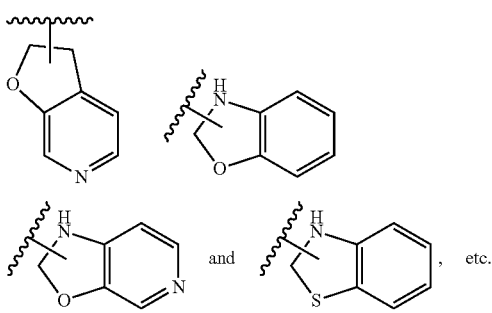

Heterocyclyl can be optionally substituted.

The term "aryl" refers to an aromatic monocyclic or fused polycyclic group containing from 6 to 14 carbon atoms, preferably 6 to 10 members, such as phenyl and naphthyl, most preferably phenyl. The aryl ring may be fused to a heteroaryl, heterocyclyl or cycloalkyl ring, wherein the ring to which the parent structure is attached is an aryl ring. Non-limiting examples include:

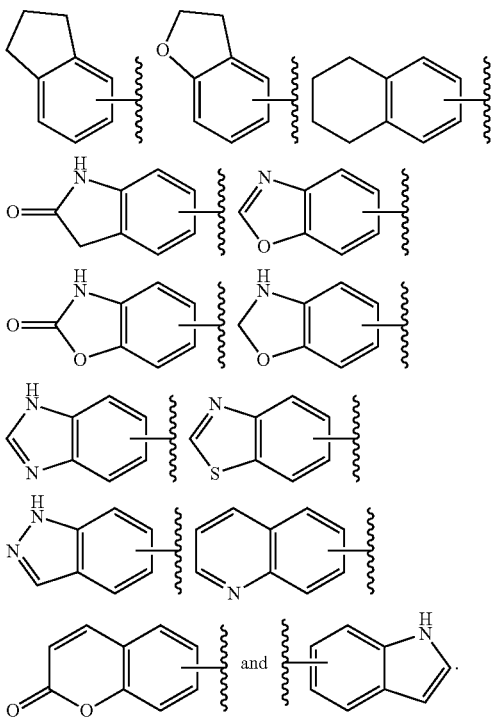

The aryl group can be optionally substituted.

The term "heteroaryl or heteroaryl ring" refers to an aromatic group containing from 5 to 14 ring atoms, wherein 1 to 4 ring atoms are heteroatoms selected from the group consisting of oxygen, sulfur and nitrogen. More preferably, heteroaryl is 5- or 6-membered, such as furyl, thienyl, pyridyl, pyrrolyl, N-alkylpyrrolyl, pyrimidinyl, pyrazinyl, pyrazolyl, imidazolyl, tetrazolyl, oxazolyl, isoxazolyl, thiazolyl, isothiazolyl, etc. The heteroaryl ring may be fused to an aryl, heterocyclic or cycloalkyl ring, wherein the ring to which the parent structure is attached is a heteroaryl ring. Non-limiting examples include:

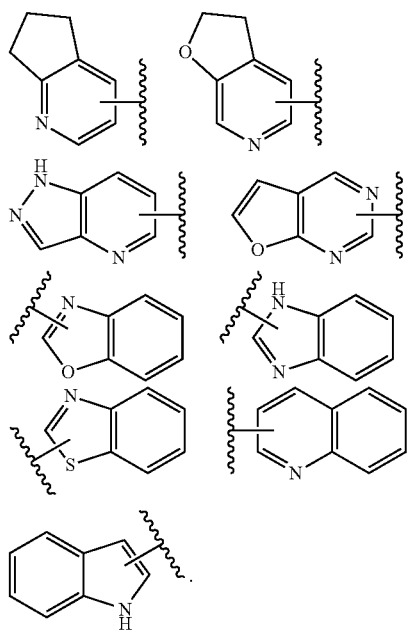

Heteroaryl can be optionally substituted.

The term "halogen" refers to fluoro, chloro, bromo or iodo.

The term "cyano" refers to —CN.

The term "optional" or "optionally" implies that the subsequently described event or environment may, but may not, occur, including the occurrence or non-occurrence of the event or environment. For example, "heterocyclyl optionally substituted by an alkyl group" implies that an alkyl group may be, but not be necessarily present, and the description includes the case where the heterocyclic group is substituted with an alkyl group and the case where the heterocyclic group is not substituted with an alkyl group.

The term "substituted" refers to one or more hydrogen atoms in the group, preferably up to 5, more preferably 1 to 3 hydrogen atoms, are independently replaced with the corresponding number of substituents. It goes without saying that the substituents are only in their possible chemical positions, and those skilled in the art will be able to determine (by experiment or theory) a substitution that may or may not be possible without much effort. For example, an amino or hydroxyl group having a free hydrogen may be unstable when combined with a carbon atom having an unsaturated (e.g., olefinic) bond.

Compounds

In a first aspect, the present invention relates to a compound represented by Formula (I') or its isomer, prodrug, stable isotope derivative, pharmaceutically acceptable salt or mixture thereof:

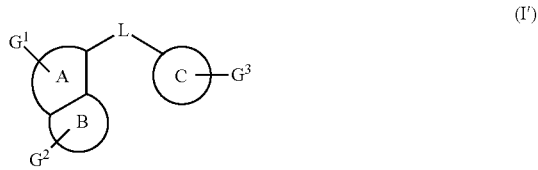

(I')

Wherein:

Ring A is a phenyl ring or a 6-membered heteroaryl ring, wherein the phenyl ring and heteroaryl ring are optionally substituted with one or more $G^1$;

Ring B is a 5-membered heteroaryl ring wherein the heteroaryl ring contains 1-4 heteroatoms independently selected from N, O, S and is optionally substituted with one or more $G^2$;

Ring C is absent, and L is $C_{1-6}$ alkyl, wherein $C_{1-6}$ alkyl is optionally substituted with one or more substituents selected from halogen, cyano, —OR, —NRR', —SR, $C_{3-6}$ cycloalkyl or 3-7 membered heterocyclyl, and/or any of —$CH_2$— within $C_{1-6}$ alkyl is optionally replaced with —O—, —$NR^1$— or —S—, or Ring C is $C_{3-8}$ cycloalkyl, $C_{3-8}$ cycloalkenyl, 3-8 membered heterocyclyl, $C_{6-10}$ aryl or 5-10 membered heteroaryl, wherein cycloalkyl, cycloalkenyl, heterocyclyl, aryl and heteroaryl are optionally substituted with one or more $G^3$;

L is independently selected from $C_{1-6}$ alkylene, —$NR^1C(O)NR^2$—, —$C(R^3)(R^4)C(O)NR^2$—, —$NR^1C(O)C(R^3)(R^4)$—, —$OC(O)NR^2$—, —$NR^1C(O)O$—, —$NR^1S(O)_mNR^2$—, —$C(R^3)(R^4)S(O)_mNR^2$, —$NR^1S(O)_mC(R^3)(R^4)$—, —$C(R^3)(R^4)NR^1C(O)$—, —$C(O)NR^2C(R^3)(R^4)$—, wherein alkylene is optionally substituted with substituents selected from halogen, cyano, —OR, —NRR', —SR, $C_{1-6}$ alkyl, $C_{3-6}$ cycloalkyl or 3-7 membered heterocyclyl, and/or any of —$CH_2$— within alkylene is optionally replaced with —O—, —$NR^1$— or —S—;

R and R' are each independently selected from H, $C_{1-6}$ alkyl, $C_{3-6}$ cycloalkyl or 3-7 membered heterocyclyl, wherein $C_{1-6}$ alkyl is optionally substituted with substituents selected from —$OR^5$, —$NR^5R^6$, —$SR^5$, and/or any of —$CH_2$— within $C_{1-6}$ alkyl is optionally replaced with —O—, —$NR^5$— or —S—;

$R^1$, $R^2$, $R^3$ and $R^4$ are each independently selected from H, —OH, $C_{1-6}$ alkyl, $C_{3-6}$ cycloalkyl or 3-7 membered heterocyclyl, wherein $C_{1-6}$ alkyl is optionally substituted with substituents selected from —$OR^5$, —$NR^5R^6$, —$SR^5$, and/or any of —$CH_2$— within $C_{1-6}$ alkyl is optionally replaced with —O—, —$NR^5$— or —S—;

Alternatively, $R^3$ and $R^4$ together with the carbon atom to which they are attached form a 3-6 membered ring optionally containing hetero atom(s);

$G^1$, $G^2$ and $G^3$ are each independently selected from halogen, cyano, $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocyclyl, $C_{6-10}$ aryl, 5-10 membered heteroaryl, —$OR^5$, —$OC(O)NR^5R^6$, —$C(O)OR^5$, —$C(O)NR^5R^6$, —$C(O)R^5$, —$NR^5R^6$, —$NR^5C(O)R^6$, —$NR^5C(O)NR^6R^7$, —$S(O)_mR^5$ or —$NR^5S(O)_mR^6$, wherein alkyl, alkenyl, alkynyl, cycloalkyl, cycloalkenyl, heterocyclyl, aryl or heteroaryl is optionally substituted with substituents selected from halogen, cyano, $C_{1-6}$ alkyl, $C_{3-8}$ cycloalkyl, $C_{3-8}$ cycloalkenyl, 3-8 membered heterocyclyl, —$OR^8$, —$OC(O)NR^8R^9$, —$C(O)OR^8$, —$C(O)NR^8R^9$, —$C(O)R^8$, —$NR^8R^9$, —$NR^8C(O)R^9$, —$NR^8C(O)NR^9R^{10}$, —$S(O)_mR^8$ or —$NR^8S(O)_mR^9$, and any of —$CH_2$— within $C_{1-6}$ alkyl is optionally replaced with —O—, —$NR^{11}$— or —S—;

$R^5$, $R^6$, $R^7$, $R^8$, $R^9$ and $R^{10}$ are each independently selected from H, $C_{1-6}$ alkyl, $C_{3-8}$ cycloalkyl, 3-8 membered heterocyclyl, 5-10 membered heteroaryl or $C_{6-10}$ aryl, wherein alkyl, cycloalkyl, heterocyclyl, heteroaryl and aryl are optionally substituted with substituents selected from halogen, cyano, —$OR^{11}$, —$NR^{11}R^{12}$, —$SR^{11}$, 4-7 membered heterocyclyl, and/or any of —$CH_2$— within alkyl is optionally replaced with —O—, —$NR^{11}$— or —S—;

$R^{11}$ and $R^{12}$ are each independently selected from H or $C_{1-4}$ alkyl; and m is 1 or 2.

With respect to the compounds represented by the above Formula (I'), in a preferred embodiment, ring A and ring B are condensed to form the following fused heterocyclic ring:

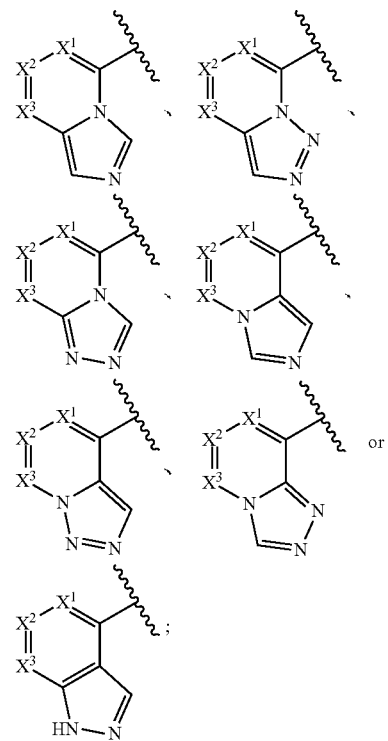

$X^1$, $X^2$ and $X^3$ are each independently selected from N or $CG^{11}$; and $G^{11}$ is selected from H, halogen, $C_{1-6}$ alkyl, —$OC_{1-6}$ alkyl, phenyl, $C_{3-7}$ cycloalkyl, $C_{3-6}$ cycloalkenyl, 4-7 membered heterocyclyl or 5-6 membered heteroaryl, wherein alkyl, cycloalkyl, cycloalkenyl, heterocyclyl, phenyl and heteroaryl are optionally substituted with one or more substituents selected from $C_{1-4}$ alkyl, halogen or —OH.

With respect to the compounds represented by the above Formula (I'), in one embodiment, ring C is absent and L is selected from $C_{1-6}$ alkyl, wherein $C_{1-6}$ alkyl is optionally substituted with one or more —OH, and/or any of —$CH_2$— within $C_{1-6}$ alkyl is optionally replaced with —NH— or —N($C_{1-6}$ alkyl)-.

With respect to the compounds represented by the above Formula (I'), in another preferred embodiment, ring C is $C_{3-7}$ cycloalkyl, $C_{6-10}$ aryl, 5-6 membered heterocyclyl or 5-6 membered heteroaryl.

With respect to the compounds represented by the above Formula (I'), in another preferred embodiment, ring C is $C_{3-7}$ cycloalkyl, preferably cyclohexyl and cyclopentyl, and more preferably cyclohexyl.

With respect to the compounds represented by the above Formula (I'), in another preferred embodiment, ring C is $C_{6-10}$ aryl, most preferably phenyl.

With respect to the compounds represented by the above Formula (I'), in another preferred embodiment, ring C is 5-6 membered heterocyclyl, preferably tetrahydropyranyl.

With respect to the compounds represented by the above Formula (I'), in another preferred embodiment, ring C is 5-6 membered heteroaryl, preferably pyridyl or pyrazolyl.

With respect to the compounds represented by the above Formula (I'), in another preferred embodiment, L is selected from —C($R^3$)($R^4$)N$R^1$C($R^3$)($R^4$)—, —N$R^1$C(O)N$R^2$—, —C($R^3$)($R^4$)C(O)N$R^2$— or —N$R^1$C(O)C($R^3$)($R^4$)—, wherein $R^1$, $R^2$, $R^3$ and $R^4$ are each independently selected from H, —OH or $C_{1-4}$ alkyl.

With respect to the compounds represented by the above Formula (I'), in another preferred embodiment, L is —CH$_2$NHCH$_2$—.

With respect to the compounds represented by the above Formula (I'), in another preferred embodiment, L is —CH$_2$N($C_{1-4}$ alkyl)CH$_2$—.

With respect to the compounds represented by the above Formula (I'), in another preferred embodiment, L is —CH($C_{1-4}$ alkyl)NHCH$_2$—.

With respect to the compounds represented by the above Formula (I'), in another preferred embodiment, L is —CH$_2$NHCH($C_{1-4}$ alkyl)-.

With respect to the compounds represented by the above Formula (I'), in another preferred embodiment, L is —NHC(O)NH—.

With respect to the compounds represented by the above Formula (I'), in another preferred embodiment, L is —CH$_2$C(O)NH—.

With respect to the compounds represented by the above Formula (I'), in another preferred embodiment, L is —CH($C_{1-4}$ alkyl)C(O)NH—.

With respect to the compounds represented by the above Formula (I'), in another preferred embodiment, L is —CH(OH)C(O)NH—.

With respect to the compounds represented by the above Formula (I'), in another preferred embodiment, L is —CH$_2$C(O)N(OH)—.

With respect to the compounds represented by the above Formula (I'), in another preferred embodiment, L is —CH$_2$C(O)N($C_{1-4}$ alkyl)-.

With respect to the compounds represented by the above Formula (I'), in another preferred embodiment, L is —NHC(O)CH$_2$—.

With respect to the compounds represented by the above Formula (I'), in another preferred embodiment, ring A is not substituted with $G^1$.

With respect to the compounds represented by the above Formula (I'), in another preferred embodiment, ring A is substituted with one, two or three $G^1$.

With respect to the compounds represented by the above Formula (I'), in another preferred embodiment, ring A is substituted with one $G^1$.

With respect to the compounds represented by the above Formula (I'), in another preferred embodiment, $G^1$ is selected from halogen, $C_{1-6}$ alkyl, —O$C_{1-6}$ alkyl, phenyl, $C_{3-7}$ cycloalkyl, $C_{3-6}$ cycloalkenyl, 4-7 membered heterocyclyl or 5-6 membered heteroaryl, wherein alkyl, cycloalkyl, cycloalkenyl, heterocyclyl, phenyl and heteroaryl are optionally substituted with one or more substituents selected from $C_{1-4}$ alkyl, halo or —OH.

With respect to the compounds represented by the above Formula (I'), in another preferred embodiment, $G^1$ is —O$C_{1-6}$ alkyl, preferably methoxy or ethoxy.

With respect to the compounds represented by the above Formula (I'), in another preferred embodiment, $G^1$ is halogen.

With respect to the compounds represented by the above Formula (I'), in another preferred embodiment, $G^1$ is phenyl which is unsubstituted or substituted by one or more halogens, such as fluorine.

With respect to the compounds represented by the above Formula (I'), in another preferred embodiment, $G^1$ is $C_{3-6}$ cycloalkenyl, preferably cyclopentenyl or cyclohexenyl, more preferably cyclopentenyl.

With respect to the compounds represented by the above Formula (I'), in another preferred embodiment, $G^1$ is 5-6 membered heteroaryl, preferably pyridyl or a pyrazolyl.

With respect to the compounds represented by the above Formula (I'), in another preferred embodiment, ring B is unsubstituted.

With respect to the compounds represented by the above Formula (I'), in another preferred embodiment, ring C is unsubstituted.

With respect to the compounds represented by the above Formula (I'), in another preferred embodiment, ring C is substituted with one, two or three $G^3$.

With respect to the compounds represented by the above Formula (I'), in another preferred embodiment, ring C is substituted with two $G^3$.

With respect to the compounds represented by the above Formula (I'), in another preferred embodiment, ring C is substituted with one $G^3$.

With respect to the compounds represented by the above Formula (I'), in another preferred embodiment, $G^3$ is selected from halogen, cyano, $C_{1-6}$ alkyl, $C_{3-7}$ cycloalkyl, 4-7 membered heterocyclyl, 5-6 membered heteroaryl, —O$R^5$, —C(O)O$R^5$, —C(O)$R^5$ or —C(O)N$R^5R^6$, wherein alkyl, cycloalkyl, heterocyclyl or heteroaryl is optionally substituted with one or more substituents selected from halogen, cyano, —OH, $C_{1-6}$ alkyl or —O$C_{1-6}$ alkyl, and any of —CH$_2$— within $C_{1-6}$ alkyl is optionally replaced with —O—, —N$R^{11}$— or —S—. $R^5$ and $R^6$ are each independently selected from H, $C_{1-6}$ alkyl or 3-7 membered heterocyclyl containing nitrogen or oxygen atom(s), wherein alkyl or heterocyclyl is optionally substituted with one or more substituents selected from halogen, cyano, —OH, —O$C_{1-4}$ alkyl, 4-7 membered heterocyclyl, and $R_{11}$ is selected from H or $C_{1-4}$ alkyl.

With respect to the compounds represented by the above Formula (I'), in another preferred embodiment, $G^3$ is cyano.

With respect to the compounds represented by the above Formula (I'), in another preferred embodiment, $G^3$ is halogen, such as chlorine.

With respect to the compounds represented by the above Formula (I'), in another preferred embodiment, $G^3$ is —O$C_{1-6}$ alkyl, such as methoxy.

With respect to the compounds represented by the above Formula (I'), in another preferred embodiment, $G^3$ is —C(O)OH or —C(O)O$C_{1-6}$ alkyl.

With respect to the compounds represented by the above Formula (I'), in another preferred embodiment, $G^3$ is —C(O)NH$_2$, —C(O)NH$C_{1-6}$ alkyl or —C(O)N($C_{1-6}$ alkyl)$_2$.

With respect to the compounds represented by the above Formula (I'), in another preferred embodiment, $G^3$ is —C(O)NH$C_{1-6}$ alkyl-OH.

With respect to the compounds represented by the above Formula (I'), in another preferred embodiment, $G^3$ is —$C_{1-6}$ alkyl-OH.

With respect to the compounds represented by the above Formula (I'), in another preferred embodiment, $G^3$ is —C(O)-(5-6 membered heterocyclyl), for example, —C(O)— morpholinyl or —C(O)-piperidinyl.

With respect to the compounds represented by the above Formula (I'), in another preferred embodiment, $G^3$ is —C(O)NH—$C_{1-6}$ alkylene-(5-6 membered heterocyclyl), for example, —C(O)NH-ethylidene-morpholinyl or —C(O)NH-propylene-morpholinyl.

With respect to the compounds represented by the above Formula (I'), in another preferred embodiment, $G^3$ is pyrazolyl optionally substituted with —$C_{1-3}$ alkylene-O—$C_{1-2}$ alkyl, for example, pyrazolyl substituted with —$C_2H_5$—O—$CH_3$.

It should be understood that the present invention also relates to any combination of preferred embodiments of the compounds represented by the above Formula (I'). Some examples of combinations are given below. However, the invention is not limited to these combinations.

An embodiment of the first aspect of the invention relates to a compound represented by the above Formula (I') or its isomer, prodrug, stable isotope derivative, pharmaceutically acceptable salt or mixture thereof, wherein:

Ring A and ring B are condensed to form the following fused heterocyclic ring:

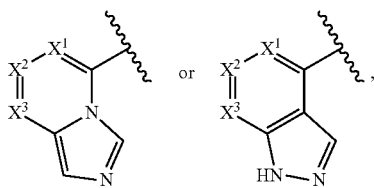

$X^1$, $X^2$ and $X^3$ are each independently selected from $CG^{11}$;

Ring C is cyclopentyl, cyclohexyl, phenyl, pyridyl, pyridonyl, pyrazolyl or tetrahydropyranyl, and is optionally substituted with one or two $G^3$;

L is selected from —$C(R^3)(R^4)NR^1C(R^3)(R^4)$—, —$NR^1C(O)NR^2$—, —$C(R^3)(R^4)C(O)NR^2$— or —$NR^1C(O)C(R^3)(R^4)$—;

$G^{11}$ is selected from H, halogen, —$OC_{1-6}$ alkyl, phenyl which is unsubstituted or substituted with one or more halogens, $C_{1-6}$ alkyl, $C_{3-7}$ cycloalkyl, $C_{4-6}$ cycloalkenyl, 4-7 membered heterocyclyl or 5-6-membered heteroaryl;

$G^3$ is selected from halogen, cyano, $C_{1-6}$ alkyl, $C_{3-7}$ cycloalkyl, 4-7 membered heterocyclyl, 5-6 membered heteroaryl, —$OR^5$, —$C(O)OR^5$, —$C(O)R^5$ or —$C(O)NR^5R^6$, wherein alkyl, cycloalkyl, heterocyclyl or heteroaryl is optionally substituted with one or more substituents selected from halogen, cyano, —OH, $C_{1-6}$ alkyl or —$OC_{1-6}$ alkyl, and any of —$CH_2$— within $C_{1-6}$ alkyl is optionally replaced with —O—, —$NR^{11}$— or —S—;

$R^1$, $R^2$, $R^3$ and $R^4$ are each independently selected from H, —OH or $C_{1-4}$ alkyl;

$R^5$ and $R^6$ are each independently selected from H, $C_{1-6}$ alkyl or 3-7 membered heterocyclyl containing nitrogen or oxygen atom(s), wherein alkyl or heterocyclyl is optionally substituted with one or more substituents selected from halogen, cyano, —OH, —$OC_{1-4}$ alkyl, 4-7 membered heterocyclyl, and $R^{11}$ is selected from H or $C_{1-4}$ alkyl.

Another embodiment of the first aspect of the invention relates to a compound represented by the above Formula (I') or its isomer, prodrug, stable isotope derivative, pharmaceutically acceptable salt or mixture thereof, wherein:

Ring A and ring B are condensed to form the following fused heterocyclic ring:

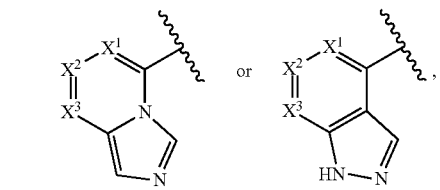

$X^1$, $X^2$ and $X^3$ are each independently selected from $CG^{11}$;

Ring C is cyclopentyl, cyclohexyl, phenyl, pyridyl, pyridonyl, pyrazolyl or tetrahydropyranyl, and is optionally substituted with one or two $G^3$;

L is selected from —$CH_2NHCH_2$—, —$CH_2N(C_{1-4}$ alkyl)$CH_2$—, —$CH(C_{1-4}$ alkyl)$NHCH_2$—, —$CH_2NHCH(C_{1-4}$ alkyl)-, —$NHC(O)NH$—, —$CH_2C(O)NH$—, —$CH(C_{1-4}$ alkyl)$C(O)NH$—, —$CH(OH)C(O)NH$—, —$CH_2C(O)N(OH)$—, —$CH_2C(O)N(C_{1-4}$ alkyl)- or —$NHC(O)CH_2$—;

$G^{11}$ is selected from H, halogen, —$OC_{1-6}$ alkyl, phenyl which is unsubstituted or substituted with one or two halogens, $C_{4-6}$ cycloalkenyl, pyridyl or pyrazolyl;

$G^3$ is selected from halogen, cyano, —$OC_{1-6}$ alkyl, —$C_{1-6}$ alkyl-OH, —$C(O)OH$, —$C(O)OC_{1-6}$ alkyl, —$C(O)NH_2$, —$C(O)NHC_{1-6}$ alkyl, —$C(O)N(C_{1-6}$ alkyl)$_2$, —$C(O)NHC_{1-6}$ alkyl-OH, —$C(O)$-(5-6 membered cycloalkyl), —$C(O)NH$—$C_{1-6}$ alkylene-(5-6 membered heterocyclyl) or pyrazolyl optionally substituted with —$C_{1-3}$ alkylene-O—$C_{1-2}$ alkyl; and The 5-6 membered heterocyclic group is selected from morpholinyl and piperidinyl and is optionally substituted with —$OC_{1-4}$ alkyl.

An embodiment of the first aspect of the invention relates to a compound represented by the above Formula (I') or its isomer, prodrug, stable isotope derivative, pharmaceutically acceptable salt or mixture thereof, wherein the compound is selected from:

| Compound number | Compound structure and name |
|---|---|
| 1. | ![structure] <br> 1-(4-cyanophenyl)-3-(imidazo[1,5-a]pyridin-5-yl)urea |
| 2. | ![structure] <br> 1-(3-cyanophenyl)-3-(imidazo[1,5-a]pyridin-5-yl)urea |
| 3. | ![structure] <br> 1-(4-chlorophenyl)-3-(imidazo[1,5-a]pyridin-5-yl)urea |

| Compound number | Compound structure and name |
|---|---|
| 4. | 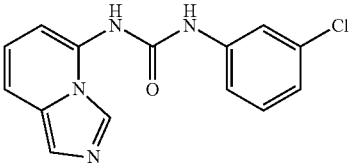 [SMILES: O=C(Nc1cccc(Cl)c1)Nc1cccc2cncn12]<br>1-(3-chlorophenyl)-3-(imidazo[1,5-a]pyridin-5-yl)urea |
| 5. | 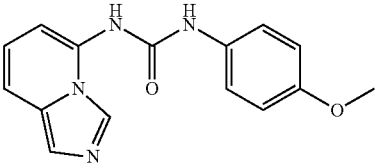 [SMILES: COc1ccc(NC(=O)Nc2cccc3cncn23)cc1]<br>1-(imidazo[1,5-a]pyridin-5-yl)-3-(4-methoxyphenyl)urea |
| 6. | 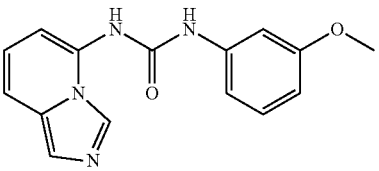 [SMILES: COc1cccc(NC(=O)Nc2cccc3cncn23)c1]<br>1-(imidazo[1,5-a]pyridin-5-yl)-3-(3-methoxyphenyl)urea |
| 7. | 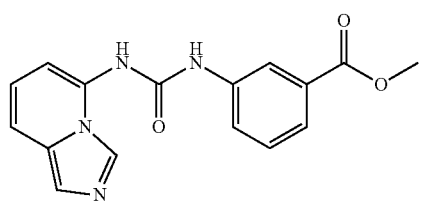 [SMILES: COC(=O)c1cccc(NC(=O)Nc2cccc3cncn23)c1]<br>methyl 3-(3-(imidazo[1,5-a]pyridin-5-yl)ureido)benzoate |
| 8. | 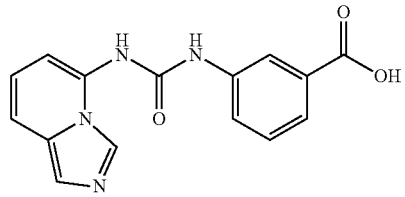 [SMILES: O=C(Nc1cccc(C(=O)O)c1)Nc1cccc2cncn12]<br>3-(3-(imidazo[1,5-a]pyridin-5-yl)ureido)benzoic acid |
| 9. | 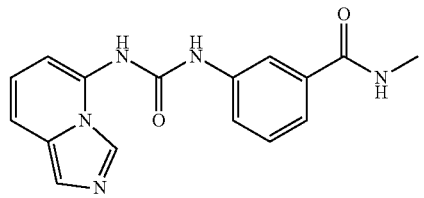 [SMILES: CNC(=O)c1cccc(NC(=O)Nc2cccc3cncn23)c1]<br>3-(3-(imidazo[1,5-a]pyridin-5-yl)ureido)-N-methylbenzamide |
| 10. | 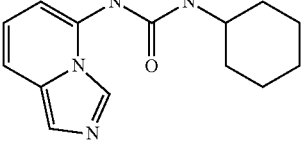<br>1-cyclohexyl-3-(imidazo[1,5-a]pyridin-5-yl)urea |
| 11. | 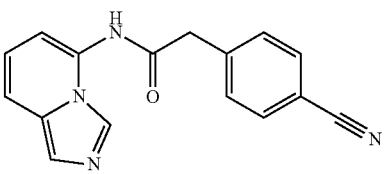 [SMILES: N#Cc1ccc(CC(=O)Nc2cccc3cncn23)cc1]<br>2-(4-cyanophenyl)-N-(imidazo[1,5-a]pyridin-5-yl)acetamide |
| 12. | 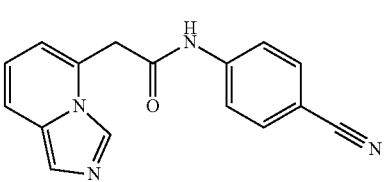 [SMILES: N#Cc1ccc(NC(=O)Cc2cccc3cncn23)cc1]<br>N-(4-cyanophenyl)-2-(imidazo[1,5-a]pyridin-5-yl)acetamide |
| 13. | 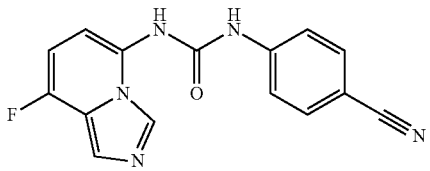 [SMILES: N#Cc1ccc(NC(=O)Nc2ccc(F)c3cncn23)cc1]<br>1-(4-cyanophenyl)-3-(8-fluoroimidazo[1,5-a]pyridin-5-yl)urea |
| 14. | 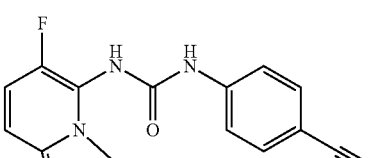<br>1-(4-cyanophenyl)-3-(6-fluoroimidazo[1,5-a]pyridin-5-yl)urea |
| 15. | 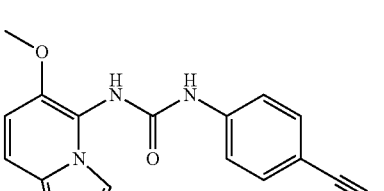<br>1-(4-cyanophenyl)-3-(6-methoxyimidazo[1,5-a]pyridin-5-yl)urea |

| Compound number | Compound structure and name |
|---|---|
| 16. | 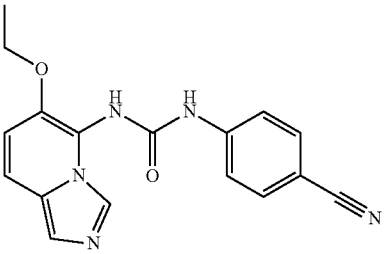 [SMILES: CCOc1ccc2cncn2c1NC(=O)Nc1ccc(C#N)cc1]<br>1-(4-cyanophenyl)-3-(6-ethoxyimidazo[1,5-a]pyridin-5-yl)urea |
| 17. | 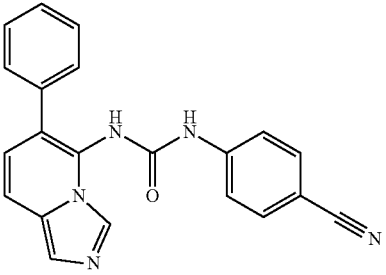 [SMILES: N#Cc1ccc(NC(=O)Nc2c(-c3ccccc3)ccc3cncn23)cc1]<br>1-(4-cyanophenyl)-3-(6-phenylimidazo[1,5-a]pyridin-5-yl)urea |
| 18. | 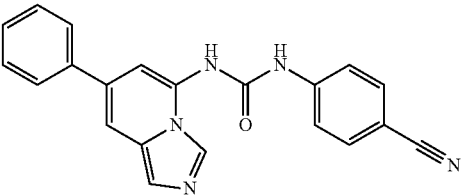 [SMILES: N#Cc1ccc(NC(=O)Nc2cc(-c3ccccc3)cc3cncn23)cc1]<br>1-(4-cyanophenyl)-3-(7-phenylimidazo[1,5-a]pyridin-5-yl)urea |
| 19. | 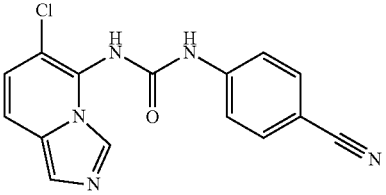 [SMILES: N#Cc1ccc(NC(=O)Nc2c(Cl)ccc3cncn23)cc1]<br>1-(6-chloroimidazo[1,5-a]pyridin-5-yl)-3-(4-cyanophenyl)urea |
| 20. | 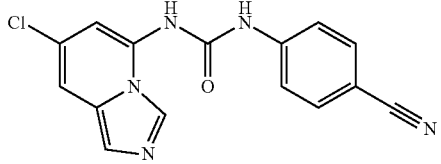 [SMILES: N#Cc1ccc(NC(=O)Nc2cc(Cl)cc3cncn23)cc1]<br>1-(7-chloroimidazo[1,5-a]pyridin-5-yl)-3-(4-cyanophenyl)urea |
| 21. | 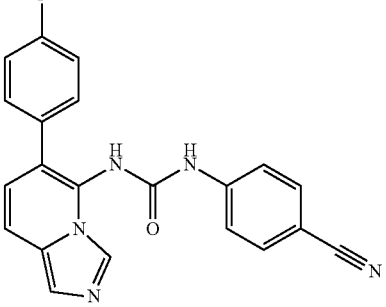<br>1-(4-cyanophenyl)-3-(6-(4-fluorophenyl)imidazo[1,5-a]pyridin-5-yl)urea |
| 22. | 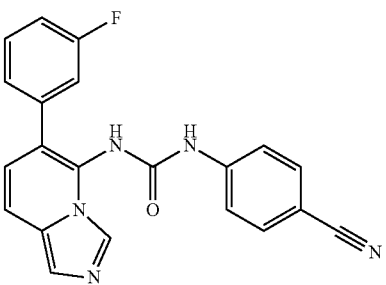 [SMILES: N#Cc1ccc(NC(=O)Nc2c(-c3cccc(F)c3)ccc3cncn23)cc1]<br>1-(4-cyanophenyl)-3-(6-(3-fluorophenyl)imidazo[1,5-a]pyridin-5-yl)urea |
| 23. | 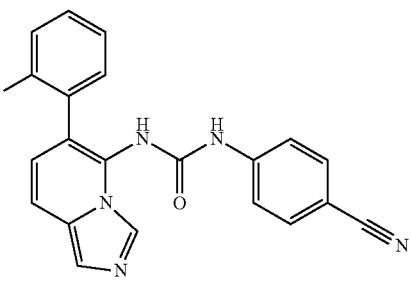<br>1-(4-cyanophenyl)-3-(6-(2-fluorophenyl)imidazo[1,5-a]pyridin-5-yl)urea |
| 24. | 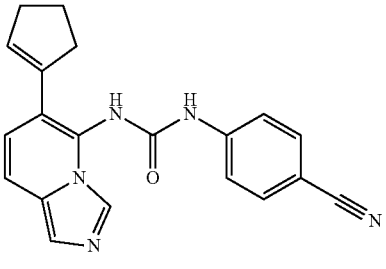 [SMILES: N#Cc1ccc(NC(=O)Nc2c(C3=CCCC3)ccc3cncn23)cc1]<br>1-(4-cyanophenyl)-3-(6-(cyclopent-1-en-1-yl)imidazo[1,5-a]pyridin-5-yl)urea |

-continued

| Compound number | Compound structure and name |
|---|---|
| 25. | 1-(4-cyanophenyl)-3-(6-(pyridin-3-yl)imidazo[1,5-a]pyridin-5-yl)urea |
| 26. | 1-(6-(1H-pyrazol-3-yl)imidazo[1,5-a]pyridin-5-yl)-3-(4-cyanophenyl)urea |
| 27. | 4-(3-(6-phenylimidazo[1,5-a]pyridin-5-yl)ureido)benzoic acid |
| 28. | N-methyl-4-(3-(6-phenylimidazo[1,5-a]pyridin-5-yl)ureido)benzamide |
| 29. | 4-(3-(6-phenylimidazo[1,5-a]pyridin-5-yl)ureido)benzamide |
| 30. | N-(2-hydroxyethyl)-4-(3-(6-phenylimidazo[1,5-a]pyridin-5-yl)ureido)benzamide |
| 31. | 1-(4-(hydroxymethyl)phenyl)-3-(6-phenylimidazo[1,5-a]pyridin-5-yl)urea |
| 32. | 1-(6-cyanopyridin-3-yl)-3-(6-phenylimidazo[1,5-a]pyridin-5-yl)urea |

| Compound number | Compound structure and name |
|---|---|
| 33. | 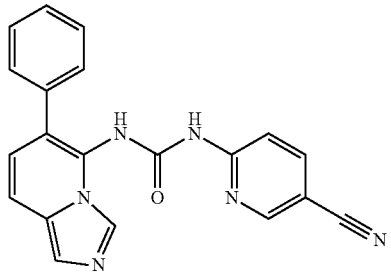 [SMILES: N#Cc1ccc(NC(=O)Nc2c(-c3ccccc3)ccc3cncn23)nc1]<br>1-(5-cyanopyridin-2-yl)-3-(6-phenylimidazo[1,5-a]pyridin-5-yl)urea |
| 34. | 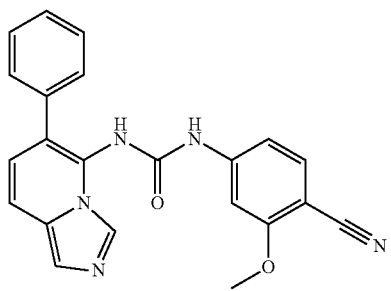 [SMILES: COc1cc(NC(=O)Nc2c(-c3ccccc3)ccc3cncn23)ccc1C#N]<br>1-(4-cyano-3-methoxyphenyl)-3-(6-phenylimidazo[1,5-a]pyridin-5-yl)urea |
| 35. | 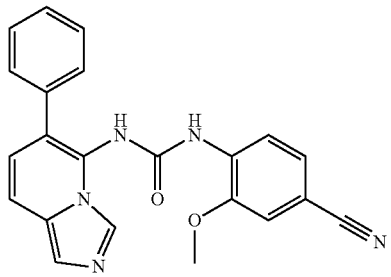 [SMILES: COc1cc(C#N)ccc1NC(=O)Nc1c(-c2ccccc2)ccc2cncn12]<br>1-(4-cyano-2-methoxyphenyl)-3-(6-phenylimidazo[1,5-a]pyridin-5-yl)urea |
| 36. | 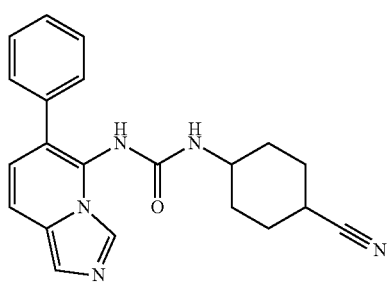 [SMILES: N#CC1CCC(NC(=O)Nc2c(-c3ccccc3)ccc3cncn23)CC1]<br>1-(4-cyanocyclohexyl)-3-(6-phenylimidazo[1,5-a]pyridin-5-yl)urea |
| 37. | 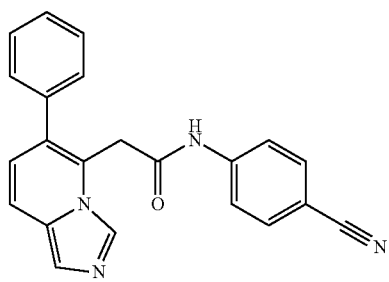 [SMILES: N#Cc1ccc(NC(=O)Cc2c(-c3ccccc3)ccc3cncn23)cc1]<br>N-(4-cyanophenyl)-2-(6-phenylimidazo[1,5-a]pyridin-5-yl)acetamide |
| 38. | 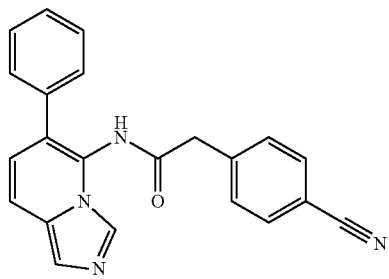 [SMILES: N#Cc1ccc(CC(=O)Nc2c(-c3ccccc3)ccc3cncn23)cc1]<br>2-(4-cyanophenyl)-N-(6-phenylimidazo[1,5-a]pyridin-5-yl)acetamide |
| 39. | 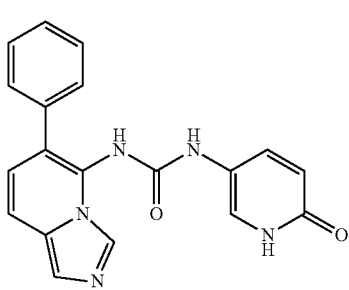 [SMILES: O=C(Nc1ccc(=O)[nH]c1)Nc1c(-c2ccccc2)ccc2cncn12]<br>1-(6-oxo-1,6-dihydropyridin-3-yl)-3-(6-phenylimidazo[1,5-a]pyridin-5-yl)urea |
| 40. | 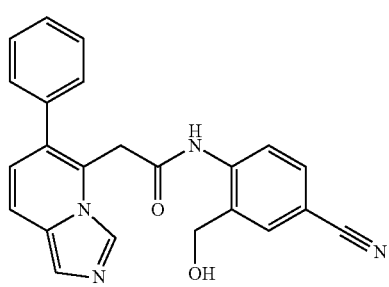 [SMILES: N#Cc1ccc(NC(=O)Cc2c(-c3ccccc3)ccc3cncn23)c(CO)c1]<br>N-(4-cyano-2-(hydroxymethyl)phenyl)-2-(6-phenylimidazo[1,5-a]pyridin-5-yl)acetamide |

| Compound number | Compound structure and name |
|---|---|
| 41. | 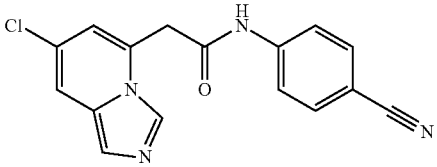 [SMILES: N#Cc1ccc(NC(=O)Cc2cc(Cl)cc3cncn23)cc1]<br>2-(7-chloroimidazo[1,5-a]pyridin-5-yl)-N-(4-cyanophenyl)acetamide |
| 42. | 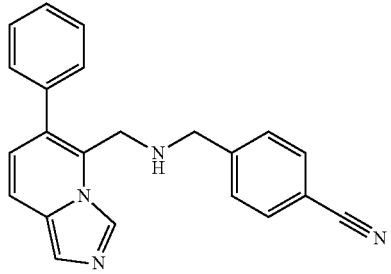 [SMILES: N#Cc1ccc(CNCc2c(-c3ccccc3)ccc3cncn23)cc1]<br>4-(((6-Phenylimidazo[1,5-a]pyridin-5-yl)methyl)amino)methyl)benzonitrile |
| 43. | 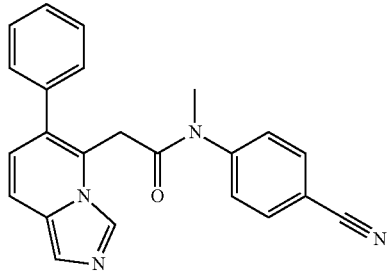 [SMILES: CN(C(=O)Cc1c(-c2ccccc2)ccc2cncn12)c1ccc(C#N)cc1]<br>N-(4-cyanophenyl)-N-methyl-2-(6-phenylimidazo[1,5-a]pyridin-5-yl)acetamide |
| 44. | 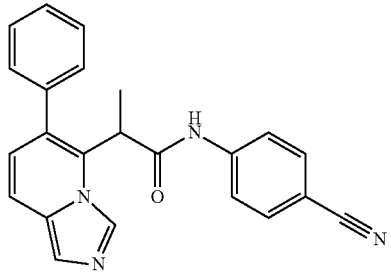 [SMILES: CC(C(=O)Nc1ccc(C#N)cc1)c1c(-c2ccccc2)ccc2cncn12]<br>N-(4-cyanophenyl)-2-(6-phenylimidazo[1,5-a]pyridin-5-yl)propanamide |
| 45. | 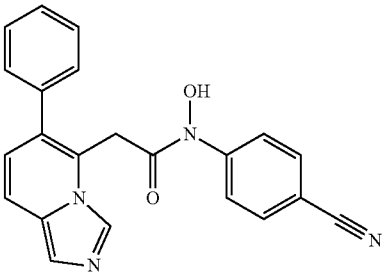 [SMILES: N#Cc1ccc(N(O)C(=O)Cc2c(-c3ccccc3)ccc3cncn23)cc1]<br>N-(4-cyanophenyl)-N-hydroxy-2-(6-phenylimidazo[1,5-a]pyridin-5-yl)acetamide |
| 46. | 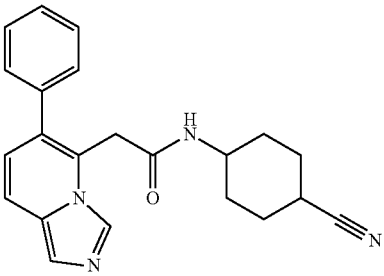 [SMILES: N#CC1CCC(NC(=O)Cc2c(-c3ccccc3)ccc3cncn23)CC1]<br>N-(4-cyanocyclohexyl)-2-(6-phenylimidazo[1,5-a]pyridin-5-yl)acetamide |
| 47. | 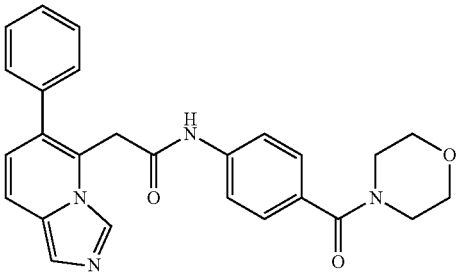 [SMILES: O=C(Cc1c(-c2ccccc2)ccc2cncn12)Nc1ccc(C(=O)N2CCOCC2)cc1]<br>N-(4-(morpholine-4-carbonyl)phenyl)-2-(6-phenylimidazo[1,5-a]pyridin-5-yl)acetamide |
| 48. | 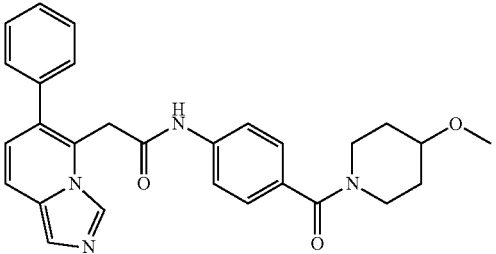 [SMILES: COC1CCN(C(=O)c2ccc(NC(=O)Cc3c(-c4ccccc4)ccc4cncn34)cc2)CC1]<br>N-(4-(4-methoxypiperidin-1-carbonyl)phenyl)-2-(6-phenylimidazo[1,5-a]pyridin-5-yl)acetamide |

| Compound number | Compound structure and name |
|---|---|
| 49. | 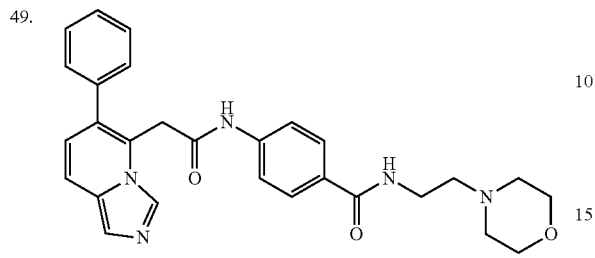<br>N-(2-morpholinoethyl)-4-(2-(6-phenylimidazo[1,5-a]pyridin-5-yl)acetamido)benzamide |
| 50. | 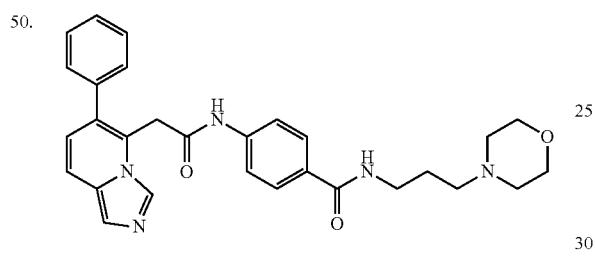<br>N-(3-morpholinopropyl)-4-(2-(6-phenylimidazo[1,5-a]pyridin-5-yl)acetamido)benzamide |
| 51. | 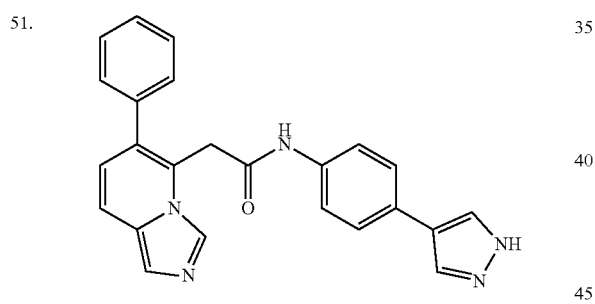<br>N-(4-(1H-pyrazol-4-yl)phenyl)-2-(6-phenylimidazo[1,5-a]pyridin-5-yl)acetamide |
| 52. | 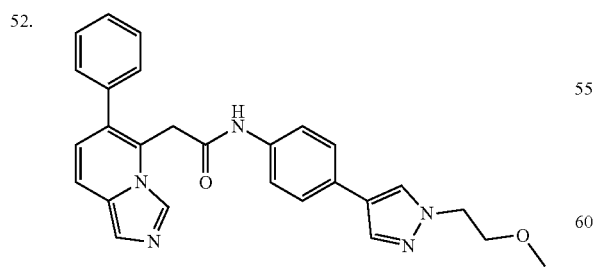<br>N-(4-(1-(2-methoxyethyl)-1H-pyrazol-4-yl)phenyl)-2-(6-phenylimidazo[1,5-a]pyridine-5-yl)acetamide |
| 53. | 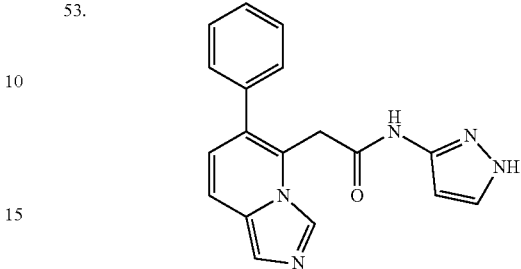<br>2-(6-Phenylimidazo[1,5-a]pyridin-5-yl)-N-(1H-pyrazol-5-yl)acetamide |
| 54. | 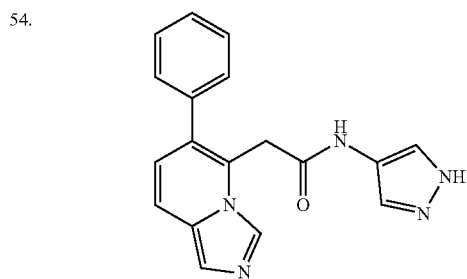<br>2-(6-Phenylimidazo[1,5-a]pyridin-5-yl)-N-(1H-pyrazol-4-yl)acetamide |
| 55. | 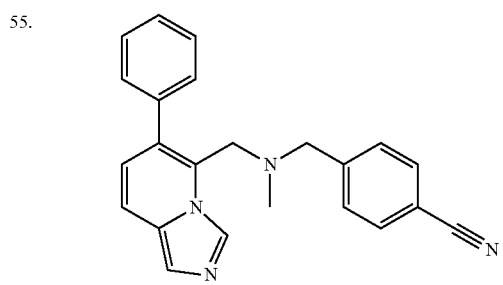<br>4-((methyl((6-phenylimidazo[1,5-a]pyridin-5-yl)methyl)amino)methyl)benzonitrile |
| 56. | 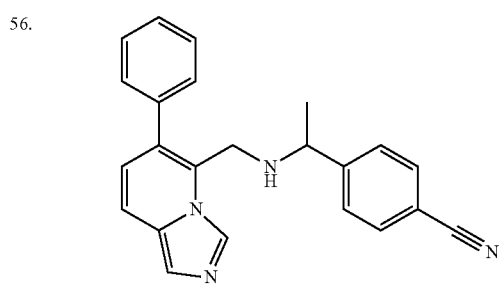<br>4-(1-((6-phenylimidazo[1,5-a]pyridin-5-yl)methyl)amino)ethyl)benzonitrile |

| Compound number | Compound structure and name |
|---|---|
| 57. | 4-(((1-(6-phenylimidazo[1,5-a]pyridin-5-yl)ethyl)amino)methyl)benzonitrile |
| 58. | N-benzyl-1-(6-phenylimidazo[1,5-a]pyridin-5-yl)methanamine |
| 59. | 1-cyclohexyl-N-((6-phenylimidazo[1,5-a]pyridin-5-yl)methyl)methanamine |
| 60. | 1-(6-phenylimidazo[1,5-a]pyridin-5-yl)-N-((tetrahydro-2H-pyran-4-yl)methyl)methanamine |
| 61. | 2-methyl-N-((6-phenylimidazo[1,5-a]pyridin-5-yl)methyl)propan-1-amine |
| 62. | 2-methyl-1-(((6-phenylimidazo[1,5-a]pyridin-5-yl)methyl)amino)propan-2-ol |
| 63. | 2-(6-Chloro-1H-indazol-4-yl)-N-(4-cyanophenyl)acetamide |
| 64. | N-(4-cyanophenyl)-2-hydroxy-2-(6-phenylimidazo[1,5-a]pyridin-5-yl)acetamide |

In a second aspect, the present invention relates to a compound represented by Formula (I) or its isomer, prodrug, stable isotope derivative, pharmaceutically acceptable salt or mixture thereof:

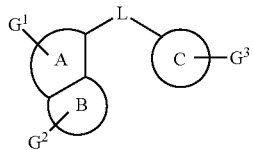

(I)

Wherein:

Ring A is a phenyl ring or a 6-membered heteroaryl ring, wherein the phenyl ring and heteroaryl ring are optionally substituted with one or more $G^1$;

Ring B is a 5-membered heteroaryl ring wherein the heteroaryl ring contains 1-4 heteroatoms independently selected from N, O, S and is optionally substituted with one or more $G^2$;

Ring C is $C_{3-8}$ cycloalkyl, $C_{3-8}$ cycloalkenyl, 3-8 membered heterocyclyl, $C_{6-10}$ aryl or 5-10 membered heteroaryl, wherein cycloalkyl, cycloalkenyl, heterocyclyl, aryl and heteroaryl are optionally substituted with one or more $G^3$;

L is independently selected from $C_{1-6}$ alkylene, —$NR^1C(O)NR^2$—, —$C(R^3)(R^4)C(O)NR^2$—, —$NR^1C(O)C(R^3)(R^4)$—, —$OC(O)NR^2$—, —$NR^1C(O)O$—, —$NR^1S(O)_mNR^2$—, —$C(R^3)(R^4)S(O)_mNR^2$—, —$NR^1S(O)_mC(R^3)(R^4)$—, —$C(R^3)(R^4)NR^1C(O)$—, —$C(O)NR^2C(R^3)(R^4)$—, wherein alkylene is optionally substituted with substituents selected from halogen, cyano, —$OR^1$, —$NR^1R^2$, —$SR^1$, $C_{3-6}$ cycloalkyl or 3-7 membered heterocyclyl, and/or any of —$CH_2$— within alkylene is optionally replaced with —O—, —$NR^1$— or —S—;

$R^1$, $R^2$, $R^3$ and $R^4$ are each independently selected from H, $C_{1-6}$ alkyl, $C_{3-6}$ cycloalkyl or 3-7 membered heterocyclyl, wherein $C_{1-6}$ alkyl is optionally substituted with substituents selected from —$OR^5$, —$NR^5R^6$, —$SR^5$, and/or any of —$CH_2$— within $C_{1-6}$ alkyl is optionally replaced with —O—, —$NR^5$— or —S—;

Alternatively, $R^3$ and $R^4$ together with the carbon atom to which they are attached form a 3-6 membered ring optionally containing hetero atom(s);

$G^1$, $G^2$ and $G^3$ are each independently selected from halogen, cyano, $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocyclyl, $C_{6-10}$ aryl, 5-10 membered heteroaryl, —$OR^5$, —$NR^5R^6$, —$C(O)OR^5$, —$C(O)NR^5R^6$, —$C(O)R^5$, —$NR^5R^6$, —$NR^5C(O)R^6$, —$NR^5C(O)NR^6R^7$, —$S(O)_mR^5$ or —$NR^5S(O)_mR^6$, wherein alkyl, alkenyl, alkynyl, cycloalkyl, cycloalkenyl, heterocyclyl, aryl or heteroaryl is optionally substituted with substituents selected from halogen, cyano, $C_{1-6}$ alkyl, $C_{3-8}$ cycloalkyl, $C_{3-8}$ cycloalkenyl, 3-8 membered heterocyclyl, —$OR^8$, —$OC(O)NR^8R^9$, —$C(O)OR^8$, —$C(O)NR^8R^9$, —$C(O)R^8$, —$NR^8R^9$, —$NR^8C(O)R^9$, —$NR^8C(O)NR^9R^{10}$, —$S(O)_mR^8$ or —$NR^8S(O)_mR^9$; $R^5$, $R^6$, $R^7$, $R^8$, $R^9$ and $R^{10}$ are each independently selected from H, $C_{1-6}$ alkyl, $C_{3-8}$ cycloalkyl, 3-8 membered heterocyclyl, 5-10 membered heteroaryl or $C_{6-10}$ aryl, wherein $C_{1-6}$ alkyl is optionally substituted with substituents selected from —$OR^{11}$, —$NR^{11}R^{12}$, —$SR^{11}$, and/or any of —$CH_2$— within $C_{1-6}$ alkyl is optionally replaced with —O—, —$NR^{11}$— or —S—;

$R^{11}$ and $R^{12}$ are each independently selected from H or $C_{1-4}$ alkyl; and m is 1 or 2.

An embodiment of the second aspect of the invention relates to a compound represented by the above Formula (I) or its isomer, prodrug, stable isotope derivative, pharmaceutically acceptable salt or mixture thereof, wherein:

Ring A and ring B are condensed to form the following fused heterocyclic ring:

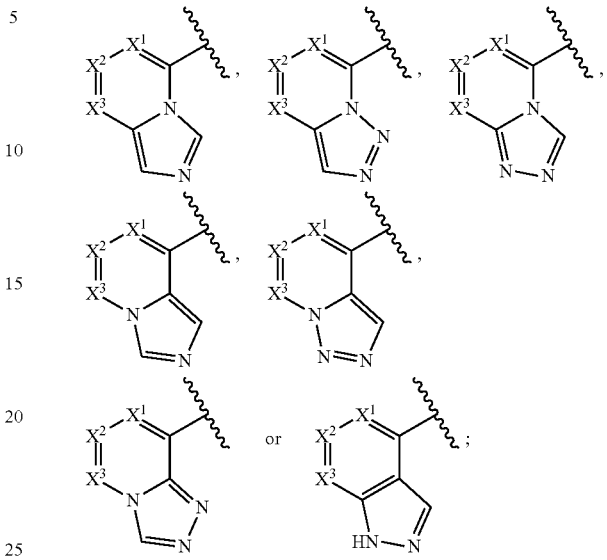

$X^1$, $X^2$ and $X^3$ are each independently selected from N or $CG^{11}$;

Ring C is $C_{3-8}$ cycloalkyl, $C_{3-8}$ cycloalkenyl, 3-8 membered heterocyclyl, $C_{6-10}$ aryl or 5-10 membered heteroaryl, and is optionally substituted with one or more $G^3$;

L is independently selected from $C_{2-6}$ alkylene, —$NR^1C(O)NR^2$—, —$C(R^3)(R^4)C(O)NR^2$—, —$NR^1C(O)C(R^3)(R^4)$—, —$OC(O)NR^2$—, —$NR^1C(O)O$—, —$NR^1S(O)_mNR^2$—, —$C(R^3)(R^4)S(O)_mNR^2$—, —$NR^1S(O)_mC(R^3)(R^4)$—, —$C(R^3)(R^4)NR^1C(O)$—, —$C(O)NR^2C(R^3)(R^4)$—, wherein alkylene is optionally substituted with substituents selected from halogen, cyano, —$OR^1$, —$NR^1R^2$, —$SR^1$, $C_{3-6}$ cycloalkyl or 3-7 membered heterocyclyl, and/or any of —$CH_2$— within alkylene is optionally replaced with —O—, —$NR^1$— or —S—;

$R^1$, $R^2$, $R^3$ and $R^4$ are each independently selected from H, $C_{1-6}$ alkyl, $C_{3-6}$ cycloalkyl or 3-7 membered heterocyclyl, wherein $C_{1-6}$ alkyl is optionally substituted with substituents selected from —$OR^5$, —$NR^5R^6$, —$SR^5$, and/or any of —$CH_2$— within $C_{1-6}$ alkyl is optionally replaced with —O—, —$NR^5$— or —S—;

Alternatively, $R^3$ and $R^4$ together with the carbon atom to which they are attached form a 3-6 membered ring optionally containing hetero atom(s);

$G^{11}$ is H and $G^3$ is selected from halogen, cyano, $C_{1-6}$ alkyl, $C_{3-8}$ cycloalkyl, $C_{3-8}$ cycloalkenyl, 3-8 membered heterocyclyl, $C_{6-10}$ aryl, 5-10 membered heteroaryl, —$OR^5$, —$C(O)OR^5$, —$C(O)NR^5R^6$, —$C(O)R^5$, —$NR^5R^6$, —$NR^5C(O)R^6$, wherein alkyl, cycloalkyl, cycloalkenyl, heterocyclyl, aryl or heteroaryl is optionally substituted with substituents selected from halogen, cyano, $C_{1-6}$ alkyl, —$OR^8$; or $G^{11}$ and $G^3$ are each independently selected from halogen, cyano, $C_{1-6}$ alkyl, $C_{3-8}$ cycloalkyl, $C_{3-8}$ cycloalkenyl, 3-8 membered heterocyclyl, $C_{6-10}$ aryl, 5-10 membered heteroaryl, —$OR^5$, —$C(O)OR^5$, —$C(O)NR^5R^6$, —$C(O)R^5$, —$NR^5R^6$, —$NR^5C(O)R^6$, wherein alkyl, cycloalkyl, cycloalkenyl, heterocyclyl, aryl or heteroaryl is optionally substituted with substituents selected from halogen, cyano, $C_{1-6}$ alkyl, —$OR^8$;

$R^5$, $R^6$, $R^8$ are each independently selected from H, $C_{1-6}$ alkyl, $C_{3-8}$ cycloalkyl or 3-8 membered monocyclic heterocyclyl, 5-6 membered heteroaryl or phenyl, wherein $C_{1-6}$ alkyl is optionally substituted with substituents selected from —$OR^{11}$, —$NR^{11}R^{12}$, —$SR^{11}$, and/or any of —$CH_2$— within $C_{1-6}$ alkyl is optionally replaced with —O—, —$NR^{11}$— or —S—;

$R^{11}$ and $R^{12}$ are each independently selected from H or $C_{1-4}$ alkyl; and m is 1 or 2.

With respect to the compounds represented by the above Formula (I), in a preferred embodiment, ring A and ring B are condensed to form the following fused heterocyclic ring:

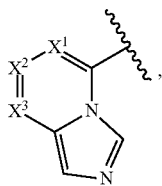

wherein $X^1$, $X^2$ and $X^3$ are each independently selected from $CG^{11}$, and $G^{11}$ is defined as described above.

With respect to the compounds represented by the above Formula (I), in another preferred embodiment, ring C is $C_{3-7}$ cycloalkyl, $C_{6-10}$ aryl or 5-6 membered heteroaryl.

With respect to the compounds represented by the above Formula (I), in another preferred embodiment, ring C is $C_{3-7}$ cycloalkyl, preferably cyclohexyl and cyclopentyl, and more preferably cyclohexyl.

With respect to the compounds represented by the above Formula (I), in another preferred embodiment, ring C is $C_{6-10}$ aryl, most preferably phenyl.

With respect to the compounds represented by the above Formula (I), in another preferred embodiment, ring C is 5-6 membered heteroaryl, preferably pyridyl.

With respect to the compounds represented by the above Formula (I), in another preferred embodiment, L is selected from $C_{2-6}$ alkylene, —$NR^1C(O)NR^2$—, —$C(R^3)(R^4)C(O)NR^2$—, —$NR^1C(O)C(R^3)(R^4)$—, —$OC(O)NR^2$—, —$NR^1C(O)O$—, —$NR^1S(O)_mNR^2$—, —$C(R^3)(R^4)S(O)_mNR^2$— or —$NR^1S(O)_mC(R^3)(R^4)$—, wherein alkylene is optionally substituted with substituents selected from —$OR^1$, —$NR^1R^2$, —$SR^1$ or 3-7 membered heterocyclyl, and/or any of —$CH_2$— within alkylene is optionally replaced with —O—, —$NR^1$— or —S—. $R^1$, $R^2$, $R^3$ and $R^4$ are each independently selected from H, $C_{1-6}$ alkyl, $C_{3-6}$ cycloalkyl or 3-7 membered heterocyclyl, wherein $C_{1-6}$ alkyl is optionally substituted with substituents selected from —$OR^5$, —$NR^5R^6$, —$SR^5$, and/or any of —$CH_2$— within $C_{1-6}$ alkyl is optionally replaced with —O—, —$NR^5$— or —S—. $R^5$ and $R^6$ are each independently selected from H or $C_{1-4}$ alkyl. And m is 1 or 2.

With respect to the compounds represented by the above Formula (I), in another preferred embodiment, L is selected from $C_{2-6}$ alkylene, —$NR^1C(O)NR^2$—, —$C(R^3)(R^4)C(O)NR^2$— or —$NR^1C(O)C(R^3)(R^4)$—, wherein alkylene is optionally substituted with substituents selected from —$OR^1$, —$NR^1R^2$, —$SR^1$ or 3-7 membered heterocyclyl, and/or any of —$CH_2$— within alkylene is optionally replaced with —O—, —$NR^1$— or —S—. $R^1$, $R^2$, $R^3$ and $R^4$ are defined as described above.

With respect to the compounds represented by the above Formula (I), in another preferred embodiment, L is —NHC(O)NH—.

With respect to the compounds represented by the above Formula (I), in another preferred embodiment, L is —$CH_2C(O)NH$—.

With respect to the compounds represented by the above Formula (I), in another preferred embodiment, L is —$NHC(O)CH_2$—.

With respect to the compounds represented by the above Formula (I), in another preferred embodiment, L is —$CH_2NR^1CH_2$—, and $R^1$ is selected from H, $C_{1-6}$ alkyl or 3-7 membered heterocyclyl containing nitrogen or oxygen atom(s), wherein $C_{1-6}$ alkyl is optionally substituted with a substituent selected from —$OR^5$, —$NR^5R^6$, —$SR^5$, and/or any of —$CH_2$— within $C_{1-6}$ alkyl is optionally replaced with —O—, —$NR^5$— or —S—. $R^5$ and $R^6$ are each independently selected from H or $C_{1-4}$ alkyl.

With respect to the compounds represented by the above Formula (I), in another preferred embodiment, L is —$CH_2NHCH_2$—.

With respect to the compounds represented by the above Formula (I), in another preferred embodiment, L is —$CH_2N(C_{1-4}\text{ alkyl})CH_2$—.

With respect to the compounds represented by the above Formula (I), in another preferred embodiment, $G^1$, $G^2$ and $G^3$ are each independently selected from halogen, cyano, $C_{1-6}$ alkyl, $C_{3-7}$ cycloalkyl, $C_{3-6}$ cycloalkenyl, 4-7 membered heterocyclyl, phenyl, 5-6 membered heteroaryl, —$OR^5$, —$C(O)OR^5$, —$C(O)R^5$ or —$C(O)NR^5R^6$, wherein alkyl, cycloalkyl, cycloalkenyl, heterocyclyl, phenyl or heteroaryl is optionally substituted with one or more substituents selected from halogen, cyano, —OH, $C_{1-4}$ alkyl or —$OC_{1-4}$ alkyl. $R^5$ and $R^6$ are each independently selected from H, $C_{1-6}$ alkyl, $C_{1-6}$ alkyl-OH, $C_{1-3}$ alkyl-O—$C_{1-3}$ alkyl or 3-7 membered heterocyclyl containing nitrogen or oxygen atom(s).

With respect to the compounds represented by the above Formula (I), in another preferred embodiment, ring A is not substituted with $G^1$.

With respect to the compounds represented by the above Formula (I), in another preferred embodiment, ring A is substituted with one, two or three $G^1$.

With respect to the compounds represented by the above Formula (I), in another preferred embodiment, ring A is substituted with one $G^1$.

With respect to the compounds represented by the above Formula (I), in another preferred embodiment, $G^1$ is selected from halogen, $C_{1-6}$ alkyl, —$OC_{1-6}$ alkyl, phenyl, $C_{3-7}$ cycloalkyl, $C_{3-6}$ cycloalkenyl, 4-7 membered heterocyclyl or 5-6 membered heteroaryl, wherein alkyl, cycloalkyl, cycloalkenyl, heterocyclyl, phenyl and heteroaryl are optionally substituted with one or more substituents selected from $C_{1-4}$ alkyl, halo or —OH.

With respect to the compounds represented by the above Formula (I), in another preferred embodiment, $G^1$ is —$OC_{1-6}$ alkyl, preferably methoxy or ethoxy.

With respect to the compounds represented by the above Formula (I), in another preferred embodiment, $G^1$ is halogen.

With respect to the compounds represented by the above Formula (I), in another preferred embodiment, $G^1$ is phenyl which is unsubstituted or substituted with one or more halogens such as fluorine.

With respect to the compounds represented by the above Formula (I), in another preferred embodiment, $G^1$ is $C_{3-6}$ cycloalkenyl, preferably cyclopentenyl or cyclohexenyl, more preferably cyclopentenyl.

With respect to the compounds represented by the above Formula (I), in another preferred embodiment, $G^1$ is 5-6 membered heteroaryl, preferably pyridyl or a pyrazolyl.

With respect to the compounds represented by the above Formula (I), in another preferred embodiment, ring B is unsubstituted.

With respect to the compounds represented by the above Formula (I), in another preferred embodiment, ring C is unsubstituted.

With respect to the compounds represented by the above Formula (I), in another preferred embodiment, ring C is substituted with one, two or three $G^3$.

With respect to the compounds represented by the above Formula (I), in another preferred embodiment, ring C is substituted with two $G^3$.

With respect to the compounds represented by the above Formula (I), in another preferred embodiment, ring C is substituted with one $G^3$.

With respect to the compounds represented by the above Formula (I), in another preferred embodiment, $G^3$ is selected from halogen, cyano, $C_{1-6}$ alkyl, $C_{3-7}$ cycloalkyl, 4-7 membered heterocyclyl, —$OR^5$, —$C(O)OR^5$, —$C(O)R^5$ or —$C(O)NR^5R^6$, wherein alkyl, cycloalkyl or heterocyclyl is optionally substituted with one or more substituents selected from halogen, cyano, —OH or —$OC_{1-4}$ alkyl. $R^5$ and $R^6$ are each independently selected from H, $C_{1-6}$ alkyl or 3-7 membered heterocyclyl containing nitrogen or oxygen atom(s), wherein $C_{1-6}$ alkyl is optionally substituted with substituents selected from —$OR^{11}$, —$NR^{11}R^{12}$, —$SR^{11}$, and/or any of —$CH_2$— within $C_{1-6}$ alkyl is optionally replaced with —O—, —$NR^{11}$— or —S—. $R^{11}$ and $R^{12}$ are each independently selected from H or $C_{1-4}$ alkyl. In a more preferred embodiment, each of $R^5$ and $R^6$ above is independently selected from H, $C_{1-6}$ alkyl, $C_{1-6}$ alkyl-OH, $C_{1-3}$ alkyl-O—$C_{1-3}$ alkyl or 3-7 membered heterocyclyl containing nitrogen atom(s).

With respect to the compounds represented by the above Formula (I), in another preferred embodiment, $G^3$ is cyano.

With respect to the compounds represented by the above Formula (I), in another preferred embodiment, $G^3$ is halogen, such as chlorine.

With respect to the compounds represented by the above Formula (I), in another preferred embodiment, $G^3$ is —$OC_{1-6}$ alkyl, such as methoxy.

With respect to the compounds represented by the above Formula (I), in another preferred embodiment, $G^3$ is —$C(O)OH$ or —$C(O)OC_{1-6}$ alkyl.

With respect to the compounds represented by the above Formula (I), in another preferred embodiment, $G^3$ is —$C(O)NH_2$, —$C(O)NHC_{1-6}$ alkyl or —$C(O)N(C_{1-6}$ alkyl$)_2$.

With respect to the compounds represented by the above Formula (I), in another preferred embodiment, $G^3$ is —$C(O)NHC_{1-6}$ alkyl-OH.

With respect to the compounds represented by the above Formula (I), in another preferred embodiment, $G^3$ is —$C_{1-6}$ alkyl-OH.

It should be understood that the present invention also relates to any combination of preferred embodiments of the compound represented by the above Formula (I). Some examples of combinations are given below. However, the invention is not limited to these combinations.

In a preferred embodiment of the second aspect of the present invention, the present invention relates to a compound represented by the above Formula (I) or its isomer, prodrug, stable isotope derivative, pharmaceutically acceptable salt or mixture thereof, wherein:
Ring A and ring B are condensed to form the following fused heterocyclic ring:

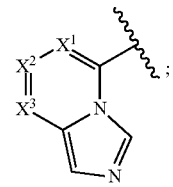

$X^1$, $X^2$ and $X^3$ are each independently selected from $CG^{11}$;

Ring C is $C_{3-8}$ cycloalkyl, phenyl or 5-6 membered heteroaryl containing nitrogen atom(s), and is optionally substituted with one, two or three $G^3$;

L is independently selected from $C_{2-6}$ alkylene, —$NR^1C(O)NR^2$—, —$C(R^3)(R^4)C(O)NR^2$—, —$NR^1C(O)C(R^3)(R^4)$—, —$OC(O)NR^2$—, —$NR^1C(O)O$—, —$NR^1S(O)_mNR^2$—, —$C(R^3)(R^4)S(O)_mNR^2$— or —$NR^1S(O)_mC(R^3)(R^4)$—, wherein alkylene is optionally substituted with substituents selected from —$OR^1$, —$NR^1R^2$, —$SR^1$ or 3-7 membered heterocyclyl, and/or any of —$CH_2$— within alkylene is optionally replaced with —O—, —$NR^1$— or —S—;

$R^1$, $R^2$, $R^3$ and $R^4$ are each independently selected from H, $C_{1-6}$ alkyl or 3-7 membered heterocyclyl containing nitrogen or oxygen atom(s), wherein $C_{1-6}$ alkyl is optionally substituted with substituents selected from —$OR^5$, —$NR^5R^6$, —$SR^5$, and/or any of —$CH_2$— within $C_{1-6}$ alkyl is optionally replaced with —O—, —$NR^5$— or —S—;

$G^{11}$ is H and $G^3$ is selected from halogen, cyano, $C_{1-6}$ alkyl, $C_{3-7}$ cycloalkyl, $C_{3-6}$ cycloalkenyl, 4-7 membered heterocyclyl, phenyl, 5-6 membered heteroaryl, —$OR^5$, —$C(O)OR^5$, —$C(O)R^5$, —$C(O)NR^5R^6$, wherein alkyl, cycloalkyl, cycloalkenyl, heterocyclyl, phenyl or heteroaryl is optionally substituted with one or more substituents selected from halogen, cyano, —OH, $C_{1-4}$ alkyl or —$OC_{1-4}$ alkyl, or $G^{11}$ and $G^3$ are each independently selected from halogen, cyano, $C_{1-6}$ alkyl, $C_{3-7}$ cycloalkyl, $C_{3-6}$ cycloalkenyl, 4-7 membered heterocyclyl, phenyl, 5-6 membered heteroaryl, —$OR^5$, —$C(O)OR^5$, —$C(O)R^5$, —$C(O)NR^5R^6$, wherein alkyl, cycloalkyl, cycloalkenyl, heterocyclyl, phenyl or heteroaryl is optionally substituted with one or more substituents selected from halogen, cyano, —OH, $C_{1-4}$ alkyl or —$OC_{1-4}$ alkyl;

$R^5$ and $R^6$ are each independently selected from H, $C_{1-6}$ alkyl or 3-7 membered heterocyclyl containing nitrogen or oxygen atom(s), wherein $C_{1-6}$ alkyl is optionally substituted with substituents selected from —$OR^{11}$, —$NR^{11}R^{12}$, —$SR^{11}$, and/or any of —$CH_2$— within $C_{1-6}$ alkyl is optionally replaced with —O—, —$NR^{11}$— or —S—;

$R^{11}$ and $R^{12}$ are each independently selected from H or $C_{1-4}$ alkyl; and m is 1 or 2.

In another preferred embodiment of the second aspect of the present invention, the present invention relates to a compound represented by the above Formula (I) or its isomer, prodrug, stable isotope derivative, pharmaceutically acceptable salt or mixture thereof, wherein:
Ring A and ring B are condensed to form the following fused heterocyclic ring

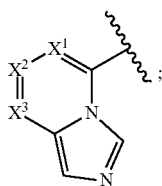

X¹, X² and X³ are each independently selected from CG¹¹;

Ring C is cyclopentyl, cyclohexyl, phenyl, pyridyl or a pyridonyl, and is optionally substituted with one or two G³;

L is selected from —CH$_2$NHCH$_2$—, —CH$_2$N(C$_{1-4}$ alkyl)CH$_2$—, —NHC(O)NH—, —CH$_2$C(O)NH— or —NHC(O)CH$_2$—;

G¹¹ is selected from H, halogen, —OC$_{1-6}$ alkyl, phenyl which is unsubstituted or substituted with one or more halogens, C$_{1-6}$ alkyl, C$_{3-7}$ cycloalkyl, C$_{4-6}$ cycloalkenyl, 4-7 membered heterocyclyl or 5-6 membered heteroaryl;

G³ is selected from halogen, cyano, C$_{1-6}$ alkyl, C$_{3-7}$ cycloalkyl, 4-7 membered heterocyclyl, —OR⁵, —C(O)OR⁵, —C(O)R⁵ or —C(O)NR⁵R⁶, wherein alkyl, cycloalkyl or heterocyclyl is optionally substituted with one or more substituents selected from halogen, cyano, —OH or —OC$_{1-4}$ alkyl;

R⁵ and R⁶ are each independently selected from H, C$_{1-6}$ alkyl or a 3-7 membered heterocyclyl containing nitrogen or oxygen atom(s), wherein C$_{1-6}$ alkyl is optionally substituted with substituents selected from —OR¹¹, —NR¹¹R¹², —SR¹¹, and/or any of —CH$_2$— within C$_{1-6}$ alkyl is optionally replaced with —O—, —NR¹¹— or —S—;

R¹¹ and R¹² are each independently selected from H or C$_{1-4}$ alkyl.

In another preferred embodiment of the second aspect of the present invention, the present invention relates to a compound represented by the above Formula (I) or its isomer, prodrug, stable isotope derivative, pharmaceutically acceptable salt or mixture thereof,
wherein:

Ring A and ring B are condensed to form the following fused heterocyclic ring

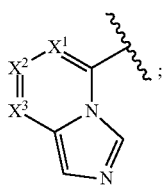

X¹, X² and X³ are each independently selected from CG¹¹;

Ring C is cyclopentyl, cyclohexyl, phenyl, pyridyl or pyridonyl, and is optionally substituted with one or two G³;

L is selected from —CH$_2$NHCH$_2$—, —NHC(O)NH—, —CH$_2$C(O)NH— or —NHC(O)CH$_2$—;

G¹¹ is selected from H, halogen, —OC$_{1-6}$ alkyl, and phenyl which is unsubstituted or substituted with one or more halogens, C$_{4-6}$ cycloalkenyl, pyridyl or pyrazolyl; and G³ is selected from halogen, cyano, —OC$_{1-6}$ alkyl, —C$_{1-6}$ alkyl-OH, —C(O)OH, —C(O)OC$_{1-6}$ alkyl, —C(O)NH$_2$, —C(O)NHC$_{1-6}$ alkyl, —C(O)N(C$_{1-6}$ alkyl)$_2$ or —C(O)NHC$_{1-6}$ alkyl-OH;

An embodiment of the second aspect of the invention relates to a compound represented by the above Formula (I) or its isomer, prodrug, stable isotope derivative, pharmaceutically acceptable salt or mixture thereof, wherein the compound is selected from:

| Compound number | Compound structure and name |
|---|---|
| 1. | 1-(4-cyanophenyl)-3-(imidazo[1,5-a]pyridin-5-yl)urea |
| 2. | 1-(3-cyanophenyl)-3-(imidazo[1,5-a]pyridin-5-yl)urea |
| 3. | 1-(4-chlorophenyl)-3-(imidazo[1,5-a]pyridin-5-yl)urea |
| 4. | 1-(3-chlorophenyl)-3-(imidazo[1,5-a]pyridin-5-yl)urea |
| 5. | 1-(imidazo[1,5-a]pyridin-5-yl)-3-(4-methoxyphenyl)urea |
| 6. | 1-(imidazo[1,5-a]pyridin-5-yl)-3-(3-methoxyphenyl)urea |

| Compound number | Compound structure and name |
|---|---|
| 7. | methyl 3-(3-(imidazo[1,5-a]pyridin-5-yl)ureido)benzoate |
| 8. | 3-(3-(imidazo[1,5-a]pyridin-5-yl)ureido)benzoic acid |
| 9. | 3-(3-(imidazo[1,5-a]pyridin-5-yl)ureido)-N-methylbenzamide |
| 10. | 1-cyclohexyl-3-(imidazo[1,5-a]pyridin-5-yl)urea |
| 11. | 2-(4-cyanophenyl)-N-(imidazo[1,5-a]pyridin-5-yl)acetamide |
| 12. | N-(4-cyanophenyl)-2-(imidazo[1,5-a]pyridin-5-yl)acetamide |
| 13. | 1-(4-cyanophenyl)-3-(8-fluoroimidazo[1,5-a]pyridin-5-yl)urea |
| 14. | 1-(4-cyanophenyl)-3-(6-fluoroimidazo[1,5-a]pyridin-5-yl)urea |
| 15. | 1-(4-cyanophenyl)-3-(6-methoxyimidazo[1,5-a]pyridin-5-yl)urea |
| 16. | 1-(4-cyanophenyl)-3-(6-ethoxyimidazo[1,5-a]pyridin-5-yl)urea |
| 17. | 1-(4-cyanophenyl)-3-(6-phenylimidazo[1,5-a]pyridin-5-yl)urea |

| Compound number | Compound structure and name |
|---|---|
| 18. | 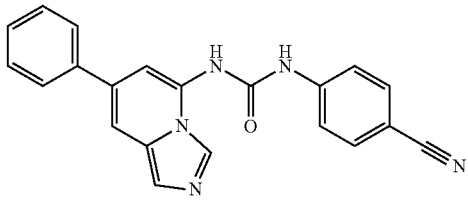<br>1-(4-cyanophenyl)-3-(7-phenylimidazo[1,5-a]pyridin-5-yl)urea |
| 19. | 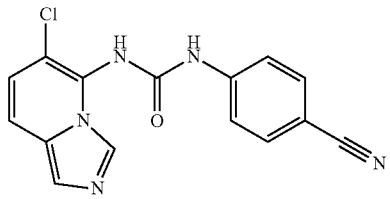<br>1-(6-chloroimidazo[1,5-a]pyridin-5-yl)-3-(4-cyanophenyl)urea |
| 20. | 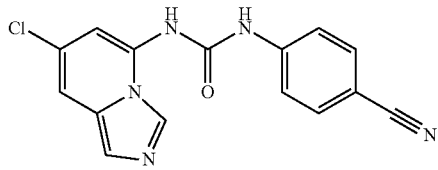<br>1-(7-chloroimidazo[1,5-a]pyridin-5-yl)-3-(4-cyanophenyl)urea |
| 21. | 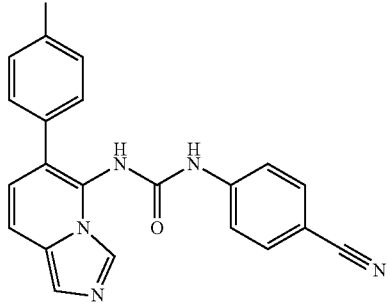<br>1-(4-cyanophenyl)-3-(6-(4-fluorophenyl)imidazo[1,5-a]pyridin-5-yl)urea |
| 22. | 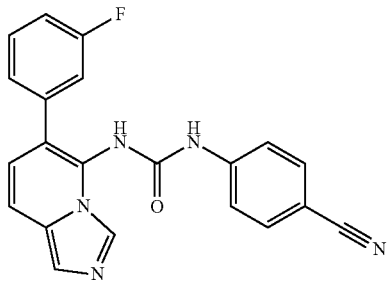<br>1-(4-cyanophenyl)-3-(6-(3-fluorophenyl)imidazo[1,5-a]pyridin-5-yl)urea |

| Compound number | Compound structure and name |
|---|---|
| 23. | 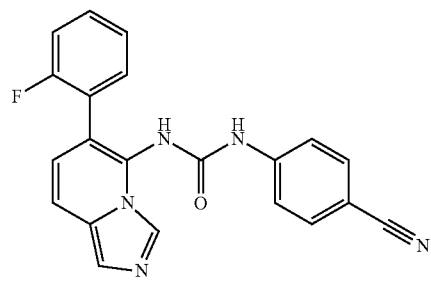<br>1-(4-cyanophenyl)-3-(6-(2-fluorophenyl)imidazo[1,5-a]pyridin-5-yl)urea |
| 24. | 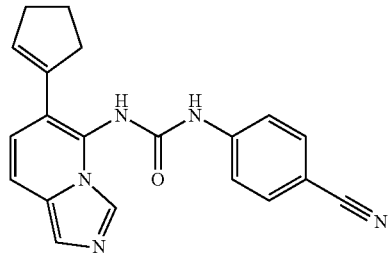<br>1-(4-cyanophenyl)-3-(6-(cyclopent-1-en-1-yl)imidazo[1,5-a]pyridin-5-yl)urea |
| 25. | 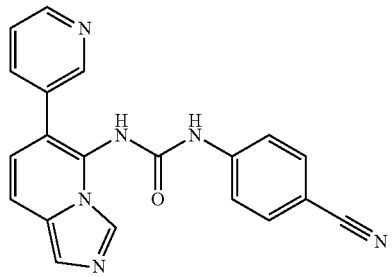<br>1-(4-cyanophenyl)-3-(6-(pyridin-3-yl)imidazo[1,5-a]pyridin-5-yl)urea |
| 26. | 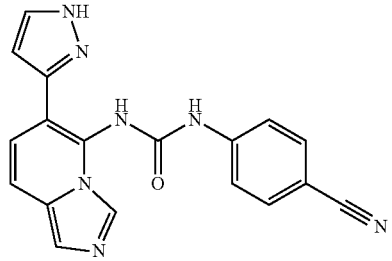<br>1-(6-(1H-pyrazol-3-yl)imidazo[1,5-a]pyridin-5-yl)-3-(4-cyanophenyl)urea |

| Compound number | Compound structure and name |
|---|---|
| 27. | 4-(3-(6-phenylimidazo[1,5-a]pyridin-5-yl)ureido)benzoic acid |
| 28. | N-methyl-4-(3-(6-phenylimidazo[1,5-a]pyridin-5-yl)ureido)benzamide |
| 29. | 4-(3-(6-phenylimidazo[1,5-a]pyridin-5-yl)ureido)benzamide |
| 30. | N-(2-hydroxyethyl)-4-(3-(6-phenylimidazo[1,5-a]pyridin-5-yl)ureido)benzamide |
| 31. | 1-(4-(hydroxymethyl)phenyl)-3-(6-phenylimidazo[1,5-a]pyridin-5-yl)urea |
| 32. | 1-(6-cyanopyridin-3-yl)-3-(6-phenylimidazo[1,5-a]pyridin-5-yl)urea |
| 33. | 1-(5-cyanopyridin-2-yl)-3-(6-phenylimidazo[1,5-a]pyridin-5-yl)urea |
| 34. | 1-(4-cyano-3-methoxyphenyl)-3-(6-phenylimidazo[1,5-a]pyridin-5-yl)urea |

| Compound number | Compound structure and name |
|---|---|
| 35. | 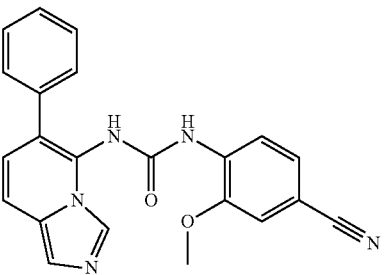<br>1-(4-cyano-2-methoxyphenyl)-3-(6-phenylimidazo[1,5-a]pyridin-5-yl)urea |
| 36. | 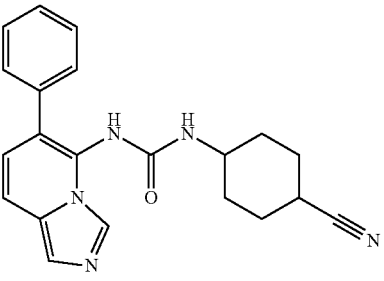<br>1-(4-cyanocyclohexyl)-3-(6-phenylimidazo[1,5-a]pyridin-5-yl)urea |
| 37. | 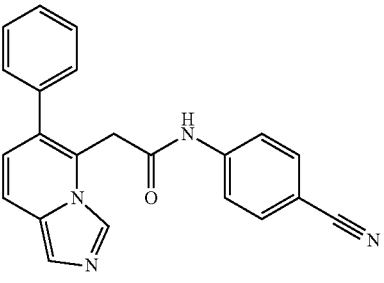<br>N-(4-cyanophenyl)-2-(6-phenylimidazo[1,5-a]pyridin-5-yl)acetamide |
| 38. | 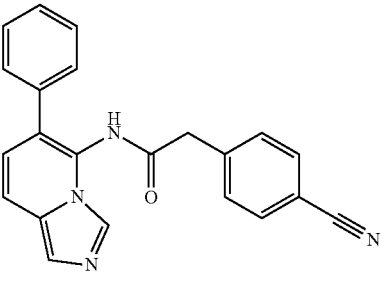<br>2-(4-cyanophenyl)-N-(6-phenylimidazo[1,5-a]pyridin-5-yl)acetamide |
| 39. | 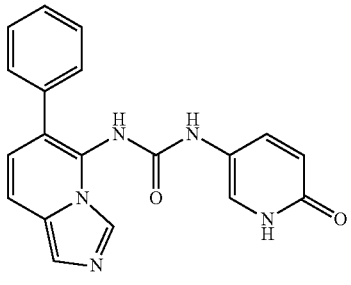<br>1-(6-oxo-1,6-dihydropyridin-3-yl)-3-(6-phenylimidazo[1,5-a]pyridin-5-yl)urea |
| 40. | 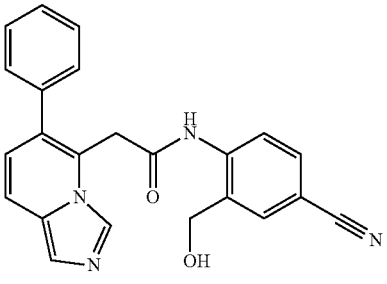<br>N-(4-cyano-2-(hydroxymethyl)phenyl)-2-(6-phenylimidazo[1,5-a]pyridin-5-yl)acetamide |
| 41. | 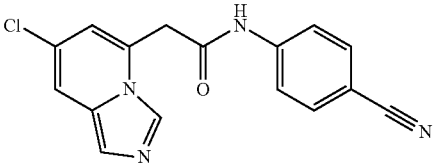<br>2-(7-chloroimidazo[1,5-a]pyridin-5-yl)-N-(4-cyanophenyl)acetamide |
| 42. | 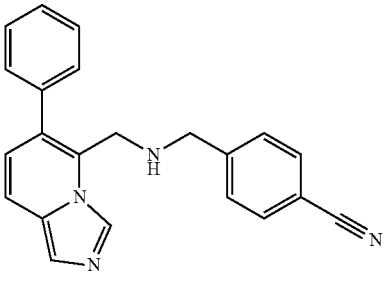<br>4-(((6-Phenylimidazo[1,5-a]pyridin-5-yl)methyl)amino)methyl)benzonitrile |

The compounds of the invention may exist in the form of optical isomers. These optical isomers are of the "R" or "S" configuration depending on the configuration of the substituents around the chiral carbon atom. Optical isomers include enantiomers and diastereomers. Methods for preparing and isolating optical isomers are known in the art.

Geometric isomers may also be present in the compounds of the invention. The present invention includes various geometric isomers and mixtures thereof resulting from the distribution of substituents around a carbon-carbon double bond, a carbon-nitrogen double bond, a cycloalkyl group or a heterocyclic group. A substituent around a carbon-carbon double bond or a carbon-nitrogen bond is designated as a Z or E configuration, and a substituent around a cycloalkyl or heterocycle is designated as a cis or trans configuration.

The compounds of the invention may also exhibit tautomerism, such as keto-enol tautomerism.

It is to be understood that the invention includes any tautomeric or stereoisomeric forms and mixtures thereof and is not limited to any one of the tautomeric or stereoisomeric forms used in the nomenclature or chemical structural formula of the compound.

The invention is also intended to include all isotopes of atoms occurring in the compounds of the invention. Isotopes include those atoms that have the same atomic number but different mass numbers. Examples of isotopes suitable for incorporation into the compounds of the invention are hydrogen, carbon, nitrogen, oxygen, phosphorus, sulfur, fluorine and chlorine, for example but not limited to $^2$H, $^3$H, $^{13}$C, $^{14}$C, $^{15}$N, $^{18}$O, $^{17}$O, $^{31}$P, $^{32}$P, $^{35}$S, $^{18}$F 和 $^{36}$Cl. Isotopically labeled compounds of the invention can generally be prepared by conventional techniques known to those skilled in the art or by methods similar to those described in the accompanying examples, using suitable isotopically labeled reagents in place of non-isotopically labeled reagents. Such compounds have a variety of potential uses, for example, as a standard and reagent in the determination of biological activity. In the case of stable isotopes, such compounds have the potential to advantageously alter biological, pharmacological or pharmacokinetic properties.

The compounds of the invention may also be administered in the form of a prodrug. Prodrugs are derivatives which are converted to the biologically active compounds of the invention under physiological conditions in vivo, for example, by oxidation, reduction, hydrolysis, etc. (each of which is carried out using an enzyme or without the participation of an enzyme). Prodrugs can be used to alter the physical and/or pharmacokinetic properties of the compounds of the invention. Examples of prodrugs are compounds wherein the amino group in the compounds of the invention is acylated, alkylated or phosphorylated, or wherein the hydroxy group is acylated, alkylated, phosphorylated or converted to borate, or the carboxyl group is esterified or amidated, or a thiol group forms a disulfide bridge with a carrier molecule, such as a peptide, that selectively delivers the drug to the target and/or to the cytosol of the cell. These compounds can be prepared from the compounds of the present invention according to known methods.

The invention further relates to pharmaceutically acceptable salts of the compound of the formula (I') or (I). A pharmaceutically acceptable salt refers to a salt made of a pharmaceutically acceptable base or acid, including an inorganic base or an acid, and an organic base or acid. Where the compounds of the invention contain one or more acidic or basic groups, the invention also includes their corresponding pharmaceutically acceptable salts. Thus, the compound of the invention containing an acidic group may be present in the form of a salt and may be used according to the invention, for example as an alkali metal salt, an alkaline earth metal salt or as an ammonium salt. More specific examples of such salts include sodium, potassium, calcium, magnesium or salts with ammonia or organic amines such as ethylamine, ethanolamine, triethanolamine or amino acids. The compound of the invention containing a basic group may be present in the form of a salt and may be used in the form of their addition salts with inorganic or organic acids according to the invention. Examples of suitable acids include hydrochloric acid, hydrobromic acid, phosphoric acid, sulfuric acid, nitric acid, methanesulfonic acid, p-toluenesulfonic acid, naphthalenedisulfonic acid, oxalic acid, acetic acid, tartaric acid, lactic acid, salicylic acid, benzoic acid, formic acid, propionic acid, pivalic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to those skilled in the art. If the compound of the present invention contains both acidic and basic groups in the molecule, the present invention includes an internal salt or a betaine in addition to the salt forms mentioned. Each salt can be obtained by conventional methods known to those skilled in the art, for example, by mixing it with an organic or inorganic acid or base in a solvent or dispersant, or by anion exchange or cation exchange with other salts.

The invention also relates to a pharmaceutical composition. The pharmaceutical composition refers to a combination containing one or more compounds of the Formula (I') or (I), or its isomer, prodrug, stable isotope derivative, pharmaceutically acceptable salt or mixture thereof, and other components such as pharmaceutically acceptable carriers and excipients. The purpose of the pharmaceutical composition is to promote the administration to the organism, which facilitates the absorption of the active ingredient and then exerts biological activity.

The invention further relates to a pharmaceutical combination comprising a therapeutically effective amount of a compound of the Formula (I') or (I), or its isomer, prodrug, stable isotope derivative, pharmaceutically acceptable salt or mixture thereof and additional anticancer agents. The different components of the pharmaceutical combination product may be present in the same pharmaceutical composition or in different pharmaceutical compositions and may be administered simultaneously or sequentially in the same or different manners.

Synthetic Methods

The compounds of the Formula (I') or (I) of the present invention can be prepared by the following exemplary methods and examples, but the methods and examples should not be construed as being limiting the scope of the invention in any ways. The compounds of the invention may also be synthesized by synthetic techniques known to those skilled in the art, or a combination of methods known in the art and methods of the invention may be employed. The product obtained in each step of the reaction is obtained by separation techniques known in the art including, but not limited to, extraction, filtration, distillation, crystallization, chromatographic separation, etc. The starting materials and chemical reagents required for the synthesis can be synthesized according to the literature or be purchased.

The compound of the Formula (I') or (I) of the present invention can be synthesized by the route described in Method A using a fused heterocyclic intermediate having an amino group: a) can be replaced with a halide under base catalysis or reductively aminated with an aldehyde to form an ammoniated target product; b) can be amidated with acid or acid chloride to form an amide target product; c) can be deprotonated with a strong base, followed by reaction with isocyanate, or can react with phosgene under a basic condition, followed by condensation with another ammonia to form a urea target product; d) can also react with chloroformate under a basic condition to form a carbamate target product.

Method A

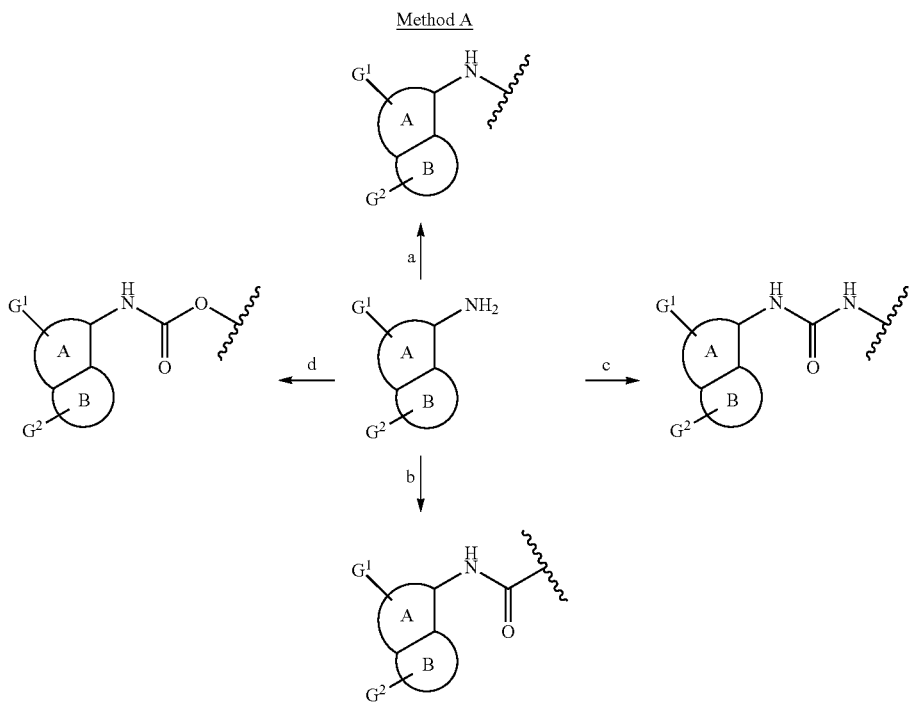

The compound of the Formula (I') or (I) of the present invention can also be synthesized by the route described in Method B using a fused heterocyclic intermediate having a carboxyl group: a) can be condensed with an amine to form an amide target product; b) can be mixed and heated with diphenyl azidophosphate (DPPA) and triethylamine, followed by reaction with another amine to form a urea target product (Curtius rearrangement). When the fused heterocyclic ring has a halogen X (such as Br) substituent, it can be further derivatized to a target product by coupling reaction at a lower temperature and in a shorter timeframe; c) can also undergo acid reduction and be further derivatized.

Method B

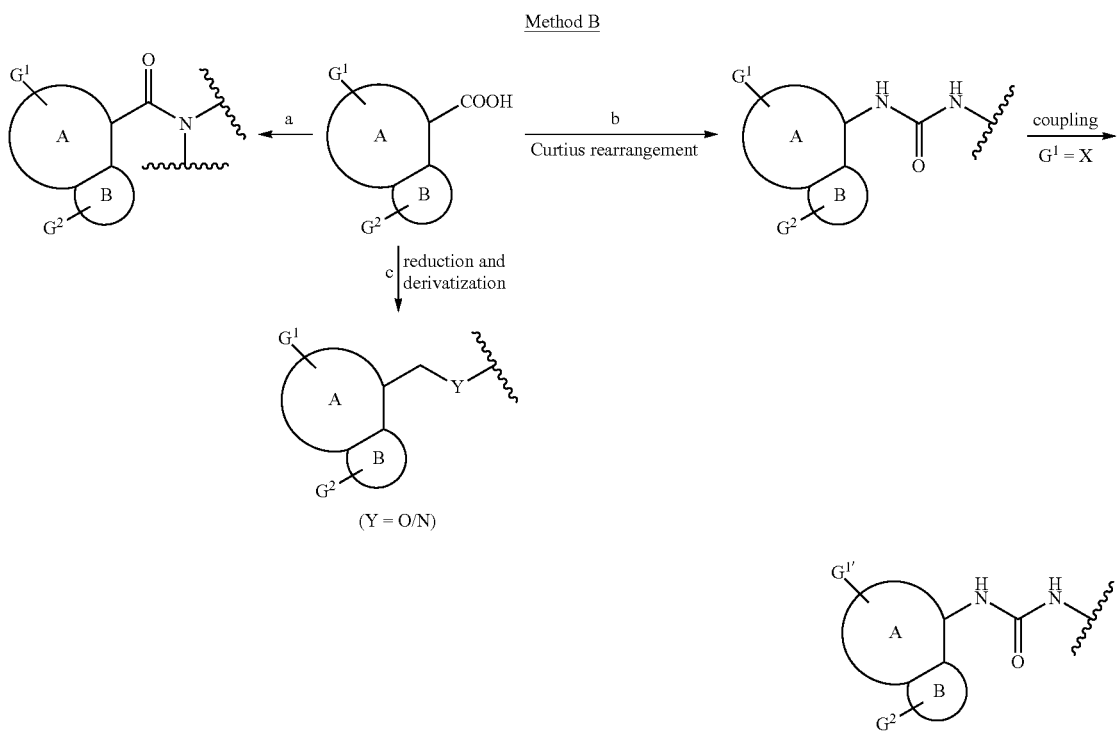

The compound of the Formula (I') or (I) of the present invention can also be synthesized by the route described in Method C using a fused heterocyclic intermediate having a halogen X: a) can be subjected to C—C coupling reactions (such as Suzuki coupling) or C—N coupling reactions (such as Buchwald coupling and Ullmann coupling); b) can be coupled with methyl tert-butyl malonate, followed by decarboxylation to an acetate derivative, and subsequently hydrolysis in the presence of a base to an acid which can undergo amide condensation to an amide target product or can be subjected to ester reduction and further derivatization.

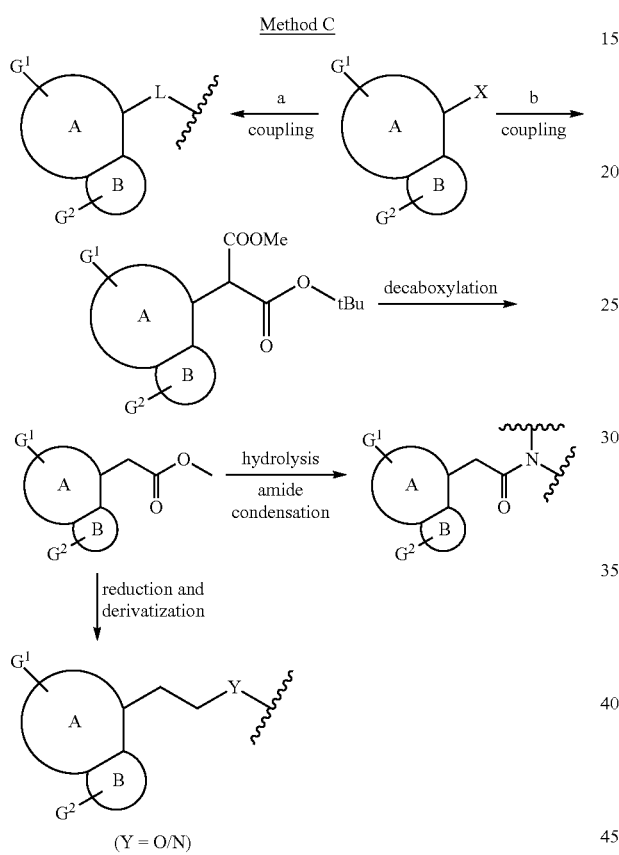

Intermediate D6 can be prepared according to the route described in Method D. The amino group of D1 is first reacted with phthalic anhydride to give D2, followed sequentially by bromination with NBS/AIBN to bromide D3, amination with hexamethylenetetramine to D4, ring closure under heat in acetic anhydride/formic acid to give intermediate D5, and finally deprotection to give D6.

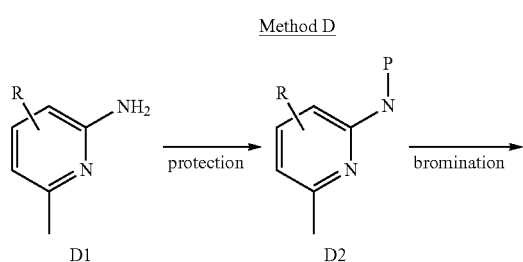

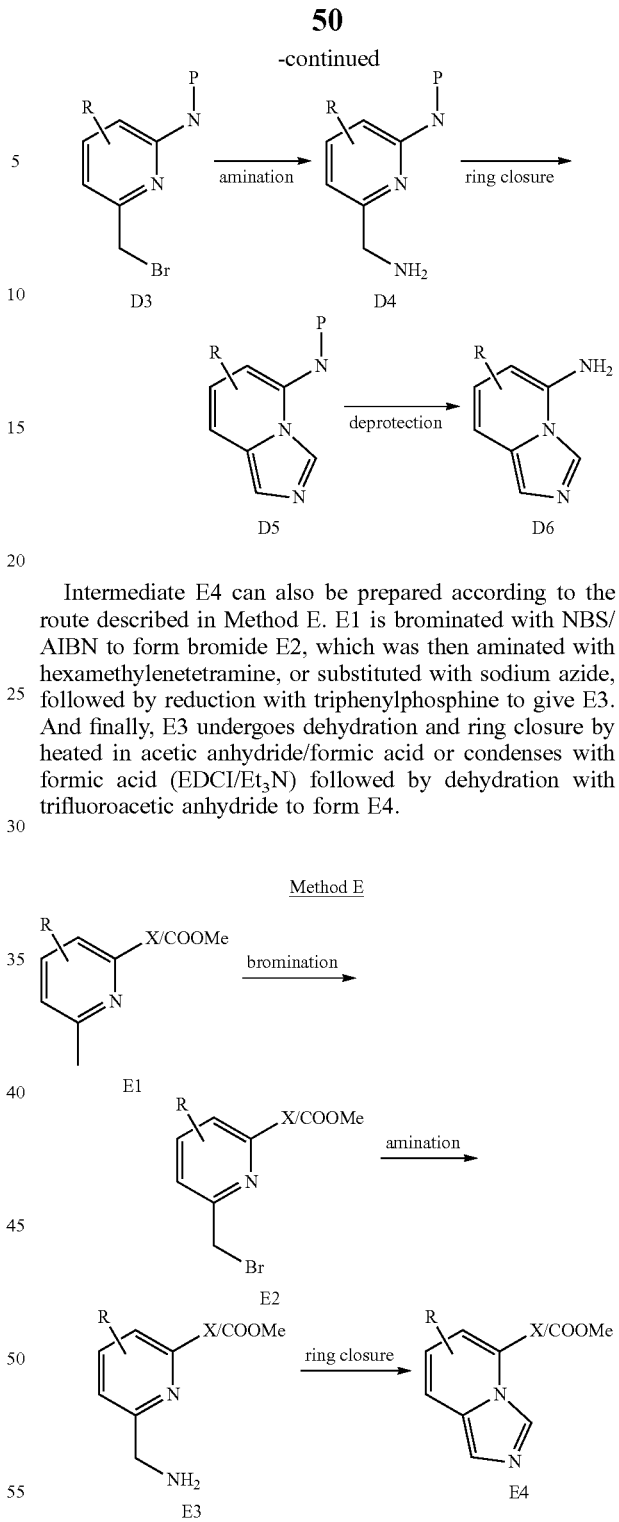

Intermediate E4 can also be prepared according to the route described in Method E. E1 is brominated with NBS/AIBN to form bromide E2, which was then aminated with hexamethylenetetramine, or substituted with sodium azide, followed by reduction with triphenylphosphine to give E3. And finally, E3 undergoes dehydration and ring closure by heated in acetic anhydride/formic acid or condenses with formic acid (EDCI/Et$_3$N) followed by dehydration with trifluoroacetic anhydride to form E4.

EXAMPLES

The compound structure was determined by nuclear magnetic resonance (NMR) or mass spectrometry (MS). NMR was measured by Bruker AVANCE-400, the solvent was deuterated dimethyl sulfoxide (DMSO-d6), deuterated chloroform (CDCl$_3$), deuterated methanol (CD$_3$OD), the internal standard was tetramethylsilane (TMS), and chemical shifts were given in units of $10^{-6}$ (ppm).

MS was measured using an Agilent SQD (ESI) mass spectrometer (manufacturer: Agilent, model: 6120).

HPLC was run using an Agilent 1200 DAD high pressure liquid chromatograph (Sunfire C18, 150×4.6 mm, 5 μm column) and a Waters 2695-2996 high pressure liquid chromatograph (Gimini C18 150×4.6 mm, 5 μm column).

Qingdao Ocean GF254 silica gel plate was used as thin-layer chromatography silica gel plate. The specification of silica gel plate used for thin-layer chromatography (TLC) was 0.15 mm~0.2 mm. The specification for thin layer chromatography separation and purification was 0.4 mm~0.5 mm.

Generally, Qingdao Ocean 200~300 mesh silica gel was used as carrier for column chromatography.

The known starting materials of the present invention can be synthesized according to methods known in the art, or can be purchased from ABCR GmbH & Co. KG, Acros Organics, Aldrich Chemical Company, Accela ChemBio Inc., Beijing Ouhe Technology Co., etc.

Unless otherwise specified, the reactions in the examples were carried out under an argon or nitrogen atmosphere.

An argon or nitrogen atmosphere means that the reaction flask is connected to an argon or nitrogen balloon of about 1 L volume.

A hydrogen atmosphere means that the reaction bottle is connected to a hydrogen balloon of about 1 L volume.

The pressurized hydrogenation reaction is conducted using a GCD-500G high purity hydrogen generator and a BLT-2000 medium pressure hydrogenator from Beijing Jiawei Kechuang Technology Co., Ltd.

The hydrogenation reaction is usually evacuated, filled with hydrogen, which is repeated for three times.

CEM Discover-SP microwave reactor was used for microwave reaction.

Unless otherwise specified in the examples, the reaction temperature was room temperature, and the temperature range was 20-30° C.

The reaction progress in the examples was monitored by thin layer chromatography (TLC), and the eluent system used was A: dichloromethane and methanol system; B: petroleum ether and ethyl acetate system, and the volume ratio of the solvents was adjusted based on polarity of the compound.

The eluent system used for purifying the compound by column chromatography and developing the thin layer chromatography included A: dichloromethane and methanol systems; B: petroleum ether and ethyl acetate system, and the volume ratio of the solvents was adjusted based on polarity of the compound. It could also be adjusted by adding a small amount of triethylamine and acidic or alkaline reagents.

The abbreviation HATU refers to 2-(7-azabenzotriazole)-N,N,N',N'-tetramethyluronium hexafluorophosphate The abbreviation $Pd_2(dba)_3$ refers to tris(dibenzylideneacetone)dipalladium.

The abbreviation BINAP refers to 2,2'-bis-(diphenylphosphino)-1,1'-binaphthyl.

The abbreviation $Pd(dppf)Cl_2 \cdot CH_2Cl_2$ refers to 1,1-bis(diphenylphosphino)ferrocene palladium chloride dichloromethane complex.

The abbreviation EDCI refers to 1-(3-dimethylaminopropyl)-3-ethylcarbodiimide hydrochloride.

Example 1

1-(4-cyanophenyl)-3-(imidazo[1,5-a]pyridin-5-yl) urea

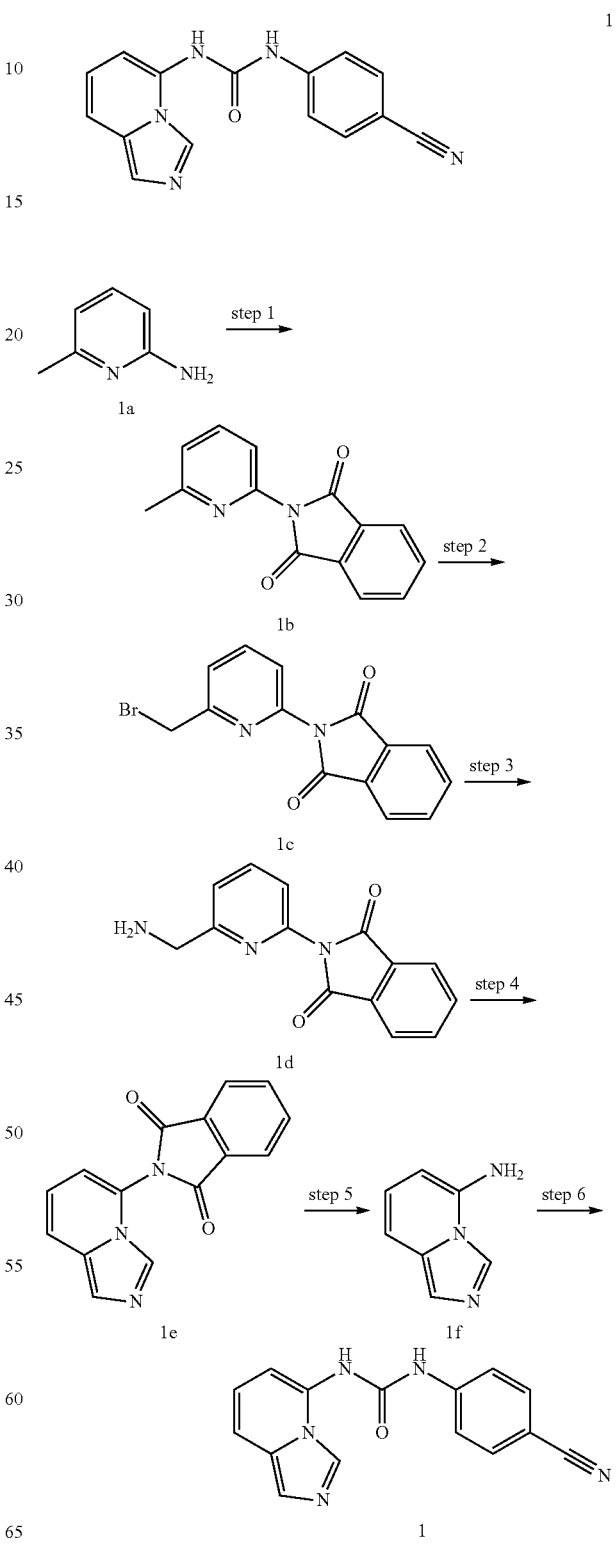

Step 1

Preparation of 2-(6-methylpyridin-2-yl)isoindoline-1,3-dione

Compound 6-methylpyridin-2-amine 1a (20 g, 185 mmol) and phthalic anhydride (27.4 g, 185 mmol) were mixed and heated to 190° C. and stirred for 2 hours. The mixture was cooled to room temperature, stirred with diethyl ether, filtered and dried to give 2-(6-methylpyridin-2-yl)isoindoline-1,3-dione 1b (43.1 g, yellow solid). Yield: 97%. The product was used in the next step without further purification.

MS m/z (ESI): 239[M+1]

Step 2

Preparation of 2-(6-(bromomethyl)pyridin-2-yl)isoindoline-1,3-dione

A mixture of 2-(6-methylpyridin-2-yl)isoindoline-1,3-dione 1b (20 g, 84 mmol), N-bromosuccinimide (17.6 g, 100 mmol), and azodiisobutyronitrile (1.36 g, 8.4 mmol) in carbon tetrachloride (200 mL) was heated to 83° C. for 8 hours. The mixture was cooled to room temperature and concentrated under reduced pressure. The residue was purified by silica gel column chromatography (dichloromethane/methanol=200/1) to give the target product 2-(6-(bromomethyl)pyridin-2-yl)isoindoline-1,3-dione 1c (11.1 g, yellow solid). Yield: 42%.

MS m/z (ESI): 317/319[M+1]

Step 3

Preparation of 2-(6-(aminomethyl)pyridin-2-yl)isoindoline-1,3-dione

A mixture of 2-(6-(bromomethyl)pyridin-2-yl)isoindoline-1,3-dione 1c (12.3 g, 38.8 mmol), and hexamethylenetetramine (8.69 g, 62.1 mmol) in dichloromethane (500 mL) was stirred at room temperature overnight. The mixture was filtered. The filtered cake was dissolved in ethanol (150 mL), added with concentrated hydrochloride (13 mL), heated to 50 OC and stirred for 2 h. The mixture was cooled to room temperature and the solvent was evaporated under reduced pressure to give the crude target product 2-(6-(aminomethyl)pyridin-2-yl)isoindoline-1,3-dione 1d (hydrochloride salt, 18.1 g, yellow solid). Yield: 100%.

MS m/z (ESI): 254[M+1]

Step 4

Preparation of 2-(imidazo[1,5-a]pyridin-5-yl)isoindoline-1,3-dione

A mixture of 2-(6-(aminomethyl)pyridin-2-yl)isoindoline-1,3-dione 1d (hydrochloride salt, 1 g, 3.4 mmol), acetic anhydride (22.2 mL) and formic acid (11.1 mL) was heated to 50° C. and stirred for 1 h. The mixture was cooled to room temperature and the solvent was evaporated under reduced pressure. The residue was poured into a 2 M aqueous solution of potassium carbonate and extracted with dichloromethane (30 mL×2). The organic phase was combined, dried over anhydrous sodium sulfate, filtered and concentrated under reduced pressure to remove the solvent. The residue was purified by silica gel column chromatography (dichloromethane/methanol=30/1) to give the target product 2-(imidazo[1,5-a]pyridin-5-yl)isoindoline-1,3-dione 1e (0.189 g, yellow solid). Yield: 21%.

MS m/z (ESI): 264[M+1]

Step 5

Preparation of imidazo[1,5-a]pyridin-5-amine

A mixture of 2-(imidazo[1,5-a]pyridin-5-yl)isoindoline-1,3-dione 1e (1.75 g, 6.65 mmol), hydrazine hydrate (11.6 mL) and methanol (175 mL) was heated to 72° C. and stirred for 1 h. The mixture was cooled to room temperature and the solvent was removed under reduced pressure. The residue was purified by silica gel column chromatography (dichloromethane/methanol=80/1) to give the target product imidazo[1,5-a]pyridin-5-amine 1f (700 mg). Yield: 78%.

MS m/z (ESI): 134[M+1]

Step 6

Preparation of 1-(4-cyanophenyl)-3-(imidazo[1,5-a]pyridin-5-yl)urea

Compound imidazo[1,5-a]pyridin-5-amine 1f (200 mg, 1.5 mmol) was dissolved in tetrahydrofuran (15 mL) and cooled to 0° C. Sodium hydride (60%, 90 mg, 2.25 mmol) was added and the resulting mixture was stirred for 30 min at 0° C. 4-Isocyanatobenzonitrile (324 mg, 2.25 mmol) was added and the mixture was stirred at room temperature for 2 h. The reaction was quenched by the addition of methanol (50 mL). The solvent was evaporated under reduced pressure. The residue was purified by silica gel column chromatography (dichloromethane/methanol=100/1 to 20/1). The obtained product was triturated in petroleum ether/ethyl acetate (1/1, 5 mL) for 1 h, filtered and dried to give the target product 1-(4-cyanophenyl)-3-(imidazo[1,5-a]pyridin-5-yl)urea 1 (80 mg, grey solid). Yield: 19%.

MS m/z (ESI): 278[M+1]

$^1$H NMR (400 MHz, DMSO-d$_6$) δ 9.80 (brs, 1H), 9.37 (brs, 1H), 8.36 (s, 1H), 7.77 (d, J=8.4 Hz, 2H), 7.68 (d, J=8.4 Hz, 2H), 7.45 (s, 1H), 7.43-7.40 (m, 1H), 6.88-6.84 (m, 2H).

Example 2

1-(3-cyanophenyl)-3-(imidazo[1,5-a]pyridin-5-yl)urea

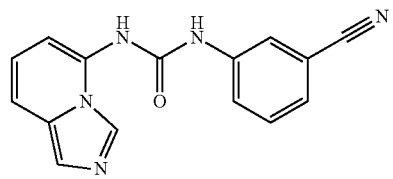 [SMILES: N#Cc1cccc(NC(=O)Nc2cccc3cncn23)c1]

2

Example 2 was synthesized according to the procedure of Example 1, but in the sixth step, 3-isocyanatobenzonitrile was used instead of 4-isocyanatobenzonitrile.

MS m/z (ESI): 278[M+1]

$^1$H NMR (400 MHz, DMSO-d$_6$) δ 9.50 (brs, 1H), 9.27 (brs, 1H), 8.30 (s, 1H), 8.01 (s, 1H), 7.75 (d, J=8.2 Hz, 1H), 7.53 (t, J=7.8 Hz, 1H), 7.47 (d, J=7.6 Hz, 1H), 7.44 (s, 1H), 7.42-7.39 (m, 1H), 6.88-6.84 (m, 2H).

Example 3

1-(4-chlorophenyl)-3-(imidazo[1,5-a]pyridin-5-yl) urea

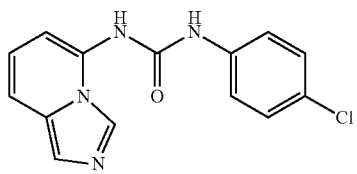 [SMILES: O=C(Nc1ccc(Cl)cc1)Nc1cccc2cncn12]

Example 3 was synthesized according to the procedure of Example 1, but in the sixth step, 1-chloro-4-isocyanatobenzene was used instead of 4-isocyanatobenzonitrile.

MS m/z (ESI): 287/289[M+1]

$^1$H NMR (400 MHz, DMSO-d$_6$) δ 9.30 (brs, 1H), 9.13 (brs, 1H), 8.29 (s, 1H), 7.53 (d, J=8.8 Hz, 2H), 7.44 (s, 1H), 7.40-7.38 (m, 1H), 7.37 (d, J=8.8 Hz, 2H), 6.87-6.85 (m, 2H).

Example 4

1-(3-chlorophenyl)-3-(imidazo[1,5-a]pyridin-5-yl) urea

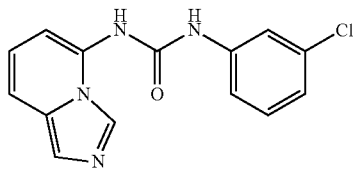 [SMILES: O=C(Nc1cccc(Cl)c1)Nc1cccc2cncn12]

Example 4 was synthesized according to the procedure of Example 1, but in the sixth step, 1-chloro-3-isocyanatobenzene was used instead of 4-isocyanatobenzonitrile.

MS m/z (ESI): 287/289[M+1]

$^1$H NMR (400 MHz, DMSO-d$_6$) δ 9.36 (brs, 1H), 9.17 (brs, 1H), 8.29 (s, 1H), 7.74 (s, 1H), 7.44 (s, 1H), 7.42-7.39 (m, 1H), 7.34-7.33 (m, 2H), 7.09-7.06 (m, 1H), 6.87-6.85 (m, 2H).

Example 5

1-(imidazo[1,5-a]pyridin-5-yl)-3-(4-methoxyphenyl) urea

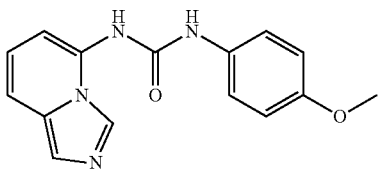 [SMILES: COc1ccc(NC(=O)Nc2cccc3cncn23)cc1]

Example 5 was synthesized according to the procedure of Example 1, but in the sixth step, 1-isocyanato-4-methoxybenzene was used instead of 4-isocyanatobenzonitrile.

MS m/z (ESI): 283[M+1]

$^1$H NMR (400 MHz, DMSO-d$_6$) δ 9.37 (brs, 2H), 8.48 (s, 1H), 7.42-7.39 (m, 3H), 7.33 (d, J=8.9 Hz, 1H), 6.96-6.83 (m, 4H), 3.73 (s, 3H).

Example 6

1-(imidazo[1,5-a]pyridin-5-yl)-3-(3-methoxyphenyl) urea

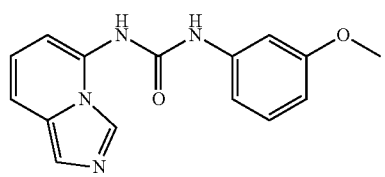 [SMILES: COc1cccc(NC(=O)Nc2cccc3cncn23)c1]

Example 6 was synthesized according to the procedure of Example 1, but in the sixth step, 1-isocyanato-3-methoxybenzene was used instead of 4-isocyanatobenzonitrile.

MS m/z (ESI): 283[M+1]

$^1$H NMR (400 MHz, DMSO-d$_6$) δ 9.15 (brs, 1H), 9.06 (brs, 1H), 8.29 (s, 1H), 7.43 (s, 1H), 7.38 (d, J=8.4 Hz, 1H), 7.24-7.20 (m, 2H), 7.00 (d, J=8 Hz, 1H), 6.90-6.84 (m, 2H), 6.61 (dd, J$_1$=8 Hz, J$_2$=2.4 Hz, 1H), 3.74 (s, 3H).

Example 7 methyl 3-(3-(imidazo[1,5-a]pyridin-5-yl)ureido) benzoate

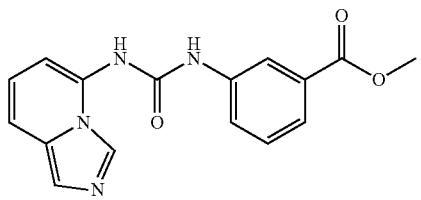 [SMILES: COC(=O)c1cccc(NC(=O)Nc2cccc3cncn23)c1]

Example 7 was synthesized according to the procedure of Example 1, but in the sixth step, methyl 3-isocyanatobenzoate was used instead of 4-isocyanatobenzonitrile.

MS m/z (ESI): 311[M+1]

$^1$H NMR (400 MHz, DMSO-d$_6$) δ 9.42 (brs, 1H), 9.14 (brs, 1H), 8.30 (s, 1H), 8.24 (s, 1H), 7.69 (d, J=8.4 Hz, 1H), 7.62 (d, J=8 Hz, 1H), 7.48 (d, J=7.9 Hz, 1H), 7.45-7.44 (m, 1H), 7.42-7.39 (m, 1H), 6.87-6.85 (m, 2H), 3.86 (s, 3H).

Example 8

3-(3-(imidazo[1,5-a]pyridin-5-yl)ureido)benzoic Acid

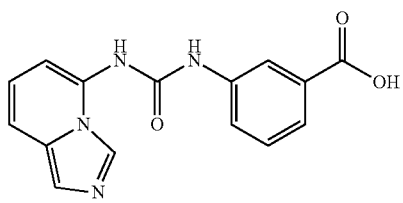 [SMILES: O=C(Nc1cccc(C(=O)O)c1)Nc1cccc2cncn12]

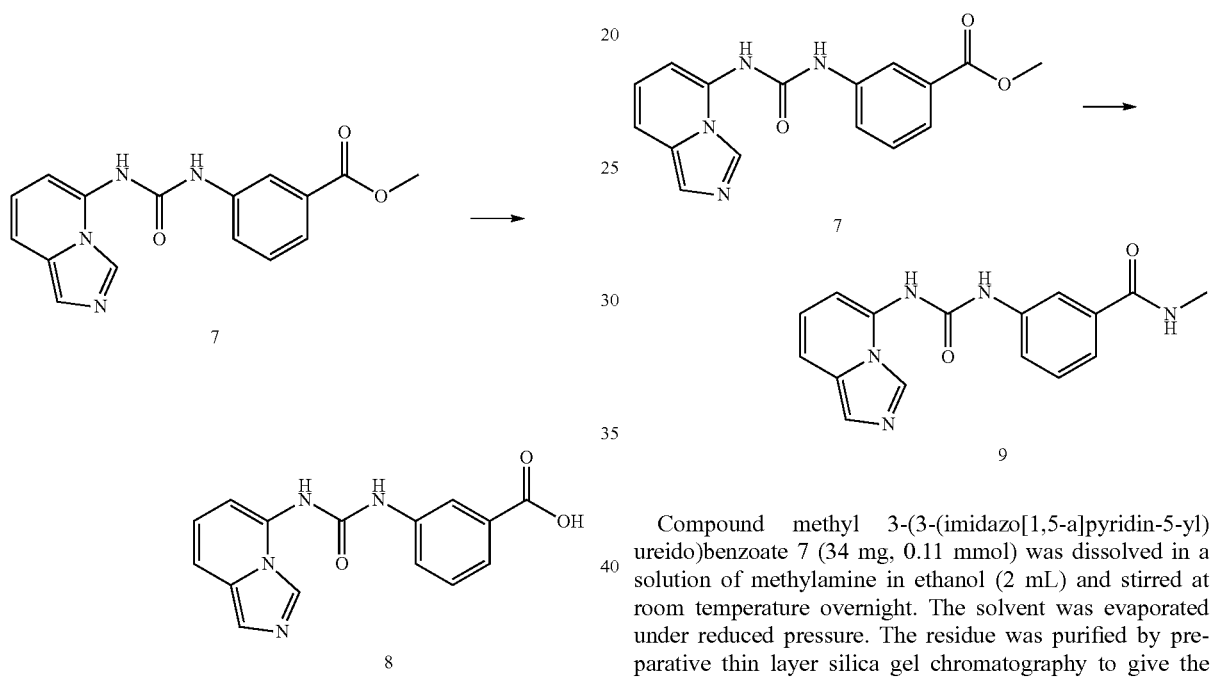

Compound methyl 3-(3-(imidazo[1,5-a]pyridin-5-yl)ureido)benzoate 7 (104 mg, 0.335 mmol) was dissolved in MeOH/THF/H$_2$O (5/5/5 mL), added with lithium hydroxide dihydrate (42 mg, 1.0 mmol) and stirred at room temperature overnight. The mixture was added with hydrochloride solution (2 N, 10 mL) and extracted with dichloromethane (50 mL×8). The organic phase was combined, dried over anhydrous sodium sulfate, filtered and concentrated under reduced pressure to remove the solvent. The residue was purified by high performance liquid chromatography to give the target product 3-(3-(imidazo[1,5-a]pyridin-5-yl)ureido)benzoic acid 8 (90 mg, grey solid). Yield: 91%.

MS m/z (ESI): 297[M+1]

$^1$H NMR (400 MHz, DMSO-d$_6$) δ 12.96 (brs, 1H), 9.40 (brs, 1H), 9.17 (brs, 1H), 8.30 (s, 1H), 8.17 (s, 1H), 7.69 (d, J=8 Hz, 1H), 7.60 (d, J=7.7 Hz, 1H), 7.46-7.39 (m, 3H), 6.89-6.86 (m, 2H).

Example 9

3-(3-(imidazo[1,5-a]pyridin-5-yl)ureido)-N-methyl-benzamide

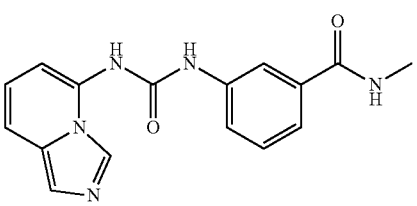 [SMILES: CNC(=O)c1cccc(NC(=O)Nc2cccc3cncn23)c1]

Compound methyl 3-(3-(imidazo[1,5-a]pyridin-5-yl)ureido)benzoate 7 (34 mg, 0.11 mmol) was dissolved in a solution of methylamine in ethanol (2 mL) and stirred at room temperature overnight. The solvent was evaporated under reduced pressure. The residue was purified by preparative thin layer silica gel chromatography to give the target product 3-(3-(imidazo[1,5-a]pyridin-5-yl)ureido)-N-methylbenzamide 9 (10 mg, grey solid). Yield: 30%.

MS m/z (ESI): 310[M+1]

$^1$H NMR (400 MHz, DMSO-d$_6$) δ 9.32 (brs, 1H), 9.14 (brs, 1H), 8.41 (brs, 1H), 8.35 (s, 1H), 7.94 (s, 1H), 7.64 (d, J=7.6 Hz, 1H), 7.46-7.39 (m, 4H), 6.90-6.87 (m, 2H), 2.78 (d, J=4.4 Hz, 3H).

Example 10

1-cyclohexyl-3-(imidazo[1,5-a]pyridin-5-yl)urea

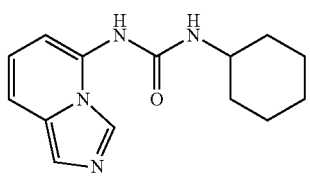 [SMILES: O=C(Nc1cccc2cncn12)NC1CCCCC1]

Example 10 was synthesized according to the procedure of Example 1, but in the sixth step, isocyanatocyclohexane was used instead of 4-isocyanatobenzonitrile.

MS m/z (ESI): 259[M+1]

$^1$H NMR (400 MHz, DMSO-d$_6$) δ 8.72 (brs, 1H), 8.23 (brs, 1H), 7.39 (brs, 1H), 7.27 (d, J=8.8 Hz, 1H), 6.90 (d, J=6.8 Hz, 1H), 6.82 (t, J=8.0 Hz, 1H), 6.64 (d, J=7.2 Hz, 1H), 3.51 (brs, 1H), 1.87-1.84 (m, 2H), 1.70-1.67 (m, 2H), 1.58-1.54 (m, 1H), 1.35-1.20 (m, 5H).

Example 11

2-(4-cyanophenyl)-N-(imidazo[1,5-a]pyridin-5-yl)acetamide

Example 12

N-(4-cyanophenyl)-2-(imidazo[1,5-a]pyridin-5-yl)acetamide

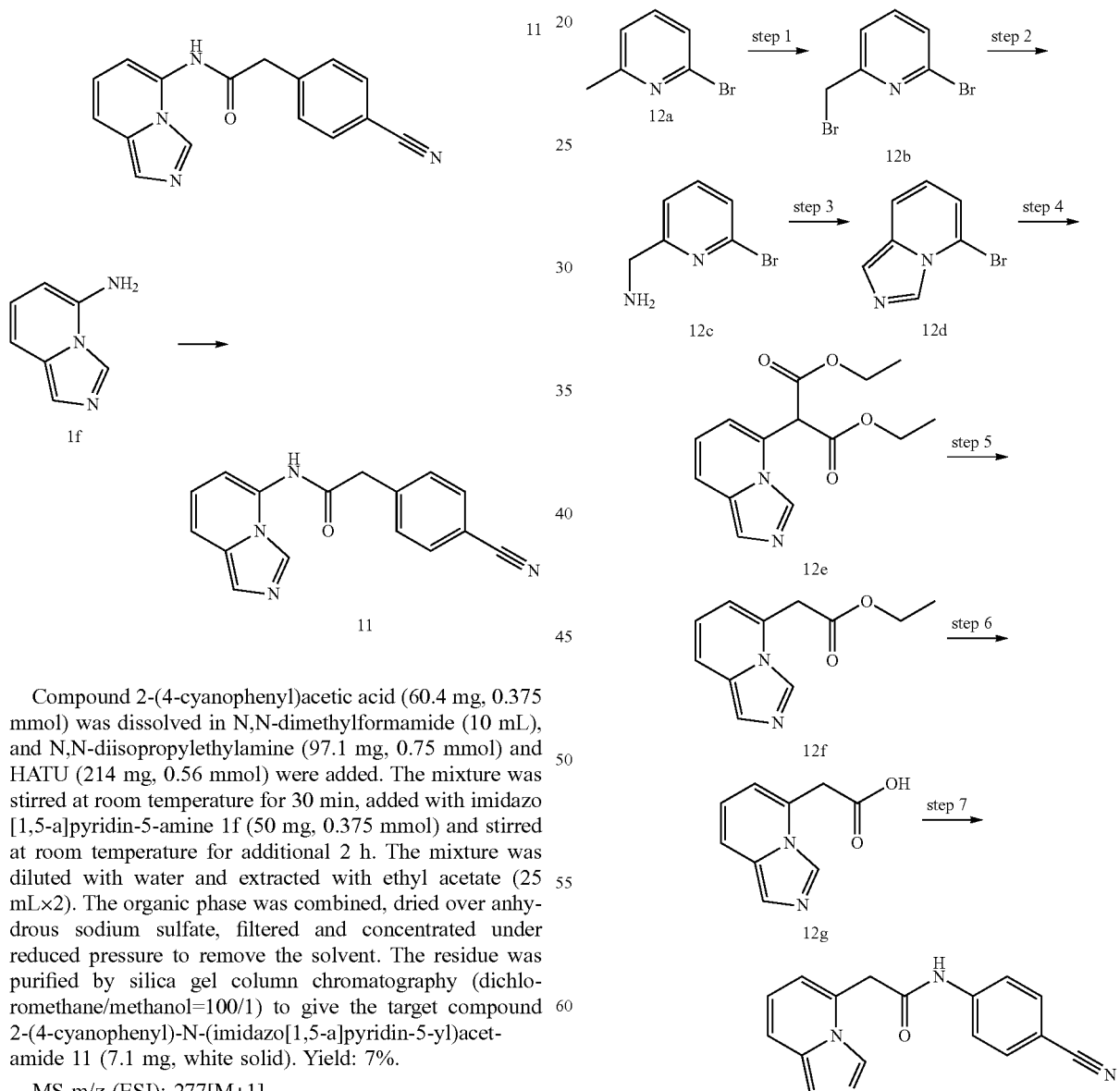

Compound 2-(4-cyanophenyl)acetic acid (60.4 mg, 0.375 mmol) was dissolved in N,N-dimethylformamide (10 mL), and N,N-diisopropylethylamine (97.1 mg, 0.75 mmol) and HATU (214 mg, 0.56 mmol) were added. The mixture was stirred at room temperature for 30 min, added with imidazo[1,5-a]pyridin-5-amine 1f (50 mg, 0.375 mmol) and stirred at room temperature for additional 2 h. The mixture was diluted with water and extracted with ethyl acetate (25 mL×2). The organic phase was combined, dried over anhydrous sodium sulfate, filtered and concentrated under reduced pressure to remove the solvent. The residue was purified by silica gel column chromatography (dichloromethane/methanol=100/1) to give the target compound 2-(4-cyanophenyl)-N-(imidazo[1,5-a]pyridin-5-yl)acetamide 11 (7.1 mg, white solid). Yield: 7%.

MS m/z (ESI): 277[M+1]

$^1$H NMR (400 MHz, DMSO-d$_6$) δ 10.63 (brs, 1H), 8.27 (s, 1H), 7.85 (d, J=7.2 Hz, 2H), 7.60 (d, J=7.6 Hz, 2H), 7.47-7.43 (m, 2H), 6.85-6.74 (m, 2H), 3.97 (s, 2H).

Step 1

Preparation of 2-bromo-6-(bromomethyl)pyridine

Compound 2-bromo-6-methylpyridine 12a (25 g, 145 mmol) was dissolved in THF (250 mL), added with N-bromosuccinimide (28.5 g, 160 mmol) and azodiisobutyronitrile (2.3 g, 14.5 mmol) and the mixture was stirred and refluxed under $N_2$ protection for 6 h. After cooled to room temperature, the mixture was filtered. The filtrate was washed with brine. The organic phase was dried over anhydrous sodium sulfate, filtered and concentrated under reduced pressure to remove the solvent to give the target compound 2-bromo-6-(bromomethyl)pyridine 12b (30 g, brown semi-solid). Yield: 83%.

MS m/z (ESI): 252[M+1]

Step 2

Preparation of (6-bromopyridin-2-yl)methanamine

2-Bromo-6-(bromomethyl)pyridine 12b (30 g, 120 mmol) was used as the starting material and the method for the synthesis of 1d in Example 1 was used to generate the titled product (6-bromopyridin-2-yl)methanamine 12c (7.6 g, brown liquid). Yield: 34%.

MS m/z (ESI): 187/189[M+1]

Step 3

Preparation of 5-bromoimidazo[1,5-a]pyridine (6-Bromopyridin-2-yl)methanamine 12c (7.6 g, 41 mmol) was used as the starting material and the method for the synthesis of 1e in Example 1 was used to generate the titled product 5-bromoimidazo[1,5-a]pyridine 12d (2.7 g, brown oil). Yield: 34%.

MS m/z (ESI): 197/199[M+1]

Step 4

Preparation of diethyl 2-(imidazo[1,5-a]pyridin-5-yl)malonate

Diethyl malonate (4.2 g, 26 mmol) was dissolved in dioxane (20 mL), added with sodium hydride (60%, 0.94 g, 24 mmol), heated to 70° C. and stirred for 1 h. The mixture was added with 5-bromoimidazo[1,5-a]pyridine 12d (1.7 g, 8.7 mmol) and cuprous bromide (0.43 g, 3 mmol), and stirred under reflux overnight. The mixture was cooled to room temperature and the solvent was evaporated under reduced pressure. The residue was added with saturated ammonium chloride solution and extracted with ethyl acetate (50 mL×3). The organic phase was combined, dried over anhydrous sodium sulfate, filtered and concentrated under reduced pressure to remove the solvent. The residue was purified by silica gel column chromatography (petroleum ether/ethyl acetate=10/1 to 1/1) to give the target compound diethyl 2-(imidazo[1,5-a]pyridin-5-yl)malonate 12e (772 mg, brown oil). Yield: 33%.

MS m/z (ESI): 277[M+1]

Step 5

Preparation of ethyl 2-(imidazo[1,5-a]pyridin-5-yl)acetate

Diethyl 2-(imidazo[1,5-a]pyridin-5-yl)malonate 12e (772 mg, 2.6 mmol) was dissolved in DMSO (7 mL), added with water (51 mg, 2.8 mmol) and lithium chloride (237 mg, 5.6 mmol), heated to 100° C. and stirred for 16 h. The mixture was cooled to room temperature, diluted with water (150 mL) and extracted with ethyl acetate (50 mL×3). The organic phase was combined, dried over anhydrous sodium sulfate, filtered and concentrated under reduced pressure to remove the solvent. The residue was purified by silica gel column chromatography (petroleum ether/ethyl acetate=10/1 to 1/1) to give the target compound ethyl 2-(imidazo[1,5-a]pyridin-5-yl)acetate 12f (350 mg, brown oil). Yield: 61%.

MS m/z (ESI): 205[M+1]

Step 6

Preparation of 2-(imidazo[1,5-a]pyridin-5-yl)acetic Acid

Ethyl 2-(imidazo[1,5-a]pyridin-5-yl)acetate 12f (200 mg, 0.98 mmol) was dissolved in MeOH (10 mL) and added with a solution of sodium hydroxide (2 M, 1 mL). The reaction mixture was stirred at room temperature for 1 h. The solvent MeOH was removed under reduced pressure. The residue was acidified with hydrochloride solution (1 N) to pH=6 and filtered. The filter cake was dried to give the target product 2-(imidazo[1,5-a]pyridin-5-yl)acetic acid 12 g (130 mg, white solid). Yield: 75%.

Step 7

Preparation of N-(4-cyanophenyl)-2-(imidazo[1,5-a]pyridin-5-yl)acetamide 2-(Imidazo[1,5-a]pyridin-5-yl)acetic acid 12 g (80 mg, 0.45 mmol) and 4-aminobenzonitrile (53 mg, 0.45 mmol) were used as the starting materials and the method for the synthesis of 11 in Example 11 was used to generate the titled product N-(4-cyanophenyl)-2-(imidazo[1,5-a]pyridin-5-yl)acetamide 12 (20 mg, green solid). Yield: 16%.

MS m/z (ESI): 277[M+1]

$^1$H NMR (400 MHz, DMSO-$d_6$) δ 10.83 (s, 1H), 8.36 (s, 1H), 7.81-7.76 (m, 4H), 7.55 (d, J=8.8 Hz, 1H), 7.44 (s, 1H), 6.81 (dd, $J_1$=8.8 Hz, $J_2$=6 Hz, 1H), 6.65 (d, J=6 Hz, 1H), 4.18 (s, 2H).

Example 13

1-(4-cyanophenyl)-3-(8-fluoroimidazo[1,5-a]pyridin-5-yl)urea

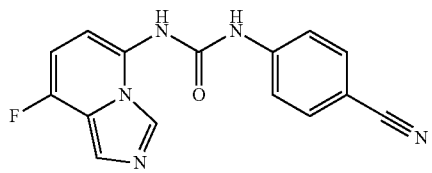 [SMILES: N#Cc1ccc(NC(=O)Nc2ccc(F)c3cncn23)cc1]

13

Example 13 was synthesized according to the procedure of Example 1 using 5-fluoro-6-methylpyridin-2-amine as the starting material.

MS m/z (ESI): 296[M+1]

$^1$H NMR (400 MHz, DMSO-$d_6$) δ 9.70 (brs, 1H), 9.23 (brs, 1H), 8.41 (d, J=2.8 Hz, 1H), 7.76 (d, J=8.8 Hz, 2H), 7.67 (d, J=8.8 Hz, 2H), 7.60 (s, 1H), 6.74 (d, J=7.6 Hz, 2H).

Example 14

1-(4-cyanophenyl)-3-(6-fluoroimidazo[1,5-a]pyridin-5-yl)urea

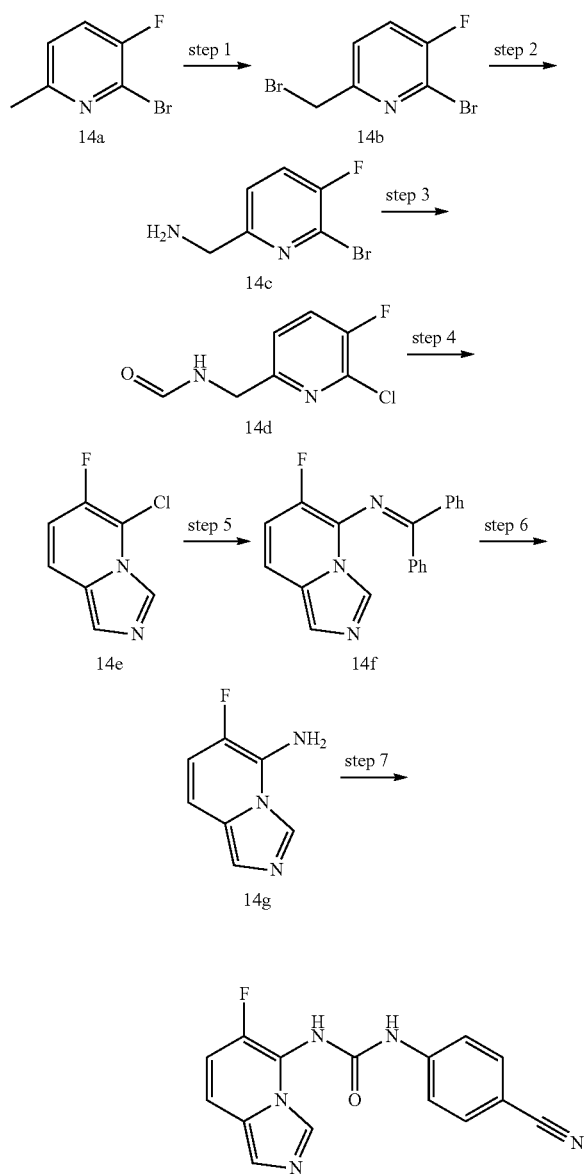

Step 1

Preparation of 2-bromo-6-(bromomethyl)-3-fluoropyridine

2-Bromo-3-fluoro-6-methylpyridine 14a (1.5 g, 7.94 mmol) was used as the starting material and the method for the synthesis of 1c in Example 1 was used to generate the titled product 2-bromo-6-(bromomethyl)-3-fluoropyridine 14b (2.3 g, brown oil). Yield: 100%.

MS m/z (ESI): 270[M+1]

Step 2

Preparation of (6-bromo-5-fluoropyridin-2-yl)methanamine

2-Bromo-6-(bromomethyl)-3-fluoropyridine 14b (2.3 g, crude, 7.94 mmol) was used as the starting material and the method for the synthesis of 1d in Example 1 was used to generate the titled product (6-bromo-5-fluoropyridin-2-yl)methanamine 14c (hydrochloride salt, 1.5 g, white solid). Yield for two steps: 78%.

MS m/z (ESI): 205/207[M+1]

Step 3

Preparation of N-((6-chloro-5-fluoropyridin-2-yl)methyl)formamide

Acetic anhydride (21 mL) and formic acid (9 mL) were mixed, heat to 60° C. and stirred for half an hour. To the above mixture was added (6-bromo-5-fluoropyridin-2-yl)methanamine 14c (hydrochloride salt, 1.5 g, 6.2 mmol) and the resulting mixture was heated to 75° C. and stirred overnight. The reaction mixture was cooled to room temperature and concentrated under reduced pressure to remove the solvent. The residue was added with water (100 mL), basified with a solution of potassium carbonate and extracted with dichloromethane (50 mL×2). The organic phase was combined, dried over anhydrous sodium sulfate, filtered and concentrated under reduced pressure to give the target compound N-((6-chloro-5-fluoropyridin-2-yl)methyl)formamide 14d (600 mg, black solid). Yield: 51%.

MS m/z (ESI): 189/191[M+1]

Step 4

Preparation of 5-chloro-6-fluoroimidazo[1,5-a]pyridine

Compound N-((6-chloro-5-fluoropyridin-2-yl)methyl)formamide 14d (600 mg, 3.18 mmol) was dissolved in toluene (10 mL) and phosphoryl trichloride (1.9 g, 12.9 mmol) was added. The reaction mixture was heated to 100° C. and stirred for 2 h. The reaction mixture was cooled to room temperature and concentrated under reduced pressure to remove the solvent. The residue was diluted with water (100 mL), basified with a solution of potassium carbonate and extracted with dichloromethane (50 mL×2). The organic phase was combined, dried over anhydrous sodium sulfate, filtered and concentrated under reduced pressure to remove the solvent. The residue was purified by silica gel column chromatography (petroleum ether/ethyl acetate=15/1 to 1/1) to give the target compound 5-chloro-6-fluoroimidazo[1,5-a]pyridine 14e (440 mg, white solid). Yield: 81%.

MS m/z (ESI): 171/173[M+1]

Step 5

Preparation of N-(6-fluoroimidazo[1,5-a]pyridin-5-yl)-1,1-diphenylmethanimine

A mixture of 5-chloro-6-fluoroimidazo[1,5-a]pyridine 14e (560 mg, 3.3 mmol), diphenylmethylamine (706 mg, 3.9 mmol), Pd$_2$(dba)$_3$ (119 mg, 0.13 mmol), BINAP (162 mg 0.26 mmol), sodium tert-butoxide (500 mg, 5.2 mmol) and toluene was heated to 100° C. and stirred for 6 h under argon protection. The reaction mixture was cooled to room temperature, diluted with water (100 mL), and extracted with ethyl acetate (50 mL×2). The organic phase was combined, dried over anhydrous sodium sulfate, filtered and concentrated under reduced pressure to remove the solvent. The residue was purified by silica gel column chromatography (petroleum ether/ethyl acetate=20/1 to 1/1) to give the target compound N-(6-fluoroimidazo[1,5-a]pyridin-5-yl)-1,1-diphenylmethanimine 14f (190 mg, red-brown solid). Yield: 18%.

MS m/z (ESI): 316[M+1]

Step 6

Preparation of 6-fluoroimidazo[1,5-a]pyridin-5-amine

To a solution of N-(6-fluoroimidazo[1,5-a]pyridin-5-yl)-1,1-diphenylmethanimine 14f (240 mg, 0.76 mmol) in THF (3 mL) was added hydrochloride solution (2 N, 3 mL) and the mixture was stirred at room temperature for 2 h. The reaction was quenched with a solution of sodium bicarbonate (50 mL) and extracted with ethyl acetate (50 mL×3). The organic phase was combined, dried over anhydrous sodium sulfate, filtered and concentrated under reduced pressure to remove the solvent. The residue was purified by silica gel column chromatography (petroleum ether/ethyl acetate=5/1 to 0/1) to give the target compound 6-fluoroimidazo[1,5-a]pyridin-5-amine 14 g (70 mg, dark green solid). Yield: 61%.

MS m/z (ESI): 152[M+1]

Step 7

Preparation of 1-(4-cyanophenyl)-3-(6-fluoroimidazo[1,5-a]pyridin-5-yl)urea

A mixture of 6-fluoroimidazo[1,5-a]pyridin-5-amine 14 g (70 mg, 0.46 mmol), 4-isocyanatobenzonitrile (200 mg, 1.4 mmol) and THF (10 mL) was heated to 70° C. and stirred for 1 h. The reaction mixture was cooled to room temperature and concentrated under reduced pressure to remove the solvent. The residue was purified by silica gel column chromatography (petroleum ether/ethyl acetate=1/1 to 0/1) to give the target compound 1-(4-cyanophenyl)-3-(6-fluoroimidazo[1,5-a]pyridin-5-yl)urea 14 (22 mg, white solid). Yield: 16%.

MS m/z (ESI): 296[M+1]

$^1$H NMR (400 MHz, DMSO-d$_6$) δ 9.88 (brs, 1H), 8.96 (brs, 1H), 8.30 (s, 1H), 7.76 (d, J=8.7 Hz, 2H), 7.66 (d, J=8.6 Hz, 2H), 7.65-7.63 (m, 1H), 7.54 (s, 1H), 7.01-6.97 (m, 1H).

Example 15

1-(4-cyanophenyl)-3-(6-methoxyimidazo[1,5-a]pyridin-5-yl)urea

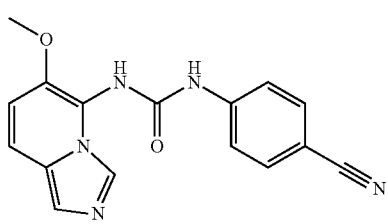 [SMILES: COc1ccc2cncn2c1NC(=O)Nc1ccc(C#N)cc1]

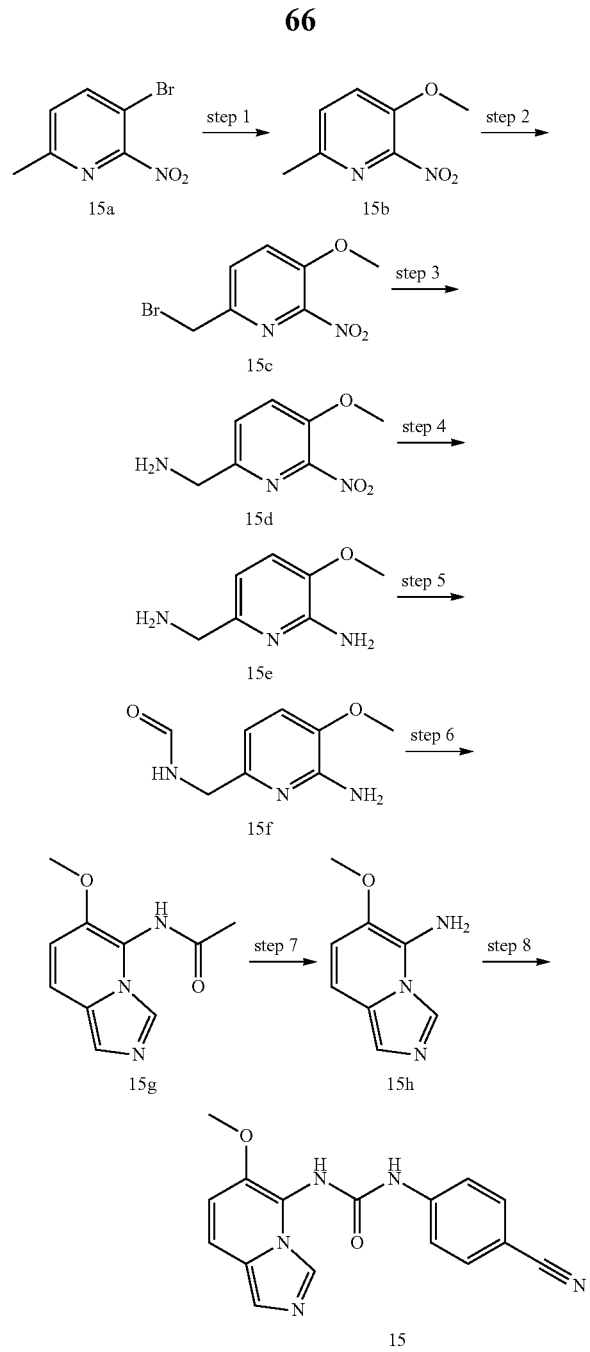

Step 1

Preparation of 3-methoxy-6-methyl-2-nitropyridine

To a solution of 6-methyl-2-nitropyridin-3-ol 15a (5.0 g, 32.46 mmol) and iodomethane (4.6 g, 32.46 mmol) in DMSO (50 mL) was added K$_2$CO$_3$ (8.96 g, 64.92 mmol) and the mixture was stirred at room temperature overnight. The mixture was diluted with water (500 mL) and filtered. The filter cake was washed with water (20 mL×2) and dried under vacuum to give the target product 3-methoxy-6-methyl-2-nitropyridine 15b (2.37 g, white solid). Yield: 43%.

MS m/z (ESI): 169[M+1]

Step 2

Preparation of 6-(bromomethyl)-3-methoxy-2-nitropyridine (3-Methoxy-6-methyl-2-nitropyridine 15b (2.37 g, 14.1 mmol) was used as the starting material and the method for the synthesis of 1c in Example 1 was used to generate the titled product 6-(bromomethyl)-3-methoxy-2-nitropyridine 15c (3 g, crude product). Yield: 86%.

MS m/z (ESI): 247/249[M+1]

Step 3

Preparation of (5-methoxy-6-nitropyridin-2-yl)methanamine 6-(bromomethyl)-3-methoxy-2-nitropyridine 15c (3 g, 12.2 mmol) was used as the starting material and the method for the synthesis of 1d in Example 1 was used to generate the titled product (5-methoxy-6-nitropyridin-2-yl)methanamine 15d (3 g, crude product, yellow solid). Yield: 100%.

MS m/z (ESI): 184[M+1]

Step 4

Preparation of 6-(aminomethyl)-3-methoxypyridin-2-amine

A mixture of (5-methoxy-6-nitropyridin-2-yl)methanamine 15d (1.5 g, crude product, 6.1 mmol), Raney-Ni and MeOH (50 mL) was stirred at room temperature under hydrogen of 1 atm pressure for 6 h. The mixture was filtered, and the filter cake was washed with MeOH (10 mL×4). The filtrate was concentrated under reduced pressure to give the titled product 6-(aminomethyl)-3-methoxypyridin-2-amine 15e (1.4 g, crude product, yellow solid). Yield: 100%.

MS m/z (ESI): 154[M+1]

Step 5

Preparation of N-((6-amino-5-methoxypyridin-2-yl)methyl)formamide 6-(Aminomethyl)-3-methoxypyridin-2-amine 15e (1.4 g, crude product, 6.1 mmol) was used as the starting material and the method for the synthesis of 14d in Example 14 was used to generate the titled product N-((6-amino-5-methoxypyridin-2-yl)methyl)formamide 15f (500 mg). Yield for three steps: 45%.

MS m/z (ESI): 182[M+1]

Step 6

Preparation of N-(6-methoxyimidazo[1,5-a]pyridin-5-yl)acetamide

A mixture of N-((6-amino-5-methoxypyridin-2-yl)methyl)formamide 15f (400 mg, 2.2 mmol) and acetic anhydride (3 mL) was heated to 80° C. and stirred for 1 h. The reaction mixture was cooled to room temperature, poured into a solution of sodium bicarbonate (50 mL) and extracted with ethyl acetate (50 mL×3). The organic phase was combined, dried over anhydrous sodium sulfate, filtered and concentrated under reduced pressure to give the target compound N-(6-methoxyimidazo[1,5-a]pyridin-5-yl)acetamide 15 g (200 mg, dark green solid). Yield: 44%.

MS m/z (ESI): 206[M+1]

Step 7

Preparation of 6-methoxyimidazo[1,5-a]pyridin-5-amine

A mixture of N-(6-methoxyimidazo[1,5-a]pyridin-5-yl)acetamide 15 g (150 mg, 0.73 mmol), hydrazine hydrate (3 mL) and MeOH (3 mL) was heated to 80° C. and stirred for 3 h. The reaction mixture was cooled to room temperature and concentrated under reduced pressure to remove the solvent. The residue was purified by silica gel column chromatography to give the target compound 6-methoxyimidazo[1,5-a]pyridin-5-amine 15h (70 mg, dark green solid). Yield: 59%.

MS m/z (ESI): 164[M+1]

Step 8

Preparation of 1-(4-cyanophenyl)-3-(6-methoxyimidazo[1,5-a]pyridin-5-yl)urea 6-methoxyimidazo[1,5-a]pyridin-5-amine 15h (60 mg, 0.37 mmol) was used as the starting material and the method for the synthesis of 1 in Example 1 was used to generate the titled product 1-(4-cyanophenyl)-3-(6-methoxyimidazo[1,5-a]pyridin-5-yl)urea 15 (3 mg, white solid). Yield: 3%.

MS m/z (ESI): 308[M+1]

$^1$H NMR (400 MHz, CD$_3$OD) δ 8.17 (s, 1H), 7.68-7.64 (m, 4H), 7.58 (d, J=9.8 Hz, 1H), 7.46 (s, 1H), 7.04 (d, J=9.8 Hz, 1H), 3.91 (s, 3H).

Example 16

1-(4-cyanophenyl)-3-(6-ethoxyimidazo[1,5-a]pyridin-5-yl)urea

16

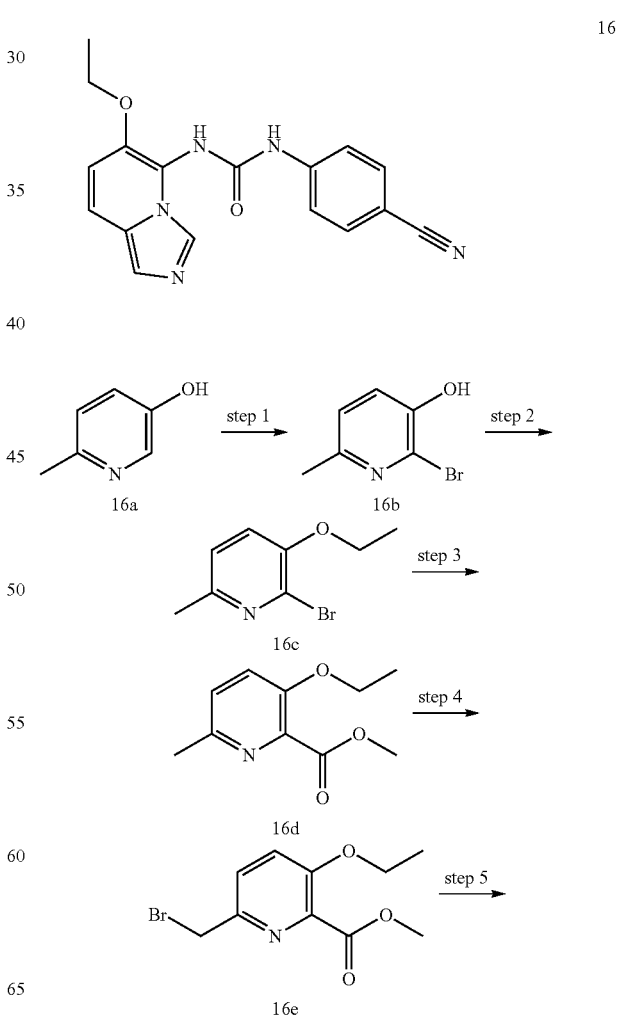

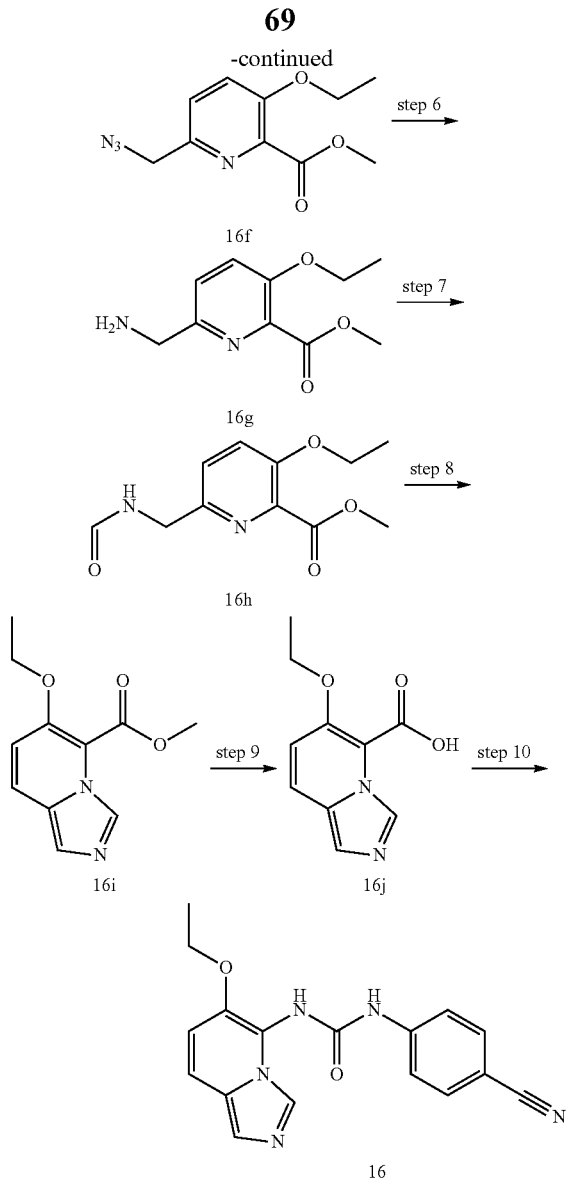

Step 1

Preparation of 2-bromo-6-methylpyridin-3-ol

Compound 6-methylpyridin-3-ol 16a (10.9 g, 100 mmol) was dissolved in pyridine (400 mL). The solution was cooled to 0° C. and added slowly with bromine (16 g, 100 mmol). The obtained mixture was stirred at room temperature overnight. The mixture was filtered, and the filtrate was concentrated under reduced pressure. The residue was added with a solution of sodium bicarbonate (200 mL) and extracted with ethyl acetate (200 mL×3). The organic phase was combined, dried over anhydrous sodium sulfate, filtered and concentrated under reduced pressure to remove the solvent. The residue was washed with petroleum ether/ethyl acetate (3/1, 50 mL) and filtered. The filter cake was dried in air. The filtrate was concentrated under reduced pressure and purified by silica gel column chromatography (petroleum ether/ethyl acetate=6/1 to 2/1). The obtained product was combined with the above filter cake to give the target compound 2-bromo-6-methylpyridin-3-ol 16b (12.2 g, light yellow solid). Yield: 65%.

$^1$H NMR (400 MHz, DMSO-$d_6$) δ 10.42 (brs, 1H), 7.18 (d, J=8 Hz, 1H), 7.09 (d, J=8 Hz, 1H), 2.34 (s, 3H).

Step 2

Preparation of 2-bromo-3-ethoxy-6-methylpyridine

To a mixture of 2-bromo-6-methylpyridin-3-ol 16b (9.4 g, 50 mmol), K$_2$CO$_3$ (13.8 g, 100 mmol) and acetonitrile (100 mL) was added iodoethane (9.36 g, 60 mmol) and the mixture was stirred under 60 OC for 4 h. The mixture was cooled to room temperature, filtered and the filtrate was concentrated under reduced pressure. The residue was added with water (200 mL) and extracted with ethyl acetate (200 mL×3). The organic phase was combined, dried over anhydrous sodium sulfate, filtered and concentrated under reduced pressure to remove the solvent. The residue was purified by silica gel column chromatography (petroleum ether/ethyl acetate=6/1) to give the target product 2-bromo-3-ethoxy-6-methylpyridine 16c (10.1 g, white solid). Yield: 94%.

MS m/z (ESI): 216/218[M+1]

Step 3

Preparation of methyl 3-ethoxy-6-methylpicolinate

A mixture of 2-bromo-3-ethoxy-6-methylpyridine 16c (2.16 g, 10 mmol), Pd(dppf)Cl$_2$·CH$_2$Cl$_2$ (0.817 g, 1.0 mmol), Et$_3$N (40 mL) and MeOH (20 mL) was bubbled with CO and then heated to 105° C. in a sealed tube for 16 h. The mixture was cooled to room temperature and concentrated under reduced pressure. The residue was added with water (100 mL) and extracted with ethyl acetate (100 mL×3). The organic phase was combined, dried over anhydrous sodium sulfate, filtered and concentrated under reduced pressure to remove the solvent. The residue was purified by silica gel column chromatography (petroleum ether/ethyl acetate=4/1) to give the target product methyl 3-ethoxy-6-methylpicolinate 16d (1.26 g, brown oil). Yield: 65%.

MS m/z (ESI): 196[M+1]

Step 4

Preparation of methyl 6-(bromomethyl)-3-ethoxypicolinate

Methyl 3-ethoxy-6-methylpicolinate 16d (1.26 g, 6.5 mmol) was used as the starting material and the method for the synthesis of 1c in Example 1 was used to generate the titled product methyl 6-(bromomethyl)-3-ethoxypicolinate 16e (0.82 g, light yellow solid). Yield: 46%.

MS m/z (ESI): 274/276[M+1]

Step 5

Preparation of methyl 6-(azidomethyl)-3-ethoxypicolinate

Compound methyl 6-(bromomethyl)-3-ethoxypicolinate 16e (0.82 g, 3 mmol) was dissolved in acetonitrile (30 mL), added with sodium azide (0.29 g, 0.45 mmol) and stirred under reflux overnight. The mixture was cooled to room temperature and concentrated under reduced pressure. The residue was added with water (40 mL) and extracted with ethyl acetate (40 mL×3). The organic phase was combined, dried over anhydrous sodium sulfate, filtered and concentrated under reduced pressure to remove the solvent. The residue was purified by silica gel column chromatography (petroleum ether/ethyl acetate=4/1) to give the target product methyl 6-(azidomethyl)-3-ethoxypicolinate 16f (0.6 g, light yellow solid). Yield: 85%.

MS m/z (ESI): 237[M+1]

Step 6

Preparation of methyl 6-(aminomethyl)-3-ethoxypicolinate

A mixture of methyl 6-(azidomethyl)-3-ethoxypicolinate 16f (0.6 g, 2.55 mmol), triphenylphosphine (1.34 g, 5.1 mmol), THF (20 mL) and H$_2$O (3 mL) was heated to 60° C. and stirred for 3 h under nitrogen protection. The mixture was cooled to room temperature and concentrated under reduced pressure. The residue was purified by silica gel column chromatography (dichloromethane/methanol=100/1 to 20/1) to give the target product methyl 6-(aminomethyl)-3-ethoxypicolinate 16 g (0.18 g, light brown oil). Yield: 34%.

MS m/z (ESI): 211[M+1]

Step 7

Preparation of methyl 3-ethoxy-6-(formamidomethyl)picolinate

Compound methyl 6-(aminomethyl)-3-ethoxypicolinate 16 g (0.18 g, 0.86 mmol) was dissolved in dichloromethane (10 mL), added with formic acid (79 mg, 1.7 mmol), EDCI (0.25 g, 1.3 mmol) and Et$_3$N (0.26 g, 2.6 mmol) and stirred at room temperature for 1 h. The mixture was diluted with dichloromethane (10 mL) and washed with water (20 mL). The organic phase was dried over anhydrous sodium sulfate, filtered and concentrated under reduced pressure to give the target product methyl 3-ethoxy-6-(formamidomethyl)picolinate 16h (0.19 g, colorless sticky oil). Yield: 93%.

MS m/z (ESI): 239[M+1]

Step 8

Preparation of methyl 6-ethoxyimidazo[1,5-a]pyridine-5-carboxylate

Compound methyl 3-ethoxy-6-(formamidomethyl)picolinate 16h (0.19 g, 0.8 mmol) was dissolved in dichloromethane (5 mL), added with trifluoroacetic anhydride (0.5 mL) and stirred at room temperature overnight. The solvent was removed under reduced pressure. The residue was dissolved in dichloromethane (20 mL) and washed with a solution of sodium bicarbonate (20 mL). The aqueous phase was extracted with dichloromethane (20 mL). The organic phase was combined, dried over anhydrous sodium sulfate, filtered and concentrated under reduced pressure to remove the solvent. The residue was purified by preparative thin layer silica gel chromatography (dichloromethane/methanol=15/1) to give the target compound methyl 6-ethoxyimidazo[1,5-a]pyridine-5-carboxylate 16i (0.16 g, yellow solid). Yield: 91%.

MS m/z (ESI): 221[M+1]

Step 9

Preparation of 6-ethoxyimidazo[1,5-a]pyridine-5-carboxylic acid

To a mixture of methyl 6-ethoxyimidazo[1,5-a]pyridine-5-carboxylate 16i (40 mg, 0.18 mmol) and MeOH (5 mL) was added a solution of NaOH (15%, 2 mL) and the mixture was stirred at room temperature for 1 h. The organic solvent was removed under reduced pressure. The residue was diluted with water (10 mL), acidified with hydrochloride solution (3 N) to pH=4 and extracted with dichloromethane/methanol (20/1, 20 mL×3). The organic phase was combined, dried over anhydrous sodium sulfate, filtered and concentrated under reduced pressure to give the target product 6-ethoxyimidazo[1,5-a]pyridine-5-carboxylic acid 16j (14 mg, light brown solid). Yield: 38%.

MS m/z (ESI): 207[M+1]

Step 10

Preparation of 1-(4-cyanophenyl)-3-(6-ethoxyimidazo[1,5-a]pyridin-5-yl)urea

To a mixture of 6-ethoxyimidazo[1,5-a]pyridine-5-carboxylic acid 16j (14 mg, 0.068 mmol), Et$_3$N (9 mg, 0.088 mmol) and toluene (2 mL) was added diphenyl azidophosphate (22 mg, 0.082 mmol), heated to 100° C. and stirred for 20 min under nitrogen protection. 4-Aminobenzonitrile (12 mg, 0.1 mmol) was added and the reaction mixture was stirred under 100° C. for 30 min. The reaction mixture was cooled to room temperature and concentrated under reduced pressure. The residue was dissolved in ethyl acetate (20 mL) and washed with water (20 mL). The organic phase was dried over anhydrous sodium sulfate, filtered and concentrated under reduced pressure to remove the solvent. The residue was purified by preparative thin layer silica gel chromatography (dichloromethane/methanol=12/1) to give the target compound 1-(4-cyanophenyl)-3-(6-ethoxyimidazo[1,5-a]pyridin-5-yl)urea 16 (6 mg, grey solid). Yield: 27%.

MS m/z (ESI): 322[M+1]

$^1$H NMR (400 MHz, DMSO-d$_6$) δ 9.70 (brs, 1H), 8.67 (s, 1H), 8.17 (s, 1H), 7.75 (d, J=8.7 Hz, 2H), 7.67 (d, J=8.7 Hz, 2H), 7.59 (d, J=9.7 Hz, 1H), 7.46 (s, 1H), 7.01 (d, J=9.8 Hz, 1H), 4.10 (q, J=7 Hz, 2H), 1.25 (t, J=7 Hz, 3H).

Example 17

1-(4-cyanophenyl)-3-(6-phenylimidazo[1,5-a]pyridin-5-yl)urea

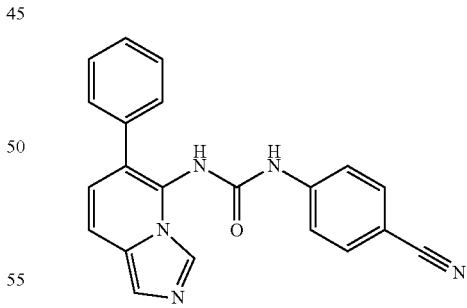

17

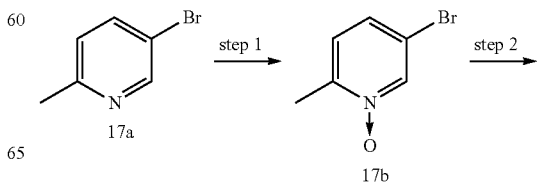

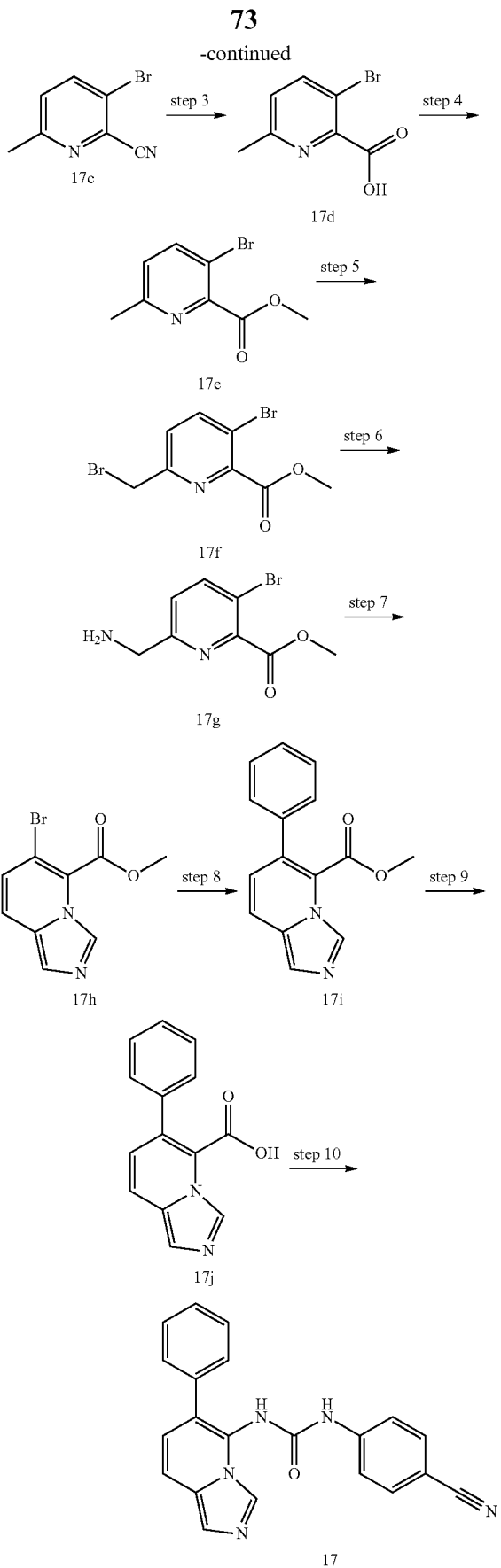

Step 1

Preparation of 5-bromo-2-methylpyridine 1-oxide

A mixture of 5-bromo-2-methylpyridine 17a (25 g, 145 mmol), mCPBA (31.35 g, 218 mmol) and chloroform (300 mL) was heated to 70° C. and stirred for 2 h. The mixture was cooled to room temperature and washed with a solution of sodium bicarbonate. The organic phase was dried over anhydrous sodium sulfate, filtered and concentrated under reduced pressure to give the target product 5-bromo-2-methylpyridine 1-oxide 17b (20.5 g, yellow solid). Yield: 75%.

MS m/z (ESI): 188[M+1]

Step 2

Preparation of 3-bromo-6-methylpicolinonitrile

A mixture of 5-bromo-2-methylpyridine 1-oxide 17b (20.5 g, 109 mmol), trimethylsilanecarbonitrile (43.25 g, 436 mmol), triethylamine (33.0 g, 327 mmol) and acetonitrile (500 mL) was heated to 100° C. and stirred overnight. The mixture was cooled to room temperature and concentrated under reduced pressure to remove the solvent. The residue was purified by silica gel column chromatography (petroleum ether/ethyl acetate=1/1) to give the target compound 3-bromo-6-methylpicolinonitrile 17c (17.1 g, yellow solid). Yield: 71%.

MS m/z (ESI): 197/199[M+1]

Step 3

Preparation of 3-bromo-6-methylpicolinic Acid

A mixture of 3-bromo-6-methylpicolinonitrile 17c (15 g, 76.1 mmol), sodium hydroxide solution (4 N, 56 mL, 228 mmol) and ethanol (150 mL) was heated to 90° C. and stirred overnight. The mixture was cooled to room temperature, acidified with hydrochloride solution and concentrated under reduced pressure to remove solvent. The residue was washed with dichloromethane to give the target compound 3-bromo-6-methylpicolinic acid 17d (15.8 g, oil). Yield: 99%.

MS m/z (ESI): 216/218[M+1]

Step 4

Preparation of methyl 3-bromo-6-methylpicolinate

A mixture of 3-bromo-6-methylpicolinic acid 17d (15.8 g, 73.1 mmol), sulfurous dichloride (6.8 mL) and methanol (30 mL) was heated to 80° C. and stirred overnight. The mixture was cooled to room temperature and concentrated under reduced pressure to remove the solvent. The residue was dissolved in ethyl acetate and washed with water. The organic phase was dried over anhydrous sodium sulfate, filtered and concentrated under reduced pressure to give the target product methyl 3-bromo-6-methylpicolinate 17e (15 g, yellow oil). Yield: 89%.

MS m/z (ESI): 230/232[M+1]

Step 5

Preparation of methyl 3-bromo-6-(bromomethyl)picolinate

Methyl 3-bromo-6-methylpicolinate 17e (15 g, 65.2 mmol) was used as the starting material and the method for the synthesis of 1c in Example 1 was used to generate the titled product methyl 3-bromo-6-(bromomethyl)picolinate 17f (16.7 g, yellow oil). Yield: 75%.

MS m/z (ESI): 310[M+1]

Step 6

Preparation of methyl 6-(aminomethyl)-3-bromopicolinate

Methyl 3-bromo-6-(bromomethyl)picolinate 17f (16.7 g, 54.0 mmol) was used as the starting material and the method for the synthesis of 1d in Example 1 was used to generate the titled product methyl 6-(aminomethyl)-3-bromopicolinate 17 g (12.1 g, white solid). Yield: 93%.

MS m/z (ESI): 245[M+1]

Step 7

Preparation of methyl 6-bromoimidazo[1,5-a]pyridine-5-carboxylate

Methyl 6-(aminomethyl)-3-bromopicolinate 17 g (12.1 g, 49.4 mmol) was used as the starting material and the method for the synthesis of 1e in Example 1 was used to generate the titled product methyl 6-bromoimidazo[1,5-a]pyridine-5-carboxylate 17h (0.73 g, yellow solid). Yield: 12%.

MS m/z (ESI): 255[M+1]

Step 8

Preparation of methyl 6-phenylimidazo[1,5-a]pyridine-5-carboxylate

A mixture of methyl 6-bromoimidazo[1,5-a]pyridine-5-carboxylate 17h (0.67 g, 2.6 mmol), phenylboronic acid (0.476 g, 3.9 mmol), Na$_2$CO$_3$ (0.827 g, 7.8 mmol), Pd(dppf)Cl$_2$·CH$_2$Cl$_2$ (0.425 g, 0.52 mmol), dioxane (20 mL) and water (5 mL) was heated to 100° C. and stirred for 5 h under nitrogen protection. The reaction mixture was cooled to room temperature and concentrated under reduced pressure to remove the solvent. The residue was added with water (50 mL) and extracted with ethyl acetate (50 mL×3). The organic phase was combined, dried over anhydrous sodium sulfate, filtered and concentrated under reduced pressure to remove the solvent. The residue was purified by silica gel column chromatography (petroleum ether/ethyl acetate=4/1) to give the target compound methyl 6-phenylimidazo[1,5-a]pyridine-5-carboxylate 17i (0.43 g, white solid). Yield: 66%.

MS m/z (ESI): 253[M+1]

Step 9

Preparation of 6-phenylimidazo[1,5-a]pyridine-5-carboxylic Acid

Methyl 6-phenylimidazo[1,5-a]pyridine-5-carboxylate 17i (0.252 g, 1.0 mmol) was used as the starting material and the method for the synthesis of 16j in Example 16 was used to generate the title product 6-phenylimidazo[1,5-a]pyridine-5-carboxylic acid 17j (0.20 g, grey solid). Yield: 84%.

MS m/z (ESI): 239[M+1]

Step 10

Preparation of 1-(4-cyanophenyl)-3-(6-phenylimidazo[1,5-a]pyridin-5-yl)urea

6-Phenylimidazo[1,5-a]pyridine-5-carboxylic acid 17j (50 mg, 0.21 mmol) was used as the starting material and the method for the synthesis of 16 in Example 16 was used to generate the titled product 6-phenylimidazo[1,5-a]pyridine-5-carboxylic acid 17 (28 mg, grey solid). Yield: 38%.

MS m/z (ESI): 354[M+1]

$^1$H NMR (400 MHz, DMSO-d$_6$) δ 9.59 (brs, 1H), 8.83 (brs, 1H), 8.31 (s, 1H), 7.71 (d, J=8.8 Hz, 2H), 7.67 (d, J=9.2 Hz, 1H), 7.56 (d, J=8.8 Hz, 2H), 7.53 (s, 1H), 7.49-7.42 (m, 4H), 7.38-7.34 (m, 1H), 6.92 (d, J=9.2 Hz, 1H).

Example 18

1-(4-cyanophenyl)-3-(7-phenylimidazo[1,5-a]pyridin-5-yl)urea

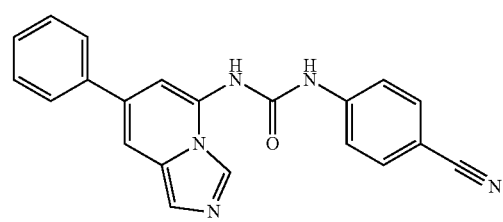 [SMILES: N#Cc1ccc(NC(=O)Nc2cc(-c3ccccc3)cc3cncn23)cc1]

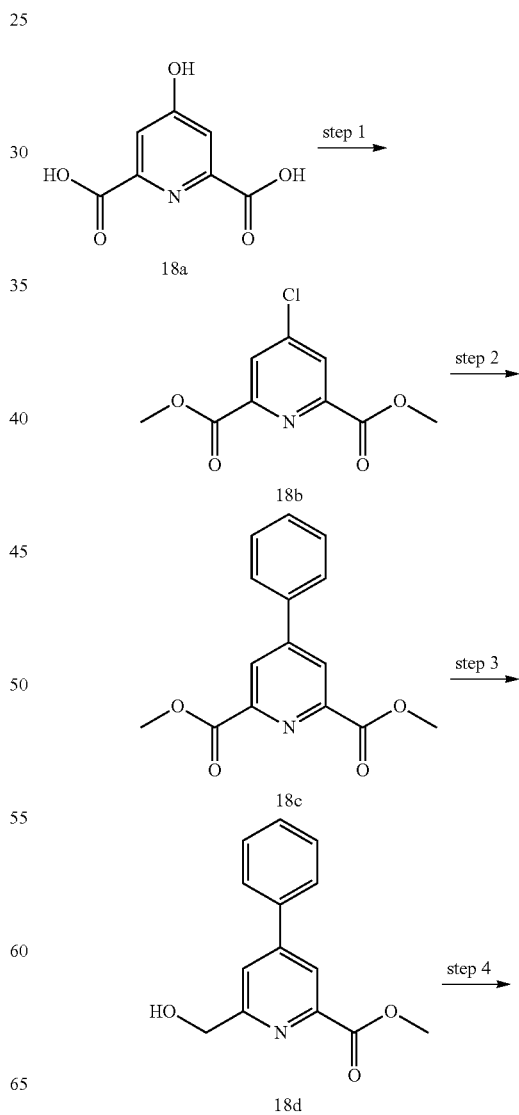

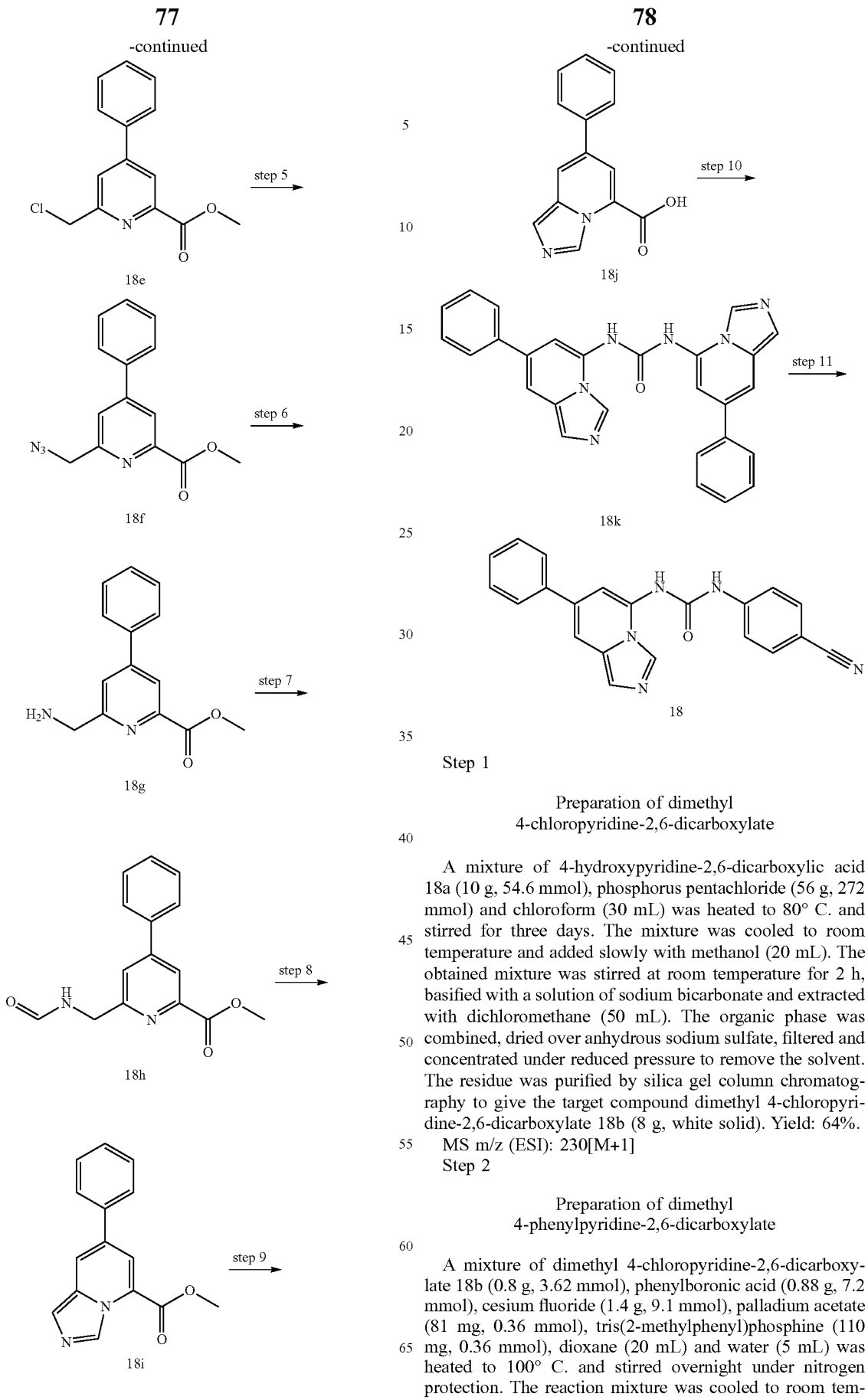

Step 1

Preparation of dimethyl 4-chloropyridine-2,6-dicarboxylate

A mixture of 4-hydroxypyridine-2,6-dicarboxylic acid 18a (10 g, 54.6 mmol), phosphorus pentachloride (56 g, 272 mmol) and chloroform (30 mL) was heated to 80° C. and stirred for three days. The mixture was cooled to room temperature and added slowly with methanol (20 mL). The obtained mixture was stirred at room temperature for 2 h, basified with a solution of sodium bicarbonate and extracted with dichloromethane (50 mL). The organic phase was combined, dried over anhydrous sodium sulfate, filtered and concentrated under reduced pressure to remove the solvent. The residue was purified by silica gel column chromatography to give the target compound dimethyl 4-chloropyridine-2,6-dicarboxylate 18b (8 g, white solid). Yield: 64%.

MS m/z (ESI): 230[M+1]

Step 2

Preparation of dimethyl 4-phenylpyridine-2,6-dicarboxylate

A mixture of dimethyl 4-chloropyridine-2,6-dicarboxylate 18b (0.8 g, 3.62 mmol), phenylboronic acid (0.88 g, 7.2 mmol), cesium fluoride (1.4 g, 9.1 mmol), palladium acetate (81 mg, 0.36 mmol), tris(2-methylphenyl)phosphine (110 mg, 0.36 mmol), dioxane (20 mL) and water (5 mL) was heated to 100° C. and stirred overnight under nitrogen protection. The reaction mixture was cooled to room temperature and concentrated under reduced pressure to remove the solvent. The residue was purified by silica gel column chromatography to give the target compound dimethyl 4-phenylpyridine-2,6-dicarboxylate 18c (0.65 g, white solid). Yield: 66%.

MS m/z (ESI): 272[M+1]

Step 3

Preparation of methyl 6-(hydroxymethyl)-4-phenylpicolinate

Compound dimethyl 4-phenylpyridine-2,6-dicarboxylate 18c (0.65 g, 2.4 mmol) was dissolved in methanol (10 mL), cooled to 0° C., added with sodium borohydride (182 mg, 4.79 mmol) and stirred for 30 min. The mixture was quenched with concentrated hydrochloride until pH=2. Methanol was removed under reduced pressure and water (30 mL) was added. The resulting mixture was extracted with dichloromethane (40 mL×3). The organic phase was combined, dried over anhydrous sodium sulfate, filtered and concentrated under reduced pressure to give the target product methyl 6-(hydroxymethyl)-4-phenylpicolinate 18d (0.5 g). Yield: 86%.

MS m/z (ESI): 244[M+1]

Step 4

Preparation of methyl 6-(chloromethyl)-4-phenylpicolinate

Compound methyl 6-(hydroxymethyl)-4-phenylpicolinate 18d (0.5 g, 2.1 mmol) was dissolved in dichloromethane (10 mL), added with sulfurous dichloride (0.5 mL) and stirred at room temperature overnight. The mixture was added with excess amount of sodium bicarbonate solution and extracted with dichloromethane. The organic phase was combined, dried over anhydrous sodium sulfate, filtered and concentrated under reduced pressure to give the target product methyl 6-(chloromethyl)-4-phenylpicolinate 18e (0.55 g). Yield: 100%.

MS m/z (ESI): 262[M+1]

Step 5

Preparation of methyl 6-(azidomethyl)-4-phenylpicolinate

Methyl 6-(chloromethyl)-4-phenylpicolinate 18e (550 mg, 2.1 mmol) was used as the starting material and the method for the synthesis of 16f in Example 16 was used to generate the titled product methyl 6-(azidomethyl)-4-phenylpicolinate 18f (0.5 g). Yield: 89%.

MS m/z (ESI): 269[M+1]

Step 6

Preparation of methyl 6-(aminomethyl)-4-phenylpicolinate

Methyl 6-(azidomethyl)-4-phenylpicolinate 18f (0.5 g, 1.86 mmol) was used as the starting material and the method for the synthesis of 16 g in Example 16 was used to generate the titled product methyl 6-(aminomethyl)-4-phenylpicolinate 18 g (0.35 g). Yield: 78%.

MS m/z (ESI): 243[M+1]

Step 7

Preparation of methyl 6-(formamidomethyl)-4-phenylpicolinate

Methyl 6-(aminomethyl)-4-phenylpicolinate 18 g (0.35 g, 1.45 mmol) was used as the starting material and the method for the synthesis of 16h in Example 16 was used to generate the titled product methyl 6-(formamidomethyl)-4-phenylpicolinate 18h (0.35 g). Yield: 89%.

MS m/z (ESI): 271[M+1]

Step 8

Preparation of methyl 7-phenylimidazo[1,5-a]pyridine-5-carboxylate

Methyl 6-(formamidomethyl)-4-phenylpicolinate 18h (0.35 g, 1.3 mmol) was used as the starting material and the method for the synthesis of 16i in Example 16 was used to generate the titled product methyl 7-phenylimidazo[1,5-a]pyridine-5-carboxylate 18i (0.25 g). Yield: 71%.

MS m/z (ESI): 253[M+1]

Step 9

Preparation of 7-phenylimidazo[1,5-a]pyridine-5-carboxylic Acid

Methyl 7-phenylimidazo[1,5-a]pyridine-5-carboxylate 18i (100 mg, 0.4 mmol) was used as the starting material and the method for the synthesis of 16j in Example 16 was used to generate the titled product 7-phenylimidazo[1,5-a]pyridine-5-carboxylic acid 18j (80 mg). Yield: 79%.

MS m/z (ESI): 239[M+1]

Step 10

Preparation of 1,3-bis(7-phenylimidazo[1,5-a]pyridin-5-yl)urea

7-Phenylimidazo[1,5-a]pyridine-5-carboxylic acid 18j (100 mg, 0.4 mmol) was used as the starting material and the method for the synthesis of 16 in Example 16 was used to generate the titled product 1,3-bis(7-phenylimidazo[1,5-a]pyridin-5-yl)urea 18k (11 mg). Yield: 11%.

MS m/z (ESI): 445[M+1]

Step 11

Preparation of 1-(4-cyanophenyl)-3-(7-phenylimidazo[1,5-a]pyridin-5-yl)urea

A mixture of 1,3-bis(7-phenylimidazo[1,5-a]pyridin-5-yl)urea 18k (50 mg, 0.11 mmol), 4-aminobenzonitrile (132 mg, 1.1 mmol) and toluene (20 mL) was heated to 110° C. and stirred for 4 h. The reaction mixture was cooled to room temperature and concentrated under reduced pressure to remove the solvent. The residue was purified by silica gel column chromatography and further purified by high performance liquid chromatography to give the target compound 1-(4-cyanophenyl)-3-(7-phenylimidazo[1,5-a]pyridin-5-yl)urea 18 (5 mg, white solid). Yield: 13%.

MS m/z (ESI): 354[M+1]

$^1$H NMR (400 MHz, DMSO-$d_6$) δ 9.70 (brs, 1H), 9.37 (brs, 1H), 8.39 (brs, 1H), 7.79-7.71 (m, 7H), 7.52-7.48 (m, 3H), 7.41-7.38 (m, 1H), 7.31 (s, 1H).

Example 19

1-(6-chloroimidazo[1,5-a]pyridin-5-yl)-3-(4-cyanophenyl)urea

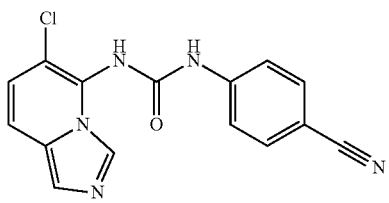 [SMILES: N#Cc1ccc(NC(=O)Nc2c(Cl)ccc3cncn23)cc1]

Using 2,3-dichloro-6-methylpyridine as the starting material, Example 19 was synthesized according to the synthesis methods of step 3 to step 10 in Example 16.

MS m/z (ESI): 312[M+1]

$^1$H NMR (400 MHz, DMSO-d$_6$) δ 9.85 (s, 1H), 9.06 (s, 1H), 8.32 (s, 1H), 7.76 (d, J=8.8 Hz, 2H), 7.68 (d, J=8.8 Hz, 2H), 7.63 (d, J=9.5 Hz, 1H), 7.54 (s, 1H), 6.94 (d, J=9.5 Hz, 1H).

Example 20

1-(7-chloroimidazo[1,5-a]pyridin-5-yl)-3-(4-cyanophenyl)urea

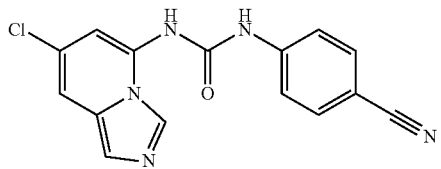 [SMILES: N#Cc1ccc(NC(=O)Nc2cc(Cl)cc3cncn23)cc1]

Using dimethyl 4-chloropyridine-2,6-dicarboxylate as the starting material, Example 20 was synthesized according to the synthesis methods of step 3 to step 10 in Example 16.

MS m/z (ESI): 312[M+1]

$^1$H NMR (400 MHz, DMSO-d$_6$) δ 9.81 (s, 1H), 9.66 (s, 1H), 8.41 (s, 1H), 7.89 (d, J=8.8 Hz, 2H), 7.70 (d, J=8.8 Hz, 2H), 7.57 (d, J=1.5 Hz, 1H), 7.44 (s, 1H), 7.01 (d, J=1.8 Hz, 1H).

Example 21

1-(4-cyanophenyl)-3-(6-(4-fluorophenyl)imidazo[1,5-a]pyridin-5-yl)urea

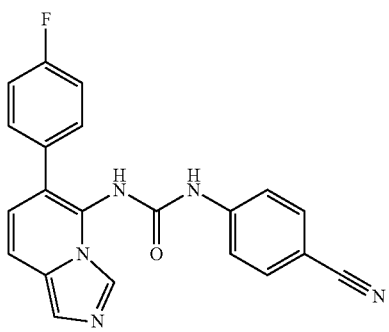 [SMILES: N#Cc1ccc(NC(=O)Nc2c(-c3ccc(F)cc3)ccc3cncn23)cc1]

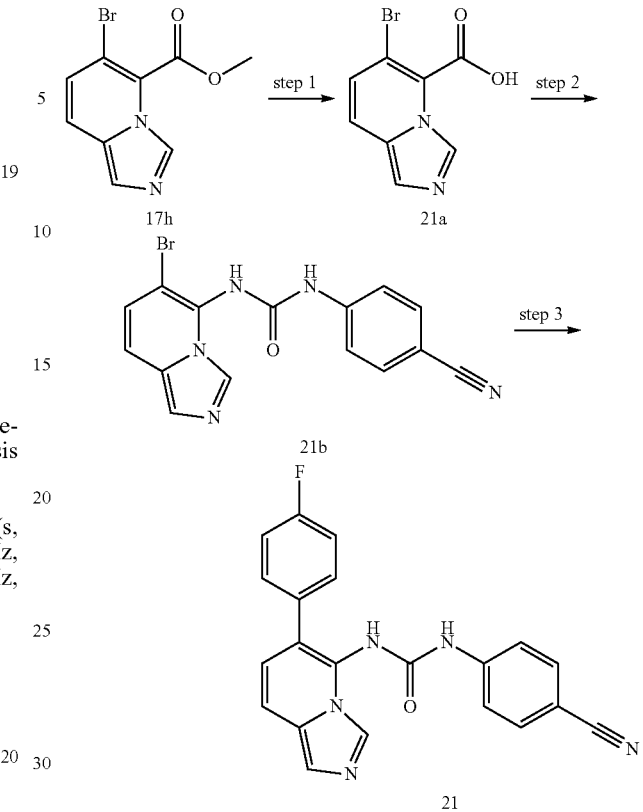

Step 1

Preparation of 6-bromoimidazo[1,5-a]pyridine-5-carboxylic Acid

Methyl 6-bromoimidazo[1,5-a]pyridine-5-carboxylate 17h (0.46 g, 1.8 mmol) was used as the starting material and the method for the synthesis of 16j in Example 16 was used to generate the titled product 6-bromoimidazo[1,5-a]pyridine-5-carboxylic acid 21a (0.35 g, white solid). Yield: 80%.

MS m/z (ESI): 241/243[M+1]

Step 2

Preparation of 1-(6-bromoimidazo[1,5-a]pyridin-5-yl)-3-(4-cyanophenyl)urea

6-Bromoimidazo[1,5-a]pyridine-5-carboxylic acid 21a (0.17 g, 0.71 mmol) was used as the starting material and the method for the synthesis of 16 in Example 16 was used to generate the titled product 1-(6-bromoimidazo[1,5-a]pyridin-5-yl)-3-(4-cyanophenyl)urea 21b (84 mg, white solid). Yield: 33%.

MS m/z (ESI): 356/358[M+1]

Step 3

Preparation of 1-(4-cyanophenyl)-3-(6-(4-fluorophenyl)imidazo[1,5-a]pyridin-5-yl)urea 1-(6-Bromoimidazo[1,5-a]pyridin-5-yl)-3-(4-cyanophenyl)urea 21b (84 mg, 0.07 mmol) was used as the starting material and the method for the synthesis of 17i in Example 17 was used to generate the titled product 1-(4-cyanophenyl)-3-(6-(4-fluorophenyl)imidazo[1,5-a]pyridin-5-yl)urea 21 (4 mg, solid). Yield: 15%.

MS m/z (ESI): 372[M+1]

¹H NMR (400 MHz, DMSO-d₆) δ 9.62 (brs, 1H), 8.84 (brs, 1H), 8.29 (s, 1H), 7.72-7.65 (m, 3H), 7.58-7.49 (m, 4H), 7.31-7.23 (m, 2H), 6.92-6.85 (m, 2H).

Example 22

1-(4-cyanophenyl)-3-(6-(3-fluorophenyl)imidazo[1,5-a]pyridin-5-yl)urea

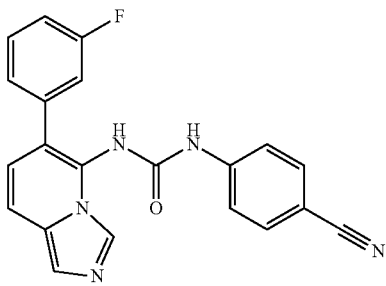 [SMILES: N#Cc1ccc(NC(=O)Nc2c(-c3cccc(F)c3)ccc3cncn23)cc1]

22

Example 22 was synthesized according to the procedure of Example 21, but in the third step, (3-fluorophenyl)boronic acid was used instead of (4-fluorophenyl)boronic acid.

MS m/z (ESI): 372[M+1]

¹H NMR (400 MHz, DMSO-d₆) δ 9.64 (brs, 1H), 8.88 (brs, 1H), 8.33 (s, 1H), 7.72-7.66 (m, 3H), 7.56-7.46 (m, 3H), 7.33-7.31 (m, 2H), 7.22-7.18 (m, 2H), 6.94 (d, J=9.2 Hz, 1H).

Example 23

1-(4-cyanophenyl)-3-(6-(2-fluorophenyl)imidazo[1,5-a]pyridin-5-yl)urea

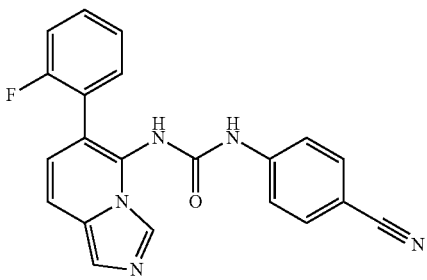 [SMILES: N#Cc1ccc(NC(=O)Nc2c(-c3ccccc3F)ccc3cncn23)cc1]

23

Example 23 was synthesized according to the procedure of Example 21, but in the third step, (2-fluorophenyl)boronic acid was used instead of (4-fluorophenyl)boronic acid.

MS m/z (ESI): 372[M+1]

¹H NMR (400 MHz, DMSO-d₆) δ 9.53 (brs, 1H), 8.85 (brs, 1H), 8.30 (s, 1H), 7.70 (d, J=8.8 Hz, 2H), 7.65 (d, J=9.2 Hz, 1H), 7.53-7.51 (m, 3H), 7.47-7.41 (m, 2H), 7.32 (d, J=9.2 Hz, 1H), 7.27 (t, J=7.4 Hz, 1H), 6.85 (d, J=9.2 Hz, 1H).

Example 24

1-(4-cyanophenyl)-3-(6-(cyclopent-1-en-1-yl)imidazo[1,5-a]pyridin-5-yl)urea

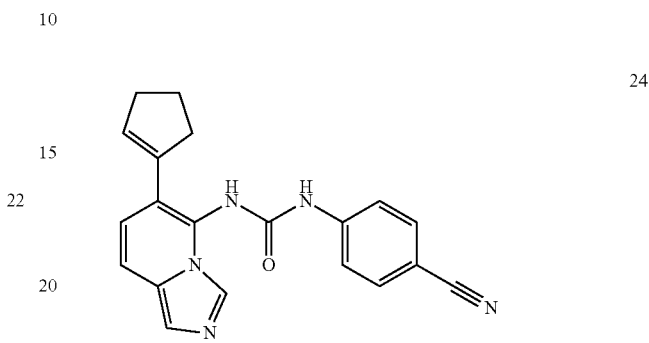

24

Example 24 was synthesized according to the procedure of Example 21, but in the third step, 2-(cyclopent-1-en-1-yl)-4,4,5,5-tetramethyl-1,3,2-dioxaborolane was used instead of (4-fluorophenyl)boronic acid.

MS m/z (ESI): 344[M+1]

¹H NMR (400 MHz, CD₃OD) δ 9.40 (s, 1H), 7.98 (s, 1H), 7.76 (d, J=9.6 Hz, 1H), 7.70 (d, J=2.8 Hz, 3H), 7.47-7.31 (m, 2H), 6.35-6.30 (m, 1H), 2.81 (t, J=6.4 Hz, 2H), 2.61-2.54 (m, 2H), 2.11-2.01 (m, 2H).

Example 25

1-(4-cyanophenyl)-3-(6-(pyridin-3-yl)imidazo[1,5-a]pyridin-5-yl)urea

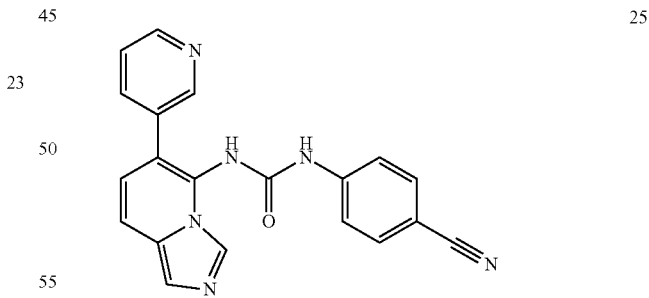

25

Example 25 was synthesized according to the procedure of Example 21, but in the third step, pyridin-3-ylboronic acid was used instead of (4-fluorophenyl)boronic acid.

MS m/z (ESI): 355[M+1]

¹H NMR (400 MHz, DMSO-d₆) δ 9.70 (brs, 1H), 8.99 (brs, 1H), 8.62 (s, 1H), 8.47 (s, 1H), 8.27 (s, 1H), 7.83-7.81 (m, 1H), 7.64-7.62 (m, 3H), 7.48-7.41 (m, 4H), 6.91-6.89 (m, 1H).

Example 26

1-(6-(1H-pyrazol-3-yl)imidazo[1,5-a]pyridin-5-yl)-3-(4-cyanophenyl)urea

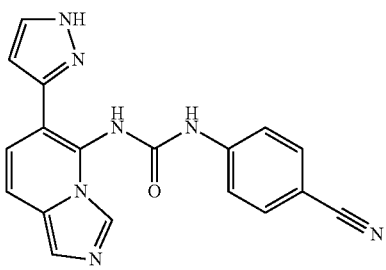

Example 26 was synthesized according to the procedure of Example 21, but in the third step, (1H-pyrazol-3-yl)boronic acid was used instead of (4-fluorophenyl)boronic acid.

MS m/z (ESI): 344[M+1]

¹H NMR (400 MHz, DMSO-d₆) δ 13.08 (brs, 1H), 10.14 (brs, 1H), 9.35 (brs, 1H), 8.16 (s, 1H), 7.67 (d, J=8.6 Hz, 2H), 7.59 (d, J=8.6 Hz, 2H), 7.54-7.47 (m, 2H), 7.38 (s, 1H), 7.32-7.29 (m, 1H), 6.65 (s, 1H).

Example 27

4-(3-(6-phenylimidazo[1,5-a]pyridin-5-yl)ureido)benzoic Acid

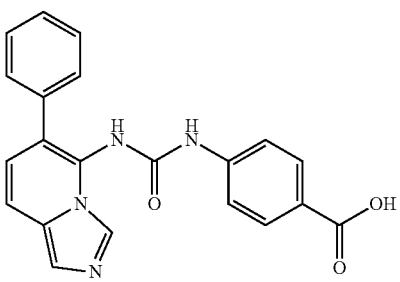

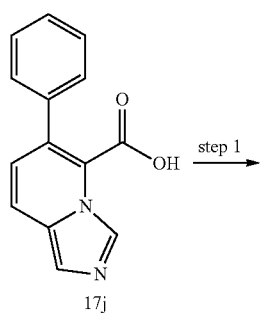

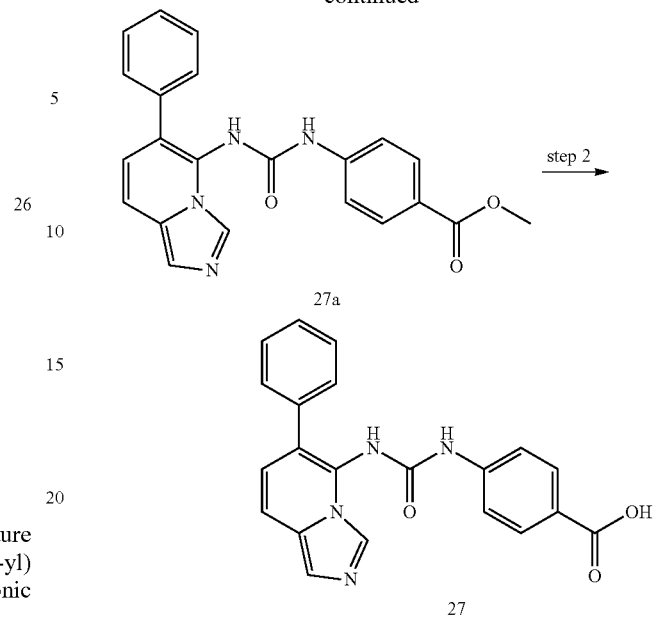

Step 1

Preparation of methyl 4-(3-(6-phenylimidazo[1,5-a]pyridin-5-yl)ureido)benzoate

6-Phenylimidazo[1,5-a]pyridine-5-carboxylic acid 17j (150 mg, 0.63 mmol) was used as the starting material and the method for the synthesis of 16 in Example 16 was used to generate the titled product methyl 4-(3-(6-phenylimidazo[1,5-a]pyridin-5-yl)ureido)benzoate 27a (55 mg, black solid). Yield: 22%.

MS m/z (ESI): 387[M+1]

Step 2

Preparation of 4-(3-(6-phenylimidazo[1,5-a]pyridin-5-yl)ureido)benzoic Acid

Compound methyl 4-(3-(6-phenylimidazo[1,5-a]pyridin-5-yl)ureido)benzoate 27a (55 mg, 0.14 mmol) was dissolved in a mixed solvent of methanol and water (10 mL, 1/1) and lithium hydroxide monohydrate (59 mg, 1.4 mmol) was added. The reaction mixture was stirred at room temperature for 16 h, acidified with diluted hydrochloride solution to pH=5 and concentrated under reduced pressure. The residue was purified by high performance liquid chromatography to give the target product 4-(3-(6-phenylimidazo[1,5-a]pyridin-5-yl)ureido)benzoic acid 27 (10 mg, white solid). Yield: 19%.

MS m/z (ESI): 373[M+1]

¹H NMR (400 MHz, CDCl₃) δ 9.53 (s, 1H), 8.10 (s, 1H), 7.95 (d, J=8.7 Hz, 2H), 7.89 (d, J=9.4 Hz, 1H), 7.62-7.44 (m, 7H), 7.37 (d, J=9.4 Hz, 1H).

Example 28

N-methyl-4-(3-(6-phenylimidazo[1,5-a]pyridin-5-yl)ureido)benzamide

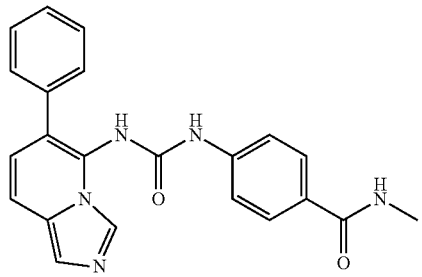

Example 28 was synthesized according to the procedure of Example 17, but in the tenth step, 4-amino-N-methylbenzamide was used instead of 4-aminobenzonitrile.

MS m/z (ESI): 386[M+1]

$^1$H NMR (400 MHz, CD$_3$OD) δ 8.33 (s, 1H), 7.76 (d, J=8.7 Hz, 2H), 7.65 (d, J=9.3 Hz, 1H), 7.56-7.44 (m, 6H), 7.39 (s, 1H), 7.25 (dd, J$_1$=30.4 Hz, J$_2$=7.8 Hz, 1H), 6.98 (d, J=9.3 Hz, 1H), 2.92 (s, 3H).

Example 29

4-(3-(6-phenylimidazo[1,5-a]pyridin-5-yl)ureido)benzamide

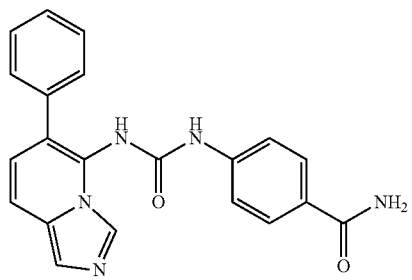

Example 29 was synthesized according to the procedure of Example 17, but in the tenth step, 4-aminobenzamide was used instead of 4-aminobenzonitrile.

MS m/z (ESI): 372[M+1]

$^1$H NMR (400 MHz, CD$_3$OD) δ 9.68 (s, 1H), 8.18 (s, 1H), 7.94 (d, J=9.5 Hz, 1H), 7.85 (d, J=8.7 Hz, 2H), 7.61-7.47 (m, 7H), 7.43 (d, J=9.5 Hz, 1H).

Example 30

N-(2-hydroxyethyl)-4-(3-(6-phenylimidazo[1,5-a]pyridin-5-yl)ureido)benzamide

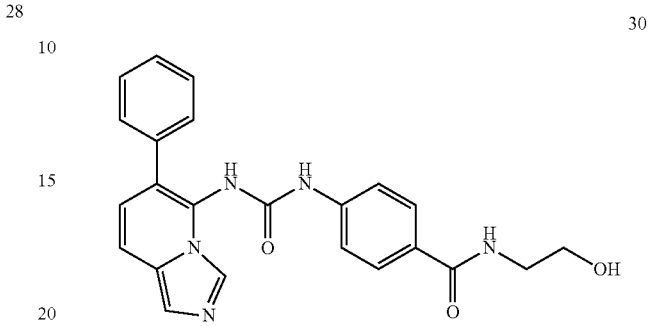

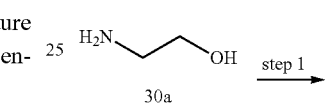

30a

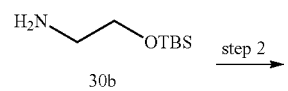

30b

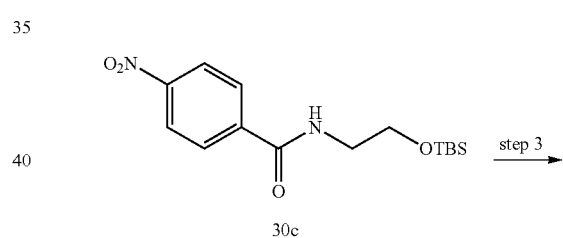

30c

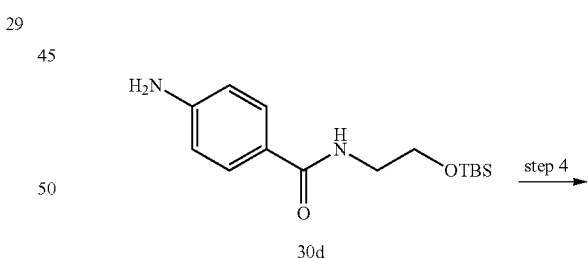

30d

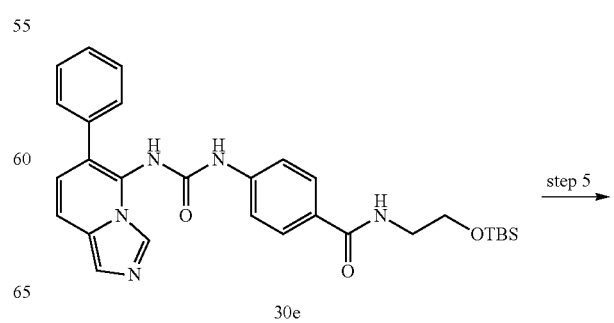

30e

-continued

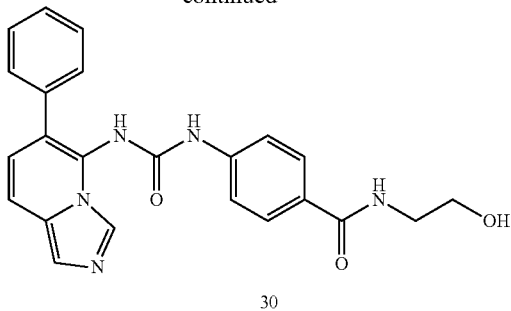

30

Step 1

Preparation of 2-((tert-butyldimethylsilyl)oxy)ethan-1-amine

To a mixture of 2-aminoethane-1-ol 30a (1.22 g, 20 mmol), imidazole (2.7 g, 40 mmol) and dichloromethane (50 mL) was added tert-butylchlorodimethylsilane (3.2 g, 21 mmol), and the reaction mixture was stirred at room temperature for 15 h. After the reaction was completed, water (20 mL) was added. The mixture was extracted with dichloromethane (20 mL×3). The organic phase was combined, dried over anhydrous sodium sulfate, filtered and concentrated under reduced give the target compound 2-((tert-butyldimethylsilyl)oxy)ethan-1-amine 30b (3.5 g, yellow oil). Yield: 100%.

MS m/z (ESI): 176[M+1]

Step 2

Preparation of N-(2-((tert-butyldimethylsilyl)oxy)ethyl)-4-nitrobenzamide

A mixture of 2-((tert-butyldimethylsilyl)oxy)ethan-1-amine 30b (3.3 g, 18.8 mmol), 4-nitrobenzoic acid (3.8 g, 22.6 mmol), HATU (8.6 g, 22.6 mmol), DIPEA (4.87 g, 37.6 mmol) and dichloromethane (100 mL) was stirred at room temperature for 15 h. The mixture was concentrated under reduced pressure, diluted with ethyl acetate and washed with brine. The organic phase was concentrated under reduced pressure. The residue was purified by silica gel column chromatography (petroleum ether/ethyl acetate=10/1 to 1/1) to give the target compound N-(2-((tert-butyldimethylsilyl)oxy)ethyl)-4-nitrobenzamide 30c (4.25 g, white solid). Yield: 70%.

MS m/z (ESI): 325[M+1]

Step 3

Preparation of 4-amino-N-(2-((tert-butyldimethylsilyl)oxy)ethyl)benzamide

A mixture of N-(2-((tert-butyldimethylsilyl)oxy)ethyl)-4-nitrobenzamide 30c (2.7 g, 8.3 mmol), Pd/C (200 mg) and methanol (100 mL) was stirred at room temperature under hydrogen for 16 h. The mixture was concentrated under reduced pressure to give the target product 4-amino-N-(2-((tert-butyldimethylsilyl)oxy)ethyl)benzamide 30d (2.15 g, yellow oil), which was used in the next step without purification.

MS m/z (ESI): 295[M+1]

Step 4

Preparation of N-(2-((tert-butyldimethylsilyl)oxy)ethyl)-4-(3-(6-phenylimidazo[1,5-a]pyridin-5-yl)ureido)benzamide 4-Amino-N-(2-((tert-butyldimethylsilyl)oxy)ethyl)benzamide 30d (280 mg g, 0.95 mmol) was used as the starting material and the method for the synthesis of 16 in Example 16 was used to generate the titled product N-(2-((tert-butyldimethylsilyl)oxy)ethyl)-4-(3-(6-phenylimidazo[1,5-a]pyridin-5-yl)ureido)benzamide 30e (70 mg, white solid). Yield: 21%.

MS m/z (ESI): 530[M+1]

Step 5

Preparation of N-(2-hydroxyethyl)-4-(3-(6-phenylimidazo[1,5-a]pyridin-5-yl)ureido)benzamide To a mixture of N-(2-((tert-butyldimethylsilyl)oxy)ethyl)-4-(3-(6-phenylimidazo[1,5-a]pyridin-5-yl)ureido)benzamide 30e (70 mg, 0.15 mmol) and dichloromethane (10 mL) was added a solution of hydrochloride in ethanol (4 M, 2 mL, 8 mmol), and the mixture was stirred at room temperature for 30 min. The reaction mixture was concentrated under reduced pressure to remove the solvent. The residue was basified with a solution of sodium bicarbonate to pH=9 and extracted with ethyl acetate (10 mL×3). The organic phase was combined, dried over anhydrous sodium sulfate, filtered and concentrated under reduced pressure to remove the solvent. The residue was purified by silica gel column chromatography (dichloromethane/methanol=15/1) to give the target compound N-(2-hydroxyethyl)-4-(3-(6-phenylimidazo[1,5-a]pyridin-5-yl)ureido)benzamide 30 (30 mg, grayish white solid). Yield: 48%.

MS m/z (ESI): 416[M+1]

$^1$H NMR (400 MHz, CD$_3$OD) δ 8.38 (s, 1H), 7.79 (d, J=8.7 Hz, 1H), 7.66 (d, J=9.3 Hz, 1H), 7.57 (s, 1H), 7.49 (dt, J$_1$=7.7 Hz, J$_2$=5.9 Hz, 3H), 7.40 (t, J=7.1 Hz, 1H), 7.30 (t, J=7.6 Hz, 1H), 7.21 (d, J=8.0 Hz, 1H), 7.10 (d, J=6.9 Hz, 1H), 7.01 (d, J=9.3 Hz, 1H), 3.72 (t, J=5.8 Hz, 2H), 3.51 (t, J=5.8 Hz, 2H).

Example 31

1-(4-(hydroxymethyl)phenyl)-3-(6-phenylimidazo[1,5-a]pyridin-5-yl)urea

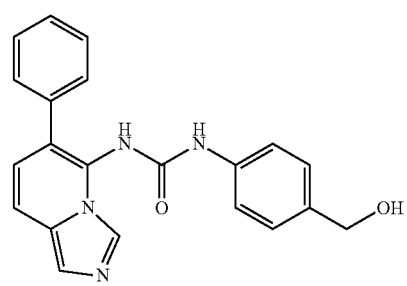

31

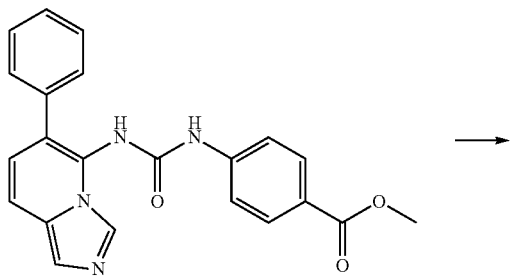

27a

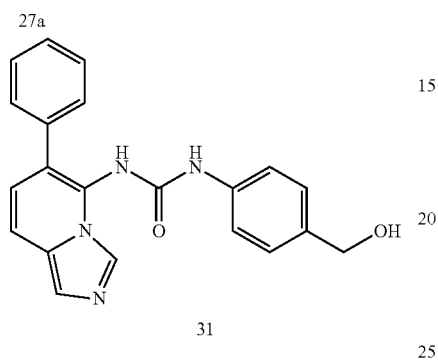

31

Compound methyl 4-(3-(6-phenylimidazo[1,5-a]pyridin-5-yl)ureido)benzoate 27a (100 mg, 0.26 mmol) was dissolved in THF (20 mL) and cooled to 0° C. Lithium aluminum hydride (42 mg, 0.78 mmol) was added. The reaction mixture was stirred for 3 h, poured into ice-water and filtered. The filtrate was concentrated under reduced pressure. The residue was purified by silica gel column chromatography (dichloromethane/methanol=10/1) to give the target compound 1-(4-(hydroxymethyl)phenyl)-3-(6-phenylimidazo[1,5-a]pyridin-5-yl)urea 31 (33 mg, white solid). Yield: 34%.

MS m/z (ESI): 359[M+1]

$^1$H NMR (400 MHz, CD$_3$OD) δ 8.31 (s, 1H), 7.63 (d, J=9.3 Hz, 1H), 7.55-7.46 (m, 5H), 7.45-7.25 (m, 5H), 6.97 (d, J=9.3 Hz, 1H), 4.56 (s, 2H).

Example 32

1-(6-cyanopyridin-3-yl)-3-(6-phenylimidazo[1,5-a]pyridin-5-yl)urea

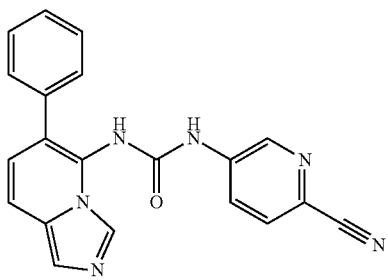

32

Example 32 was synthesized according to the procedure of Example 17, but in the tenth step, 5-aminopicolinonitrile was used instead of 4-aminobenzonitrile.

MS m/z (ESI): 355[M+1]

$^1$H NMR (400 MHz, CD$_3$OD) δ 8.60 (s, 1H), 8.37 (s, 1H), 8.11 (d, J=7.5 Hz, 1H), 7.77 (d, J=8.6 Hz, 1H), 7.67 (d, J=9.3 Hz, 1H), 7.58-7.34 (m, 6H), 6.98 (d, J=9.3 Hz, 1H).

Example 33

1-(5-cyanopyridin-2-yl)-3-(6-phenylimidazo[1,5-a]pyridin-5-yl)urea

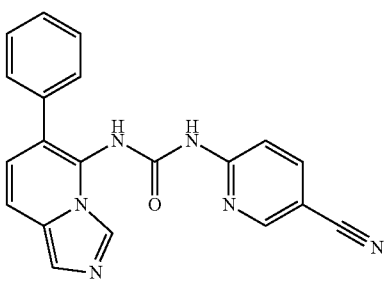

33

Example 33 was synthesized according to the procedure of Example 17, but in the tenth step, 6-aminonicotinonitrile was used instead of 4-aminobenzonitrile.

MS m/z (ESI): 355[M+1]

$^1$H NMR (400 MHz, CD$_3$OD) δ 9.68 (s, 1H), 8.56 (d, J=2.2 Hz, 1H), 8.19 (d, J=1.2 Hz, 1H), 8.07 (dd, J$_1$=8.8 Hz, J$_2$=2.2 Hz, 1H), 7.96 (d, J=9.5 Hz, 1H), 7.61-7.35 (m, 7H).

Example 34

1-(4-cyano-3-methoxyphenyl)-3-(6-phenylimidazo[1,5-a]pyridin-5-yl)urea

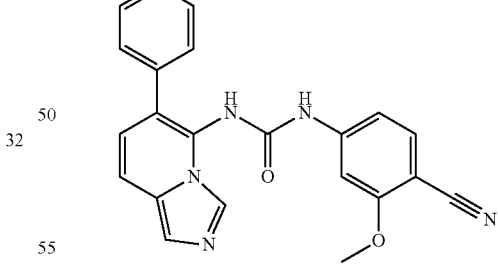

34

Example 34 was synthesized according to the procedure of Example 17, but in the tenth step, 4-amino-2-methoxybenzonitrile was used instead of 4-aminobenzonitrile.

MS m/z (ESI): 384[M+1]

$^1$H NMR (400 MHz, CD$_3$OD) δ 8.38-8.24 (m, 2H), 7.65 (d, J=9.3 Hz, 1H), 7.55 (s, 1H), 7.50 (dd, J$_1$=10.8 Hz, J$_2$=4.4 Hz, 4H), 7.45-7.26 (m, 3H), 6.98 (d, J=9.3 Hz, 1H), 3.96 (s, 3H).

Example 35

1-(4-cyano-2-methoxyphenyl)-3-(6-phenylimidazo[1,5-a]pyridin-5-yl)urea

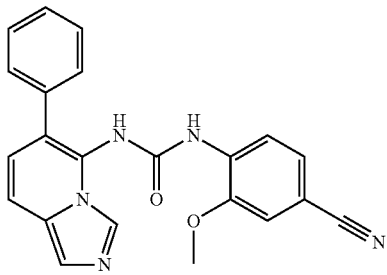

Example 35 was synthesized according to the procedure of Example 17, but in the tenth step, 4-amino-3-methoxybenzonitrile was used instead of 4-aminobenzonitrile.

MS m/z (ESI): 384[M+1]

$^1$H NMR (400 MHz, CD$_3$OD) δ 8.34 (s, 1H), 7.66 (d, J=9.3 Hz, 1H), 7.57-7.37 (m, 8H), 7.01-6.91 (m, 2H), 3.90 (s, 3H).

Example 36

1-(4-cyanocyclohexyl)-3-(6-phenylimidazo[1,5-a]pyridin-5-yl)urea

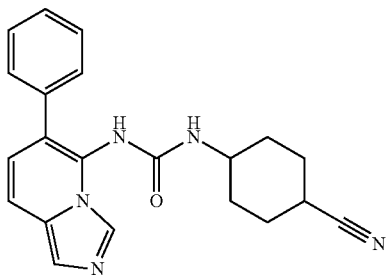

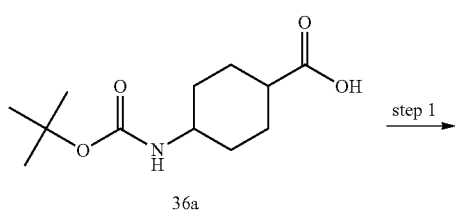

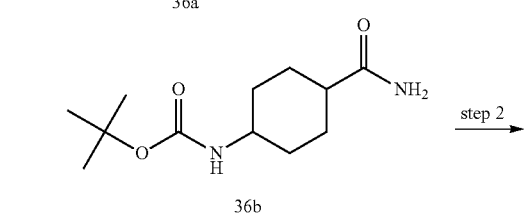

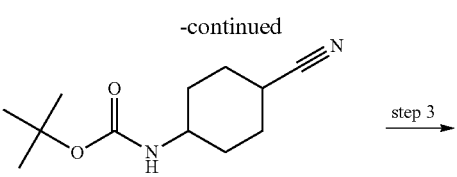

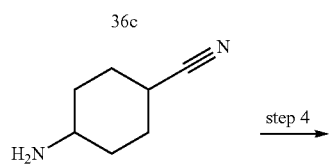

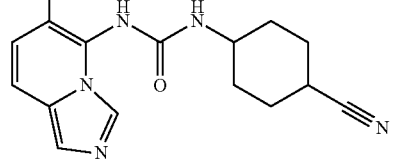

Step 1

Preparation of tert-butyl (4-carbamoylcyclohexyl)carbamate

Compound 4-((tert-butoxycarbonyl)amino)cyclohexane-1-carboxylic acid 36a (972 mg, 4.0 mmol), DIPEA (774 mg, 6.0 mmol) and HATU (1.8 g, 4.8 mmol) was dissolved in N,N-dimethylformamide (20 mL), and ammonium chloride (1.06 g, 20.0 mmol) was added. The mixture was stirred at room temperature for 14 h and concentrated under reduced pressure. The residue was added with water (20 mL) and extracted with ethyl acetate (20 mL×3). The organic phase was combined, washed with brine and concentrated under reduced pressure to remove the solvent. The residue was purified by silica gel column chromatography (dichloromethane/methanol=20/1) to give the target compound tert-butyl (4-carbamoylcyclohexyl)carbamate 36b (500 mg, grey solid). Yield: 52%.

MS m/z (ESI): 243[M+1]

Step 2

Preparation of tert-butyl (4-cyanocyclohexyl)carbamate

A mixture of tert-butyl (4-carbamoylcyclohexyl)carbamate 36b (500 mg, 2.07 mmol) and pyridine (5 mL) was cooled to 0° C. and added with phosphoryl trichloride (1.58 g, 10.35 mmol). The mixture was stirred for 30 min, poured into ice-water and extracted with ethyl acetate (20 mL×3). The organic phase was combined, washed with brine and concentrated under reduced pressure to remove the solvent. The residue was purified by silica gel column chromatography (petroleum ether/ethyl acetate=10/1) to give the target compound tert-butyl (4-cyanocyclohexyl)carbamate 36c (140 mg). Yield: 30%.

MS m/z (ESI): 225[M+1]

Step 3

Preparation of 4-aminocyclohexane-1-carbonitrile

Compound tert-butyl (4-cyanocyclohexyl)carbamate 36c (140 mg, 0.63 mmol) was dissolved in dichloromethane and added with a solution of hydrochloride in ethanol (4 M, 2 mL). The mixture was stirred at room temperature for 2 h and concentrated under reduced pressure to give the target compound 4-aminocyclohexane-1-carbonitrile 36d (100 mg, crude product).

MS m/z (ESI): 125[M+1]

Step 4

Preparation of 1-(4-cyanocyclohexyl)-3-(6-phenylimidazo[1,5-a]pyridin-5-yl)urea

4-Aminocyclohexane-1-carbonitrile 36d (100 mg, crude) was used as the starting material and the method for the synthesis of 16 in Example 16 was used to generate the titled product 1-(4-cyanocyclohexyl)-3-(6-phenylimidazo[1,5-a]pyridin-5-yl)urea 36 (27 mg, white solid). Yield for two steps: 24%.

MS m/z (ESI): 360[M+1]

$^1$H NMR (400 MHz, CD$_3$OD) δ 8.28 (s, 1H), 7.62 (d, J=9.3 Hz, 1H), 7.54 (s, 1H), 7.50-7.38 (m, 5H), 6.99 (d, J=9.3 Hz, 1H), 3.59 (t, J=9.7 Hz, 1H), 3.05-2.92 (m, 1H), 1.99-1.69 (m, 6H), 1.56 (dd, J$_1$=17.3 Hz, J$_2$=7.1 Hz, 2H).

Example 37

N-(4-cyanophenyl)-2-(6-phenylimidazo[1,5-a]pyridin-5-yl)acetamide

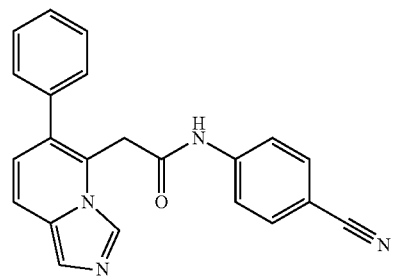

37

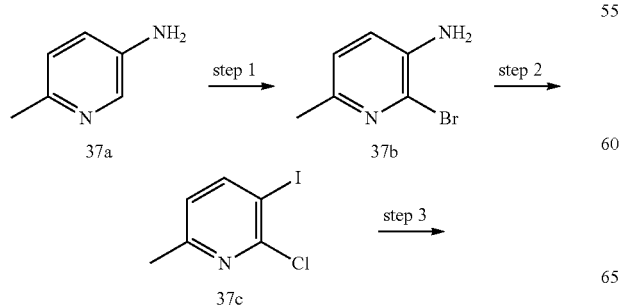

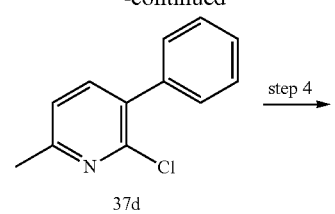

37d

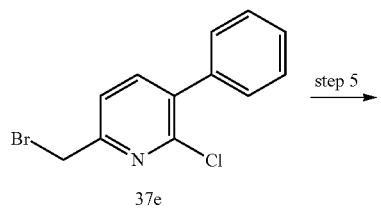

37e

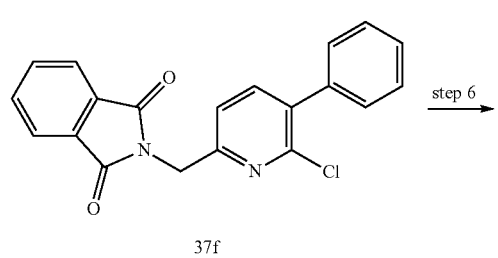

37f

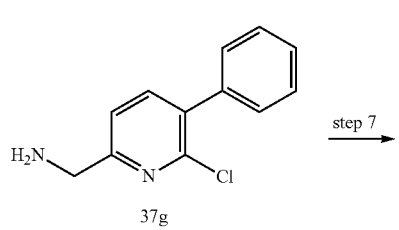

37g

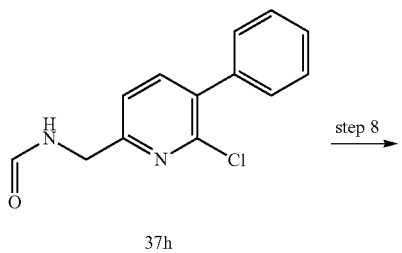

37h

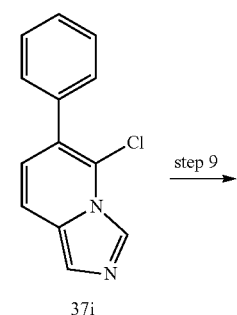

37i

97

-continued

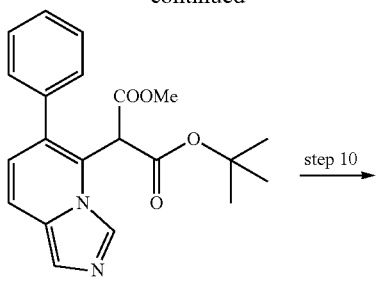

37j

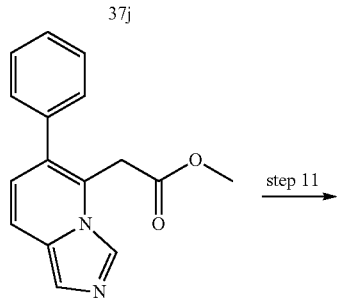

37k

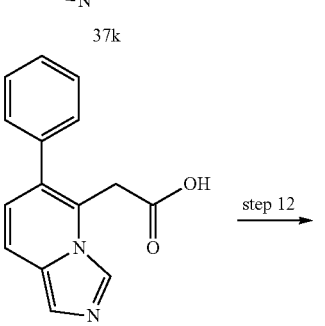

37l

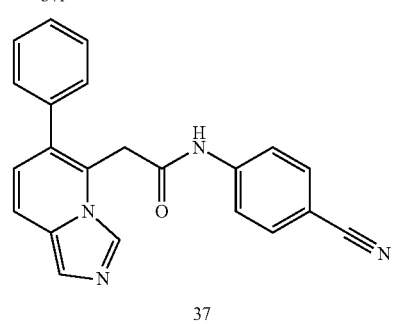

37

Step 1

Preparation of 2-bromo-6-methylpyridin-3-amine

Compound 6-methylpyridin-3-amine 37a (10.8 g, 100 mmol) was dissolved in dichloromethane (500 mL) and cooled to 0° C. N-Bromosuccinimide (17.8 g, 100 mmol) was added slowly within 1 h. Then the reaction mixture was stirred at 0° C. for 30 min. The mixture was washed with saturated aqueous sodium bicarbonate solution (200 mL). The organic phase was dried over anhydrous sodium sulfate, filtered and concentrated under reduced pressure to give the target product 2-bromo-6-methylpyridin-3-amine 37b (17.3 g, light brown solid). Yield: 93%.

MS m/z (ESI): 187/189[M+1]

98

Step 2

Preparation of 2-chloro-3-iodo-6-methylpyridine

Compound 2-bromo-6-methylpyridin-3-amine 37b (17.3 g, 92.5 mmol) was dissolved in concentrated hydrochloride solution (37%, 200 mL) and cooled to 0° C. A solution (40 mL) of sodium nitrite (12.8 g, 185 mmol) was added slowly, while keeping the temperature of the reaction system under 5° C. Then the reaction mixture was stirred at 0° C. for 20 min. Potassium iodide (46.1 g, 278 mmol) was dissolved in water (50 mL) and the solution was added slowly to the above reaction system, while keeping the temperature under 10° C. Then the reaction mixture was stirred at 10-15° C. for 30 min. The reaction mixture was neutralized with sodium hydroxide and extracted with ethyl acetate (500 mL×3). The organic phase was combined, dried over anhydrous sodium sulfate, filtered and concentrated under reduced pressure to remove the solvent. The residue was purified by silica gel column chromatography (petroleum ether/ethyl acetate=20/1) to give the target compound 2-chloro-3-iodo-6-methylpyridine 37c (14 g, white solid). Yield: 60%.

MS m/z (ESI): 254[M+1]

Step 3

Preparation of 2-chloro-6-methyl-3-phenylpyridine

A mixture of 2-chloro-3-iodo-6-methylpyridine 37c (9.0 g, 35.6 mmol), phenylboronic acid (6.5 g, 53.4 mmol), $Na_2CO_3$ (7.5 g, 71.2 mmol), $Pd(dppf)Cl_2 \cdot CH_2Cl_2$ (2.9 g, 3.56 mmol), dioxane (200 mL) and water (50 mL) was heated to 60° C. and stirred overnight under nitrogen protection. The reaction mixture was cooled to room temperature, diluted with water (200 mL) and extracted with ethyl acetate (500 mL×3). The organic phase was combined, dried over anhydrous sodium sulfate, filtered and concentrated under reduced pressure to remove the solvent. The residue was purified by silica gel column chromatography (petroleum ether/ethyl acetate=20/1) to give the target compound 2-chloro-6-methyl-3-phenylpyridine 37d (4.5 g, yellow oil). Yield: 62%.

$^1$H NMR (400 MHz, $CDCl_3$) δ 7.57 (d, J=7.6 Hz, 1H), 7.44-7.40 (m, 5H), 7.16 (d, J=7.6 Hz, 1H), 2.59 (s, 3H).

Step 4

Preparation of 6-(bromomethyl)-2-chloro-3-phenylpyridine

2-Chloro-6-methyl-3-phenylpyridine 37d (7 g, 34.5 mmol) was used as the starting material and the method for the synthesis of 1c in Example 1 was used to generate the title product 6-(bromomethyl)-2-chloro-3-phenylpyridine 37e (5 g). Yield: 51%.

$^1$H NMR (400 MHz, $CDCl_3$) δ 7.65 (d, J=7.6 Hz, 1H), 7.44-7.40 (m, 5H), 7.33 (d, J=7.6 Hz, 1H), 4.05 (s, 2H).

Step 5

Preparation of 2-((6-chloro-5-phenylpyridin-2-yl)methyl)isoindoline-1,3-dione

A mixture of 6-(bromomethyl)-2-chloro-3-phenylpyridine 37e (15 g, 46.2 mmol), potassium phthalimide (12.8 g, 69.2 mmol) and acetonitrile (150 mL) was heated to reflux and stirred for 2 h. The mixture was cooled to room temperature and concentrated under reduced pressure. The residue was added with water (500 mL) and extracted with ethyl acetate (500 mL×3). The organic phase was combined, dried over anhydrous sodium sulfate, filtered and concentrated under reduced pressure to remove the solvent. The residue was purified by silica gel column chromatography (petroleum ether/ethyl acetate=4/1) to give the target compound 2-((6-chloro-5-phenylpyridin-2-yl)methyl)isoindoline-1,3-dione 37f (15 g, white solid). Yield: 94%.

MS m/z (ESI): 349/351[M+1]

Step 6

Preparation of (6-chloro-5-phenylpyridin-2-yl)methanamine

A mixture of 2-((6-chloro-5-phenylpyridin-2-yl)methyl)isoindoline-1,3-dione 37f (15 g, 43.1 mmol), hydrazine hydrate (4.3 g, 86.2 mmol) and ethanol (100 mL) was heated to reflux and stirred for 2 h. The mixture was cooled to room temperature and concentrated under reduced pressure. The residue was added with dichloromethane and filtered. The filtrate was concentrated under reduced pressure to give the target product (6-chloro-5-phenylpyridin-2-yl)methanamine 37 g (7 g). Yield: 75%.

MS m/z (ESI): 219/221[M+1]

Step 7

Preparation of N-((6-chloro-5-phenylpyridin-2-yl)methyl)formamide (6-Chloro-5-phenylpyridin-2-yl)methanamine 37 g (7 g, 32.1 mmol) was used as the starting material and the method for the synthesis of 18h in Example 18 was used to generate the title product N-((6-chloro-5-phenylpyridin-2-yl)methyl)formamide 37h (8 g). Yield: 100%.

MS m/z (ESI): 247/249[M+1]

Step 8

Preparation of 5-chloro-6-phenylimidazo[1,5-a]pyridine

N-((6-Chloro-5-phenylpyridin-2-yl)methyl)formamide 37h (7 g, 28.5 mmol) was used as the starting material and the method for the synthesis of 16i in Example 16 was used to generate the title product 5-chloro-6-phenylimidazo[1,5-a]pyridine 37i (5 g, yellow solid). Yield: 77%.

MS m/z (ESI): 229/231[M+1]

Step 9

Preparation of 1-(tert-butyl) 3-methyl 2-(6-phenylimidazo[1,5-a]pyridin-5-yl)malonate A mixture of 5-chloro-6-phenylimidazo[1,5-a]pyridine 37i (0.343 g, 1.5 mmol), methyl tert-butyl malonate (1.57 g, 9 mmol), cesium carbonate (2.45 g, 7.5 mmol), $Pd_2(dba)_3$ (0.275 g, 0.3 mmol), 9,9-dimethyl-4,5-bis(diphenylphosphino)xanthene (0.347 g, 0.6 mmol) and N,N-dimethylacetamide (10 mL) was heated to 150° C. and stirred under nitrogen protection for 6 h. The reaction mixture was cooled to room temperature and concentrated under reduced pressure to remove the solvent. The residue was added with water (50 mL) and extracted with ethyl acetate (50 mL). The organic phase was dried over anhydrous sodium sulfate, filtered and concentrated under reduced pressure to remove the solvent. The residue was purified by silica gel column chromatography (dichloromethane/methanol=100/1) to give the target compound 1-(tert-butyl) 3-methyl 2-(6-phenylimidazo[1,5-a]pyridin-5-yl)malonate 37j (0.2 g, dark brown sticky oil). Yield: 36%.

MS m/z (ESI): 367[M+1]

Step 10

Preparation of methyl 2-(6-phenylimidazo[1,5-a]pyridin-5-yl)acetate

Compound 1-(tert-butyl) 3-methyl 2-(6-phenylimidazo[1,5-a]pyridin-5-yl)malonate 37j (0.2 g, 0.55 mmol) was dissolved in dichloromethane (10 mL) and trifluoroacetic acid (5 mL) was added. The reaction mixture was stirred at room temperature for 2 h and concentrated under reduced pressure to remove the solvent. The residue was dissolved in dichloromethane (20 mL) and washed with saturated aqueous sodium bicarbonate solution (20 mL). The organic phase was dried over anhydrous sodium sulfate, filtered and concentrated under reduced pressure to remove the solvent. The residue was purified by preparative thin layer silica gel chromatography (dichloromethane/methanol=16/1) to give the target product methyl 2-(6-phenylimidazo[1,5-a]pyridin-5-yl)acetate 37k (70 mg, dark brown sticky oil). Yield: 47%.

MS m/z (ESI): 267[M+1]

Step 11

Preparation of 2-(6-phenylimidazo[1,5-a]pyridin-5-yl)acetic Acid

Methyl 2-(6-phenylimidazo[1,5-a]pyridin-5-yl)acetate 37k (70 mg, 0.26 mmol) was used as the starting material and the method for the synthesis of 16j in Example 16 was used to generate the title product 2-(6-phenylimidazo[1,5-a]pyridin-5-yl)acetic acid 37l (15 mg). Yield: 11%.

MS m/z (ESI): 253[M+1]

Step 12

Preparation of N-(4-cyanophenyl)-2-(6-phenylimidazo[1,5-a]pyridin-5-yl)acetamide Compound 2-(6-phenylimidazo[1,5-a]pyridin-5-yl)acetic acid 37l (15 mg, 0.059 mmol) and HATU (34 mg, 0.089 mmol) was dissolved in N,N-dimethylformamide (3 mL) and 4-aminobenzonitrile (14 mg, 0.12 mmol) and DIPEA (23 mg, 0.18 mmol) were added. The reaction mixture was stirred at room temperature for 1 h and concentrated under reduced pressure. The residue was dissolved in dichloromethane (10 mL) and washed with water (10 mL). The organic phase was dried over anhydrous sodium sulfate, filtered and concentrated under reduced pressure to remove the solvent. The residue was purified by preparative thin layer silica gel chromatography (dichloromethane/methanol=16/1) to give the target product N-(4-cyanophenyl)-2-(6-phenylimidazo[1,5-a]pyridin-5-yl)acetamide 37 (3.4 mg, grey solid). Yield: 16%.

MS m/z (ESI): 353[M+1]

$^1$H NMR (400 MHz, DMSO-$d_6$) δ 10.79 (s, 1H), 8.40 (s, 1H), 7.82-7.75 (m, 4H), 7.66 (d, J=9.1 Hz, 1H), 7.51-7.44 (m, 6H), 6.85 (d, J=9.2 Hz, 1H), 4.13 (s, 2H).

Example 38

2-(4-cyanophenyl)-N-(6-phenylimidazo[1,5-a]pyridin-5-yl)acetamide

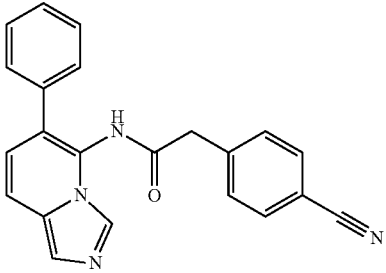

38

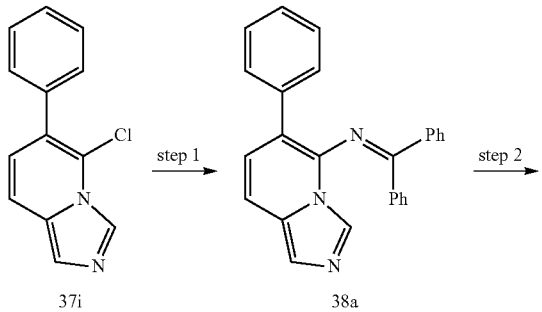

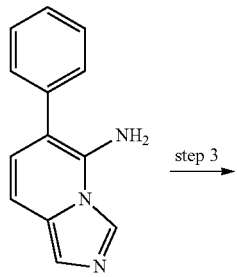

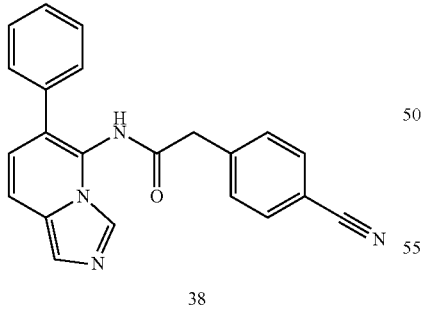

38

Step 1

Preparation of 1,1-diphenyl-N-(6-phenylimidazo[1,5-a]pyridin-5-yl)methanimine

5-Chloro-6-phenylimidazo[1,5-a]pyridine 37i (0.30 g, 1.3 mmol) was used as the starting material and the method for the synthesis of 14f in Example 14 was used to generate the titled product 1,1-diphenyl-N-(6-phenylimidazo[1,5-a]pyridin-5-yl)methanimine 38a (0.48 g, white solid). Yield: 99%.

MS m/z (ESI): 374[M+1]

Step 2

Preparation of 6-phenylimidazo[1,5-a]pyridin-5-amine 1,1-Diphenyl-N-(6-phenylimidazo[1,5-a]pyridin-5-yl)methanimine 38a (0.48 g, 1.28 mmol) was the used as starting material and the method for the synthesis of 14 g in Example 14 was used to generate the title product 6-phenylimidazo[1,5-a]pyridin-5-amine 38b (80 mg, white solid). Yield: 29%.

MS m/z (ESI): 210[M+1]

Step 3

Preparation of 2-(4-cyanophenyl)-N-(6-phenylimidazo[1,5-a]pyridin-5-yl)acetamide Compound 6-phenylimidazo[1,5-a]pyridin-5-amine 38b (28 mg, 0.13 mmol) was dissolved in a mixed solvent of dichloromethane (1.5 mL) and N,N-dimethylformamide (0.15 mL), and to which 2-(4-cyanophenyl)acetic acid (33 mg, 0.2 mmol), EDCI (52 mg, 0.26 mmol) and DMAP (50 mg, 0.4 mmol) were added. The reaction mixture was stirred at room temperature for 4 h, diluted with water (50 mL) and extracted with dichloromethane (30 mL×3). The organic phase was combined, dried over anhydrous sodium sulfate, filtered and concentrated under reduced pressure to remove the solvent. The residue was purified by preparative thin layer silica gel chromatography to give the target compound 2-(4-cyanophenyl)-N-(6-phenylimidazo[1,5-a]pyridin-5-yl)acetamide 38 (10 mg, white solid). Yield: 21%.

MS m/z (ESI): 353[M+1]

$^1$H NMR (400 MHz, DMSO-d6) δ 8.56 (brs, 1H), 8.12 (brs, 1H), 7.57-7.46 (m, 4H), 7.39-7.32 (m, 3H), 7.24-7.19 (m, 3H), 6.82 (d, J=8.9 Hz, 1H), 3.72 (s, 2H).

Example 39

1-(6-oxo-1,6-dihydropyridin-3-yl)-3-(6-phenylimidazo[1,5-a]pyridin-5-yl)urea

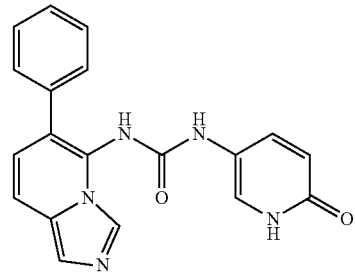

39

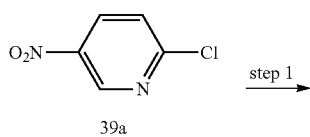

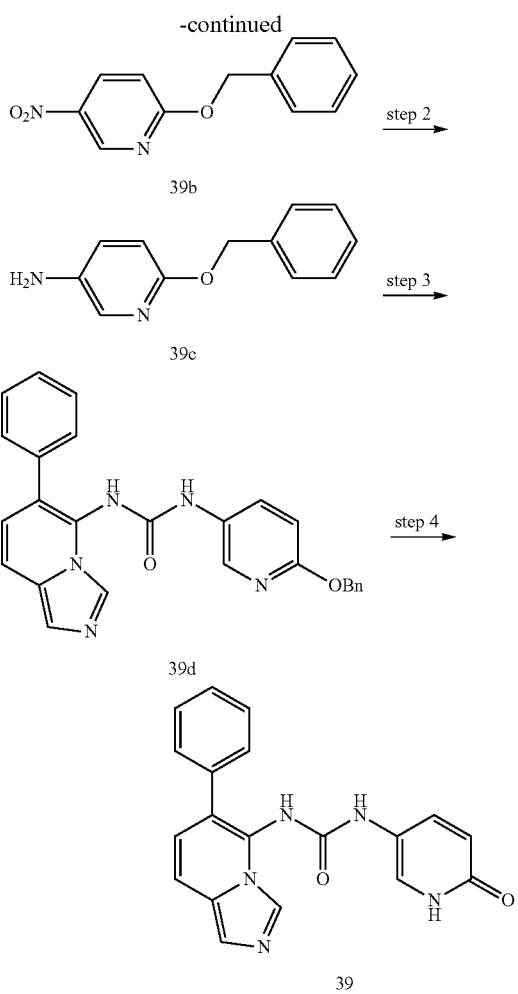

Step 1

Preparation of 2-(benzyloxy)-5-nitropyridine

Compound 2-chloro-5-nitropyridine 39a (324 mg, 3.0 mmol) was dissolved in THF (20 mL), sodium hydride (60%, 180 mg, 4.5 mmol) was added at 0° C. and the resulting mixture was stirred for 30 min. Then 2-chloro-5-nitropyridine (476 mg, 3.0 mmol) was added and the mixture was stirred at room temperature for 2 h. The mixture was added with water (20 mL) and extracted with ethyl acetate (20 mL×3). The organic phase was combined, washed with brine and concentrated under reduced pressure to remove the solvent. The residue was purified by silica gel column chromatography (petroleum ether/ethyl acetate=100/1) to give the target compound 2-(benzyloxy)-5-nitropyridine 39b (500 mg, yellow solid). Yield: 72%.

MS m/z (ESI): 231[M+1]

Step 2

Preparation of 6-(benzyloxy)pyridin-3-amine

Compound 2-(benzyloxy)-5-nitropyridine 39b (500 mg, 2.17 mmol) was dissolved in a mixed solvent of THF and water (30 mL, 1/1). Iron powder (200 mg, 3.57 mmol) and ammonium chloride (1.16 g, 21.7 mmol) were added successively. The reaction mixture was heated under reflux for 24 h. After cooled to room temperature, the mixture was filtered. The filtrate was extracted with ethyl acetate (20 mL×3). The organic phase was combined, washed with brine and concentrated under reduced pressure to remove the solvent. The residue was purified by silica gel column chromatography (dichloromethane/methanol=20/1) to give the target product 6-(benzyloxy)pyridin-3-amine 39c (310 mg). Yield: 71%.

MS m/z (ESI): 201[M+1]

Step 3

Preparation of 1-(6-(benzyloxy)pyridin-3-yl)-3-(6-phenylimidazo[1,5-a]pyridin-5-yl)urea 6-(Benzyloxy)pyridin-3-amine 39c (189 mg, 0.95 mmol) was used as the starting material and the method for the synthesis of 16 in Example 16 was used to generate the title product 1-(6-(benzyloxy)pyridin-3-yl)-3-(6-phenylimidazo [1,5-a]pyridin-5-yl)urea 39d (80 mg, white solid). Yield: 29%.

MS m/z (ESI): 436[M+1]

Step 4

Preparation of 1-(6-oxo-1,6-dihydropyridin-3-yl)-3-(6-phenylimidazo[1,5-a]pyridin-5-yl)urea A mixture of 1-(6-(benzyloxy)pyridin-3-yl)-3-(6-phenylimidazo[1,5-a]pyridin-5-yl)urea 39d (80 mg, 0.18 mmol), Pd/C (20 mg), ethyl acetate (10 mL) and methanol (10 mL) was stirred at room temperature under hydrogen for 6 h. The mixture was filtered, and the filtrate was concentrated under reduced pressure. The residue was purified by silica gel column chromatography (dichloromethane/methanol=20/1) to give the target product 1-(6-oxo-1,6-dihydropyridin-3-yl)-3-(6-phenylimidazo[1,5-a]pyridin-5-yl)urea 39 (20 mg, grey solid). Yield: 32%.

MS m/z (ESI): 346[M+1]

1H NMR (400 MHz, CD$_3$OD) δ 8.34 (s, 1H), 7.64 (d, J=9.3 Hz, 1H), 7.58-7.46 (m, 6H), 7.45-7.37 (m, 2H), 6.98 (d, J=9.3 Hz, 1H), 6.51 (d, J=9.6 Hz, 1H).

Example 40

N-(4-cyano-2-(hydroxymethyl)phenyl)-2-(6-phenylimidazo[1,5-a]pyridin-5-yl)acetamide

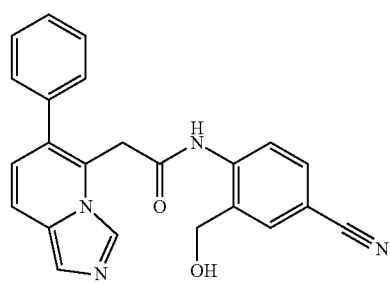

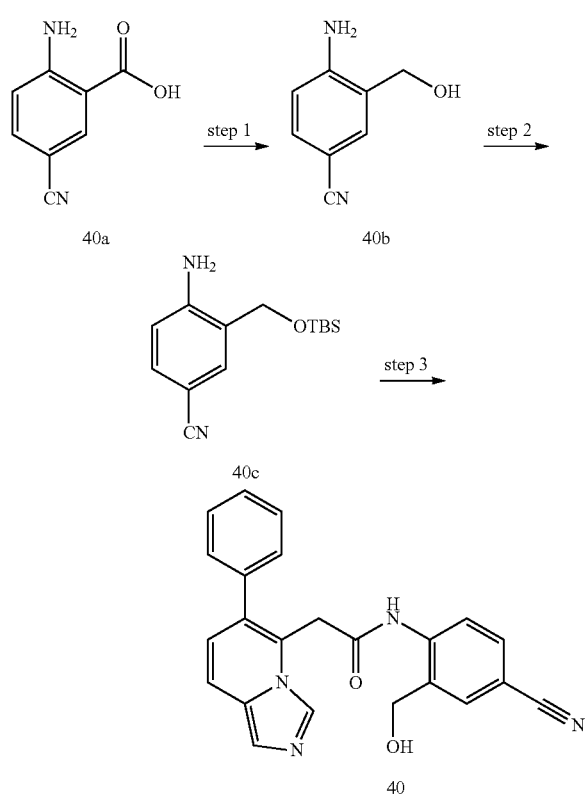

Step 1

Preparation of 4-amino-3-(hydroxymethyl)benzonitrile

Compound 2-amino-5-cyanobenzoic acid 40a (162 mg, 1.0 mmol) was dissolved in THF (20 mL). After cooled to 0° C., the solution was added dropwise with a solution of borane-dimethyl sulfide adduct in THF (2 M, 1.5 mL, 3.0 mmol). The reaction mixture was warmed gradually to room temperature and stirred for 6 h. The reaction was quenched with methanol and the resulting mixture was concentrated under reduced pressure. The residue was purified by silica gel column chromatography (dichloromethane/methanol=10/1) to give the target product 4-amino-3-(hydroxymethyl)benzonitrile 40b (50 mg, white solid). Yield: 34%.

MS m/z (ESI): 149[M+1]

Step 2

Preparation of 4-amino-3-(((tert-butyldimethylsilyl)oxy)methyl)benzonitrile

Compound 4-amino-3-(hydroxymethyl)benzonitrile 40b (210 mg, 1.4 mmol) was mixed with imidazole (190 mg, 2.8 mmol), dichloromethane (20 mL) and tert-butylchlorodimethylsilane (255 mg, 1.7 mmol) successively at 0° C. Then the mixture was stirred at room temperature for 3 h. After the reaction was completed, the mixture was washed with brine. The organic phase was dried over anhydrous sodium sulfate and concentrated under reduced pressure to remove the solvent. The residue was purified by silica gel column chromatography (petroleum ether/ethyl acetate=10/1) to give the target product 4-amino-3-(((tert-butyldimethylsilyl)oxy)methyl)benzonitrile 40c (330 mg, yellow oil). Yield: 90%.

$^1$H NMR (400 MHz, CDCl$_3$) δ 7.39 (dd, J=8.3, 1.9 Hz, 1H), 7.32 (d, J=1.7 Hz, 1H), 6.66 (d, J=8.3 Hz, 1H), 4.67 (s, 2H), 0.91 (s, 9H), 0.11-0.08 (s, 6H).

Step 3

Preparation of N-(4-cyano-2-(hydroxymethyl)phenyl)-2-(6-phenylimidazo[1,5-a]pyridin-5-yl)acetamide Compounds 4-amino-3-(((tert-butyldimethylsilyl)oxy)methyl)benzonitrile 40c (20 mg, 0.08 mmol) and 2-(6-phenylimidazo[1,5-a]pyridin-5-yl)acetic acid 371 (36 mg, 0.12 mmol) were dissolved in N,N-dimethylformamide (5 mL), and HATU (38 mg, 0.1 mmol) and DIPEA (20 mg, 0.24 mmol) were added. The reaction mixture was stirred at room temperature for 2 h and then heated to 65° C. and stirred for 3 h. The reaction mixture was concentrated under reduced pressure, added with water and extracted with ethyl acetate (10 mL×3). The organic phase was combined and concentrated under reduced pressure to remove the solvent. The residue was purified by high performance liquid chromatography to give the target product N-(4-cyano-2-(hydroxymethyl)phenyl)-2-(6-phenylimidazo[1,5-a]pyridin-5-yl)acetamide 40 (1.7 mg, white solid). Yield: 6%.

MS m/z (ESI): 383[M+1]

$^1$H NMR (400 MHz, CDCl$_3$) δ 8.38 (d, J=8.0 Hz, 1H), 8.02 (s, 1H), 7.53-7.43 (m, 7H), 7.39-7.32 (m, 2H), 6.93 (d, J=9.3 Hz, 1H), 4.58 (s, 2H), 4.07 (s, 2H).

Example 41

2-(7-chloroimidazo[1,5-a]pyridin-5-yl)-N-(4-cyanophenyl)acetamide

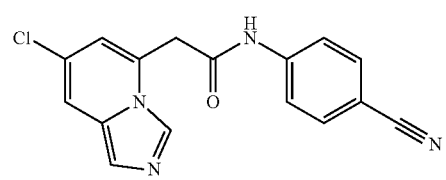

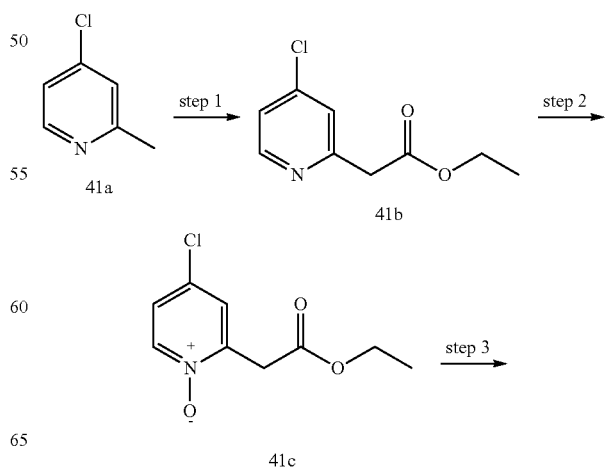

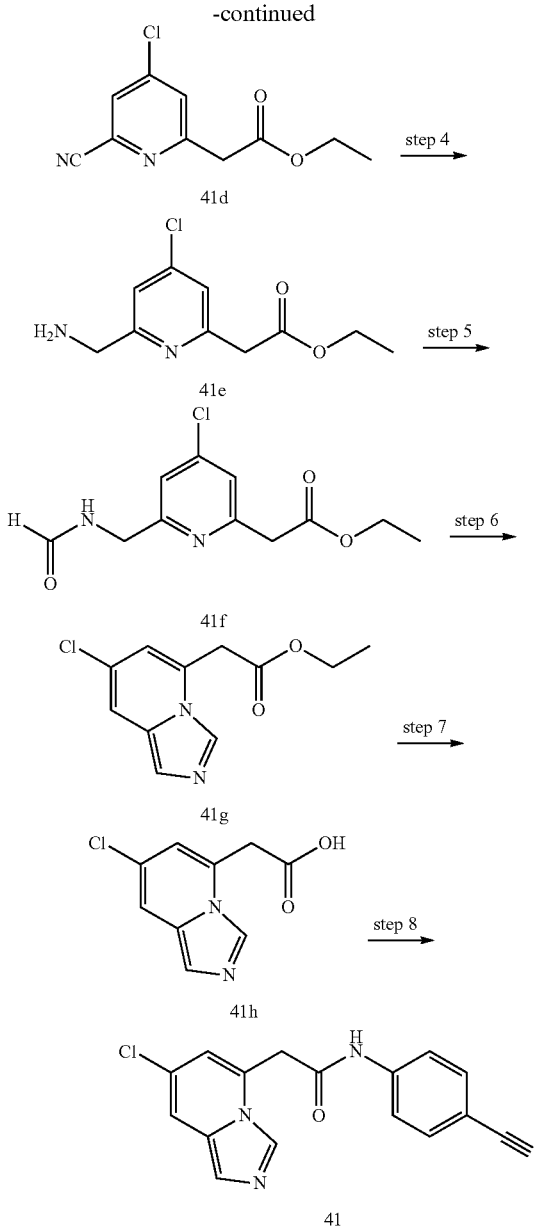

Step 1

Preparation of ethyl 2-(4-chloropyridin-2-yl)acetate

A solution of lithium bis(trimethylsilyl)amide (1.3 M, 46 mL, 60 mmol) in THF (50 mL) was cooled to 0° C. and a solution of 4-chloro-2-methylpyridine 41a (2.55 g, 20 mmol) in THF (10 mL) was added dropwise. The reaction mixture was stirred at room temperature for 2 h. Diethyl carbonate (4.72 g, 40 mmol) was added and the resulting mixture was stirred for 2 h. The reaction was quenched with saturated ammonium chloride solution (10 mL) and concentrated under reduced pressure. The residue was added with water (100 mL) and extracted with ethyl acetate (100 mL×3). The organic phase was combined, dried over anhydrous sodium sulfate, filtered and concentrated under reduced pressure to remove the solvent. The residue was purified by silica gel column chromatography (petroleum ether/ethyl acetate=10/1) to give the target product ethyl 2-(4-chloropyridin-2-yl)acetate 41b (3.4 g, light yellow liquid). Yield: 85%.

MS m/z (ESI): 200[M+1]

Step 2

Preparation of 4-chloro-2-(2-ethoxy-2-oxoethyl)pyridine 1-oxide

Compound ethyl 2-(4-chloropyridin-2-yl)acetate 41b (3.4 g, 17 mmol) was dissolved in dichloromethane (100 mL) and mCPBA (5.86 g, 34 mmol) was added. The mixture was stirred at room temperature for 30 min, washed with saturated sodium thiosulfate solution (50 mL) and saturated sodium bicarbonate solution (50 mL). The organic phase was dried over anhydrous sodium sulfate, filtered and concentrated under reduced pressure to remove the solvent. The residue was purified by silica gel column chromatography (petroleum ether/ethyl acetate=4/1 to 1/1) to give the target product 4-chloro-2-(2-ethoxy-2-oxoethyl)pyridine 1-oxide 41c (1.45 g, light yellow oil). Yield: 40%.

MS m/z (ESI): 216[M+1]

Step 3

Preparation of ethyl 2-(4-chloro-6-cyanopyridin-2-yl)acetate

Compound 4-chloro-2-(2-ethoxy-2-oxoethyl)pyridine 1-oxide 41c (1.45 g, 6.72 mmol) was dissolved in acetonitrile (10 mL) and triethylamine (40 mL), and trimethylsilanecarbonitrile (6.67 g, 67.2 mmol) was added. The reaction mixture was heated to 90° C. in a sealed tube and stirred for 24 h. After cooled to room temperature, the mixture was concentrated under reduced pressure. The residue was purified by silica gel column chromatography (petroleum ether/ethyl acetate=10/1 to 1/1) to give the target product ethyl 2-(4-chloro-6-cyanopyridin-2-yl)acetate 41d (230 mg, light brown oil). Yield: 15%.

MS m/z (ESI): 225[M+1]

Step 4

Preparation of ethyl 2-(6-(aminomethyl)-4-chloropyridin-2-yl)acetate

Compound ethyl 2-(4-chloro-6-cyanopyridin-2-yl)acetate 41d (112 mg, 0.5 mmol) was dissolved in ethanol (20 mL) and Raney-Ni (0.4 g) was added. The reaction mixture was degassed with hydrogen for 6 times and stirred at room temperature under balloon pressure of hydrogen for 2 h. The mixture was filtered and the filtrate was concentrated under reduced pressure to give the target product ethyl 2-(6-(aminomethyl)-4-chloropyridin-2-yl)acetate 41e (130 mg, brown oil, crude product). Yield: 100%. The product was used in the next step without purification.

MS m/z (ESI): 229[M+1]

Step 5

Preparation of ethyl 2-(4-chloro-6-(formamidomethyl)pyridin-2-yl)acetate

Compound ethyl 2-(6-(aminomethyl)-4-chloropyridin-2-yl)acetate 41e (130 mg, 0.5 mmol) was dissolved in dichloromethane (5 mL) and added successively with formic acid (35 mg, 0.75 mmol), triethyl amine (152 mg, 1.5 mmol) and EDCI (144 mg, 0.75 mmol). The mixture was stirred at room temperature for 30 min, diluted with dichloromethane (20 mL) and washed with water (20 mL). The organic phase was dried over anhydrous sodium sulfate, filtered and concentrated under reduced pressure to remove the solvent. The residue was purified by silica gel column chromatography (petroleum ether/ethyl acetate=4/1 to 1/1) to give the target product ethyl 2-(4-chloro-6-(formamidomethyl)pyridin-2-yl)acetate 41f (65 mg, colorless oil). Yield for two steps: 50%.

MS m/z (ESI): 257[M+1]

Step 6

Preparation of ethyl 2-(7-chloroimidazo[1,5-a]pyridin-5-yl)acetate

Compound ethyl 2-(4-chloro-6-(formamidomethyl)pyridin-2-yl)acetate 41f (65 mg, 0.25 mmol) was dissolved in dichloromethane (5 mL), added with trifluoroacetic anhydride 2 mL) and stirred at room temperature for 10 min. The solvent was removed under reduced pressure. The residue was dissolved in dichloromethane (20 mL) and washed with a solution of sodium bicarbonate (20 mL). The organic phase was dried over anhydrous sodium sulfate, filtered and concentrated under reduced pressure to give the target product ethyl 2-(7-chloroimidazo[1,5-a]pyridin-5-yl)acetate 41 g (60 mg, light yellow solid). Yield: 100%.

MS m/z (ESI): 239[M+1]

Step 7

Preparation of 2-(7-chloroimidazo[1,5-a]pyridin-5-yl)acetic Acid

To a mixture of ethyl 2-(7-chloroimidazo[1,5-a]pyridin-5-yl)acetate 41 g (60 mg, 0.25 mmol), methanol (4 mL) and water (1 mL) was added sodium hydroxide (50 mg, 1.25 mmol). The reaction mixture was stirred at room temperature for 10 min. The organic solvent was removed under reduced pressure. The residue was added with water (5 mL), acidified with hydrochloride solution (2 M) to pH=3 and extracted with ethyl acetate (10 mL×3). The organic phase was combined, dried over anhydrous sodium sulfate, filtered and concentrated under reduced pressure to give the target product 2-(7-chloroimidazo[1,5-a]pyridin-5-yl)acetic acid 41h (42 mg, white solid). Yield: 80%.

MS m/z (ESI): 211[M+1]

Step 8

Preparation of 2-(7-chloroimidazo[1,5-a]pyridin-5-yl)-N-(4-cyanophenyl)acetamide Compound 2-(7-chloroimidazo[1,5-a]pyridin-5-yl)acetic acid 41h (42 mg, 0.2 mmol) was dissolved in N,N-dimethylformamide (5 mL) and HATU (114 mg, 0.3 mmol) was added. The mixture was stirred at room temperature for 5 min. Then 4-aminobenzonitrile (47 mg, 0.4 mmol) and triethylamine (61 mg, 0.6 mmol) were added and the reaction mixture was stirred for 5 min. The reaction mixture was concentrated under reduced pressure, added with water (10 mL) and extracted with ethyl acetate (10 mL×3). The organic phase was combined and concentrated under reduced pressure to remove the solvent. The residue was purified by preparative thin layer silica gel chromatography (dichloromethane/methanol=20/1) to give the target product 2-(7-chloroimidazo[1,5-a]pyridin-5-yl)-N-(4-cyanophenyl) acetamide 41 (30 mg, white solid). Yield: 48%.

MS m/z (ESI): 311[M+1]

$^1$H NMR (400 MHz, DMSO-d6) 10.82 (s, 1H), 8.40 (s, 1H), 7.81-7.75 (m, 4H), 7.73 (d, J=1.6 Hz, 1H), 7.42 (s, 1H), 6.76 (d, J=1.9 Hz, 1H), 4.23 (s, 2H).

Example 42

4-(((((6-phenylimidazo[1,5-a]pyridin-5-yl)methyl)amino)methyl)benzonitrile

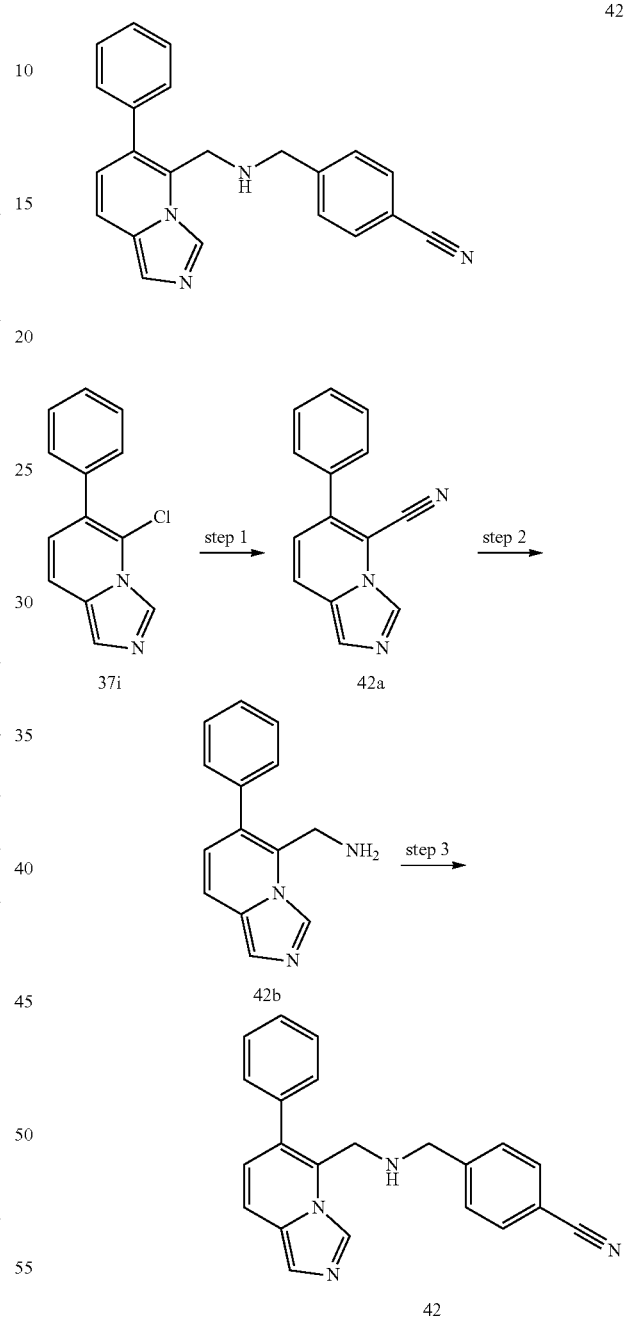

Step 1

Preparation of 6-phenylimidazo[1,5-a]pyridine-5-carbonitrile

A mixture of 5-chloro-6-phenylimidazo[1,5-a]pyridine 37i (0.2 g, 0.87 mmol), zinc cyanide (62 mg, 0.52 mmol), zinc powder (17 mg, 0.26 mmol), Pd$_2$(dba)$_3$ (156 mg, 0.17 mmol), dppf (95 mg, 0.17 mmol) and N,N-dimethylacetamide (10 mL) was heated to 150° C. and stirred for 2 h under nitrogen protection. After cooled to room temperature, the mixture was filtered. The filtrate was concentrated under reduced pressure and the residue was purified by silica gel column chromatography to give the target product 6-phenylimidazo[1,5-a]pyridine-5-carbonitrile 42a (200 mg). Yield: 100%.

MS m/z (ESI): 220[M+1]

Step 2

Preparation of (6-phenylimidazo[1,5-a]pyridin-5-yl) methanamine

A mixture of 6-phenylimidazo[1,5-a]pyridine-5-carbonitrile 42a (200 mg, 0.87 mmol) and borane tetrahydrofuran complex (1 M, 5 mL, 5 mmol) was heated to reflux and stirred under nitrogen protection for 2 h. After cooled to room temperature, the mixture was added with methanol and stirred overnight. The mixture was concentrated under reduced pressure to give the target product (6-phenylimidazo[1,5-a]pyridin-5-yl)methanamine 42b (120 mg).

Yield for two steps: 62%.

MS m/z (ESI): 224[M+1]

Step 3

Preparation of 4-(((((6-phenylimidazo[1,5-a]pyridin-5-yl)methyl)amino)methyl)benzonitrile Compound (6-phenylimidazo[1,5-a]pyridin-5-yl)methanamine 42b (75 mg, 0.34 mmol) was dissolve in methanol (5 mL), 4-formylbenzonitrile (66 mg, 0.5 mmol) was added and the reaction mixture was stirred at room temperature for 2 h. After cooled to 0° C., the reaction mixture was added with sodium triacetoxyborohydride (214 mg, 1.10 mmol) and stirred at room temperature for 1 h. The mixture was poured into water (50 mL) and extracted with dichloromethane (30 mL×3). The organic phase was combined, dried over anhydrous sodium sulfate, filtered and concentrated under reduced pressure to remove the solvent. The residue was purified by preparative thin layer silica gel chromatography (petroleum ether/ethyl acetate=2/1) to give the target product 4-((((6-phenylimidazo[1,5-a]pyridin-5-yl)methyl) amino)methyl)benzonitrile 42 (37 mg, brown oil). Yield: 33%.

MS m/z (ES): 339[M+1]

$^1$H NMR (400 MHz, DMSO-d6) δ 8.60 (s, 1H), 7.70 (d, J=8.3 Hz, 2H), 7.60 (d, J=9.2 Hz, 1H), 7.49 (s, 1H), 7.46-7.36 (m, 7H), 6.76 (d, J=9.2 Hz, 1H), 3.89 (s, 2H), 3.75 (s, 2H).

Example 43

N-(4-cyanophenyl)-N-methyl-2-(6-phenylimidazo[1,5-a]pyridin-5-yl)acetamide

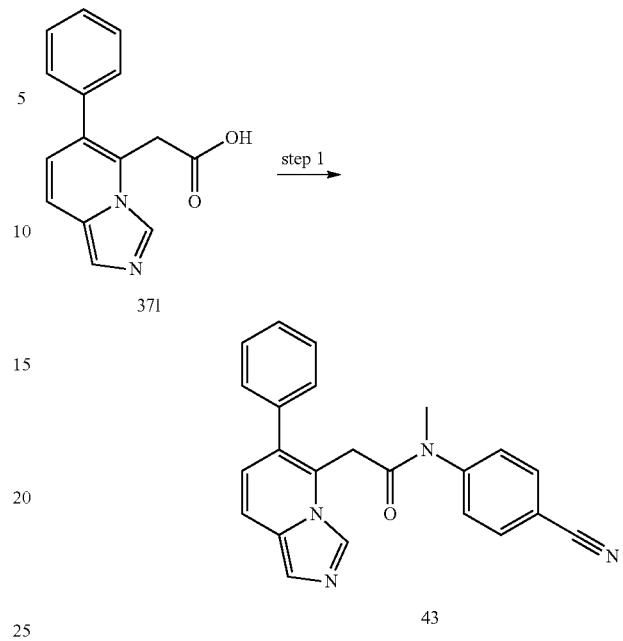

Preparation of N-(4-cyanophenyl)-N-methyl-2-(6-phenylimidazo[1,5-a]pyridin-5-yl)acetamide A mixture of 2-(6-phenylimidazo[1,5-a]pyridin-5-yl)acetic acid 371 (30 mg, 0.12 mmol), HATU (68 mg, 0.18 mmol), 4-(methylamino)benzonitrile (24 mg, 0.18 mmol), DIPEA (31 mg, 0.24 mmol) and dichloromethane (10 mL) was stirred at room temperature for 1 h. The mixture was diluted with dichloromethane and washed with water. The organic phase was dried over anhydrous sodium sulfate, filtered and concentrated under reduced pressure to remove the solvent. The residue was purified by preparative thin layer silica gel chromatography to give the target product N-(4-cyanophenyl)-N-methyl-2-(6-phenylimidazo[1,5-a]pyridin-5-yl)acetamide 43 (3 mg, white solid). Yield: 7%.

MS m/z (ESI): 367[M+1]

$^1$H NMR (400 MHz, CDCl$_3$) δ 7.95 (s, 1H), 7.68 (d, J=6.3 Hz, 2H), 7.51-7.37 (m, 9H), 6.75 (d, J=8.1 Hz, 1H), 3.71 (s, 2H), 3.35 (s, 3H).

Example 44

N-(4-cyanophenyl)-2-(6-phenylimidazo[1,5-a]pyridin-5-yl)propanamide

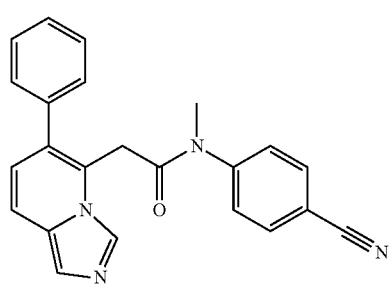

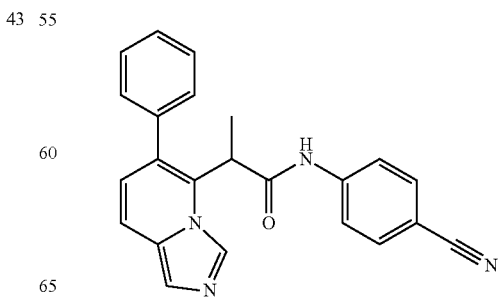

113

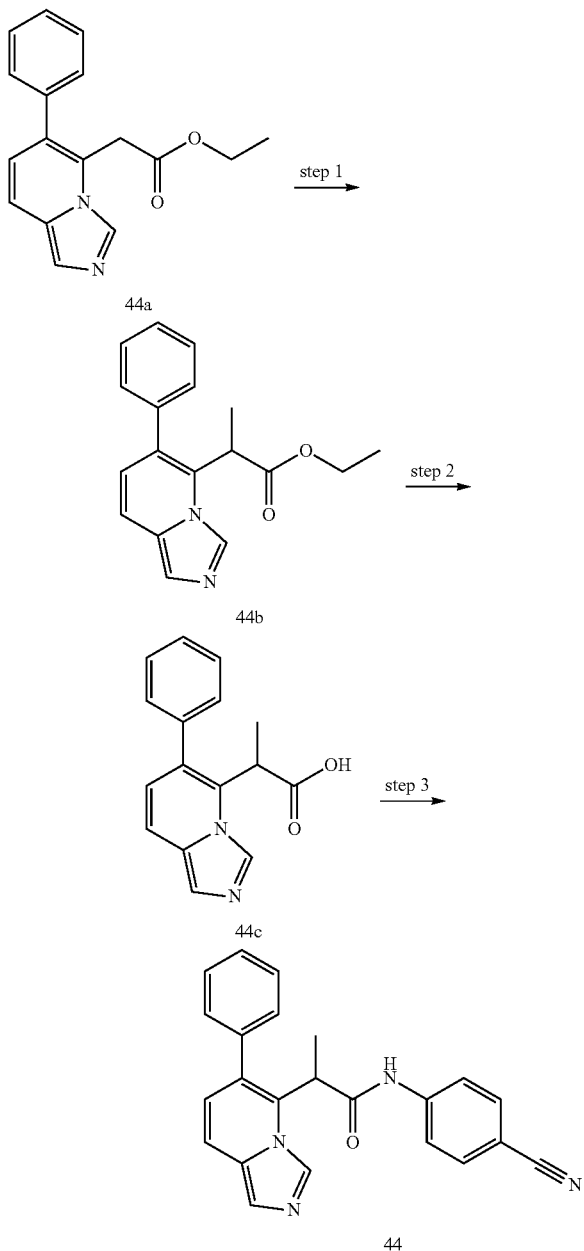

44a

44b

44c

44

Step 1

Preparation of ethyl 2-(6-phenylimidazo[1,5-a]pyridin-5-yl)propanoate

Diisopropylamine (48 mg, 0.48 mmol) was dissolved in THF (3 mL) and the solution was cooled to −78° C. Then a solution of n-BuLi in hexane (2.4 M, 0.2 mL, 0.48 mmol) was added under nitrogen. The reaction mixture was warmed gradually to −40° C. and stirred for 1 h. A solution of ethyl 2-(6-phenylimidazo[1,5-a]pyridin-5-yl)acetate 44a (67 mg, 0.24 mmol) in THF (0.5 mL) was added and the resulting mixture was stirred at −40° C. for 1 h. Iodomethane (102 mg, 0.72 mmol) was added. The reaction mixture was warmed gradually to 0° C., added with water (10 mL) and extracted with ethyl acetate (20 mL×2). The organic phase was combined and concentrated under reduced pressure to give the target product ethyl 2-(6-phenylimidazo[1,5-a]pyridin-5-yl)propanoate 44b (68 mg, crude product). The product was used directly in the next step without further purification.

MS m/z (ESI): 295[M+1]

Step 2

Preparation of 2-(6-phenylimidazo[1,5-a]pyridin-5-yl)propanoic Acid

Ethyl 2-(6-phenylimidazo[1,5-a]pyridin-5-yl)propanoate 44b (68 mg, crude product) was dissolved in a mixed solvent of methanol (1 mL) and water (0.1 mL), and sodium hydroxide (37 mg, 0.92 mmol) was added. The reaction mixture was stirred at room temperature for 1 h, acidified with hydrochloride solution (1 M) to pH=5 and extracted with ethyl acetate (10 mL×8). The organic phase was combined and concentrated under reduced pressure to give the target product 2-(6-phenylimidazo[1,5-a]pyridin-5-yl)propanoic acid 44c (38 mg, crude product). The product was used directly in the next step without further purification.

MS m/z (ESI): 267[M+1]

Step 3

Preparation of N-(4-cyanophenyl)-2-(6-phenylimidazo[1,5-a]pyridin-5-yl)propenamide Compound 2-(6-phenylimidazo[1,5-a]pyridin-5-yl)propanoic acid 44c (38 mg, crude product) was dissolved in dichloromethane (1 mL), then oxalyl chloride (0.2 mL) and N,N-dimethylformamide (0.025 mL) were added and the reaction mixture was stirred for 1 h. The mixture was concentrated under reduced pressure. The residue was dissolved in dichloromethane (1 mL) and added dropwise to the mixture of 4-aminobenzonitrile (20 mg, 0.17 mmol) and sodium hydride (60%, 9 mg, 0.21 mmol). The reaction mixture was stirred at room temperature for 1 h, quenched with water (10 mL) and extracted with dichloromethane (10 mL×3). The organic phase was combined, dried over anhydrous sodium sulfate, filtered and concentrated under reduced pressure to remove the solvent. The residue was purified by high performance liquid chromatography to give the target product N-(4-cyanophenyl)-2-(6-phenylimidazo[1,5-a]pyridin-5-yl)propenamide 44 (3.2 mg, white solid). Yield for three steps: 4%.

MS m/z (ES): 367[M+1]

$^1$H NMR (400 MHz, DMSO-$d_6$) δ 10.13 (s, 1H), 8.40 (s, 1H), 7.72 (d, J=8.8 Hz, 2H), 7.59 (dd, J=9.0, 2.9 Hz, 3H), 7.50 (s, 1H), 7.43-7.16 (m, 5H), 6.68 (d, J=9.2 Hz, 1H), 4.40 (q, J=7.2 Hz, 1H), 1.60 (d, J=7.3 Hz, 3H).

Example 45

N-(4-cyanophenyl)-N-hydroxy-2-(6-phenylimidazo[1,5-a]pyridin-5-yl)acetamide

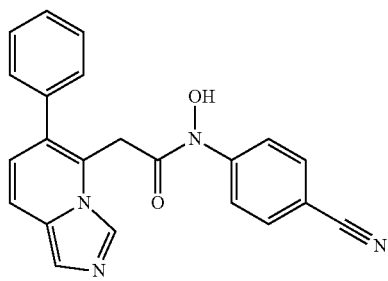

45

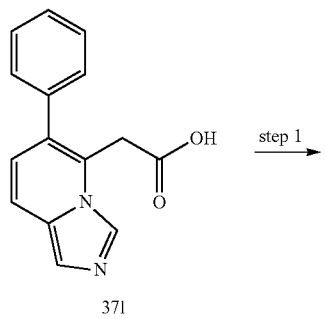

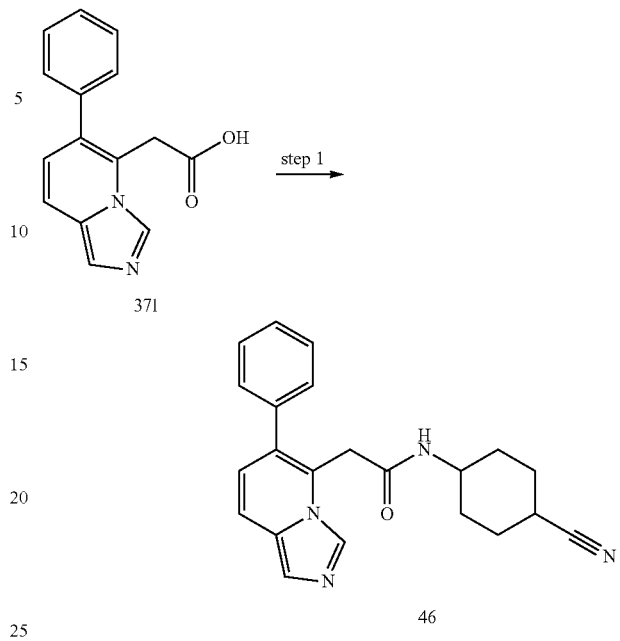

Preparation of N-(4-cyanophenyl)-N-hydroxy-2-(6-phenylimidazo[1,5-a]pyridin-5-yl)acetamide Compound 2-(6-phenylimidazo[1,5-a]pyridin-5-yl)acetic acid 371 (63 mg, 0.25 mmol) was dissolved in dichloromethane (10 mL), then oxalyl chloride (95 mg, 0.75 mmol) and N,N-dimethylformamide (0.025 mL) were added and the reaction mixture was stirred for 1 h. The mixture was concentrated under reduced pressure. The residue was dissolved in dichloromethane (1 mL) and added dropwise to a mixture of 4-(hydroxyamino)benzonitrile (101 mg, 0.75 mmol) and DIPEA (0.5 mL) in THF (10 mL). The reaction mixture was stirred at 0° C. for 1 h. After the reaction was completed, the reaction mixture was concentrated under reduced pressure. The residue was purified by silica gel column chromatography (dichloromethane/methanol=100/1 to 10/1) to give the target product N-(4-cyanophenyl)-N-hydroxy-2-(6-phenylimidazo[1,5-a]pyridin-5-yl)acetamide 45 (13 mg, white solid). Yield: 14%.

MS m/z (ESI): 369[M+1]

$^1$H NMR (400 MHz, CD$_3$OD) δ 8.26 (s, 1H), 7.96 (d, J=8.9 Hz, 2H), 7.75 (d, J=8.9 Hz, 2H), 7.65 (d, J=9.3 Hz, 1H), 7.85-7.39 (m, 6H), 6.92 (d, J=9.3 Hz, 1H), 4.45 (s, 2H).

Example 46

N-(4-cyanocyclohexyl)-2-(6-phenylimidazo[1,5-a]pyridin-5-yl)acetamide

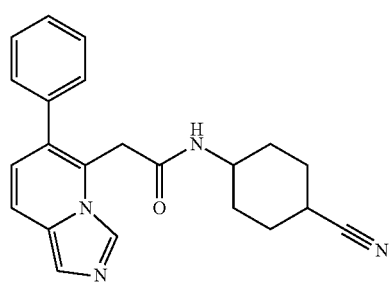

Preparation of N-(4-cyanocyclohexyl)-2-(6-phenylimidazo[1,5-a]pyridin-5-yl)acetamide A mixture of 2-(6-phenylimidazo[1,5-a]pyridin-5-yl)acetic acid 371 (40 mg, 0.16 mmol), HATU (121 mg, 0.32 mmol), 4-aminocyclohexane-1-carbonitrile (hydrochloride salt, 31 mg, 0.19 mmol), and triethylamine (48 mg, 0.48 mmol) in dichloromethane (15 mL) was stirred at room temperature for 30 min. The mixture was washed with water (5 mL×3). The organic phase was dried over anhydrous sodium sulfate, filtered and concentrated under reduced pressure to remove the solvent. The residue was purified by reversed phase high performance liquid preparative chromatography [XBridge C18, 30×150 mm, 5 μm; acetonitrile-water (containing 0.1% formic acid) from 10% to 90%, 25 mL/min] to give the target product N-(4-cyanocyclohexyl)-2-(6-phenylimidazo[1,5-a]pyridin-5-yl)acetamide 46 (4.1 mg, solid). Yield: 4.2%.

MS m/z (ESI): 359[M+1]

$^1$H NMR (400 MHz, DMSO-d6) δ 8.38 (d, J=7.9 Hz, 1H), 8.25 (s, 1H), 7.60 (d, J=9.2 Hz, 1H), 7.48-7.43 (m, 6H), 6.81 (d, J=9.2 Hz, 1H), 3.81 (s, 2H), 3.71-3.64 (m, 1H), 3.04-3.03 (m, 1H), 1.92-1.87 (m, 2H), 1.78-1.72 (m, 2H), 1.71-1.64 (m, 2H), 1.53-1.45 (m, 2H).

Example 47

N-(4-(morpholine-4-carbonyl)phenyl)-2-(6-phenylimidazo[1,5-a]pyridin-5-yl)acetamide

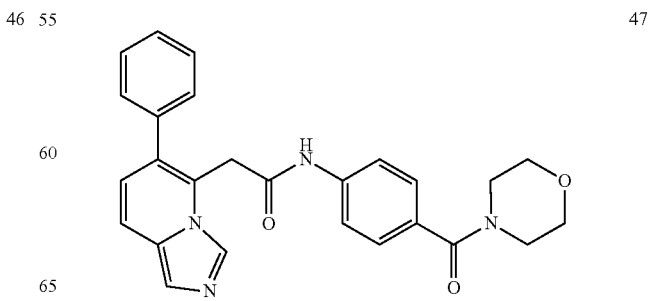

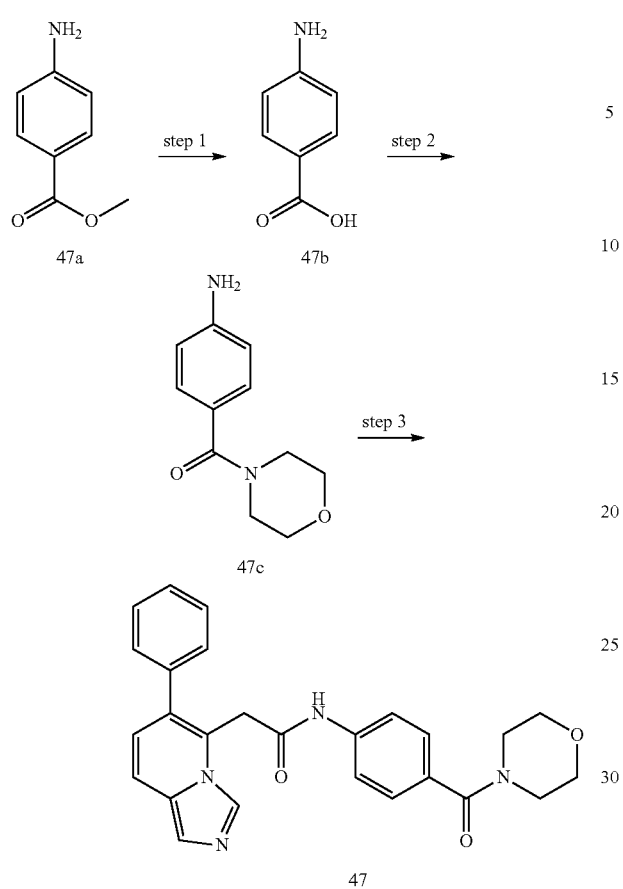

47

Step 1

Preparation of 4-aminobenzoic Acid

A mixture of methyl 4-aminobenzoate 47a (2.26 g, 15 mmol), potassium hydroxide (2.52 g, 45 mmol), water (30 mL) and methanol (30 mL) was stirred at 55° C. for 3 h. After cooled to room temperature, the mixture was concentrated under reduced pressure. The residue was dissolved in water (100 mL), acidified with hydrochloride solution (1 M) to pH=4 and extracted with ethyl acetate (50 mL×3). The organic phase was combined, dried over anhydrous sodium sulfate, filtered and concentrated under reduced pressure to give the target product 4-aminobenzoic acid 47b (1.6 g, brown solid). Yield: 78%.

MS m/z (ESI): 138[M+1]

Step 2

Preparation of (4-aminophenyl)(morpholino)methanone

A mixture of 4-aminobenzoic acid 47b (137 g, 1 mmol), morpholine (96 mg, 1.1 mmol), DIPEA (387 mg, 3 mmol), and HATU (380 mg, 1 mmol) in N,N-dimethylformamide (5 mL) was stirred at room temperature for 2 h. The reaction was quenched with water and extracted with ethyl acetate (50 mL×2). The organic phase was combined and concentrated under reduced pressure to remove the solvent. The residue was purified by silica gel column chromatography (dichloromethane/methanol=100/1 to 10/1) to give the target product (4-aminophenyl)(morpholino)methanone 47c (103 mg, brown oil). Yield: 50%.

MS m/z (ESI): 207[M+1]

Step 3

Preparation of N-(4-(morpholine-4-carbonyl)phenyl)-2-(6-phenylimidazo[1,5-a]pyridin-5-yl)acetamide A mixture of 2-(6-phenylimidazo[1,5-a]pyridin-5-yl)acetic acid 37l (50 mg, 0.2 mmol), HATU (76 mg, 0.2 mmol), (4-aminophenyl)(morpholino)methanone 47c (80 mg, 0.4 mmol), and DIPEA (129 mg, 1 mmol) in N,N-dimethylformamide (2 mL) was stirred at room temperature for 1 h. The mixture was diluted with dichloromethane and washed with water. The organic phase was dried over anhydrous sodium sulfate, filtered and concentrated under reduced pressure to remove the solvent. The residue was purified by reversed phase high performance liquid preparative chromatography to give the target product N-(4-(morpholine-4-carbonyl)phenyl)-2-(6-phenylimidazo[1,5-a]pyridin-5-yl)acetamide 47 (11 mg, white solid). Yield: 12%.

MS m/z (ES): 441[M+1]

$^1$H NMR (400 MHz, CD$_3$OD) δ 8.33 (s, 1H), 7.68 (d, J=8.6 Hz, 2H), 7.63 (d, J=9.3 Hz, 1H), 7.51-7.42 (m, 8H), 6.90 (d, J=9.3 Hz, 1H), 4.12 (s, 2H), 3.71-3.52 (m, 8H).

Example 48

N-(4-(4-methoxypiperidine-1-carbonyl)phenyl)-2-(6-phenylimidazo[1,5-a]pyridin-5-yl)acetamide

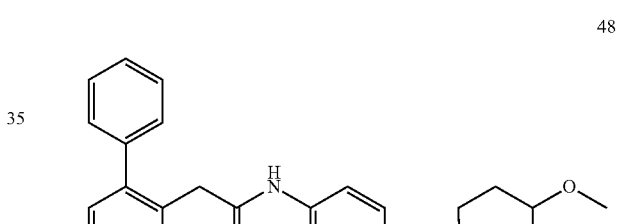

48

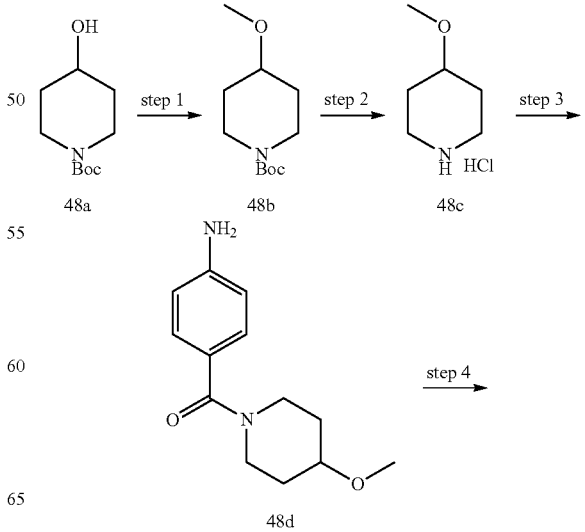

119

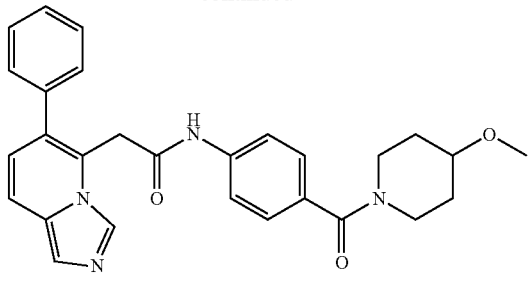

48

Step 1

Preparation of tert-butyl 4-methoxypiperidine-1-carboxylate

A mixture of tert-butyl 4-hydroxypiperidine-1-carboxylate 48a (1.0 g, 5 mmol) and N,N-dimethylformamide (20 mL) was cooled to 0° C., and added with sodium hydride (60%, 360 mg, 15 mmol). The reaction mixture was stirred at 0° C. for 30 min, added with iodomethane (2.13 g, 15 mmol), then warmed to room temperature and stirred for 2 h. The reaction was quenched with saturated aqueous ammonium chloride solution and extracted with ethyl acetate (50 mL×2). The organic phase was combined and concentrated under reduced pressure to remove the solvent. The residue was purified by silica gel column chromatography (petroleum ether/ethyl acetate=100/0 to 1/1) to give the target product tert-butyl 4-methoxypiperidine-1-carboxylate 48b (700 mg, brown oil). Yield: 65%.

MS m/z (ESI): 160[M+1-56]

Step 2

Preparation of 4-methoxypiperidine

Compound tert-butyl 4-methoxypiperidine-1-carboxylate 48b (242 mg, 1.12 mmol) was dissolved in ethyl acetate (12 mL) and added with a solution of hydrochloride in ethanol (33%, 3 mL). The reaction mixture was stirred at room temperature for 2 h and concentrated under reduced pressure to give the target product 4-methoxypiperidine 48c (hydrochloride salt, 180 mg, brown solid). Yield: 100%.

MS m/z (ESI): 116[M+1]

Step 3

Preparation of (4-aminophenyl)(4-methoxypiperidin-1-yl)methanone

A mixture of 4-aminobenzoic acid 47b (153 mg, 1.12 mmol), 4-methoxypiperidine 48c (hydrochloride salt, 180 mg, 1.12 mmol), DIPEA (816 mg, 6.72 mmol), and HATU (446 mg, 1.17 mmol) in N,N-dimethylformamide (5 mL) was stirred at room temperature for 2 h. The mixture was quenched with water and extracted with ethyl acetate (50 mL×2). The organic phase was combined and concentrated under reduced pressure to remove the solvent. The residue was purified by silica gel column chromatography (dichloromethane/methanol=100/1 to 10/1) to give the target product (4-aminophenyl)(4-methoxypiperidin-1-yl)methanone 48d (160 mg, brown oil). Yield: 61%.

MS m/z (ESI): 235[M+1]

120

Step 4

Preparation of N-(4-(4-methoxypiperidine-1-carbonyl)phenyl)-2-(6-phenylimidazo[1,5-a]pyridin-5-yl)acetamide A mixture of 2-(6-phenylimidazo[1,5-a]pyridin-5-yl)acetic acid 37l (82 mg, 0.271 mmol), HATU (105 mg, 0.271 mmol), (4-aminophenyl)(4-methoxypiperidin-1-yl)methanone 48d (80 mg, 0.34 mmol), and DIPEA (179 mg, 1.35 mmol) in N,N-dimethylformamide (2 mL) was stirred at room temperature for 1 h. After completed, the reaction was quenched with water and extracted with ethyl acetate (50 mL×2). The organic phase was combined, dried over anhydrous sodium sulfate, filtered and concentrated under reduced pressure to remove the solvent. The residue was purified by silica gel column chromatography (dichloromethane/methanol=100/1 to 10/1) and further purified by reversed phase high performance liquid preparative chromatography to give the target product N-(4-(4-methoxypiperidine-1-carbonyl)phenyl)-2-(6-phenylimidazo[1,5-a]pyridin-5-yl)acetamide 48 (13 mg, white solid). Yield: 10%.

MS m/z (ES): 469[M+1]

$^1$H NMR (400 MHz, CD$_3$OD) δ 8.38 (s, 1H), 7.70-7.64 (m, 3H), 7.54-7.41 (m, 8H), 6.93 (d, J=9.3 Hz, 1H), 4.14 (s, 2H), 4.02 (s, 1H), 3.66 (s, 1H), 3.57-3.52 (m, 3H), 3.39 (s, 3H), 2.04-1.89 (m, 2H), 1.64-1.43 (m, 2H).

Example 49

N-(2-morpholinoethyl)-4-(2-(6-phenylimidazo[1,5-a]pyridin-5-yl)acetamido)benzamide

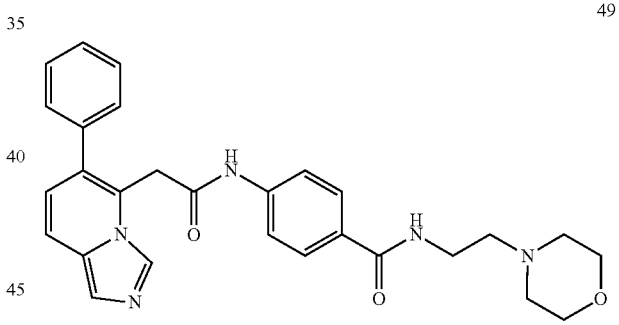

49

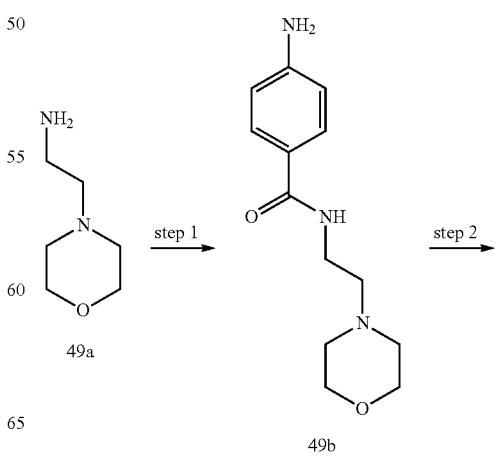

-continued

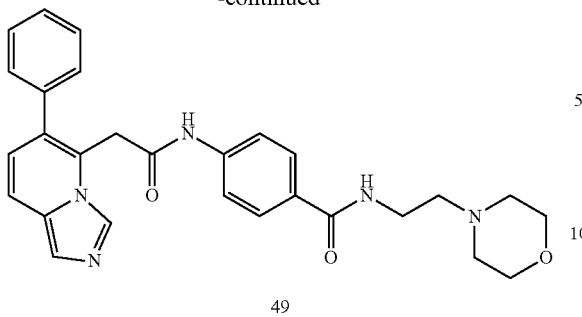

49

Step 1

Preparation of 4-amino-N-(2-morpholinoethyl)benzamide

A mixture of 4-aminobenzoic acid 47b (102 mg, 0.75 mmol), 2-morpholinoethan-1-amine 49a (117 mg, 0.9 mmol), DIPEA (290 mg, 2.25 mmol), and HATU (313 mg, 0.825 mmol) in N,N-dimethylformamide (5 mL) was stirred at room temperature for 2 h. The reaction was quenched with water and extracted with ethyl acetate (50 mL×2). The organic phase was combined and concentrated under reduced pressure to remove the solvent. The residue was purified by silica gel column chromatography (dichloromethane/methanol=100/1 to 10/1) to give the target product 4-amino-N-(2-morpholinoethyl)benzamide 49b (66 mg, brown oil). Yield: 35%.

MS m/z (ESI): 250[M+1]

Step 2

Preparation of N-(2-morpholinoethyl)-4-(2-(6-phenylimidazo[1,5-a]pyridin-5-yl)acetamido)benzamide A mixture of 2-(6-phenylimidazo[1,5-a]pyridin-5-yl)acetic acid 37l (70 mg, 0.277 mmol), HATU (105 mg, 0.277 mmol), 4-amino-N-(2-morpholinoethyl)benzamide 49b (66 mg, 0.265 mmol), and DIPEA (179 mg, 1.385 mmol) in N,N-dimethylformamide (2 mL) was stirred at room temperature for 2 h. The reaction was quenched with water and extracted with ethyl acetate (50 mL×2). The organic phase was combined, dried over anhydrous sodium sulfate, filtered and concentrated under reduced pressure to remove the solvent. The residue was purified by silica gel column chromatography (dichloromethane/methanol=100/1 to 10/1), and further purified by reversed phase high performance liquid preparative chromatography to give the target product N-(2-morpholinoethyl)-4-(2-(6-phenylimidazo[1,5-a]pyridin-5-yl)acetamido)benzamide 49 (11 mg, white solid). Yield: 8%.

MS m/z (ES): 484[M+1]

$^1$H NMR (400 MHz, CD$_3$OD) δ 8.36 (s, 1H), 7.85 (d, J=8.7 Hz, 2H), 7.70 (d, J=8.7 Hz, 2H), 7.65 (d, J=9.3 Hz, 1H), 7.54 (s, 1H), 7.50-7.43 (m, 5H), 6.92 (d, J=9.3 Hz, 1H), 4.15 (s, 2H), 3.79-3.75 (m, 4H), 3.61 (t, J=6.5 Hz, 2H), 2.78-2.74 (m, 6H).

Example 50

N-(3-morpholinopropyl)-4-(2-(6-phenylimidazo[1,5-a]pyridin-5-yl)acetamido)benzamide

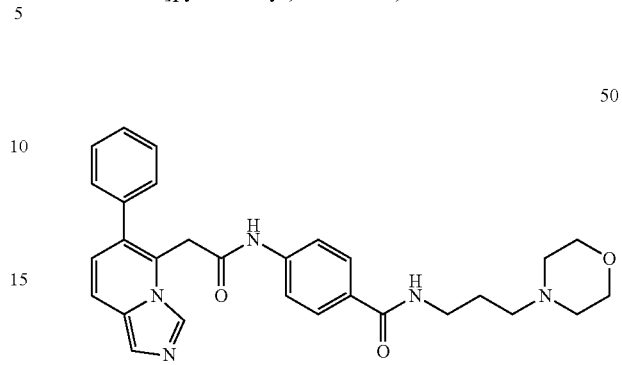

50

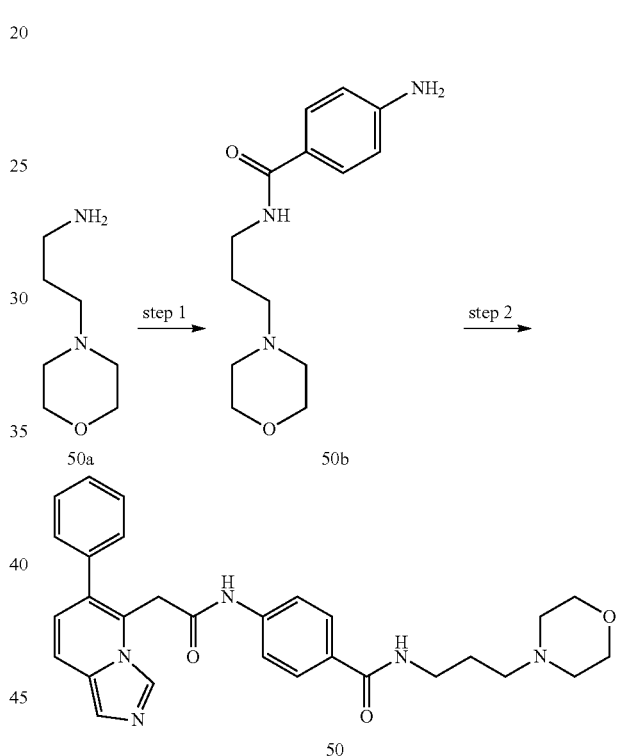

Step 1

Preparation of 4-amino-N-(3-morpholinopropyl)benzamide

A mixture of 4-aminobenzoic acid 47b (137 mg, 1 mmol), 3-morpholinopropan-1-amine 50a (158 mg, 1.1 mmol), DIPEA (516 mg, 4 mmol), and HATU (418 mg, 1.1 mmol) in N,N-dimethylformamide (5 mL) was stirred at room temperature for 2 h. The reaction was quenched with water and extracted with ethyl acetate (50 mL×2). The organic phase was combined and concentrated under reduced pressure to remove the solvent. The residue was purified by silica gel column chromatography (dichloromethane/methanol=100/1 to 10/1) to give the target product 4-amino-N-(3-morpholinopropyl)benzamide 50b (66 mg, brown oil). Yield: 35%.

MS m/z (ESI): 264[M+1]

Step 2

Preparation of N-(3-morpholinopropyl)-4-(2-(6-phenylimidazo[1,5-a]pyridin-5-yl)acetamido)benzamide A mixture of 2-(6-phenylimidazo[1,5-a]pyridin-5-yl)acetic acid 37l (70 mg, 0.277 mmol), HATU (105 mg, 0.277 mmol), 4-amino-N-(3-morpholinopropyl)benzamide 50b (80 mg, 0.3 mmol), and DIPEA (179 mg, 1.385 mmol) in N,N-dimethylformamide (2 mL) was stirred at room temperature for 2 h. The reaction was quenched with water and extracted with ethyl acetate (50 mL×2). The organic phase was combined, dried over anhydrous sodium sulfate, filtered and concentrated under reduced pressure to remove the solvent. The residue was purified by silica gel column chromatography (dichloromethane/methanol=100/1 to 10/1) to give the crude product, which was further purified by reversed phase high performance liquid preparative chromatography to give the target product N-(3-morpholinopropyl)-4-(2-(6-phenylimidazo[1,5-a]pyridin-5-yl)acetamido)benzamide 50 (13 mg, white solid). Yield: 10%.

MS m/z (ES): 498[M+1]

$^1$H NMR (400 MHz, CD$_3$OD) δ 8.36 (s, 1H), 7.85 (d, J=8.7 Hz, 2H), 7.69 (d, J=8.7 Hz, 2H), 7.65 (d, J=9.3 Hz, 1H), 7.53-7.42 (m, 6H), 6.92 (d, J=9.3 Hz, 1H), 4.14 (s, 2H), 3.83 (t, J=4.5 Hz, 4H), 3.48 (t, J=6.6 Hz, 2H), 2.88-2.80 (m, 6H), 2.01-1.95 (m, 2H).

Example 51

N-(4-(1H-pyrazol-4-yl)phenyl)-2-(6-phenylimidazo[1,5-a]pyridin-5-yl)acetamide

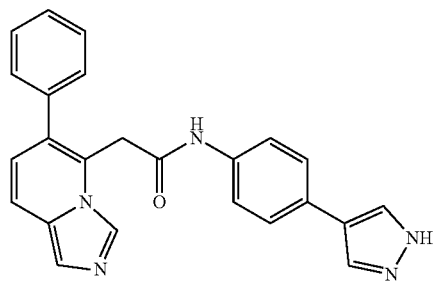

51

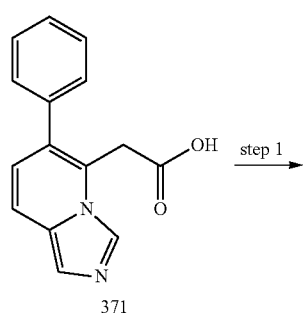

371

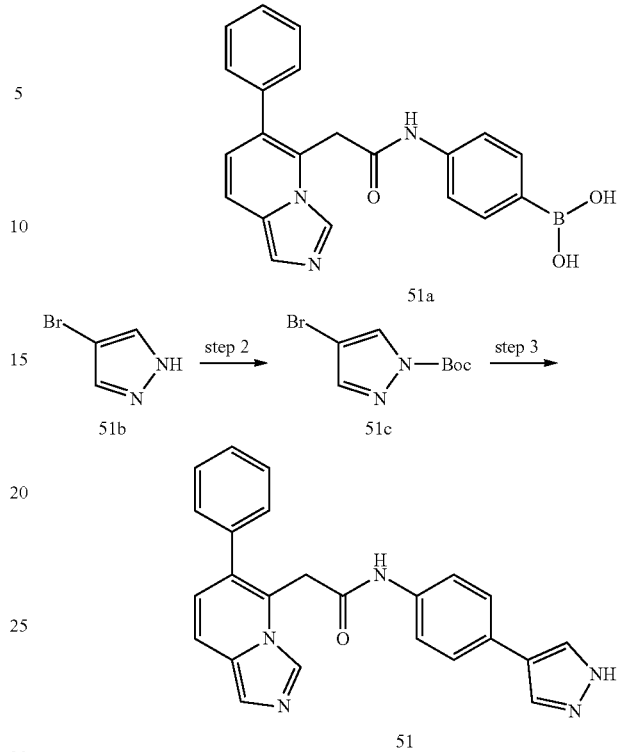

Step 1

Preparation of (4-(2-(6-phenylimidazo[1,5-a]pyridin-5-yl)acetamido)phenyl)boronic Acid A mixture of 2-(6-phenylimidazo[1,5-a]pyridin-5-yl)acetic acid 37l (200 mg, 0.79 mmol), HATU (452 mg, 1.19 mmol), (4-aminophenyl)boronic acid (26 mg, 0.317 mmol), and DIPEA (307 mg, 2.38 mmol) in N,N-dimethylformamide (10 mL) was stirred at room temperature for 3 h. After completed, the reaction was quenched with water and extracted with ethyl acetate (10 mL×3). The organic phase was combined, dried over anhydrous sodium sulfate, filtered and concentrated under reduced pressure to remove the solvent. The residue was purified by silica gel column chromatography (dichloromethane/methanol=100/1 to 10/1) to give the target product (4-(2-(6-phenylimidazo[1,5-a]pyridin-5-yl)acetamido)phenyl)boronic acid 51a (80 mg, white solid). Yield: 27%.

MS m/z (ESI): 372[M+1]

Step 2

Preparation of tert-butyl 4-bromo-1H-pyrazole-1-carboxylate

To a solution of 4-bromo-1H-pyrazole 51b (146 mg, 1 mmol) in dichloromethane was added successively with triethylamine (303 mg, 3 mmol) and di-tert-butyl dicarbonate (327 mg, 1.5 mmol), and the mixture was stirred at room temperature for 3 h. The mixture was concentrated under reduced pressure and the residue was purified by silica gel column chromatography (petroleum ether/ethyl acetate=100/1 to 10/1) to give the target product tert-butyl 4-bromo-1H-pyrazole-1-carboxylate 51c (150 mg, white solid). Yield: 61%.

MS m/z (ESI): 247[M+1]

Step 3

Preparation of N-(4-(1H-pyrazol-4-yl)phenyl)-2-(6-phenylimidazo[1,5-a]pyridin-5-yl)acetamide A mixture of (4-(2-(6-phenylimidazo[1,5-a]pyridin-5-yl)acetamido)phenyl)boronic acid 51a (20 mg, 0.054 mmol), tert-butyl 4-bromo-1H-pyrazole-1-carboxylate 51c (16 mg, 0.065 mmol), Pd(dppf)Cl$_2$ (1.2 mg, 0.0016 mmol), Cs$_2$CO$_3$ (26 mg, 0.081 mmol), dioxane (10 mL) and water (2 mL) was heated to 80° C. and stirred for 18 h under nitrogen protection. The reaction mixture was cooled to room temperature and extracted with ethyl acetate (10 mL×3). The organic phase was combined, washed with brine (10 mL×3), dried over anhydrous sodium sulfate, filtered and concentrated under reduced pressure to remove the solvent. The residue was purified by silica gel column chromatography (dichloromethane/methanol=100/1 to 10/1) to give the target product N-(4-(1H-pyrazol-4-yl)phenyl)-2-(6-phenylimidazo[1,5-a]pyridin-5-yl)acetamide 51 (3 mg, white solid). Yield: 14%.

MS m/z (ESI): 394[M+1]

$^1$H NMR (400 MHz, CD$_3$OD) δ 8.38 (s, 1H), 7.95 (s, 2H), 7.65 (d, J=9.3 Hz, 1H), 7.58 (s, 4H), 7.54 (s, 1H), 7.52-7.42 (m, 6H), 6.93 (d, J=9.3 Hz, 1H), 4.13 (s, 2H).

Example 52

N-(4-(1-(2-methoxyethyl)-1H-pyrazol-4-yl)phenyl)-2-(6-phenylimidazo[1,5-a]pyridin-5-yl)acetamide

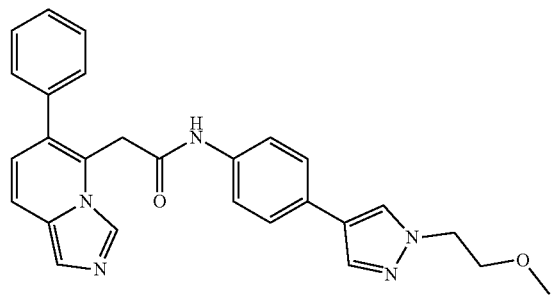

52

Step 1

Preparation of 4-bromo-1-(2-methoxyethyl)-1H-pyrazole

To a mixture of 4-bromo-1H-pyrazole 51b (146 mg, 1 mmol), 1-chloro-2-methoxyethane (94 mg, 1 mmol) and acetonitrile (5 mL) was added sodium hydroxide (48 mg, 1.2 mmol) and the resulting mixture was stirred at room temperature for 18 h. The mixture was filtered, and the filtrate was concentrated under reduced pressure. The residue was purified by silica gel column chromatography (petroleum ether/ethyl acetate=100/1 to 10/1) to give the target product 4-bromo-1-(2-methoxyethyl)-1H-pyrazole 52a (150 mg, white solid). Yield: 74%.

MS m/z (ESI): 205[M+1]

Step 2

Preparation of N-(4-(1-(2-methoxyethyl)-1H-pyrazol-4-yl)phenyl)-2-(6-phenylimidazo[1,5-a]pyridin-5-yl)acetamide A mixture of (4-(2-(6-phenylimidazo[1,5-a]pyridin-5-yl)acetamido)phenyl)boronic acid 51a (20 mg, 0.054 mmol), 4-bromo-1-(2-methoxyethyl)-1H-pyrazole 52a (11 mg, 0.054 mmol), Pd(dppf)Cl$_2$ (1.2 mg, 0.0016 mmol), Cs$_2$CO$_3$ (21 mg, 0.065 mmol), dioxane (5 mL) and water (2 mL) was heated to 80° C. and stirred for 18 h under nitrogen protection. The reaction mixture was cooled to room temperature and extracted with ethyl acetate (10 mL×3). The organic phase was combined, washed with brine (10 mL×3), dried over anhydrous sodium sulfate, filtered and concentrated under reduced pressure to remove the solvent. The residue was purified by silica gel column chromatography (dichloromethane/methanol=100/1 to 19/1) to give the target product N-(4-(1-(2-methoxyethyl)-1H-pyrazol-4-yl)phenyl)-2-(6-phenylimidazo[1,5-a]pyridin-5-yl)acetamide 52 (4 mg, white solid). Yield: 16%.

MS m/z (ESI): 452[M+1]

$^1$H NMR (400 MHz, CDCl$_3$) δ 8.82-8.77 (m, 1H), 7.64 (s, 1H), 7.55 (d, J=14.3 Hz, 2H), 7.48-7.39 (m, 8H), 7.28 (d, J=7.1 Hz, 2H), 6.84 (d, J=9.2 Hz, 1H), 6.30-5.25 (m, 1H), 4.22 (t, J=5.0 Hz, 2H), 4.09 (s, 2H), 3.69 (t, J=5.0 Hz, 2H), 3.27 (s, 3H).

Example 53

2-(6-phenylimidazo[1,5-a]pyridin-5-yl)-N-(1H-pyrazol-3-yl)acetamide

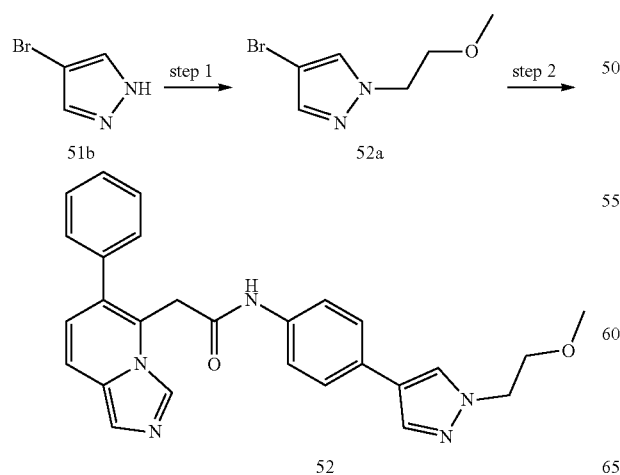

52

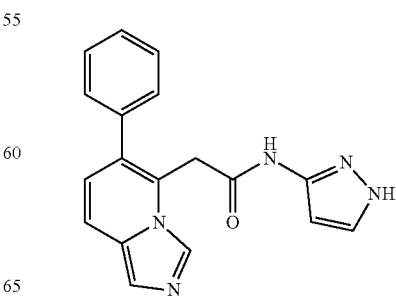

53

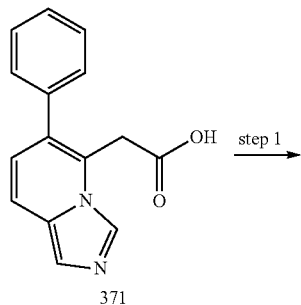

Preparation of 2-(6-phenylimidazo[1,5-a]pyridin-5-yl)-N-(1H-pyrazol-3-yl)acetamide A mixture of 2-(6-phenylimidazo[1,5-a]pyridin-5-yl)acetic acid 371 (40 mg, 0.158 mmol), HATU (66 mg, 0.173 mmol), 1H-pyrazol-3-amine (26 mg, 0.317 mmol), and DIPEA (81 mg, 0.632 mmol) in N,N-dimethylformamide (2 mL) was stirred at room temperature for 4 h. After completed, the reaction was quenched with water and extracted with ethyl acetate (20 mL×3). The organic phase was combined, dried over anhydrous sodium sulfate, filtered and concentrated under reduced pressure to remove the solvent. The residue was purified by reversed phase high performance liquid chromatography to give the target product 2-(6-phenylimidazo[1,5-a]pyridin-5-yl)-N-(1H-pyrazol-3-yl)acetamide 53 (12.3 mg, white solid). Yield: 21%.

MS m/z (ESI): 318[M+1]

$^1$H NMR (400 MHz, CD$_3$OD) δ 8.20 (s, 1H), 7.52 (d, J=8.9 Hz, 1H), 7.44 (s, 1H), 7.40-7.36 (m, 6H), 6.80 (d, J=9.4 Hz, 1H), 6.40 (s, 1H), 4.00 (s, 2H).

Preparation of 2-(6-phenylimidazo[1,5-a]pyridin-5-yl)-N-(1H-pyrazol-4-yl)acetamide A mixture of 2-(6-phenylimidazo[1,5-a]pyridin-5-yl)acetic acid 371 (40 mg, 0.158 mmol), HATU (66 mg, 0.173 mmol), 1H-pyrazol-4-amine (26 mg, 0.317 mmol), and DIPEA (81 mg, 0.632 mmol) in N,N-dimethylformamide (2 mL) was stirred at room temperature for 4 h. After completed, the reaction was quenched with water and extracted with ethyl acetate (20 mL×3). The organic phase was combined, dried over anhydrous sodium sulfate, filtered and concentrated under reduced pressure to remove the solvent. The residue was purified by reversed phase high performance liquid chromatography to give the target product 2-(6-phenylimidazo[1,5-a]pyridin-5-yl)-N-(1H-pyrazol-4-yl)acetamide 54 (11.9 mg, white solid). Yield: 20%.

MS m/z (ESI): 318[M+1]

$^1$H NMR (400 MHz, CD$_3$OD) δ 8.31 (s, 1H), 7.74 (s, 2H), 7.62 (d, J=9.1 Hz, 1H), 7.53-7.42 (m, 6H), 6.91 (d, J=8.6 Hz, 1H), 4.06 (s, 2H).

Example 54

2-(6-phenylimidazo[1,5-a]pyridin-5-yl)-N-(1H-pyrazol-4-yl)acetamide

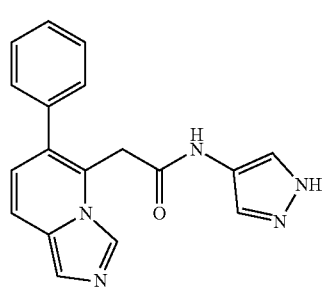

Example 55

4-((methyl((6-phenylimidazo[1,5-a]pyridin-5-yl)methyl)amino)methyl)benzonitrile

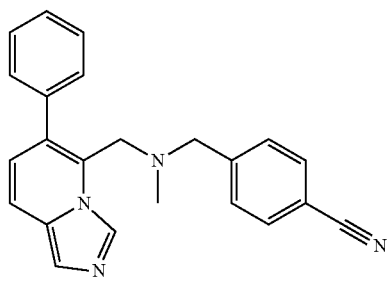

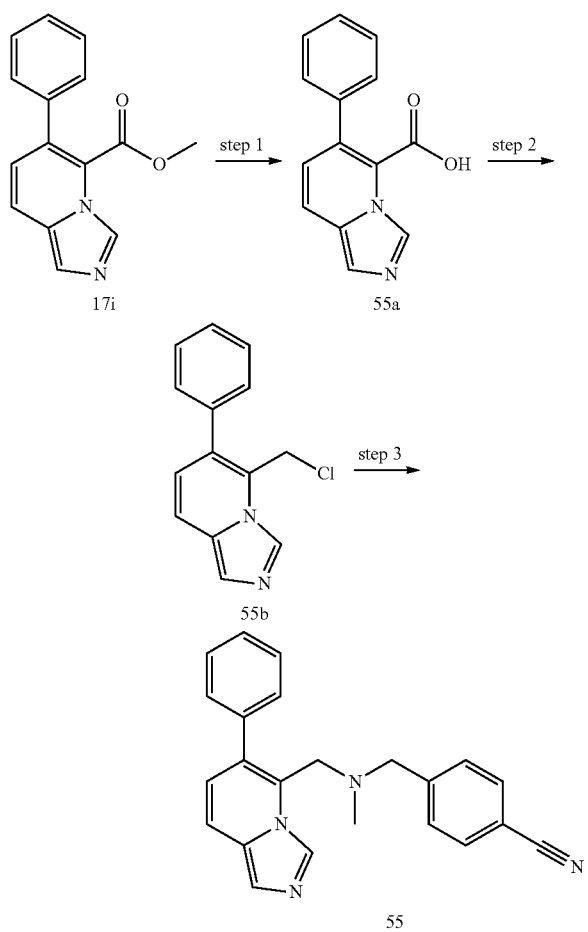

Step 1

Preparation of (6-phenylimidazo[1,5-a]pyridin-5-yl)methanol

Compound methyl 6-phenylimidazo[1,5-a]pyridine-5-carboxylate 17i (338 mg, 1.34 mmol) was dissolved in THF (10 mL) and cooled to 0° C. in ice-water bath. Then lithium aluminum hydride (22.6 mg, 0.595 mmol) was added and the reaction mixture was stirred at 0° C. for 1 h. The reaction mixture was filtered. The filtrate was concentrated under reduced pressure. The residue was purified by silica gel column chromatography (petroleum ether/ethyl acetate=100/1 to 1/1) to give the target compound (6-phenylimidazo[1,5-a]pyridin-5-yl)methanol 55a (300 mg, yellow solid). Yield: 100%.

MS m/z (ESI): 225[M+1]

Step 2

Preparation of 5-(chloromethyl)-6-phenylimidazo[1,5-a]pyridine

Compound (6-phenylimidazo[1,5-a]pyridin-5-yl)methanol 55a (300 mg, 1.34 mmol) was dissolved in dichloromethane (5 mL), added with sulfurous dichloride (316 mg, 2.68 mmol) and stirred at room temperature for 1 h. The reaction was quenched with water and extracted with ethyl acetate. The organic phase was combined, dried over anhydrous sodium sulfate, filtered and concentrated under reduced pressure. The residue was purified by silica gel column chromatography (petroleum ether/ethyl acetate=100/1 to 1/1) to give the target product 5-(chloromethyl)-6-phenylimidazo[1,5-a]pyridine 55b (150 mg, yellow solid). Yield: 46%.

MS m/z (ESI): 243[M+1]

Step 3

Preparation of 4-((methyl((6-phenylimidazo[1,5-a]pyridin-5-yl)methyl)amino)methyl)benzonitrile Compound 5-(chloromethyl)-6-phenylimidazo[1,5-a]pyridine 55b (25 mg, 0.103 mmol), 4-((methylamino)methyl)benzonitrile (29 mg, 0.2 mmol), $K_2CO_3$ (69 mg, 0.5 mmol) and acetonitrile (5 mL) were mixed at room temperature, heated to 55° C. and stirred for 18 h. After cooled to room temperature, the mixture was filtered. The filtrate was concentrated under reduced pressure. The residue was purified by silica gel column chromatography (petroleum ether/ethyl acetate=1/1 to 1/3) to give the target product 4-((methyl((6-phenylimidazo[1,5-a]pyridin-5-yl)methyl)amino)methyl)benzonitrile 55 (25 mg, light yellow oil). Yield: 71%.

MS m/z (ESI): 353[M+1]

$^1$H NMR (400 MHz, CDCl$_3$) δ 8.64 (s, 1H), 7.64-7.42 (m, 7H), 7.38-7.22 (m, 4H), 6.70 (d, J=9.2 Hz, 1H), 3.89 (s, 2H), 3.44 (s, 2H), 2.11 (s, 3H).

Example 56

4-(1-(((6-phenylimidazo[1,5-a]pyridin-5-yl)methyl)amino)ethyl)benzonitrile

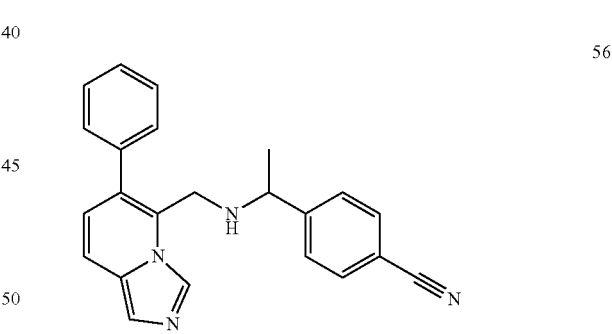

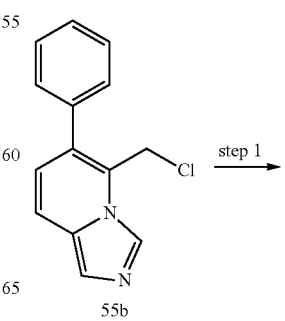

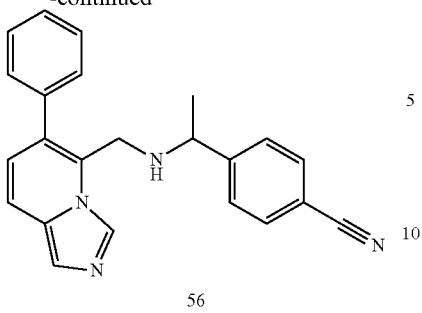

56

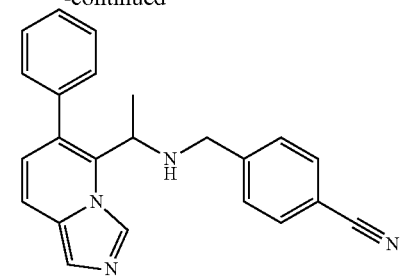

57

Preparation of 4-(1-(((6-phenylimidazo[1,5-a]pyridin-5-yl)methyl)amino)ethyl)benzonitrile Compound 5-(chloromethyl)-6-phenylimidazo[1,5-a]pyridine 55b (49 mg, 0.2 mmol), 4-(1-aminoethyl)benzonitrile (29 mg, 0.2 mmol), $K_2CO_3$ (138 mg, 1 mmol), KI (33 mg, 0.2 mmol) and acetonitrile (5 mL) were mixed at room temperature, heated to 55° C. and stirred for 18 h. After cooled to room temperature, the mixture was filtered. The filtrate was concentrated under reduced pressure. The residue was purified by silica gel column chromatography (petroleum ether/ethyl acetate=1/1 to 1/3) to give the target product 4-(1-(((6-phenylimidazo[1,5-a]pyridin-5-yl)methyl)amino)ethyl)benzonitrile 56 (15 mg, light yellow oil). Yield: 21%.

MS m/z (ESI): 353[M+1]

$^1$H NMR (400 MHz, CDCl$_3$) δ 8.47 (s, 1H), 7.52 (d, J=8.2 Hz, 3H), 7.46-7.41 (m, 4H), 7.31-7.24 (m, 5H), 6.70 (d, J=9.2 Hz, 1H), 3.92 (q, J=13.2 Hz, 2H), 3.74 (q, J=6.6 Hz, 1H), 1.33 (d, J=6.6 Hz, 3H).

Example 57

4-(((1-(6-phenylimidazo[1,5-a]pyridin-5-yl)ethyl)amino)methyl)benzonitrile

57

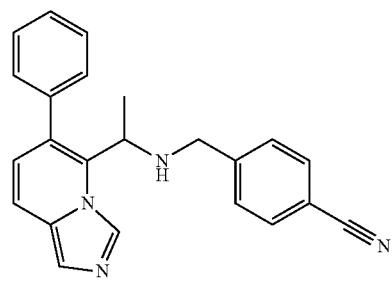

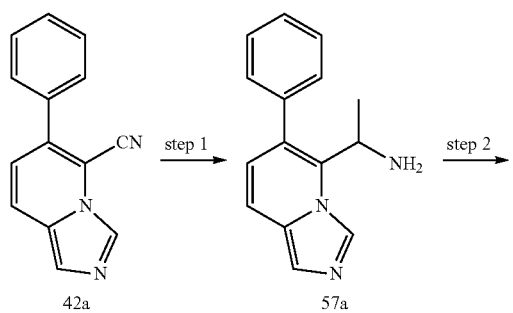

Step 1

Preparation of 1-(6-phenylimidazo[1,5-a]pyridin-5-yl)ethan-1-amine

Compound 6-phenylimidazo[1,5-a]pyridine-5-carbonitrile 42a (45 mg, 0.2 mmol) was dissolved in THF (5 mL), added with a solution of methylmagnesium bromide in THF (3 M, 1 mL, 3 mmol) and heated at 50° C. for 5 min. The reaction mixture was cooled to 0° C. and added with methanol (5 mL) and sodium borohydride (38 mg, 1 mmol). The mixture was stirred at room temperature for 15 h and concentrated under reduced pressure. The residue was dissolved in dichloromethane (50 mL), washed with water and concentrated under reduced pressure. The residue was purified by silica gel column chromatography (dichloromethane/methanol=20/1 to 15/1) to give the target product 1-(6-phenylimidazo[1,5-a]pyridin-5-yl)ethan-1-amine 57a (31 mg, yellow oil). Yield: 65%.

MS m/z (ESI): 238[M+1]

Step 2

Preparation of 4-(((1-(6-phenylimidazo[1,5-a]pyridin-5-yl)ethyl)amino)methyl)benzonitrile Compound 1-(6-phenylimidazo[1,5-a]pyridin-5-yl)ethan-1-amine 57a (31 mg, 0.13 mmol) was dissolved in dichloromethane (5 mL), added with 4-formylbenzonitrile (17 mg, 0.13 mmol) and acetic acid (0.05 mL), and stirred at room temperature for 2 h. After cooled to 0° C., the mixture was added with sodium triacetoxyborohydride (138 mg, 0.65 mmol) and stirred at room temperature for 72 h. The reaction mixture was diluted with dichloromethane (50 mL) and washed with water (10 mL). The organic phase was concentrated under reduced pressure. The residue was purified by silica gel column chromatography (dichloromethane/methanol=20/1 to 15/1) to give the target product 4-(((1-(6-phenylimidazo[1,5-a]pyridin-5-yl)ethyl)amino)methyl)benzonitrile 57 (27 mg, colorless oil). Yield: 59%.

MS m/z (ESI): 353[M+1]

$^1$H NMR (400 MHz, CDCl$_3$) δ 9.25 (s, 1H), 7.45 (s, 1H), 7.29-7.25 (m, 6H), 7.23-7.20 (m, 4H), 6.63 (d, J=9.2 Hz, 1H), 4.45-4.40 (m, 1H), 3.67-3.54 (m, 2H), 1.64 (d, J=8 Hz, 3H).

Example 58

N-benzyl-1-(6-phenylimidazo[1,5-a]pyridin-5-yl)methanamine

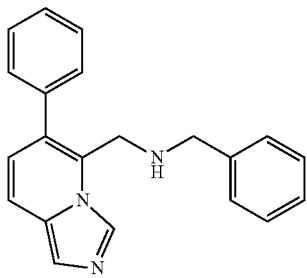

58

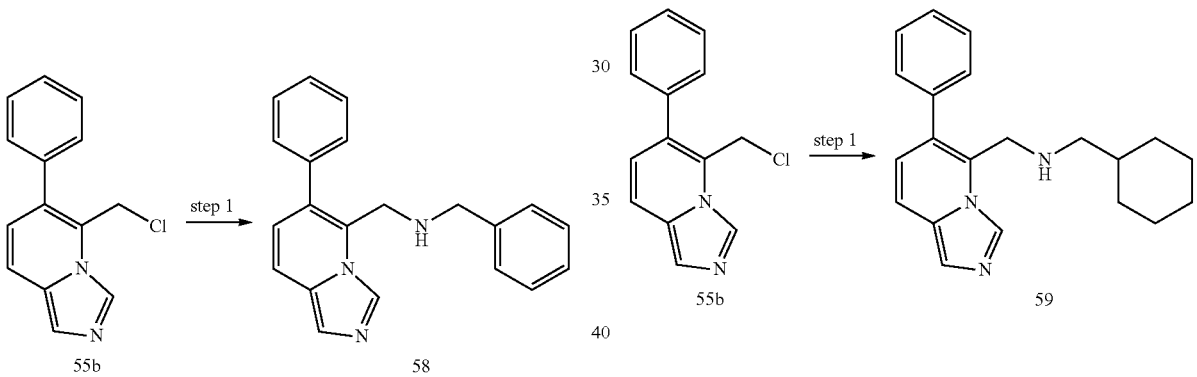

Preparation of N-benzyl-1-(6-phenylimidazo[1,5-a]pyridin-5-yl)methanamine

Compound 5-(chloromethyl)-6-phenylimidazo[1,5-a]pyridine 55b (20 mg, 0.083 mmol), benzylamine (18 mg, 0.165 mmol), K$_2$CO$_3$ (23 mg, 0.165 mmol), KI (1.4 mg, 0.008 mmol) and acetonitrile (5 mL) were mixed at room temperature, heated to 55° C. and stirred for 18 h. After cooled to room temperature, the mixture was filtered. The filtrate was concentrated under reduced pressure. The residue was purified by silica gel column chromatography (dichloromethane/methanol=100/1 to 9/1) to give the target product N-benzyl-1-(6-phenylimidazo[1,5-a]pyridin-5-yl)methanamine 58 (7.5 mg, yellow solid). Yield: 29%.

MS m/z (ESI): 314[M+1]

$^1$H NMR (400 MHz, CDCl$_3$) δ 8.42 (s, 1H), 7.50 (s, 1H), 7.45-7.41 (m, 4H), 7.34-7.28 (m, 5H), 7.24-7.21 (m, 3H), 6.71 (d, J=9.2 Hz, 1H), 4.00 (s, 2H), 3.77 (s, 2H).

Example 59

1-cyclohexyl-N-((6-phenylimidazo[1,5-a]pyridin-5-yl)methyl)methanamine

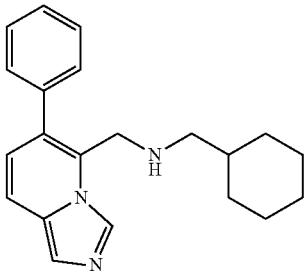

59

Preparation of 1-cyclohexyl-N-((6-phenylimidazo[1,5-a]pyridin-5-yl)methyl)methanamine Compound 5-(chloromethyl)-6-phenylimidazo[1,5-a]pyridine 55b (20 mg, 0.083 mmol), cyclohexylmethanamine (19 mg, 0.165 mmol), K$_2$CO$_3$ (23 mg, 0.165 mmol), KI (1.4 mg, 0.008 mmol) and acetonitrile (5 mL) were mixed at room temperature, heated to 55° C. and stirred for 18 h. After cooled to room temperature, the mixture was filtered. The filtrate was concentrated under reduced pressure. The residue was purified by silica gel column chromatography (dichloromethane/methanol=100/1 to 9/1) to give the target product 1-cyclohexyl-N-((6-phenylimidazo[1,5-a]pyridin-5-yl)methyl)methanamine 59 (6 mg, white solid). Yield: 23%.

MS m/z (ESI): 320[M+1]

$^1$H NMR (400 MHz, CDCl$_3$) δ 8.49 (s, 1H), 7.50 (s, 1H), 7.49-7.38 (m, 4H), 7.35 (d, J=7.7 Hz, 2H), 6.72 (d, J=9.2 Hz, 1H), 3.96 (s, 2H), 2.42 (d, J=6.6 Hz, 2H), 1.73-1.64 (m, 5H), 1.20-1.12 (m, 3H), 0.91-0.82 (m, 3H).

Example 60

1-(6-phenylimidazo[1,5-a]pyridin-5-yl)-N-((tetrahydro-2H-pyran-4-yl)methyl)methanamine

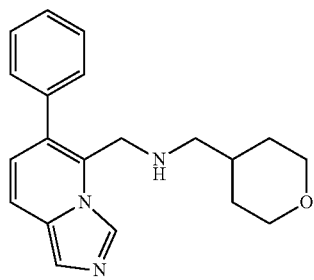

60

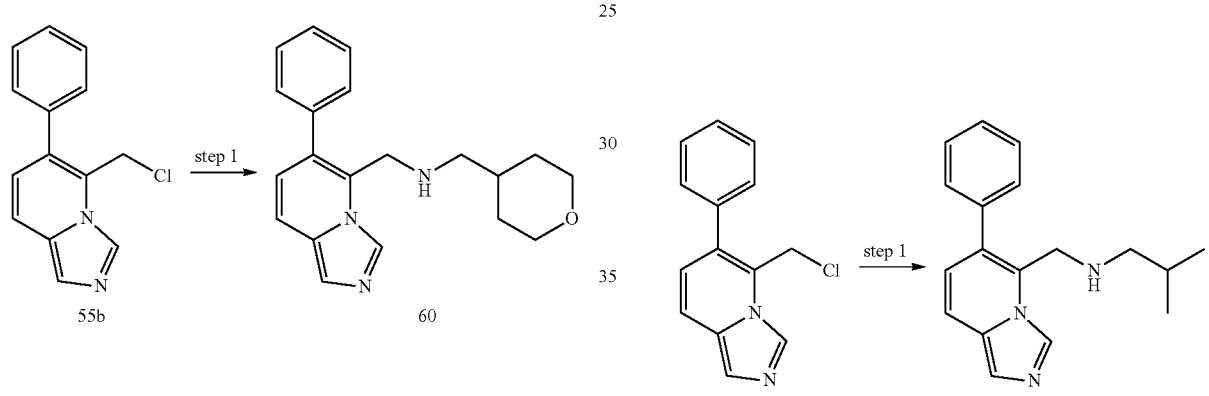

Preparation of 1-(6-phenylimidazo[1,5-a]pyridin-5-yl)-N-((tetrahydro-2H-pyran-4-yl)methyl)methanamine Compound 5-(chloromethyl)-6-phenylimidazo[1,5-a]pyridine 55b (20 mg, 0.083 mmol), (tetrahydro-2H-pyran-4-yl)methanamine (19 mg, 0.165 mmol), $K_2CO_3$ (23 mg, 0.165 mmol), KI (1.4 mg, 0.008 mmol) and acetonitrile (5 mL) were mixed at room temperature, heated to 55° C. and stirred for 18 h. After cooled to room temperature, the mixture was filtered. The filtrate was concentrated under reduced pressure. The residue was purified by silica gel column chromatography (dichloromethane/methanol=100/1 to 9/1) to give the target product 1-(6-phenylimidazo[1,5-a]pyridin-5-yl)-N-((tetrahydro-2H-pyran-4-yl)methyl)methanamine 60 (8.1 mg, white solid). Yield: 30%.

MS m/z (ESI): 322[M+1]

$^1$H NMR (400 MHz, CDCl$_3$) δ 8.48 (s, 1H), 7.51 (s, 1H), 7.48-7.41 (m, 4H), 7.35 (d, J=7.1 Hz, 2H), 6.73 (d, J=9.2 Hz, 1H), 4.00 (s, 2H), 3.93 (dd, J=11.2, 4.1 Hz, 2H), 3.30 (t, J=11.6 Hz, 2H), 2.47 (d, J=6.2 Hz, 2H), 1.57-1.50 (m, 4H), 1.23-1.20 (m, 1H).

Example 61

2-methyl-N-((6-phenylimidazo[1,5-a]pyridin-5-yl)methyl)propan-1-amine

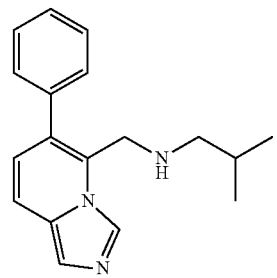

61

Preparation of 2-methyl-N-((6-phenylimidazo[1,5-a]pyridin-5-yl)methyl)propan-1-amine Compound 5-(chloromethyl)-6-phenylimidazo[1,5-a]pyridine 55b (24 mg, 0.1 mmol), 2-methylpropan-1-amine (15 mg, 0.2 mmol), $K_2CO_3$ (23 mg, 0.165 mmol) and acetonitrile (4 mL) were mixed at room temperature, heated to 55° C. and stirred for 12 h. After cooled to room temperature, the mixture was filtered. The filtrate was concentrated under reduced pressure. The residue was purified by preparative thin layer silica gel chromatography (dichloromethane/methanol=15/1) to give the target product 2-methyl-N-((6-phenylimidazo[1,5-a]pyridin-5-yl)methyl)propan-1-amine 61 (6.8 mg, white solid). Yield: 24%.

MS m/z (ESI): 280[M+1]

$^1$H NMR (400 MHz, CDCl$_3$) δ 8.51 (s, 1H), 7.51 (s, 1H), 7.47-7.41 (m, 4H), 7.37-7.35 (m, 2H), 6.73 (d, J=9.2 Hz, 1H), 3.98 (s, 2H), 2.41 (d, J=6.7 Hz, 2H), 1.66-1.62 (m, 1H), 0.87 (d, J=6.6 Hz, 6H).

Example 62

2-methyl-1-(((6-phenylimidazo[1,5-a]pyridin-5-yl)methyl)amino)propan-2-ol

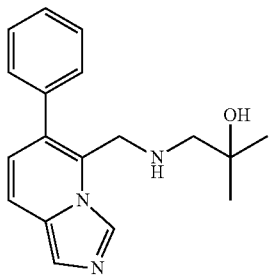

62

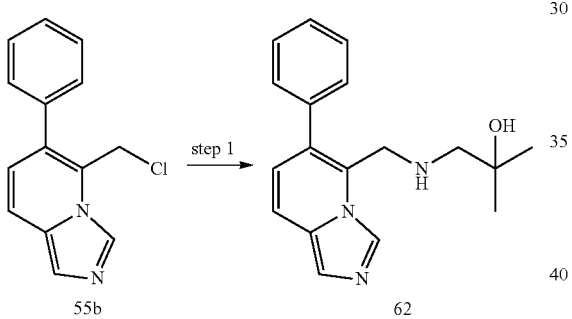

Preparation of 2-methyl-1-(((6-phenylimidazo[1,5-a]pyridin-5-yl)methyl)amino)propan-2-ol Compound 5-(chloromethyl)-6-phenylimidazo[1,5-a]pyridine 55b (35 mg, 0.14 mmol), 1-amino-2-methylpropan-2-ol (29 mg, 0.33 mmol), $K_2CO_3$ (83 mg, 0.6 mmol) and acetonitrile (4 mL) were mixed at room temperature, heated to 55° C. and stirred for 12 h. After cooled to room temperature, the mixture was filtered. The filtrate was concentrated under reduced pressure. The residue was purified by preparative thin layer silica gel chromatography (dichloromethane/methanol=15/1) to give the target product 2-methyl-1-(((6-phenylimidazo[1,5-a]pyridin-5-yl)methyl)amino)propan-2-ol 62 (24 mg, white solid). Yield: 75%.

MS m/z (ESI): 296[M+1]

$^1$H NMR (400 MHz, $CD_3OD$) δ 9.60 (s, 1H), 8.09 (s, 1H), 7.96 (d, J=9.4 Hz, 1H), 7.62-7.52 (m, 5H), 7.20 (d, J=9.4 Hz, 1H), 4.80 (s, 2H), 2.85 (s, 2H), 1.16 (s, 6H).

Example 63

2-(6-chloro-1H-indazol-4-yl)-N-(4-cyanophenyl)acetamide

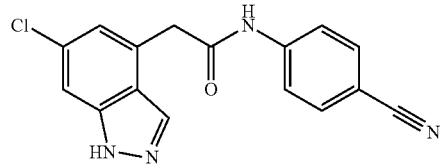

63

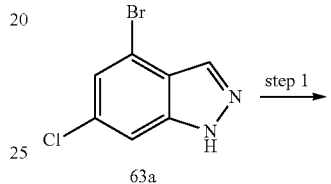

63a

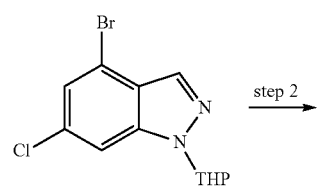

63b

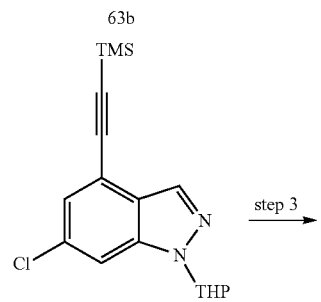

63c

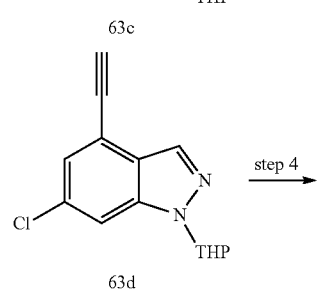

63d

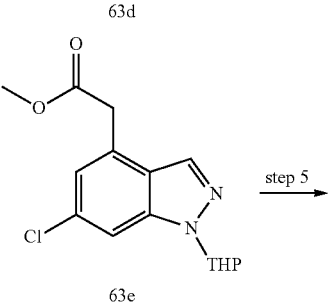

63e

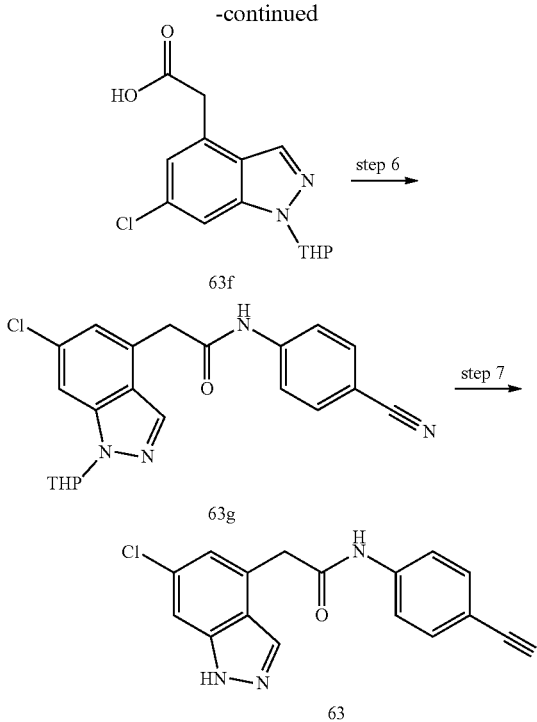

Step 1

Preparation of 4-bromo-6-chloro-1-(tetrahydro-2H-pyran-2-yl)-1H-indazole

Compound 4-bromo-6-chloro-1H-indazole 63a (2 g, 8.68 mmol) was dissolved in THF (40 mL), added with 3,4-dihydro-2H-pyran (2.2 g, 26 mmol) and L-camphorsulfonic acid (0.2 g, 0.87 mmol), heated to 55° C. and stirred for 2 h. After cooled to room temperature, the mixture was basified with triethylamine to pH=7 and concentrated under reduced pressure. The residue was purified by silica gel column chromatography (petroleum ether/ethyl acetate=10/1) to give the target product 4-bromo-6-chloro-1-(tetrahydro-2H-pyran-2-yl)-1H-indazole 63b (2.5 g, orange solid). Yield: 92%.

MS m/z (ESI): 231/233[M+1]

Step 2

Preparation of 6-chloro-1-(tetrahydro-2H-pyran-2-yl)-4-((trimethylsilyl)ethynyl)-1H-indazole A mixture of 4-bromo-6-chloro-1-(tetrahydro-2H-pyran-2-yl)-1H-indazole 63b (300 mg, 0.95 mmol), ethynyltrimethylsilane (111 mg, 1.14 mmol), Pd(PPh$_3$)$_2$Cl$_2$ (35 mg, 0.05 mmol), and CuI (1.9 mg, 0.01 mmol) in THF (1 mL) was heated to 80° C. under microwave irradiation and stirred under nitrogen for 2 h. After cooled to room temperature, the mixture was diluted with water (30 mL) and extracted with ethyl acetate (30 mL×3). The organic phase was combined, washed with brine (40 mL×2), dried over anhydrous sodium sulfate, filtered and concentrated under reduced pressure to remove the solvent. The residue was purified by silica gel column chromatography (petroleum ether/ethyl acetate=10/1) to give the target product 6-chloro-1-(tetrahydro-2H-pyran-2-yl)-4-((trimethylsilyl)ethynyl)-1H-indazole 63c (311 mg, pink solid). Yield: 99%.

MS m/z (ESI): 333[M+1]

Step 3

Preparation of 6-chloro-4-ethynyl-1-(tetrahydro-2H-pyran-2-yl)-1H-indazole

Compound 6-chloro-1-(tetrahydro-2H-pyran-2-yl)-4-((trimethylsilyl)ethynyl)-1H-indazole 63c (310 mg, 0.93 mmol) was dissolved in dichloromethane (2 mL) and methane (1 mL), and added with potassium carbonate (150 mg, 1.12 mmol). The reaction mixture was stirred at room temperature for 1 h, diluted with water (20 mL) and extracted with ethyl acetate (20 mL×3). The organic phase was combined, washed with brine (20 mL×2), dried over anhydrous sodium sulfate, filtered and concentrated under reduced pressure to remove the solvent. The residue was purified by silica gel column chromatography (petroleum ether/ethyl acetate=10/1) to give the target product 6-chloro-4-ethynyl-1-(tetrahydro-2H-pyran-2-yl)-1H-indazole 63d (200 mg, white solid). Yield: 82%.

MS m/z (ESI): 261[M+1]

Step 4

Preparation of methyl 2-(6-chloro-1-(tetrahydro-2H-pyran-2-yl)-1H-indazol-4-yl)acetate To a mixture of 6-chloro-4-ethynyl-1-(tetrahydro-2H-pyran-2-yl)-1H-indazole 63d (100 mg, 0.56 mmol), and methyltrioxorhenium (14 mg, 0.057 mmol) in methanol (5 mL) was added dropwise hydrogen peroxide solution (33%, 3 mL, 1.7 mmol). The mixture was stirred at room temperature for 5 days, diluted with water (20 mL) and extracted with ethyl acetate (20 mL×3). The organic phase was combined, washed with brine (20 mL×2), dried over anhydrous sodium sulfate, filtered and concentrated under reduced pressure to remove the solvent. The residue was purified by silica gel column chromatography (petroleum ether/ethyl acetate=5/1) to give the target product methyl 2-(6-chloro-1-(tetrahydro-2H-pyran-2-yl)-1H-indazol-4-yl)acetate 63e (50 mg, white solid). Yield: 58%.

MS m/z (ESI): 309[M+1]

Step 5

Preparation of 2-(6-chloro-1-(tetrahydro-2H-pyran-2-yl)-1H-indazol-4-yl)acetic Acid To a mixture of methyl 2-(6-chloro-1-(tetrahydro-2H-pyran-2-yl)-1H-indazol-4-yl)acetate 63e (200 mg, 0.64 mmol), THF (1 mL) and H$_2$O (1 mL) was added lithium hydroxide monohydrate (40 mg, 0.98 mmol). The mixture was stirred at room temperature for 2 h, adjusted with hydrochloride solution (2 M) until pH=7, diluted with water (20 mL) and extracted with ethyl acetate (20 mL×3). The organic phase was combined, washed with brine (20 mL×2), dried over anhydrous sodium sulfate, filtered and concentrated under reduced pressure to remove the solvent. The residue was purified by silica gel column chromatography (dichloromethane/methanol=10/1) to give the target product 2-(6-chloro-1-(tetrahydro-2H-pyran-2-yl)-1H-indazol-4-yl)acetic acid 63f (90 mg, white solid). Yield: 48%.

MS m/z (ESI): 295[M+1]

Step 6

Preparation of 2-(6-chloro-1-(tetrahydro-2H-pyran-2-yl)-1H-indazol-4-yl)-N-(4-cyanophenyl)acetamide A mixture of 2-(6-chloro-1-(tetrahydro-2H-pyran-2-yl)-1H-indazol-4-yl)acetic acid 63f (60 mg, 0.2 mmol), HATU (90 mg, 0.23 mmol), 4-aminobenzonitrile (30 mg, 0.25 mmol), and DIPEA (104 mg, 0.8 mmol) in N,N-dimethylformamide (2 mL) was stirred at room temperature for 3 h. After completed, the reaction mixture was diluted with water (20 mL) and extracted with ethyl acetate (20 mL×3). The organic phase was combined, washed with brine (20 mL×2), dried over anhydrous sodium sulfate, filtered and concentrated under reduced pressure to remove the solvent. The residue was purified by silica gel column chromatography (petroleum ether/ethyl acetate=1/2) to give the target product 2-(6-chloro-1-(tetrahydro-2H-pyran-2-yl)-1H-indazol-4-yl)-N-(4-cyanophenyl)acetamide 63 g (36 mg, yellow solid). Yield: 45%.

MS m/z (ESI): 395[M+1]

Step 7

Preparation of 2-(6-chloro-1H-indazol-4-yl)-N-(4-cyanophenyl)acetamide

To a solution of 2-(6-chloro-1-(tetrahydro-2H-pyran-2-yl)-1H-indazol-4-yl)-N-(4-cyanophenyl)acetamide 63 g (36 mg, 0.091 mmol) in methanol (2 mL) was added a solution of hydrochloride in ethanol (33%, 1 mL). The reaction mixture was stirred at room temperature for 2 h, adjusted to pH=7 and extracted with ethyl acetate (20 mL×3). The organic phase was combined, washed with brine (20 mL×2), dried over anhydrous sodium sulfate, filtered and concentrated under reduced pressure to remove the solvent. The residue was purified by reversed phase high performance liquid chromatography to give the target product 2-(6-chloro-1H-indazol-4-yl)-N-(4-cyanophenyl)acetamide 63 (4.3 mg, white solid). Yield: 15%.

MS m/z (ESI): 311[M+1]

$^1$H NMR (400 MHz, DMSO-d6) δ 13.23 (s, 1H), 10.74 (s, 1H), 8.20 (s, 1H), 7.78 (s, 3H), 7.53 (s, 1H), 7.10 (d, J=1.4 Hz, 1H), 4.04 (s, 2H).

Example 64

N-(4-cyanophenyl)-2-hydroxy-2-(6-phenylimidazo[1,5-a]pyridin-5-yl)acetamide

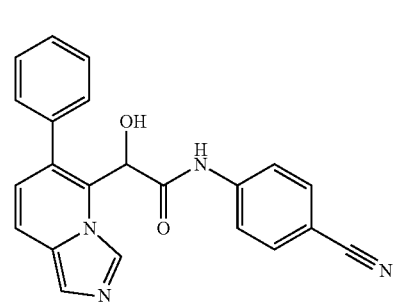

64

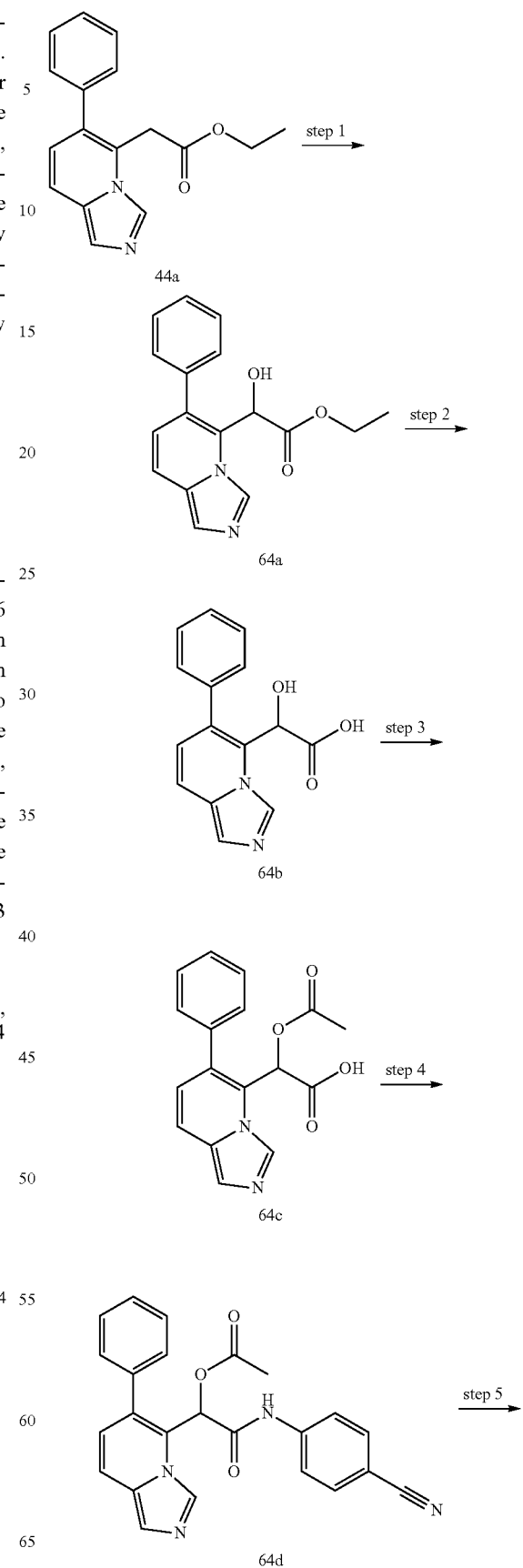

143
-continued

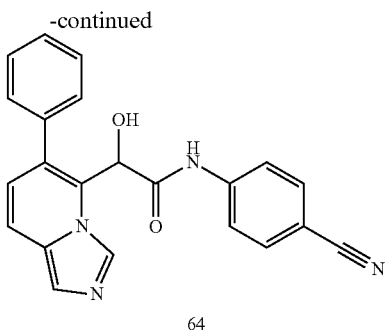

64

Step 1

Preparation of ethyl 2-hydroxy-2-(6-phenylimidazo[1,5-a]pyridin-5-yl)acetate

A solution of ethyl 2-(6-phenylimidazo[1,5-a]pyridin-5-yl)acetate 44a (280 mg, 1 mmol) in THF (10 mL) was cooled to 0° C. and added a solution of sodium bis(trimethylsilyl) amide in THF (2 M, 0.375 mL, 0.75 mmol). The mixture was warmed to room temperature, stirred for 5 min and cooled to −78° C. A solution of (camphorsulfonyl)oxaziridine (230 mg, 1 mmol) in THF (5 mL) was added and the reaction mixture was warmed to room temperature and stirred for 1 h. The reaction was quenched with water and extracted with ethyl acetate (50 mL×2). The organic phase was combined, dried over anhydrous sodium sulfate, filtered and concentrated under reduced pressure to remove the solvent. The residue was purified by silica gel column chromatography (dichloromethane/methanol=100/1 to 15/1) to give the target product ethyl 2-hydroxy-2-(6-phenylimidazo[1,5-a]pyridin-5-yl)acetate 64a (122 mg, white solid). Yield: 43%.

MS m/z (ESI): 297[M+1]

Step 2

Preparation of 2-hydroxy-2-(6-phenylimidazo[1,5-a]pyridin-5-yl)acetic Acid

Compound ethyl 2-hydroxy-2-(6-phenylimidazo[1,5-a]pyridin-5-yl)acetate 64a (122 mg, 0.42 mmol) was dissolved in THF (2 mL) and water (2 mL), and sodium hydroxide (50 mg, 1.26 mmol) was added. The mixture was stirred at room temperature for 2 h, adjusted with hydrochloride solution until pH=5 and concentrated under reduced pressure. The residue was purified by reversed phase high performance liquid chromatography to give the target product 2-hydroxy-2-(6-phenylimidazo[1,5-a]pyridin-5-yl)acetic acid 64b (70 mg, yellow solid). Yield: 70%.

MS m/z (ESI): 269[M+1]

Step 3

Preparation of 2-acetoxy-2-(6-phenylimidazo[1,5-a]pyridin-5-yl)acetic Acid

To a solution of 2-hydroxy-2-(6-phenylimidazo[1,5-a]pyridin-5-yl)acetic acid 64b (20 mg, 0.074 mmol) in dichloromethane (10 mL) was added acetyl chloride (0.1 mL) at 0° C. and the reaction mixture was stirred for 3 h. After the reaction was completed, the mixture was concentrated under reduced pressure to give the target product 2-acetoxy-2-(6-phenylimidazo[1,5-a]pyridin-5-yl)acetic acid 64c (33 mg, brown solid). Yield: 100%.

MS m/z (ESI): 311[M+1]

Step 4

Preparation of 2-((4-cyanophenyl)amino)-2-oxo-1-(6-phenylimidazo[1,5-a]pyridin-5-yl)ethyl Acetate A mixture of 2-acetoxy-2-(6-phenylimidazo[1,5-a]pyridin-5-yl)acetic acid 64c (22 mg, 0.07 mmol), HATU (54 mg, 0.141 mmol), 4-aminobenzonitrile (17 mg, 0.141 mmol), and DIPEA (54 mg, 0.42 mmol) in N,N-dimethylformamide (2 mL) was stirred at 60° C. for 12 h. After completed, the reaction was quenched with water and extracted with ethyl acetate (50 mL×2). The organic phase was combined, dried over anhydrous sodium sulfate, filtered and concentrated under reduced pressure to remove the solvent. The residue was purified by silica gel column chromatography (dichloromethane/methanol=100/1 to 15/1) to give the target product 2-((4-cyanophenyl)amino)-2-oxo-1-(6-phenylimidazo[1,5-a]pyridin-5-yl)ethyl acetate 64d (30 mg, crude product). The product was used directly in the next step without purification.

MS m/z (ES): 411[M+1]

Step 5

Preparation of N-(4-cyanophenyl)-2-hydroxy-2-(6-phenylimidazo[1,5-a]pyridin-5-yl)acetamide To a solution of 2-((4-cyanophenyl)amino)-2-oxo-1-(6-phenylimidazo[1,5-a]pyridin-5-yl)ethyl acetate 64d (30 mg, crude product) in methanol (5 mL) was added potassium carbonate (30 mg, 0.22 mmol). The mixture was stirred at room temperature for 1 h and filtered. The filtrate was concentrated under reduced pressure and the residue was purified by reversed phase high performance liquid chromatography to give the target product N-(4-cyanophenyl)-2-hydroxy-2-(6-phenylimidazo[1,5-a]pyridin-5-yl)acetamide 64 (4.6 mg, brown solid). Yield for two steps: 17%.

MS m/z (ES): 369[M+1]

$^1$H NMR (400 MHz, CD$_3$OD) δ 9.49 (s, 1H), 8.13 (s, 1H), 7.94-7.88 (m, 3H), 7.72-7.77 (m, 2H), 7.62-7.60 (m, 2H), 7.56-7.49 (m, 3H), 7.31 (d, J=9.5 Hz, 1H), 5.86 (s, 1H).

IDO Enzyme Activity Inhibition Testing

The effects of the compounds of the invention on the activity of indoleamine 2,3-dioxygenase (IDO) were evaluated by the Ehrlich method.

The experimental principle is summarized as follows: IDO1 catalyzes oxidation of tryptophan to form N-formyl kynurenine, N-formyl kynurenine is subsequently hydrolyzed by trichloroacetic acid to form kynurenine, and kynurenine further reacts with the Ehrlich reagent to make the solution yellow. The absorbance at 490 nm (OD490) is directly proportional to the activity of IDO1.

The experimental methods are summarized as follows:

The reaction buffer was 50 mM 2-(N-morpholine)ethanesulfonic acid-hydrate (Sigma, Cat. No. 69889); the full-length human recombinant IDO1 protein was purchased from the Tsinghua Protein Research Technology Center and diluted to a 33.6 ng/μL enzyme solution with the reaction buffer; the substrate solution was prepared with the reaction buffer containing 20 mM vitamin C (Sigma, Cat. No. A5960), 150 μM L-tryptophan (Sigma, Cat. No. T0254), 2250 UI/mL catalase (Sigma, Cat. No. C30), and 10 μM methylene blue (Sigma, Cat. No. 28514); the reaction termination solution was 30% (mass/volume) trichloroacetic acid (Sigma, Cat. No. T9159) aqueous solution; the Ehrlich reagent was 2% p-dimethylaminobenzaldehyde (Sigma, Cat. No. 156477) acetic acid (Macklin, Cat. No. A801295) solution.

A compound was dissolved in DMSO (Sigma, Cat. No. D5879) and diluted to 1 mM, then serially diluted 3-fold with DMSO to a minimum concentration of 50.8 nM, and each concentration was further diluted 25-fold with the reaction buffer. If a compound's IC50 value was very low, the initial concentration of the compound was decreased.

A 10-μL compound solution and a 10-μL enzyme solution were added to a 96-well plate (Sigma, Cat. No. CLS3695), mixed well and incubated at room temperature. After 15 min, a 20-μL substrate solution was added and incubated at 60° C. after mixing for 30 min. The reaction plate was equilibrated to room temperature and 60 μL of the Ehrlich reagent was added. After incubation for 15 min, OD490 of each well was measured.

In this experiment, OD490 without enzyme was referred as $OD490_{100\%\ inhibition}$, and OD490 with enzyme added but without compound was referred as $OD490_{0\%\ inhibition}$. The percentage of inhibition on the IDO1 activity by a compound was calculated using the following formula:

Inhibition %=100−100*($OD490_{compound}$−$OD490_{100\%\ inhibition}$)/($OD490_{0\%\ inhibition}$−$OD490_{100\%\ inhibition}$)

The IC50 value of a compound was obtained by fitting 10 concentration points using XLfit software (ID Business Solutions Ltd., UK) following the formula below:

Y=Bottom+(Top−Bottom)/(1+10^((log $IC_{50}$−X)*slope factor))

Where Y is the percentage of inhibition, Bottom is the bottom platform value of the S-curve, Top is the top platform value of the S-curve, X is the logarithm of the concentration of the test compound, and slope factor is the slope coefficient of the curve.

The activity data for some representative example compounds are listed as follows:

| Compound number | $IC_{50}$ |
| --- | --- |
| 1 | B |
| 3 | B |
| 14 | A |
| 15 | B |
| 16 | B |
| 17 | A |
| 19 | A |
| 20 | A |
| 21 | B |
| 22 | A |
| 23 | A |
| 24 | A |
| 27 | B |
| 28 | B |
| 29 | B |
| 30 | B |
| 32 | A |
| 33 | B |
| 34 | A |
| 35 | A |
| 37 | A |
| 40 | B |
| 41 | A |
| 42 | A |
| 45 | A |
| 47 | A |
| 48 | A |
| 49 | A |
| 50 | A |
| 51 | A |
| 52 | A |
| 53 | A |
| 54 | B |
| 55 | B |

-continued

| Compound number | $IC_{50}$ |
| --- | --- |
| 58 | B |
| 59 | B |
| 61 | B |
| 62 | A |
| 63 | B |

A: <250 nM;
B: 250~1.5 μM.

Conclusion: The compounds of the invention have an inhibitory effect on the activity of IDO1.

IDO Intracellular Activity Inhibition Testing

The effects of the compounds of the invention on the activity of indoleamine 2,3-dioxygenase (IDO) in Hela cells induced by IFN-γ were evaluated by the Ehrlich method.

The experimental principle is summarized as follows: IDO expression is low in Hela cells under no induction, but a certain concentration of IFN-γ can induces Hela cells to express IDO which catalyzes the conversion of tryptophan to N-formyl kynurenine, which in turn is hydrolyzed by trichloroacetic acid to give kynurenine. Kynurenine then reacts with the Ehrlich reagent to give a color enabling detection of the IDO activity. The absorbance at 490 nm (OD490) is directly proportional to the IDO activity.

A compound was dissolved in DMSO (Sigma, Cat. No. D5879) and diluted to 5 mM, then serially diluted 3-fold with DMSO to a minimum concentration of 2.29 μM, and each concentration point was diluted 50-fold with FBS-free DMEM medium (ThermoFisher, Cat. No. 11995073). If a compound's IC50 value is very low, the initial concentration of the compound was lowered.

Hela cells (ATCC, Cat. No. CCL-2) were cultured in DMEM complete medium containing 10% FBS (GBICO, Cat. No. 10099-141) and 100 U/mL streptomycin mixture (ThermoFisher, Cat. No. 15140122). When covering the culture vessel 80-90%, the cells were digested with 0.25% trypsin (containing EDTA) (ThermoFisher, Cat. No. 25200056) and planted in 96-well plates (Corning, Cat. No. 3599), 20000 cells per well (80 μL of DMEM medium). The plates were then incubated in a 37° C., 5% $CO_2$ incubator overnight (18-20 hours).

After overnight, 10 μL of DMEM-diluted compound and 10 μL of 500 ng/mL of INF-γ were added to each well, and gently mixed and the 96-well plates were placed in a 37° C., 5% $CO_2$ incubator for further culturing. After 24 hours, they were removed and centrifuged at room temperature 2000×g for 5 min, and then the supernatants were transferred to reaction plates (Sigma, Cat. No. CLS3695). One-twentieth of trichloroacetic acid (Sigma, Cat. No. T9159) was added and incubated at 60° C. After 30 min, the reaction plates were centrifuged at room temperature 2000×g for 5 min. The supernatants were transferred to clean reaction plates, an equal volume of the Ehrlich reagent was added, mixed, and incubated at room temperature. After 15 min, OD490 of each well was measured.

In this experiment, OD490 without IFN-γ but with DMEM medium replacement was referred as $OD490_{100\%\ inhibition}$. OD490 with IFN-γ and 0.2% DMSO was referred as $OD490_{0\%\ inhibition}$. The percentage of inhibition on the IDO1 activity in Hela cells by a compound was calculated using the following formula:

Inhibition %=100−100*($OD490_{compound}$−$OD490_{100\%\ inhibition}$)/($OD490_{0\%\ inhibition}$−$OD490_{100\%\ inhibition}$)

The IC50 value of a compound was obtained by fitting 8 concentration points using XLfit software (ID Business Solutions Ltd., UK) following the formula below:

Y=Bottom+(Top−Bottom)/(1+10^((log $IC_{50}$−X)*slope factor))

Where Y is the percentage of inhibition, Bottom is the bottom platform value of the S-curve, Top is the top platform value of the S-curve, X is the logarithm of the concentration of the test compound, and slope factor is the slope coefficient of the curve.

The activity data for part of representative example compounds are listed as follows:

| Compound number | $IC_{50}$ | Compound number | $IC_{50}$ |
| --- | --- | --- | --- |
| 17 | A | 19 | B |
| 21 | B | 22 | A |
| 23 | A | 24 | B |
| 36 | A | 37 | A |
| 49 | A | 50 | A |
| 51 | A | 53 | B |
| 54 | B | 64 | A |

A: <1 μM;
B: 1~10 μM.

Conclusion: The compounds of the invention have an inhibitory effect on the activity of IDO1 in Hela cells.

What is claimed is:

1. A compound of Formula (I') or a pharmaceutically acceptable salt thereof:

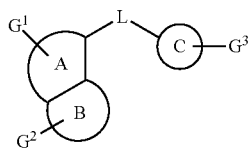

(I')

wherein
Ring A and ring B are condensed to form the following fused heterocyclic ring:

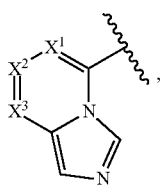

$X^1$, $X^2$ and $X^3$ are each independently selected from $CG^{11}$;
Ring C is phenyl or pyridyl, and is optionally substituted with one or two $G^3$;
L is selected from —$CH_2NHCH_2$—, —NHC(O)NH—, —$CH_2C(O)NH$—, and —NHC(O)$CH_2$—;
$G^{11}$ is selected from H, halogen, —$OC_{1-6}$ alkyl, phenyl which is unsubstituted or substituted with one or two halogens, $C_{4-6}$ cycloalkenyl, pyridyl or pyrazolyl; and
$G^3$ is selected from halogen, cyano, —$OC_{1-6}$ alkyl, —$C_{1-6}$ alkyl-OH, —C(O)OH, —C(O)O$C_{1-6}$ alkyl,
—C(O)$NH_2$, —C(O)NH$C_{1-6}$ alkyl, —C(O)N($C_{1-6}$ alkyl)$_2$, and —C(O)NH$C_{1-6}$ alkyl-OH.

2. A compound or a pharmaceutically acceptable salt thereof, wherein the compound is selected from:

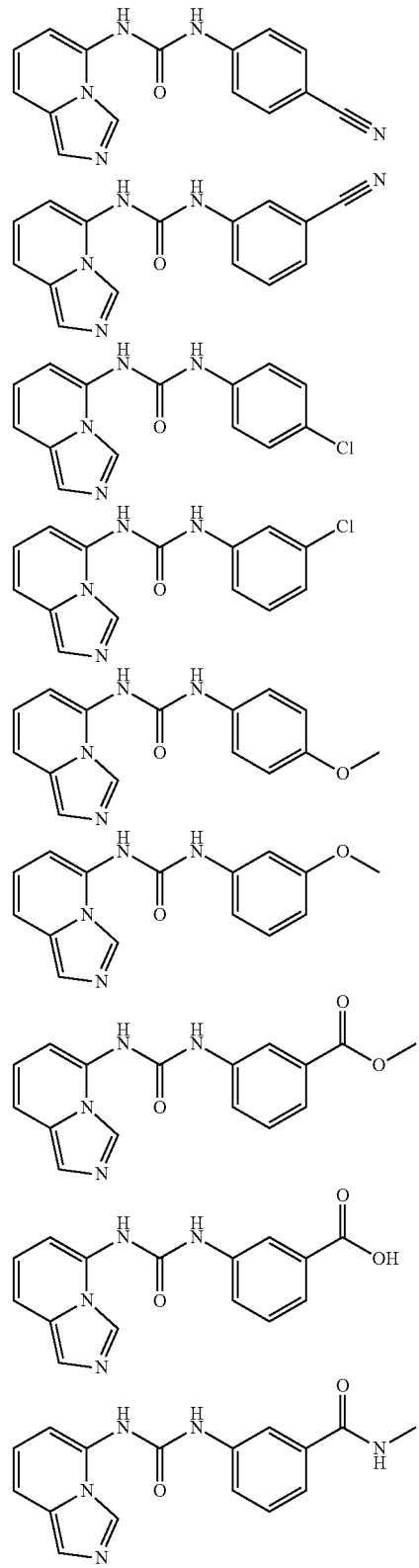

149
-continued
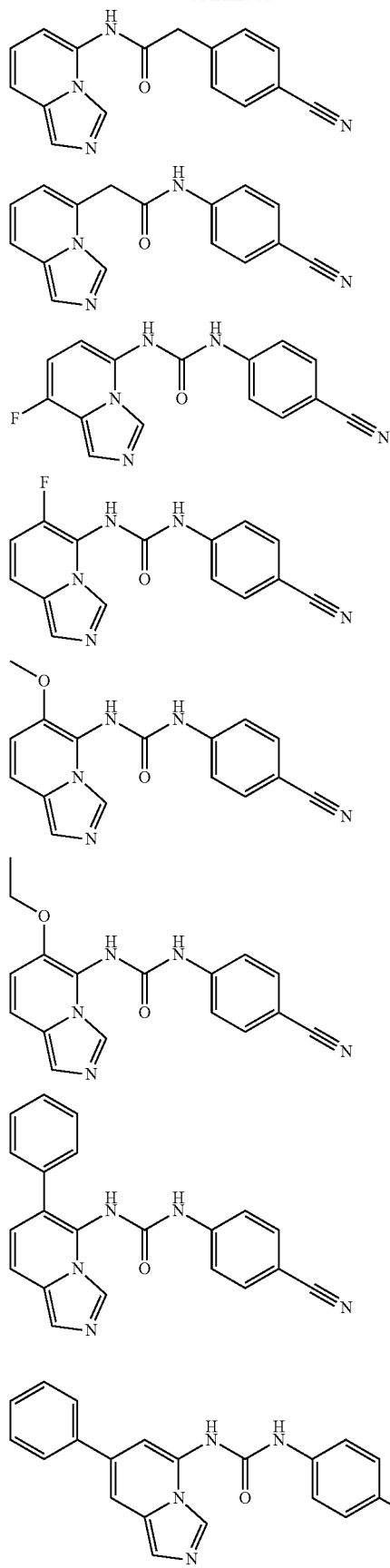
150
-continued
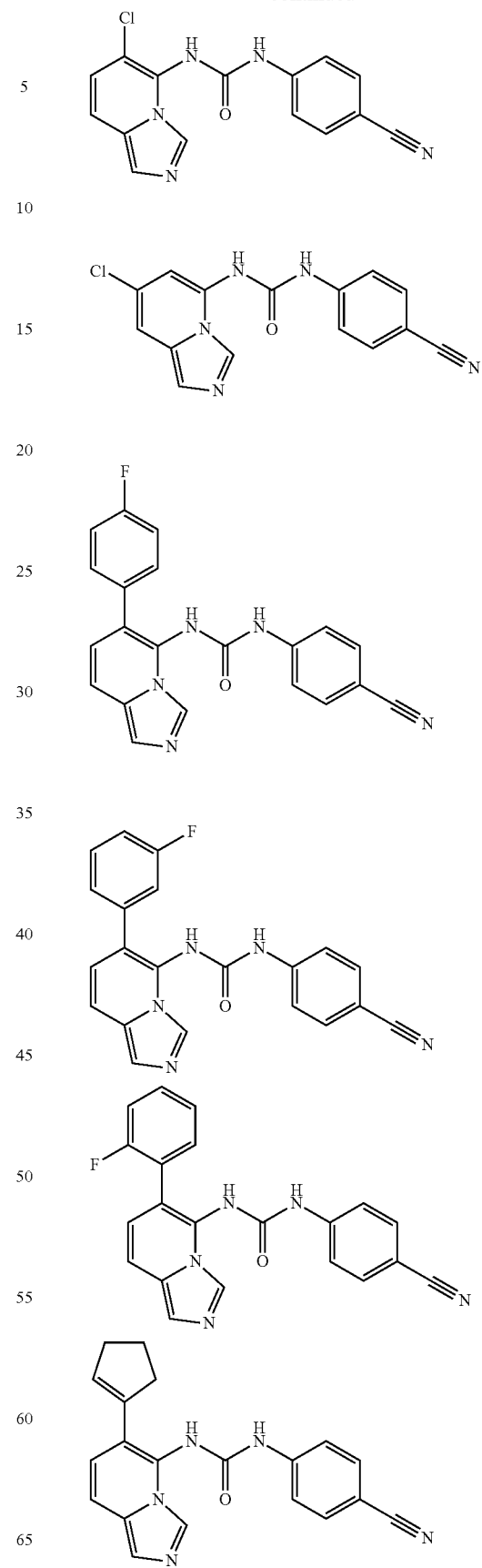

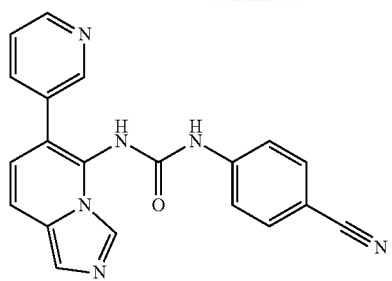 [SMILES: N#Cc1ccc(NC(=O)Nc2c(-c3cccnc3)ccc3cncn23)cc1]
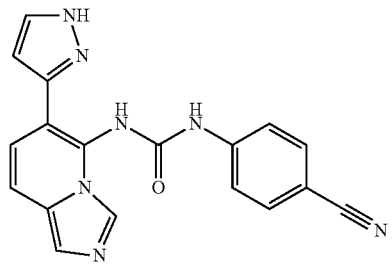 [SMILES: N#Cc1ccc(NC(=O)Nc2c(-c3cc[nH]n3)ccc3cncn23)cc1]
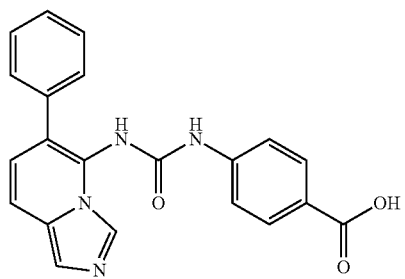 [SMILES: O=C(Nc1ccc(C(=O)O)cc1)Nc1c(-c2ccccc2)ccc2cncn12]
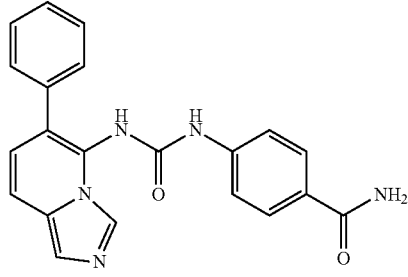 [SMILES: NC(=O)c1ccc(NC(=O)Nc2c(-c3ccccc3)ccc3cncn23)cc1]
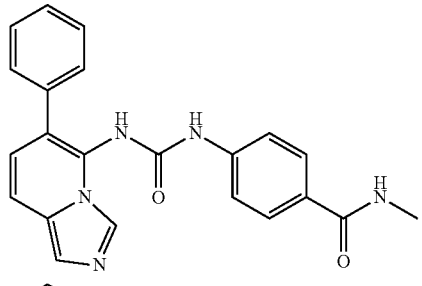
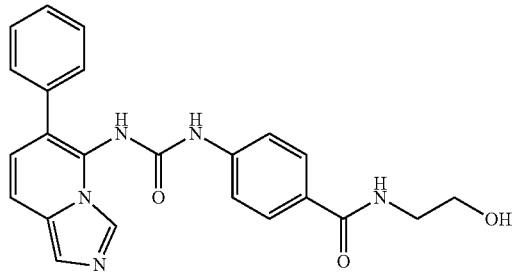 [SMILES: O=C(Nc1ccc(C(=O)NCCO)cc1)Nc1c(-c2ccccc2)ccc2cncn12]
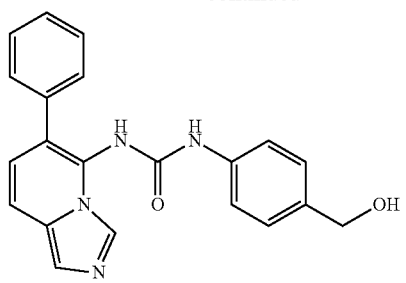 [SMILES: O=C(Nc1ccc(CO)cc1)Nc1c(-c2ccccc2)ccc2cncn12]
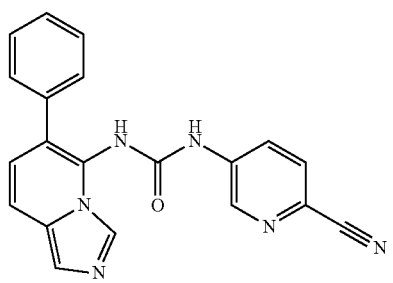 [SMILES: N#Cc1ccc(NC(=O)Nc2c(-c3ccccc3)ccc3cncn23)cn1]
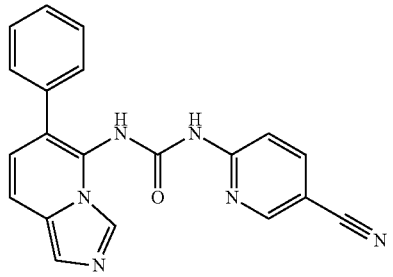
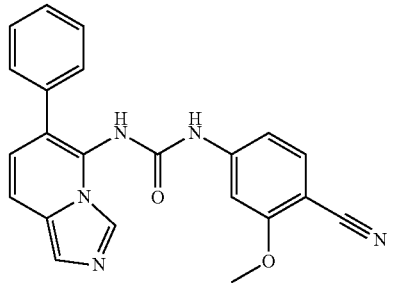 [SMILES: COc1cc(NC(=O)Nc2c(-c3ccccc3)ccc3cncn23)ccc1C#N]
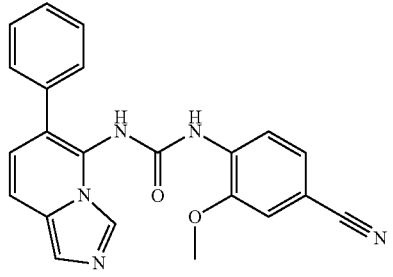 [SMILES: COc1cc(C#N)ccc1NC(=O)Nc1c(-c2ccccc2)ccc2cncn12]
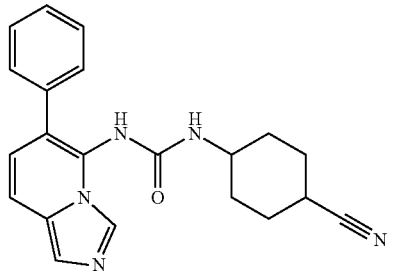 [SMILES: N#CC1CCC(NC(=O)Nc2c(-c3ccccc3)ccc3cncn23)CC1]

153
-continued

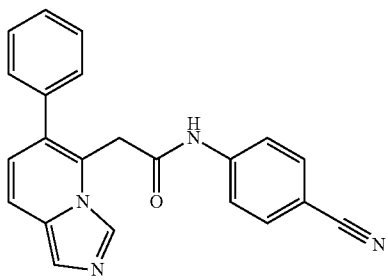 [SMILES: N#Cc1ccc(NC(=O)Cc2c(-c3ccccc3)ccc3cncn23)cc1]

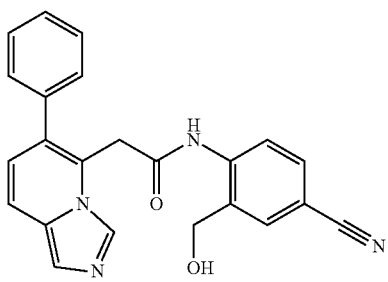 [SMILES: N#Cc1ccc(NC(=O)Cc2c(-c3ccccc3)ccc3cncn23)c(CO)c1]

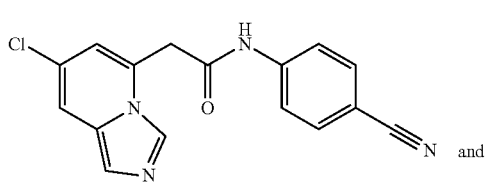

and

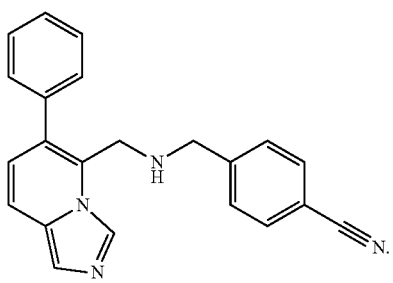

3. A pharmaceutical composition comprising a therapeutically effective amount of a compound according to claim 1 or 2, or a pharmaceutically acceptable salt thereof, and pharmaceutically acceptable carriers and excipients.

4. The pharmaceutical composition of claim 3, further comprising one or more other anticancer agents.

5. A compound or a pharmaceutically acceptable salt thereof, wherein the compound is selected from:

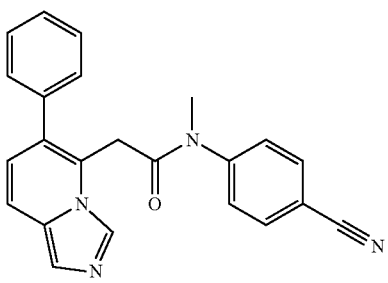

154
-continued

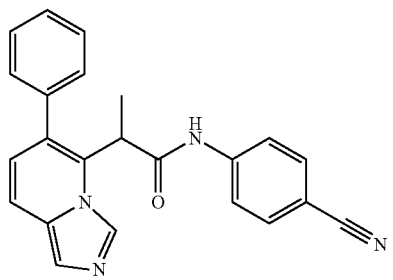

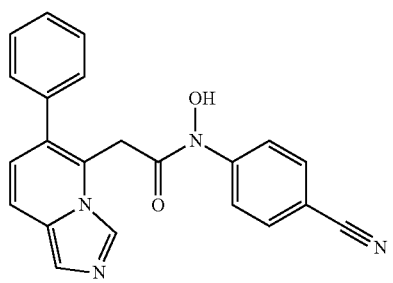

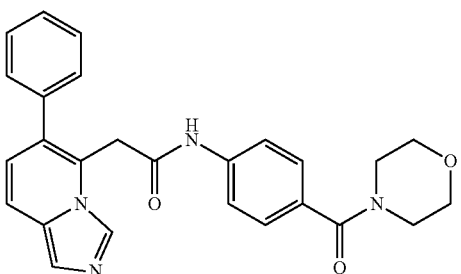

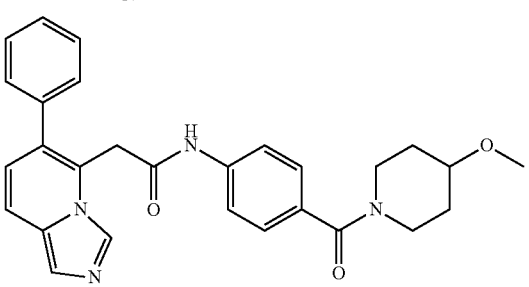

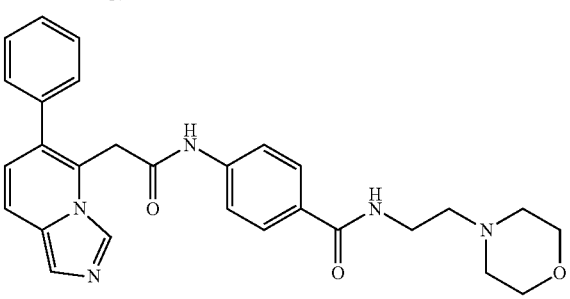

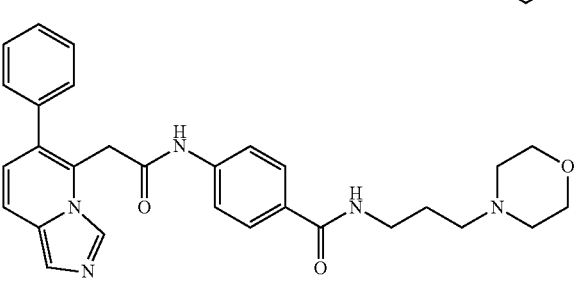

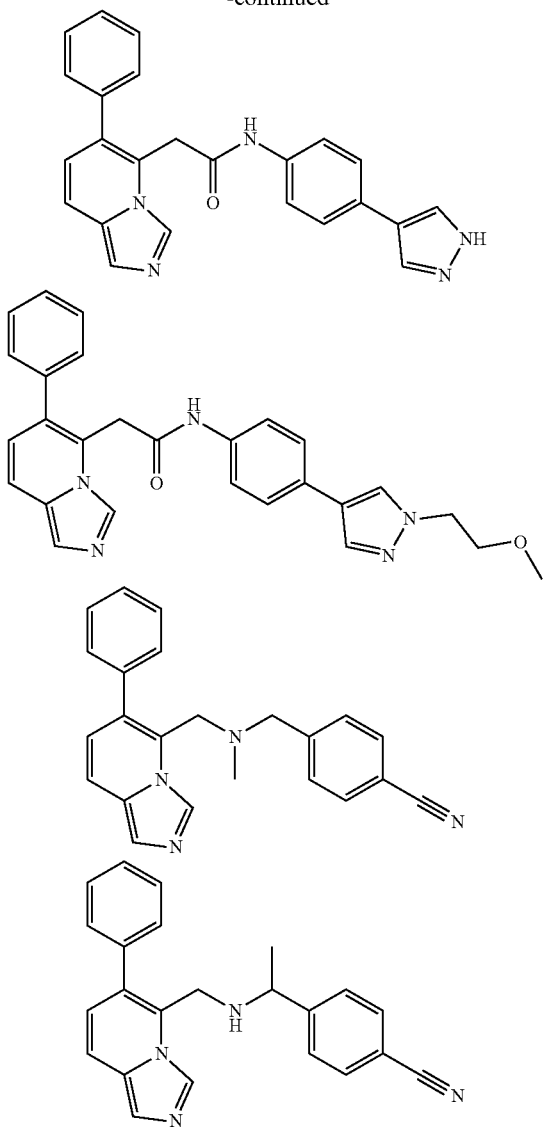
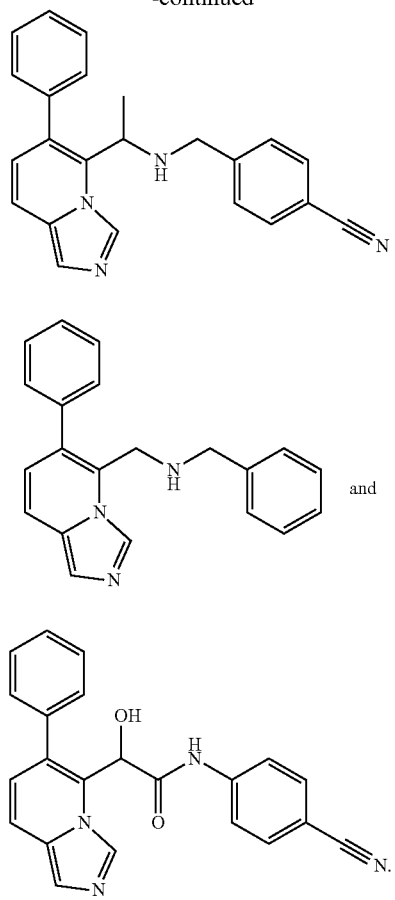
6. A pharmaceutical composition comprising a therapeutically effective amount of a compound according to claim 5, or a pharmaceutically acceptable salt thereof, and pharmaceutically acceptable carriers and excipients.
7. The pharmaceutical composition of claim 6, further comprising one or more other anticancer agents.
* * * * *